(12) United States Patent
Foster et al.

(10) Patent No.: US 12,365,712 B2
(45) Date of Patent: Jul. 22, 2025

(54) SINGLE-CHAIN TNF RECEPTOR 2 AGONIST FUSION PROTEINS

(71) Applicant: Relinia, Inc., Euless, TX (US)

(72) Inventors: David C. Foster, Euless, TX (US); Lutz B. Giebel, San Mateo, CA (US); Leonard G. Presta, San Francisco, CA (US)

(73) Assignee: Relinia, Inc., Euless, TX (US)

( * ) Notice: Subject to any disclaimer, the term of this patent is extended or adjusted under 35 U.S.C. 154(b) by 0 days.

(21) Appl. No.: 18/052,180

(22) Filed: Nov. 2, 2022

(65) Prior Publication Data

US 2024/0076334 A1 Mar. 7, 2024

Related U.S. Application Data

(62) Division of application No. 16/618,233, filed as application No. PCT/US2018/036139 on Jun. 5, 2018, now Pat. No. 11,530,247.

(60) Provisional application No. 62/515,643, filed on Jun. 6, 2017.

(51) Int. Cl.
| | | |
|---|---|---|
| *C07K 19/00* | (2006.01) | |
| *A61K 39/00* | (2006.01) | |
| *A61P 29/00* | (2006.01) | |
| *C07K 14/525* | (2006.01) | |
| *C07K 16/46* | (2006.01) | |
| *C12N 5/00* | (2006.01) | |
| *C12N 15/00* | (2006.01) | |
| *A61K 38/00* | (2006.01) | |
| *C12N 5/07* | (2010.01) | |
| *C12N 15/62* | (2006.01) | |

(52) U.S. Cl.
CPC ............ *C07K 14/525* (2013.01); *A61P 29/00* (2018.01); *A61K 38/00* (2013.01); *A61K 39/00* (2013.01); *C07K 16/46* (2013.01); *C07K 19/00* (2013.01); *C07K 2319/02* (2013.01); *C07K 2319/30* (2013.01); *C07K 2319/50* (2013.01); *C07K 2319/70* (2013.01); *C12N 5/06* (2013.01); *C12N 15/62* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,816,567 A | 3/1989 | Cabilly et al. |
| 5,648,237 A | 7/1997 | Carter |
| 5,739,277 A | 4/1998 | Presta et al. |
| 5,789,199 A | 8/1998 | Joly et al. |
| 5,840,523 A | 11/1998 | Simmons et al. |
| 5,959,177 A | 9/1999 | Hein et al. |
| 6,040,498 A | 3/2000 | Stomp et al. |
| 6,133,426 A | 10/2000 | Gonzalez et al. |
| 6,417,429 B1 | 7/2002 | Hein et al. |
| 6,420,548 B1 | 7/2002 | Vezina et al. |
| 6,946,292 B2 | 9/2005 | Kanda et al. |
| 7,064,191 B2 | 6/2006 | Shinkawa et al. |
| 7,125,978 B1 | 10/2006 | Vezina et al. |
| 7,691,568 B2 | 4/2010 | Niwa et al. |
| 7,700,099 B2 | 4/2010 | Strohl |
| 7,749,753 B2 | 7/2010 | Kanda et al. |
| 8,450,460 B2 | 5/2013 | Hill et al. |
| 9,724,390 B2 | 8/2017 | Gurney |
| 11,142,558 B2 | 10/2021 | Fischer et al. |
| 2003/0157108 A1 | 8/2003 | Presta |
| 2004/0093621 A1 | 5/2004 | Shitara et al. |
| 2004/0110704 A1 | 6/2004 | Yamane et al. |
| 2004/0132140 A1 | 7/2004 | Satoh et al. |
| 2005/0265962 A1 | 12/2005 | Desjarlais et al. |
| 2011/0135657 A1* | 6/2011 | Hu .................. C07K 16/18 435/69.6 |
| 2014/0322212 A1* | 10/2014 | Brogdon ............ A61K 38/1774 435/328 |
| 2015/0056159 A1 | 2/2015 | Kontermann et al. |
| 2016/0222130 A1* | 8/2016 | Kamohara ............. C12N 15/63 |

(Continued)

FOREIGN PATENT DOCUMENTS

| | | |
|---|---|---|
| WO | 1997/11971 A1 | 4/1997 |
| WO | 1999/058572 A1 | 11/1999 |

(Continued)

OTHER PUBLICATIONS

Boschert et al. "Single chain TNF derivatives with individually mutated receptor binding sites reveal differential stoichiometry of ligand receptor complex formation for TNFR1 and TNER2," Cellular Signaling 22 (2010) 1088-1096.

Chopra et al. "Exogenous TNFR2 activation protects from acute GvHD via host T reg cell expansion," J. Exp. Med. Aug. 15, 2016, 2016, 1-20.

Dong et al. "Essential protective role of tumor necrosis factor receptor 2 in neurodegeneration," PNAS, vol. 113, No. 43, Oct. 25, 2016, pp. 12304-12309.

(Continued)

*Primary Examiner* — Elizabeth C. Kemmerer
*Assistant Examiner* — Regina M DeBerry
(74) *Attorney, Agent, or Firm* — Goodwin Procter LLP

(57) ABSTRACT

This invention provides for a fusion protein between a single chain TNFR2 Selective Agonist protein (scTNFR2 Selective Agonist) and a dimerization domain, such as an IgGFc protein. The single chain TNFR2 Selective Agonist moiety provides a therapeutic activity by selectively activating the TNFR2 form of the TNF-α receptor, thus selectively stimulating Tregs and/or increasing myelin deposition.

7 Claims, 15 Drawing Sheets

Specification includes a Sequence Listing.

(56) References Cited

U.S. PATENT DOCUMENTS

| | | | |
|---|---|---|---|
| 2017/0107270 A1* | 4/2017 | Pons | A61K 47/6811 |
| 2017/0320959 A1* | 11/2017 | Swanson | A61K 39/4611 |
| 2020/0102362 A1 | 4/2020 | Fischer et al. | |
| 2022/0026741 A1 | 1/2022 | Tranvouez-Bernardin et al. | |

FOREIGN PATENT DOCUMENTS

| | | |
|---|---|---|
| WO | 2004/42072 A2 | 5/2004 |
| WO | 2007/106585 A1 | 9/2007 |
| WO | 2008/079246 A2 | 7/2008 |
| WO | 2010/010051 A1 | 1/2010 |
| WO | 2015/148708 A1 | 10/2015 |
| WO | 2016/070156 A2 | 5/2016 |
| WO | 2016/156291 A1 | 10/2016 |
| WO | 2017/040312 A1 | 3/2017 |
| WO | 201822675 A1 | 2/2018 |
| WO | 2018185247 A1 | 10/2018 |
| WO | 2020260368 A1 | 12/2020 |
| WO | 2023095913 A1 | 6/2023 |
| WO | 2024200987 A1 | 10/2024 |
| WO | 2024200988 A1 | 10/2024 |
| WO | 2024201144 A1 | 10/2024 |
| WO | 2024204896 A1 | 10/2024 |

OTHER PUBLICATIONS

Faustman and Davis. "TNF receptor 2 and disease: autoimmunity and regenerative medicine," Frontiers in Immunology, Dec. 2013, vol. 4, Article 478, pp. 1-8.

Faustman and Davis. "TNF receptor 2 pathway: drug target for autoimmune diseases," Nature Reviews, Jun. 2010, vol. 9, pp. 482-493.

Fischer et al. "A TNF Receptor 2 Selective Agonist Rescues Human Neurons from Oxidative Stress-Induced Cell Death," PLoS One Nov. 2011, vol. 6, Issue 11, pp. 1-11.

Fischer et al. "Astrocyte-Specific Activation of TNFR2 Promotes Oligodendrocyte Maturation by Secretion of Leukemia Inhibitory Factor," GLIA 2014; 62:272-283.

Fischer et al. "Novel strategies to mimic transmembrane tumor necrosis factor-dependent activation of tumor necrosis factor receptor 2," Scientific Reports, Jul. 26, 2017, 7:6607, 1-13.

Fischer et al. "Selective Activation of Tumor Necrosis Factor Receptor II Induces Anti-inflammatory Responses and Alleviates Experimental Arthritis," Arthritis & Rheumatology, vol. 70, No. 5, May 2018, 722-735.

Fischer et al. "Targeting sTNF-TNFR1 Signaling as a New Therapeutic Strategy," Antibodies 2015, 4, 48-70.

Gao et al. "Opposing Functions of Microglial and Macrophagic TNFR2 in the Pathogenesis of Experimental Autoimmune Encephalomyelitis," Cell Reports Jan. 3, 2017, 18, 198-212.

He et al. "A TNFR2-Agonist Faciliatates High Purity Expansion of Low Purity Treg Cells," PLoS One, May 25, 2016, vol. 11, Iss. 5, E01563311, pp. 1-17.

Hutt et al. "Superior Properties of Fc-comprising scTRAIL Fusion Proteins," Mol Cancer Ther; 16(12) Dec. 2017, 2792-2802.

Krippner-Heidenreich et al. "Single-Chain TNF, a TNF Derivative with Enhanced Stability and Antitumoral Activity," J Immunol 2008; 180:8176-8183.

Liu et al. "Pharmacokinetics of IgG1 monoclonal antibodies produced in humanized Pichia pastoris with specific glycoforms: A comparative study with CHO prodcued materials." Biologicals 39: 205-210 (2011).

Loetscher et al. "Human Tumor Necrosis Factor a (TNF'a) Mutants with Exclusive Specificity for the 55-kDa or 75-kDTaN F' Receptors," J. Bio. Chem., vol. 268, No. 36, Issue of Dec. 15, 1993, pp. 26360-26367.

Madsen et al. "Oligodendroglial TNFR2 Mediates Membrane TNF Dependent Repair in Experimental Autoimmune Encephalomyelitis by Promoting Oligodendrocyte Differentiation and Remyelination," Journal of Neuroscience, May 4, 2016, vol. 36, No. 18, pp. 5128-5413.

Oganesyan Vaheh et al. "Structural characterization of a human Fc fragment engineered for lack of effector functions," Acta Crystallographica Section D Biological Crystallography, vol. 64, No. 6, Jun. 1, 2008, pp. 700-704.

Okubo et al. "Homogeneous Expansion of Human T-Regulatory Cells Via Tumor Necrosis Factor Receptor 2," Scientific Reports, Nov. 2013, 3:3153, 1-11.

Okubo et al. "Treg activation defect in type 1 diabetes: correction with TNFR2 agonism," Clinical & Translational Immunology (2016) 5, e56, 1-9.

Seifert et al. "The IgM CH2 Domain as Covalently Linked Homodimerization Module for the Generation of Fusion Proteins with Dual Specificity," Protein Engineering, Design & Selection, Sep. 17, 2012, vol. 25, No. 10, pp. 603-612.

Alegre, M L et al. "A non-activating "humanized" anti-CD3 monoclonal antibody retains immunosuppressive properties in vivo." Transplantation vol. 57,11 (1994): 1537-43.

Angal, S et al. "A single amino acid substitution abolishes the heterogeneity of chimeric mouse/human (IgG4) antibody." Molecular immunology vol. 30,1 (1993): 105-8.

Armour, K L et al. "Recombinant human IgG molecules lacking Fcgamma receptor I binding and monocyte triggering activities." European journal of immunology vol. 29,8 (1999): 2613-24.

Armour, Kathryn L et al. "Differential binding to human FcgammaRIIa and FcgammaRIIb receptors by human IgG wildtype and mutant antibodies." Molecular immunology vol. 40,9 (2003): 585-93.

Bolt, S et al. "The generation of a humanized, non-mitogenic CD3 monoclonal antibody which retains in vitro immunosuppressive properties." European journal of immunology vol. 23,2 (1993): 403-11.

Brenner, Dirk et al. "Regulation of tumour necrosis factor signalling: live or let die." Nature reviews. Immunology vol. 15,6 (2015): 362-74.

Challener, "Fusion Proteins Pose Manufacturability Challenges." BioPharm International, May 1, 2017 30(5): 30-31, 37.

Chen, Xiaoying et al. "Fusion protein linkers: property, design and functionality." Advanced drug delivery reviews vol. 65,10 (2013): 1357-69.

Chu, Seung Y et al. "Inhibition of B cell receptor-mediated activation of primary human B cells by coengagement of CD19 and FcgammaRIIb with Fc-engineered antibodies." Molecular immunology vol. 45, 15 (2008): 3926-33.

Cole, M S et al. "HuM291, a humanized anti-CD3 antibody, is immunosuppressive to T cells while exhibiting reduced mitogenicity in vitro." Transplantation vol. 68,4 (1999): 563-71.

Evans et al. "Design of Nonpeptidal Ligands for a Peptide Receptor: Cholecystokinin" (1987) J. Med. Chem., 30: 1229-1239.

Gerngross, Tillman U. "Advances in the production of human therapeutic proteins in yeasts and filamentous fungi." Nature biotechnology vol. 22,11 (2004): 1409-14.

Graham, F L et al. "Characteristics of a human cell line transformed by DNA from human adenovirus type 5." The Journal of general virology vol. 36,1 (1977): 59-74.

Grell, M et al. "The transmembrane form of tumor necrosis factor is the prime activating ligand of the 80 kDa tumor necrosis factor receptor." Cell vol. 83,5 (1995): 793-802.

Hutchins et al. "Improved biodistribution, tumor targetting, reduced immunogenicity in mice with a gamma4 variant of Campath-1H." (1995) Proc Natl Acad Sci USA 92: 11980-11984.

Kanda, Yutaka et al. "Comparison of cell lines for stable production of fucose-negative antibodies with enhanced ADCC." Biotechnology and bioengineering vol. 94,4 (2006): 680-8.

Lazar, Greg A et al. "Engineered antibody Fc variants with enhanced effector function." Proceedings of the National Academy of Sciences of the United States of America vol. 103,11 (2006): 4005-10.

Li, Huijuan et al. "Optimization of humanized IgGs in glycoengineered Pichia pastoris." Nature biotechnology vol. 24,2 (2006): 210-5.

Lightle, Sandra et al. "Mutations within a human IgG2 antibody form distinct and homogeneous disulfide isomers but do not affect

(56) References Cited

OTHER PUBLICATIONS

Fc gamma receptor or C1q binding." Protein science : a publication of the Protein Society vol. 19,4 (2010): 753-62.

Mather, J P et al. "Culture of testicular cells in hormone-supplemented serum-free medium." Annals of the New York Academy of Sciences vol. 383 (1982): 44-68.

Mather, J P. "Establishment and characterization of two distinct mouse testicular epithelial cell lines." Biology of reproduction vol. 23,1 (1980): 243-52.

McEarchern, Julie A et al. "Engineered anti-CD70 antibody with multiple effector functions exhibits in vitro and in vivo antitumor activities." Blood vol. 109,3 (2007): 1185-92.

Naismith, J H et al. "Crystallographic evidence for dimerization of unliganded tumor necrosis factor receptor." The Journal of biological chemistry vol. 270,22 (1995): 13303-7.

Okazaki, Akira et al. "Fucose depletion from human IgG1 oligosaccharide enhances binding enthalpy and association rate between IgG1 and FcgammaRIIIa." Journal of molecular biology vol. 336,5 (2004): 1239-49.

Peters, Shirley J et al. "Engineering an improved IgG4 molecule with reduced disulfide bond heterogeneity and increased Fab domain thermal stability." The Journal of biological chemistry vol. 287,29 (2012): 24525-33.

Reddy, M P et al. "Elimination of Fc receptor-dependent effector functions of a modified IgG4 monoclonal antibody to human CD4." Journal of immunology (Baltimore, Md. : 1950) vol. 164,4 (2000): 1925-33.

Ripka et al. "Two Chinese Hamster Ovary Glycosylation Mutants Affected in the Conversion of GDP-Mannose to GDP-Fucose" (1986) Arch. Biochem. Biophys. 249: 533-545.

Rizo and Gierasch "Constrained Peptides: Models of Bioactive Peptides and Protein SUBSTRUCTURES" (1992) Ann. Rev. Biochem. 61: 387-416.

Sazinsky, Stephen L et al. "Aglycosylated immunoglobulin G1 variants productively engage activating Fc receptors." Proceedings of the National Academy of Sciences of the United States of America vol. 105,51 (2008): 20167-72.

Shields, R L et al. "High resolution mapping of the binding site on human IgG1 for Fc gamma RI, Fc gamma RII, Fc gamma RIII, and FcRn and design of IgG1 variants with improved binding to the Fc gamma R." The Journal of biological chemistry vol. 276,9 (2001): 6591-604.

U.S. Appl. No. 18/942,121, filed Nov. 8, 2024, Title: TNF-Alpha Variant Fusion Molecules.

Urlaub, G, and L A Chasin. "Isolation of Chinese hamster cell mutants deficient in dihydrofolate reductase activity." Proceedings of the National Academy of Sciences of the United States of America vol. 77,7 (1980): 4216-20.

White et al. "Conformation of the human immunoglobulin G2 hinge imparts superagonistic properties to immunostimulatory anticancer antibodies." Cancer Cell Jan. 12, 2015;27(1):138-48.

Xu, D et al. "In vitro characterization of five humanized OKT3 effector function variant antibodies." Cellular immunology vol. 200,1 (2000): 16-26.

Yamane-Ohnuki, Naoko et al. "Establishment of FUT8 knockout Chinese hamster ovary cells: an ideal host cell line for producing completely defucosylated antibodies with enhanced antibody-dependent cellular cytotoxicity." Biotechnology and bioengineering vol. 87,5 (2004): 614-22.

Yazaki and Wu, Methods in Molecular Biology, vol. 248 (B.K.C. Lo, ed., Humana Press, Totowa, NJ), pp. 255-268 (2003).

* cited by examiner

MSTESMIRDVELAEEALPKKTGGPQGSRRCLFLSLFSFLIVAGATTLFCLLHFGVIG*PQR*
*EEFPRDLSLISPLAQAVRSSSRTPSDK*PVAHVVANPQAEGQLQWLNRRANALLANGVELR
DNQLVVPSEGLYLIYSQVLFKGQGCPSTHVLLTHTISRIAVSYQTKVNLLSAIKSPCQRE
TPEGAEAKPWYEPIYLGGVFQLEKGDRLSAEINRPDYLDFAESGQVYFGIIAL
　　　　　　　　　　　　　　　　　　　　　　↑↑

Figure 2

*VRSSSRTPSDK*PVAHVVANPQAEGQLQWLNRRANALLANGVELR
DNQLVVPSEGLYLIYSQVLFKGQGCPSTHVLLTHTISRIAVSYQTKVNLLSAIKSPCQRE
TPEGAEAKPWYEPIYLGGVFQLEKGDRLSAEINRPDYLDFAESGQVYFGIIAL

Figure 3

PVAHVVANPQAEGQLQWLNRRANALLANGVELR
DNQLVVPSEGLYLIYSQVLFKGQGCPSTHVLLTHTISRIAVSYQTKVNLLSAIKSPCQRE
TPEGAEAKPWYEPIYLGGVFQLEKGDRLSAEINRPDYLNFRESGQVYFGIIAL

Figure 4

VRSS SRTPSDK

Figure 5

Human IgG1 Fc fusions with FcgR & C1Q knock-out
trimeric TNF at Fc N-terminus

Version 1
v1g1  EPKSCDKTHTCPPCPAPELLGGPSVFLFPPKPKDTLMISRTPEVTCVVVDVSHEDPEVKFNWYVDGVEVHNA
v1g1 KTKPREEQYNSTYRVVSVLTVLHQDWLNGKEYKCKVSNKALPAPIEKTISKAKGQPREPQVYTLPPSRDELT
v1g1 KNQVSLTCLVKGFYPSDIAVEWESNGQPENNYKTTPPVLDSDGSFFLYSKLTVDKSRWQQGNVFSCSVMHEA
v1g1 LHNHYTQKSLSLSPGK
C => S
L234A L235A P331S
v1g1 EPKSSDKTHTCPPCPAPEAAGGPSVFLFPPKPKDTLMISRTPEVTCVVVDVSHEDPEVKFNWYVDGVEVHNA
v1g1 KTKPREEQYNSTYRVVSVLTVLHQDWLNGKEYKCKVSNKALPASIEKTISKAKGQPREPQVYTLPPSRDELT
v1g1 KNQVSLTCLVKGFYPSDIAVEWESNGQPENNYKTTPPVLDSDGSFFLYSKLTVDKSRWQQGNVFSCSVMHEA
v1g1 LHNHYTQKSLSLSPGK Version 2 with GGGGS between Fc and trimeric TNF
v2g1 GGGGSEPKSCDKTHTCPPCPAPELLGGPSVFLFPPKPKDTLMISRTPEVTCVVVDVSHEDPEVKFNWYVDGVEVHNA
v2g1 KTKPREEQYNSTYRVVSVLTVLHQDWLNGKEYKCKVSNKALPAPIEKTISKAKGQPREPQVYTLPPSRDELT
v2g1 KNQVSLTCLVKGFYPSDIAVEWESNGQPENNYKTTPPVLDSDGSFFLYSKLTVDKSRWQQGNVFSCSVMHEA
v2g1 LHNHYTQKSLSLSPGK
C => S
L234A L235A P331S
v2g1 GGGGSEPKSSDKTHTCPPCPAPEAAGGPSVFLFPPKPKDTLMISRTPEVTCVVVDVSHEDPEVKFNWYVDGVEVHNA
v2g1 KTKPREEQYNSTYRVVSVLTVLHQDWLNGKEYKCKVSNKALPASIEKTISKAKGQPREPQVYTLPPSRDELT
v2g1 KNQVSLTCLVKGFYPSDIAVEWESNGQPENNYKTTPPVLDSDGSFFLYSKLTVDKSRWQQGNVFSCSVMHEA
v2g1 LHNHYTQKSLSLSPGK

FIG. 6A

Human IgG1 Fc fusions with FcgR & C1Q knock-out
trimeric TNF at Fc C-terminus

Version 3 v3g1 EPKSCDKTHTCPPCPAPELLGGPSVFLFPPKPKDTLMISRTPEVTCVVVDVSHEDPEVKFNWYVDGVEVHNA
v3g1 KTKPREEQYNSTYRVVSVLTVLHQDWLNGKEYKCKVSNKALPAPIEKTISKAKGQPREPQVYTLPPSRDELT
v3g1 KNQVSLTCLVKGFYPSDIAVEWESNGQPENNYKTTPPVLDSDGSFFLYSKLTVDKSRWQQGNVFSCSVMHEA
v3g1 LHNHYTQKSLSLSP(GGGGS) n=1-5

C => S

L234A L235A P331S v3g1 EPKSSDKTHTCPPCPAPEAAGGPSVFLFPPKPKDTLMISRTPEVTCVVVDVSHEDPEVKFNWYVDGVEVHNA
v3g1 KTKPREEQYNSTYRVVSVLTVLHQDWLNGKEYKCKVSNKALPASIEKTISKAKGQPREPQVYTLPPSRDELT
v3g1 KNQVSLTCLVKGFYPSDIAVEWESNGQPENNYKTTPPVLDSDGSFFLYSKLTVDKSRWQQGNVFSCSVMHEA
v3g1 LHNHYTQKSLSLSP(GGGGS) n=1-5

FIG. 6B

Human IgG4 Fc fusions
trimeric TNF at Fc N-terminus

Version 1
v1g4  ESKYGPPCPSCPAPEFLGGPSVFLFPPKPKDTLMISRTPEVTCVVVDVSQEDPEVQFNWYVDGVEVHNA
v1g4  KTKPREEQFNSTYRVVSVLTVLHQDWLNGKEYKCKVSNKGLPSSIEKTISKAKGQPREPQVYTLPPSQEEMT
v1g4  KNQVSLTCLVKGFYPSDIAVEWESNGQPENNYKTTPPVLDS

```
Human IgG4 Fc fusions
trimeric TNF at Fc C-terminus

Version 3
v3g4     ESKYGPPCPSCPAPEFLGGPSVFLFPPKPKDTLMISRTPEVTCVVVDVSQEDPEVQFNWYVDGVEVHNA
v3g4 KTKPREEQFNSTYRVVSVLTVLHQDWLNGKEYKCKVSNKGLPSSIEKTISKAKGQPREPQVYTLPPSQEEMT
v3g4 KNQVSLTCLVKGFYPSDIAVEWESNGQPENNYKTTPPVLDSDGSFFLYSRLTVDKSRWQEGNVFSCSVMHEA
v3g4 LHNHYTQKSLSLSL(GGGGS) n=1-5
S => P
v3g4     ESKYGPPCPPCPAPEFLGGPSVFLFPPKPKDTLMISRTPEVTCVVVDVSQEDPEVQFNWYVDGVEVHNA
v3g4 KTKPREEQFNSTYRVVSVLTVLHQDWLNGKEYKCKVSNKGLPSSIEKTISKAKGQPREPQVYTLPPSQEEMT
v3g4 KNQVSLTCLVKGFYPSDIAVEWESNGQPENNYKTTPPVLDSDGSFFLYSRLTVDKSRWQEGNVFSCSVMHEA
v3g4 LHNHYTQKSLSLSL(GGGGS) n=1-5
```

FIG. 7B

```
Human IgG2 Fc fusions with C1q knock-out
trimeric TNF at Fc N-terminus

Version 1
v1g2    ERKCCVECPPCPAPPVAGPSVFLFPPKPKDTLMISRTPEVTCVVVDVSHEDPEVQFNWYVDGVEVHNA
v1g2 KTKPREEQFNSTFRVVSVLTVVHQDWLNGKEYKCKVSNKGLPAPIEKTISKTKGQPREPQVYTLPPSREEM
v1g2 TKNQVSLTCLVKGFYPSDIAVEWESNGQPENNYKTTPPMLDSDGSFFLYSKLTVDKSRWQQGNVFSCSVMH
v1g2 EALHNHYTQKSLSLSPGK
C => S
P331S
v1g2    ERKSSVECPPCPAPPVAGPSVFLFPPKPKDTLMISRTPEVTCVVVDVSHEDPEVQFNWYVDGVEVHNA
v1g2 KTKPREEQFNSTFRVVSVLTVVHQDWLNGKEYKCKVSNKGLPASIEKTISKTKGQPREPQVYTLPPSREEM
v1g2 TKNQVSLTCLVKGFYPSDIAVEWESNGQPENNYKTTPPMLDSDGSFFLYSKLTVDKSRWQQGNVFSCSVMH
v1g2 EALHNHYTQKSLSLSPGK Version 2  with GGGGS between Fc and trimeric TNF
v1g2 GGGGSERKCCVECPPCPAPPVAGPSVFLFPPKPKDTLMISRTPEVTCVVVDVSHEDPEVQFNWYVDGVEVHNA
v1g2 KTKPREEQFNSTFRVVSVLTVVHQDWLNGKEYKCKVSNKGLPAPIEKTISKTKGQPREPQVYTLPPSREEM
v1g2 TKNQVSLTCLVKGFYPSDIAVEWESNGQPENNYKTTPPMLDSDGSFFLYSKLTVDKSRWQQGNVFSCSVMH
v1g2 EALHNHYTQKSLSLSPGK
C => S
P331S
v1g2 GGGGSERKSSVECPPCPAPPVAGPSVFLFPPKPKDTLMISRTPEVTCVVVDVSHEDPEVQFNWYVDGVEVHNA
v1g2 KTKPREEQFNSTFRVVSVLTVVHQDWLNGKEYKCKVSNKGLPASIEKTISKTKGQPREPQVYTLPPSREEM
v1g2 TKNQVSLTCLVKGFYPSDIAVEWESNGQPENNYKTTPPMLDSDGSFFLYSKLTVDKSRWQQGNVFSCSVMH
v1g2 EALHNHYTQKSLSLSPGK
```

FIG. 8A

```
Human IgG2 Fc fusions
trimeric TNF at Fc C-terminus

Version 3
v1g2     ERKCCVECPPCPAPPVAGPSVFLFPPKPKDTLMISRTPEVTCVVVDVSHEDPEVQFNWYVDGVEVHNA
v1g2 KTKPREEQFNSTFRVVSVLTVVHQDWLNGKEYKCKVSNKGLPAPIEKTISKTKGQPREPQVYTLPPSREEM
v1g2 TKNQVSLTCLVKGFYPSDIAVEWESNGQPENNYKTTPPMLDSDGSFFLYSKLTVDKSRWQQGNVFSCSVMH
v1g2 EALHNHYTQKSLSLSP(GGGGS) n=1-5
C => S
P331S
v1g2     ERKSSVECPPCPAPPVAGPSVFLFPPKPKDTLMISRTPEVTCVVVDVSHEDPEVQFNWYVDGVEVHNA
v1g2 KTKPREEQFNSTFRVVSVLTVVHQDWLNGKEYKCKVSNKGLPASIEKTISKTKGQPREPQVYTLPPSREEM
v1g2 TKNQVSLTCLVKGFYPSDIAVEWESNGQPENNYKTTPPMLDSDGSFFLYSKLTVDKSRWQQGNVFSCSVMH
v1g2 EALHNHYTQKSLSLSP(GGGGS) n=1-5
```

FIG. 8B v3g1 EPKSSDKTHTCPPCPAPEAAGGPSVFLFPPKPKDTLMISRTPEVTCVVVDVSHEDPEVKFNWYVDGVEVHNA
v3g1 KTKPREEQYNSTYRVVSVLTVLHQDWLNGKEYKCKVSNKALPASIEKTISKAKGQPREPQVYTLPPSRDELT
v3g1 KNQVSLTCLVKGFYPSDIAVEWESNGQPENNYKTTPPVLDSDGSFFLYSKLTVDKSRWQQGNVFSCSVMHEA
v3g1 LHMHYTQKSLSLSP(ELQLEESSAEAQDGELDG)

FIG. 9

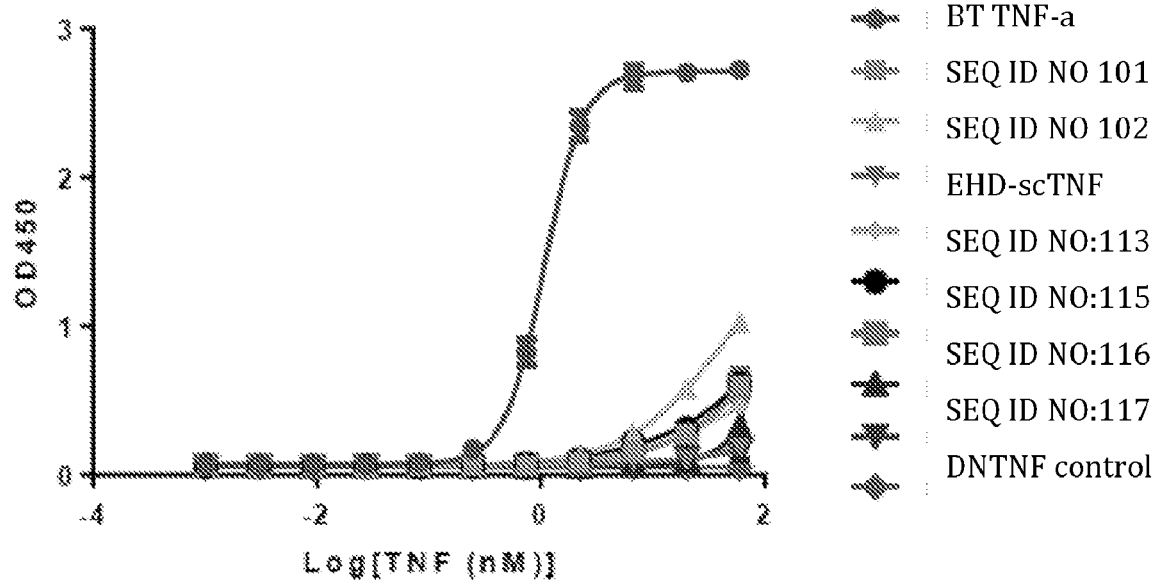
Figure 11A Binding of TNF Variants to immobilized TNFR1
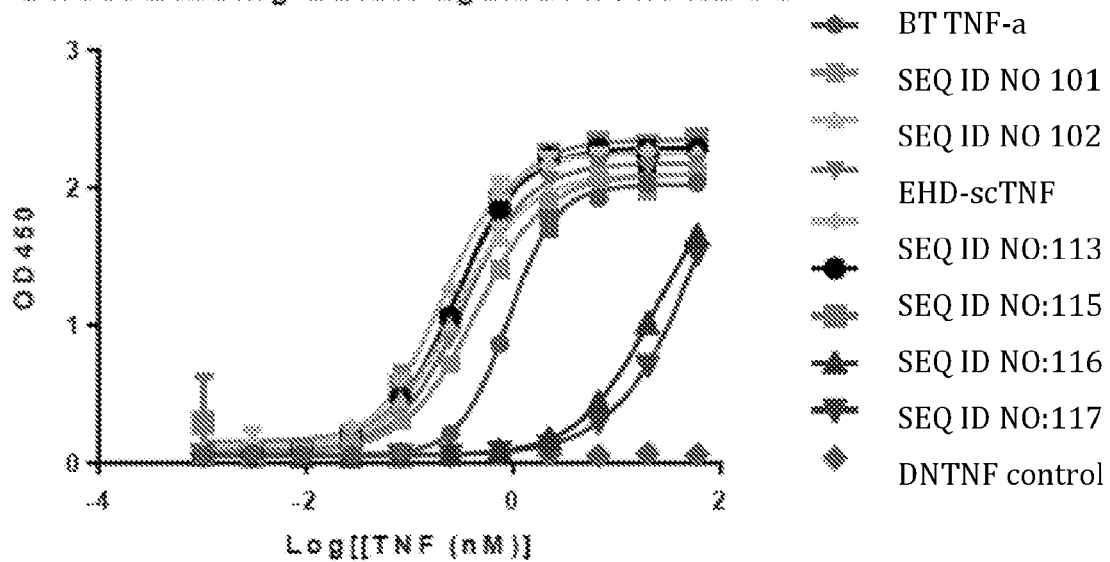
Figure 11B Binding of TNF Variants to immobilized TNFR2

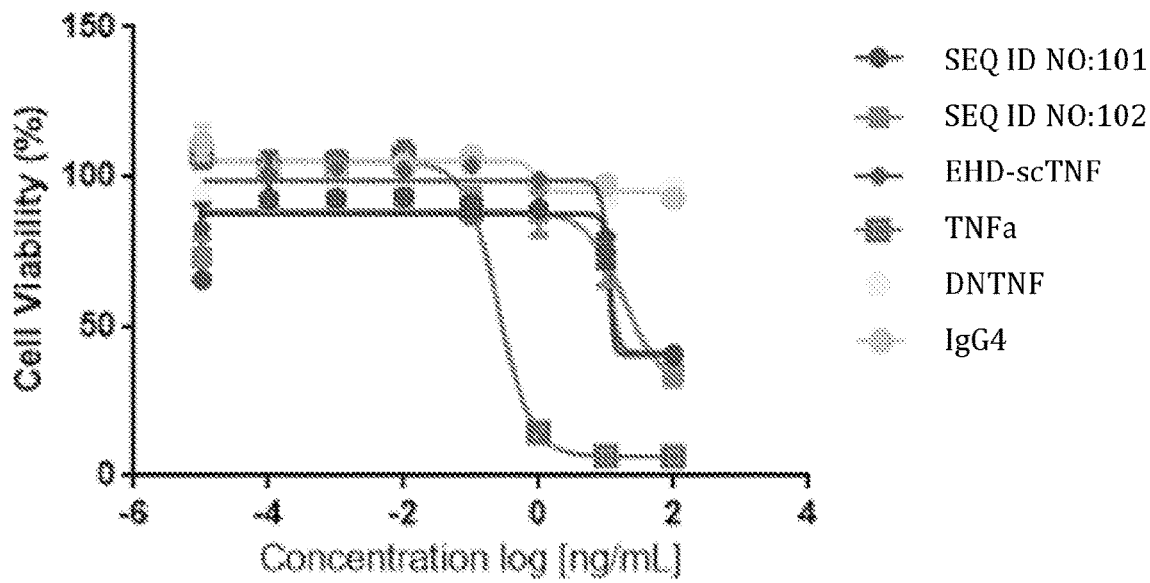
Figure 12a Kym-1 Cell Viability assay in the presence of TNF variants
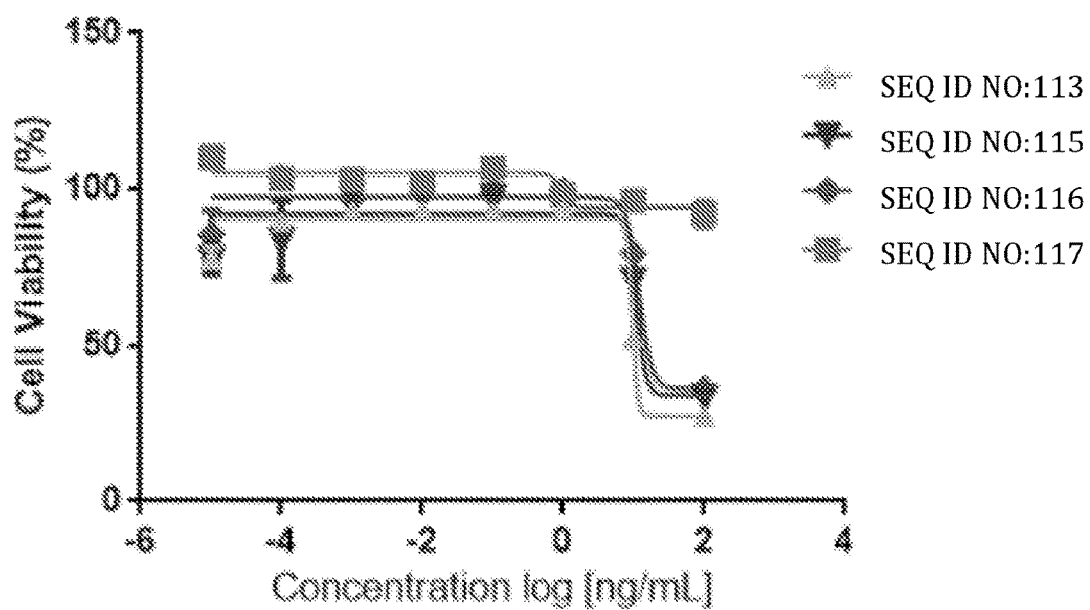
Figure 12b Kym-1 Cell Viability assay in the presence of TNF variants.

SINGLE-CHAIN TNF RECEPTOR 2 AGONIST FUSION PROTEINS

This application is a divisional of U.S. application Ser. No. 16/618,233, filed Nov. 29, 2019, now U.S. Pat. No. 11,530,247, which is a 371 of International Patent Application No. PCT/US2018/036139, filed Jun. 5, 2018, which claims the benefit of U.S. Provisional Application No. 62/515,643, filed Jun. 6, 2017, the contents of which are incorporated in its entirety by reference.

STATEMENT REGARDING FEDERALLY FUNDED RESEARCH

None

REFERENCE TO SEQUENCE LISTING

A listing of the sequences follows the specification and is expressly included in or incorporated herein by reference. This application contains a Sequence Listing which has been submitted electronically in XML format. The Sequence Listing XML is incorporated herein by reference. Said XML file, created on Sep. 7, 2023, is named TBI-100D1_SL.xml and is 179,025 bytes in size.

BACKGROUND

I. Field of the Invention

The present invention relates generally to the fields of TNF Receptor 2 agonist molecules and uses thereof.

II. Description of Related Art

Tumor necrosis factor-a (TNF-a) is a cytokine that is responsible for diverse biological effects such as inflammation and immune modulation. It is a target of a variety of therapeutic agents including antibodies such as Humira and Remicade.

SUMMARY

In one embodiment the present disclosure provides a fusion protein comprising a first TNF homology domain (THD) comprising D143N/A145R mutations, wherein the THD has at least 95% identity to SEQ ID NO: 3; a second THD comprising D143N/A145R mutations, wherein the THD has at least 95% identity to SEQ ID NO: 3; a third THD comprising D143N/A145R mutations, wherein the THD has at least 95% identity to SEQ ID NO: 3; an immunoglobulin Fc domain; and a first linker peptide covalently linking the first and second THDs and a second linker covalently linking the second and third THDs.

In some embodiments the linkers in the fusion protein are composed of from 1-31 or 2-15 or 3-10 amino acids and in some embodiments include at least some stalk region from TNF-a.

In some embodiments the Fc in the fusion protein is covalently linked to the N-terminus of the N-terminal THD or the C-terminus of the C-terminal THD.

In some embodiments the Fc is covalently linked to the THD by a linker, although in some embodiments the Fc and THD are directly connected.

In some embodiments the TNFR2 agonist-Fc fusion protein selectively activates TNFR2 over TNFR1, and in some embodiments upon administration to a subject, this fusion protein selectively activates a TNFR2 in the subject over TNFR1 in the subject. In some embodiments the TNFR2 agonist-Fc fusion protein preferentially activates T regulatory cells in the subject relative to conventional T cells in the subject. In some embodiments the TNFR2 agonist-Fc fusion protein increases myelination in a subject compared to control administration.

In some embodiments the present disclosure provides a nucleic acid encoding a fusion protein as described above.

In some embodiments the present disclosure provides a method of increasing myelin deposition in a patient in need thereof comprising administering a fusion protein as described herein to said patient.

In some embodiments the present disclosure provides method of treating demyelinating disease in a patient in need thereof comprising administering a fusion protein as described herein to said patient. In some embodiments the demyelinating disease is optic neuritis or multiple sclerosis.

In some embodiments the present disclosure provides a method of treating pain in a patient in need thereof comprising administering a fusion protein as described herein to said patient.

It is contemplated that any embodiment of a method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.p FIG. 1A shows domains of scTNFR2 agonist fusion proteins. FIG. 1B shows a scTNFR2 agonist fusion protein comprising N-terminal Fc, linker 1, stalk sequence, THD, linker 2, stalk sequence, THD, linker 2, stalk sequence THD. FIG. 1C shows a scTNFR2 agonist fusion protein comprising N-terminal Fc, linker 1, stalk sequence variation, THD, linker 2, stalk sequence variation, THD, linker 2, stalk sequence, THD. FIG. 1D shows a scTNFR2 agonist fusion protein comprising N-terminal Fc, linker 1, THD, linker 2, THD, linker 2, THD. FIG. 1E shows a scTNFR2 agonist fusion protein comprising N-terminal Fc, linker 1, stalk sequence, THD, linker 2, THD, linker 2, THD. FIG. 1F shows a scTNFR2 agonist fusion protein comprising N-terminal Fc, stalk sequence, THD, linker 2, THD, linker 2, THD. FIG. 1G shows a scTNFR2 agonist fusion protein comprising N-terminal THD, linker 2, THD, linker 2, THD, linker 1, Fc.

FIG. 2 Depicts sequence of wild type TNF-a. (SEQ ID NO:1) Bold indicates ADAM17 cleavage site between A and V. Italics indicate stalk region (amino acids 57-87). Underline indicates THD (amino acids 88-233). Arrows indicate amino acids to be mutated to form TNFR2 agonist.

FIG. 3 Depicts sequence of mature, soluble TNF-a. (SEQ ID NO:2)

FIG. 4 Depicts the TNF homology domain (THD) containing D143N/A145R mutations. (SEQ ID NO:3)

FIG. 5 Depicts the sequence from the ADAM17 cleavage site in the stalk region to the C-terminus of the stalk region. (SEQ ID NO:4)

FIG. 6A Version 1—Depicts Human IgG1 Fc sequence (SEQ ID NO:5) with FcγR and C1q knockout (SEQ ID NO:6). The C-terminus of the scTNFR2 agonist can be fused directly to Fc N-terminus. Version 2—Depicts Human IgG1 Fc sequence like Version 1 with the exception that linker GGGGS (SEQ ID NO: 25) is placed between the N-terminus of the Fc and C-terminus of the scTNFR2 agonist. (SEQ ID NO:7 and SEQ ID NO:8)

FIG. 6B Version 3—Depicts Human IgG1 Fc sequence with FcγR and C1Q knockout. The scTNFR2 agonist is at the Fc C-terminus contains a spacer of (GGGGS)$_n$, wherein n=1=5 (SEQ ID NO: 44). (SEQ ID NO:9 and SEQ ID NO: 10)

FIG. 7A Version 1—Depicts Human IgG4 Fc sequence. (SEQ ID NQ:11) and a variant containing Ser to Pro mutation (SEQ ID NO: 12) The C-terminus of the scTNFR2 agonist can be fused directly to Fc-N-terminus. Version 2—Depicts Human IgG4 Fc sequence like Version 1 with the exception that linker GGGGS (SEQ ID NO: 25) is placed between the N-terminus of the Fc and C-terminus of the scTNFR2 agonist. (SEQ ID NO: 13 and SEQ ID NO: 14)

FIG. 7B Version 3—Depicts Human IgG4 Fc sequence. The scTNFR2 agonist is at the Fc C-terminus which contains a spacer of (GGGGS)$_n$, wherein n=1=5 (SEQ ID NO: 44). (SEQ ID NO: 15 and SEQ ID NO: 16)

FIG. 8A Version 1—Depicts Human IgG2 Fc sequence (SEQ ID NO:17) with C1q knockout (SEQ ID NO: 18). The C-terminus of the scTNFR2 agonist can be fused directly to Fc-N-terminus. Version 2—Depicts Human IgG2 Fc sequence like Version 1 with the exception that linker GGGGS (SEQ ID NO: 25) is placed between the N-terminus of the Fc and C-terminus of the scTNFR2 agonist. (SEQ ID NO: 19 and SEQ ID NO:20)

FIG. 8B Version 3—Depicts Human IgG2 Fc sequence with C1Q knockout. The scTNFR2 agonist is at the Fc C-terminus contains a spacer of (GGGGS)$_n$, wherein n=1=5 (SEQ ID NO: 44). (SEQ ID NO:21 and SEQ ID NO:22)

FIG. 9 Depicts human IgG sequence including a C-terminal extension (SEQ ID NO:40).

FIG. 10B Electrophoregram of SEQ ID NO: 101 under non-reducing conditions.

FIGS. 11A-11B-FIG. 11A Binding of TNF Variants to immobilized TNFR1. FIG. 11B Binding of TNF Variants to immobilized TNFR2

FIGS. 12A-12B-FIG. 12a Kym-1 Cell Viability assay in the presence of TNF variants.

FIG. 12B Kym-1 Cell Viability assay in the presence of TNF variants.

DESCRIPTION

Figure 1A:
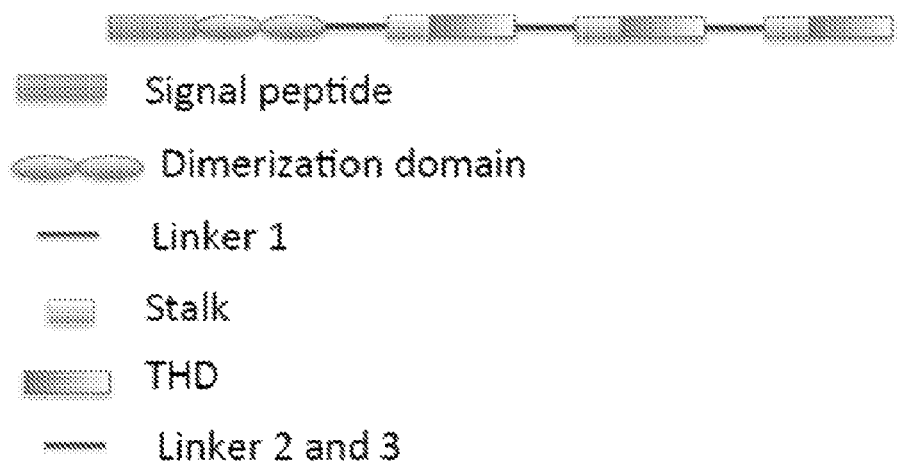
FIGS. 1A-1G: Configurations of scTNFR2 agonist fusion proteins.
Figure 1B:
Figure 1C:
Figure 1D:
Figure 1E:
Figure 1F:
Figure 1G:

TNF-a is found in both soluble forms and transmembrane forms as a homotrimer. The transmembrane precursor is cleaved, resulting in soluble form. The soluble and transmembrane form signal through two distinct receptors, TNFR1 and TNFR2, resulting in distinct biological effects. Soluble TNF-a (sTNF-a) signaling through TNFR1 is thought to mediate inflammation while transmembrane TNF-a (tmTNF-a) signaling through TNFR2 is thought to modulate immune response, stimulation of regulatory T-cells (Tregs) and myelin regulation.

While current products and methods of inhibiting TNF-a are effective and account for a significant therapeutic market, the current therapies are not without deleterious side effects. These range from immunosuppression to demyelination of neurons. For instance, therapeutics that are effective immunomodulators in the periphery are contraindicated for treatment of neuro inflammatory disorders. Currently marketed TNF-a inhibitors are labeled with a BLACK BOX WARNING specifically warning against treatment of neurological diseases because they cause demyelination resulting in worsening of the condition. These current TNF-a inhibitors block signaling by both soluble and tmTNF-a, resulting in the beneficial anti-inflammatory effects but also leading to deleterious side effects. Accordingly, there is a significant need for the development of molecules that stimulate signaling through the TNFR2 but not TNFR1.

Accordingly, the present disclosure provides novel TNFR2 agonist molecules. These find use as improved compositions and methods for treating disorders such as, but not limited to pain, nerve injury and/or demyelinating diseases such as, but not limited to multiple sclerosis and optic neuritis.

Definitions

"At least a percent (eg. 97%) sequence identify to Sequence ID No. X" as used herein refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs. For example, computer programs such as BLAST2, BLASTN, BLASTP, Gapped BLAST, etc., generate alignments and provide percent identity between sequences of interest. The algorithm of Karlin and Altschul (Karlin and Altschul, Proc. Natl. Acad. Sci USA 67:22264-2268, 1990) modified as in Karlin and Altschul, Proc. Natl. Acad. Sci USA 90:5873-5877, 1993 is incorporated into the NBLAST and XBLAST programs of Altschul et al. (Altschul, et al. J. Mol. Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL world-wide web address of: "ncbi.nlm.nih.gov" for these programs. In a specific embodiment, percent identity is calculated using BLAST2 with default parameters as provided by the NCBI.

"N-terminus" refers to the end of a peptide or polypeptide that bears an amino group in contrast to the carboxyl end bearing a carboxyl acid group.

"C-terminus" refers to the end of a peptide or polypeptide that bears a carboxylic acid group in contrast to the amino terminus bearing an amino group.

"C-terminal IgG Fc protein moiety" refers to a portion of a fusion protein that derives from two identical protein fragments, each having a hinge region, a second constant domain, and a third constant domains of the IgG molecule's two heavy chains, and consisting of the carboxy-terminal heavy chains disulphide bonded to each other through the hinge region.

It is functionally defined as that part of the IgG molecule that interacts with the complement protein C1q and the IgG-Fc receptors (FcγR), mediating Complement-dependent cytotoxicity (CDC) and antibody-dependent cellular cytotoxicity (ADCC) effector functions. The sequence can be modified to decrease effector functions, to increase circulating half-life, and to eliminate glycosylation sites.

Single-Chain TNF-a Variants

The single chain TNF-a variant fusion proteins described herein are generally composed of contiguous amino acids having the following domain structure:

DD-L1-THD-L2-THD-L3-THD or THD-L2-THD-L3-THD-L1-DD, where DD is a dimerization domain as described herein. LI, L2 and L3 are linkers that may be the same or different and THD is a TNF-a homology domain as defined herein. In preferred embodiments the fusion protein is encoded by contiguous nucleotides and expressed as a single contiguous polypeptide.

"N-terminal human TNF-a variant protein moiety" or "N-terminal scTNFR2 Agonist (scTNFR2)" refers to an N-terminal domain of a fusion protein that is derived from a wild type TNF-a protein structurally and functionally defined herein and that is composed of three THDs.

"C-terminal human TNF-a variant protein moiety" or "C-terminal scTNFR2 Agonist (scTNFR2)" refers to a C-terminal domain of a fusion protein that is derived from a wild type TNF-a protein structurally and functionally defines above.

Tregs

"Tregs" or "Treg cells" refer to Regulatory T cells. Regulatory T cells are a class of T cells that suppress the activity of other immune cells, and are defined using flow cytometry by the cell marker phenotype CD4+CD25+ FOXP3+. Because FOXP3 is an intracellular protein and requires cell fixation and permeablization for staining, the cell surface phenotype CD4+CD25+CD127− can be used for defining live Tregs. Tregs also include various Treg subclasses, such as tTregs (thymus-derived) and pTregs (peripherally-derived, differentiated from naive T cells in the periphery).

Peptide Linkers

"Peptide linker" is defined as an amino acid sequence located between the two proteins comprising a fusion protein, such that the linker peptide sequence is not derived from either partner protein. Peptide linkers are incorporated into fusion proteins as spacers in order to promote proper protein folding and stability of the component protein moieties, to improve protein expression, or to enable better bioactivity of the two fusion partners (Chen, et al., 2013, Adv Drug Deliv Rev. 65(10).1357-69). Peptide linkers can be divided into the categories of unstructured flexible peptides or rigid structured peptides.

Fc Fusion Proteins

An "Fc fusion protein" is a protein made by recombinant DNA technology in which the translational reading frame of the Fc domain of a mammalian IgG protein is fused to that of another protein ("Fc fusion partner") to produce a novel single recombinant polypeptide.

Fc fusion proteins are typically produced as disulfide-linked dimers, joined together by disulfide bonds located in the hinge region.

Functional Activation

"Bioactivity" refers to the measurement of biological activity in a quantitative cell-based in vitro assay.

"Functional activation of Treg cells" is defined a TNF-a-mediated response in Tregs. Assay readouts for functional activation of Treg cells includes stimulation of pSTAT5, Treg cell proliferation, and stimulation of the levels of Treg effector proteins.

Design and Construction

There are multiple options for the design and construction of an Fc fusion protein, and the choices among these design options are presented below to permit the generation of a molecule with the desired biological activity and pharmaceutical characteristics. Key design options are: (1) the nature of the TNF-ot Selective Agonist, (2) the choice of the dimerization domain protein moiety, i.e. Fc, (3) the configuration of fusion partners in the fusion protein, and (4) the amino acid sequence at the junction between the dimerization domain and the fusion partner protein as well as between the three THDs.

General Methods

In general, preparation of the fusion proteins of the invention can be accomplished by procedures disclosed herein and by recognized recombinant DNA techniques involving, e.g., polymerase chain amplification reactions (PCR), preparation of plasmid DNA, cleavage of DNA with restriction enzymes, preparation of oligonucleotides, ligation of DNA, isolation of mRNA, introduction of the DNA into a suitable cell, transformation or transfection of a host, culturing of the host. Additionally, the fusion molecules can be isolated and purified using chaotropic agents and well known electrophoretic, centrifugation and chromatographic methods. See generally, Sambrook et al., Molecular Cloning: A Laboratory Manual (2nd ed. (1989); and Ausubel et al., Current Protocols in Molecular Biology, John Wiley & Sons, New York (1989) for disclosure relating to these methods.

The genes encoding the fusion proteins of this invention involve restriction enzyme digestion and ligation as the basic steps employed to yield DNA encoding the desired fusions. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of E. coli. Numerous cloning vectors suitable for construction of the expression construct are known in the art (X.ZAP and pBLUESCRIPT SK-1, Stratagene, LaJolla, Calif., pET, Novagen Inc., Madison, Wis.—cited in Ausubel et al., 1999) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization and PCR analyses.

Site-directed mutagenesis is typically used to introduce specific mutations into the genes encoding the fusion proteins of this invention by methods known in the art. See, for example, U.S. Patent Application Publication 2004/0171154; Storici et al., 2001, Nature Biotechnology 19: 773-776; Kren et al., 1998, Nat. Med. 4: 285-290; and Calissano and Macino, 1996, Fungal Genet. Newslett. 43: 15-16. Any site-directed mutagenesis procedure can be used in the present invention. There are many commercial kits available that can be used to prepare the variants of this invention.

Various promoters (transcriptional initiation regulatory region) may be used according to the invention. The selection of the appropriate promoter is dependent upon the proposed expression host. Promoters from heterologous sources may be used as long as they are functional in the chosen host.

Various signal sequences may be used to facilitate expression of the proteins described herein. Signal sequence are selected or designed for efficient secretion and processing in the expression host may also be used. A signal sequence, which is homologous to the TCR coding sequence or the mouse IL-2 coding sequence may be used for mammalian cells. Other suitable signal sequence/host cell pairs include the B. subtilis sacB signal sequence for secretion in B. subtilis, and the Saccharomyces cerevisiae a-mating factor or P. pastoris acid phosphatase phol signal sequences for P. pastoris secretion. The signal sequence may be joined directly through the sequence encoding the signal peptidase cleavage site to the protein coding sequence, or through a short nucleotide bridge.

Elements for enhancing transcription and translation have been identified for eukaryotic protein expression systems. For example, positioning the cauliflower mosaic virus (CaMV) promoter 1000 bp on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10 fold.

The expression cassette(s) are joined to appropriate vectors compatible with the host that is being employed. The vector must be able to accommodate the DNA sequence coding for the fusion proteins to be expressed. Suitable host cells include eukaryotic and prokaryotic cells, preferably those cells that can be easily transformed and exhibit rapid growth in culture medium. Specifically preferred hosts cells include prokaryotes such as E. coli. Bacillus subtillus, etc. and eukaryotes such as animal cells and yeast strains, e.g., S. cerevisiae. Mammalian cells are generally preferred, particularly HEK, J558, NSO, SP2-O or CHO. Other suitable hosts include, e.g., insect cells such as Sf9. Conventional culturing conditions are employed. See Sambrook, supra. Stable transformed or transfected cell lines can then be selected. In vitro transcription-translation systems can also be employed as an expression system.

Nucleic acid encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, micro injection, viral transduction and/or integration. Suitable methods for transfecting host cells can be found in Sambrook et al. supra, and other laboratory textbooks.

Alternatively, one can use synthetic gene construction for all or part of the construction of the proteins described herein. This entails in vitro synthesis of a designed polynucleotide molecule to encode a polypeptide molecule of interest. Gene synthesis can be performed utilizing a number of techniques, such as the multiplex microchip-based technology described by Tian, et. al., (Tian, et. al., Nature 432:1050-1054) and similar technologies wherein oligonucleotides are synthesized and assembled upon photoprogrammable microfluidic chips.

The fusion proteins of this invention are isolated from harvested host cells or from the culture medium. Standard protein purification techniques are used to isolate the proteins of interest from the medium or from the harvested cells. In particular, the purification techniques can be used to express and purify a desired fusion protein on a large-scale (i.e. in at least milligram quantities) from a variety of approaches including roller bottles, spinner flasks, tissue culture plates, bioreactor, or a fermentor. •

The TNFR2 Selective Agonist Moiety and Fusion Proteins

In one embodiment the molecules described herein are single-chain, trimeric TNF-a molecules. By "single-chain" is meant that a single polypeptide comprises 3 THDs as described herein.

The single chain TNF-a variant fusion proteins described herein are generally composed of contiguous amino acids having the following domain structure: DD-L1-THD-L2-THD-L3-THD or THD-L2-THD-L3-THD-L1-DD, where DD is a dimerization domain as described herein. L1, L2 and L3 are linkers that may be the same or different and THD is a TNF-a homology domain as defined herein. In preferred embodiments the fusion protein is encoded by contiguous nucleotides and expressed as a single contiguous polypeptide.

Full length human TNF-a has the sequence as set forth in FIG. 2 (SEQ ID NO:1). It is a type 2 transmembrane protein that is cleaved by the protease ADAMI7 to produce the cleaved, soluble TNF-a and uncleaved transmembrane TNF-a. Both soluble and transmembrane molecules signal through cognate receptors. Soluble TNF-a signals primarily through TNFR1, while transmembrane TNF-a signals primarily through TNFR2. The cleaved, soluble TNF-a has the sequence shown in SEQ ID NO:2. C-terminal to the cleavage site is a domain that forms the TNF-homology domain (THD), which is a sequence and structurally similar domain found in members of the TNF superfamily, that makes up the receptor binding domain of the molecule. Of note, a region N-terminal to the THD domain and including the ADAM17 cleavage site is a domain of the molecule referred to as the "stalk region". This stalk region does not appear to be found in the receptor-binding portion of the molecule. Accordingly, domains of TNF-a include from N- to C-terminus: N-terminal intracellular domain, a transmembrane domain, stalk region, ADAM 17 cleavage site within the stalk region and THD domain. The transmembrane domain terminates at amino acid 56. The stalk region is defined as amino acids 57-87 of the full-length sequence. The ADAM1 7 cleavage site is found between amino acids 76/77. The THD domain begins at amino acid 88 and extends to amino acid 233. This is summarized in FIG. 2.

Mutations in the THD have been identified that abrogate binding to TNFR1 and result in a molecule that agonizes TNFR2. The mutations are D143N and A145R, wherein the numbering is based on the sequence of soluble TNF-a. This corresponds to D219N and A221R wherein the numbering is based on the full length TNF-a sequence. That is, at these positions, the native sequences of D and A are mutated to an N and R, respectively. These mutations will be referred to as TNFR2 agonist sequences herein.

Accordingly, the present disclosure provides single-chain TNFR2 agonists (scTNFR2) comprising a first, second and third THD domain comprising the TNFR2 agonist sequences. In some embodiments all three of the THD domains of the scTNFR2 agonist comprise the TNFR2 agonist sequences. Sequence of the THD domain comprising the TNFR2 agonist sequences is found in SEQ ID NO:3.

The variants of this invention optionally include conservatively substituted Variants that apply to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed base and/or deoxyinosine residues (Batzer et al., Nucleic Acid Res. 19:5081 (1991); Ohtsuka et al., J. Biol. Chern. 260:2605-2608 (1985); Rossolini et al., Mol. Cell. Probes 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are silent variations, which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

With regard to conservative substitution of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a conservatively modified variant where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:

1) Alanine (A), Glycine (G);
2) Serine (5), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W).

Dimerization Domains

One design choice is the nature of the dimerization domains of the fusion protein. Without being bound by theory, it is thought that dimerization enhances signaling by the TNFR2 agonist and also may improve half-life of the fusion protein. There are many different dimerization domains, such as Fc fusion proteins derived from other dimerizing molecules, such as IgE heavy chain domain 2 (EHD2) and IgM heavy chain domain 2 (MHD2).

Fc Protein Moiety

The main therapeutic applications of Fc fusion proteins are (1) endowing the fusion partner protein with immunoglobulin Fc effector functions; or (2) increasing the circulating half-life of the fusion partner protein (Czajkowsky, et al., 2012, EMBO Mol Med. 4:1015-28). The primary effector functions of IgG proteins are Complement-Dependent Cytotoxicity (CDC) and Antibody-Dependent Cellular Cytotoxicity (ADCC), functions mediated by Fc binding to complement protein C1q and to IgG-Fc receptors (FcγR), respectively. These effector functions are important when the therapeutic protein is used to direct or enhance the immune response to a particular antigen target or cell. The fusion protein of this invention is designed solely to increase the circulating half-life of the TNFR2 Selective Agonist moiety, and effector functions are not needed and can even be toxic, and thus in some embodiments not desired. For instance, a scTNFR2 agonist-Fc fusion protein with an effector function-competent Fc can potentially kill the Treg cells that the fusion protein of this invention is seeking to activate and expand, exactly the opposite of the therapeutic goal for autoimmune diseases. There are four human IgG subclasses that differ in effector functions (CDC, ADCC), circulating half-life, and stability (Salfeld, J. G., 2007, Nature Biotechnology 25:1369-72). IgG1 possesses Fc effector functions, is the most abundant IgG subclass, and is the most commonly used subclass in US FDA-approved therapeutic proteins. IgG2 is deficient in Fc effector functions, but is subject to dimerization with other IgG2 molecules, and is also subject to instability due to scrambling of disulfide bonds in the hinge region. IgG3 possesses Fc effector functions, and has an extremely long, rigid hinge region. IgG4 is deficient in Fc effector functions, has a shorter circulating half-life than the other subclasses, and the IgG4 dimer is biochemically unstable due to only a single disulfide bond in the hinge region leading to the exchange of H chains between different IgG4 molecules. A skilled artisan would recognize that Fc protein moieties from IgG2 and IgG4 do not possess effector functions and can be used in this invention. The skilled artisan would also recognize that Fc sequence modifications have been described in the art that such that the hinge region of IgG2 Fc can be modified to prevent aggregation, or that the hinge region of IgG4 Fc can be modified to stabilize dimers. It will be appreciated by those of ordinary skill in the art that the IgG described in the sequences of the fusion constructs disclosed herein may be changed. That is, where an IgG1 sequence is disclosed, this can be exchanged with an IgG2 or IgG4 and the like.

Alternatively, effector function-deficient variants of IgG1 have been generated. One such variant has an amino acid substitution at position N297, the location of an N-linked glycosylation site. Substitution of this asparagine residue removes the glycosylation site and significantly reduces ADCC and CDC activity (Tao, M. H., et al., 1989, J Immunol. 143:2595-2601). This variant is used as an exemplary case in the invention herein. Another effector function deficient IgG1 variant is IgG1(L234F/L235E/P331S) (Oganesyan, et al., 2008, Acta Crystallogr D Biol Crystallogr. 64:700-4), which mutates amino acids in the C1q and FcγR binding sites, and one skilled in the art would consider using these or similar Fc variants to generate effector-deficient and stable scTNFR2 agonist-Fc fusion proteins. Other mutations at these sites, such as L234A and L235A can also be used in the fusion protein described herein. Exemplary IgG sequences and variants are shown in FIGS. 6A-6B, 7A-7B, and 8A-8B and in SEQ ID NOs:5-22.

A skilled artisan would also recognize that forms of Fc protein moieties engineered to be stable monomers rather than dimers (Dumont, J. A., et., al., 2006, BioDrugs 20:151-60; Liu Z, et al., J Biol Chem. 2015 20; 290:7535-62) can also be combined with the TNFR2 selective agonist of this invention. In addition, a skilled artisan would recognize that a functionally monomeric heterodimer composed of a TNFR2 agonist-Fc H chain polypeptide combined with an Fc H chain polypeptide and assembled using bispecific antibody technology (Zhu Z, et al., 1997 Protein Sci. 6:781-8) can also be combined with the TNFR2 Selective Agonist of this invention. In addition, a skilled artisan will recognize that Fc variants that lack some or all of the hinge region can be used with this invention.

Fc fusion proteins can be made in two configurations, indicated here as X-Fc, where X, the scTNFR2 agonist fusion partner protein, is at the N-terminus and Fc is at the C-terminus, and Fc-X, where the Fc is at the N-terminus, and the scTNFR2 agonist fusion partner protein is at the C-terminus (FIGS. 1A-1G). There are examples in the literature showing that different fusion partners can have distinct preferences for N- or C-terminal Fc fusions. For instance, FGF21 has been shown to have a strong preference for the Fc-X configuration. Fc-FGF21 has receptor-activating bioactivity essentially the same as FGF21 itself, while FGF21-Fc has 1000-fold reduced bioactivity (Hecht, et al., 2012, PLoS One. 7(1 1):e49345). A number of IL2 agonist Fc fusion proteins have been made for various applications, and these have been reported to have good IL-2 bioactivity when directly fused to Fc in both the Fc-X (Gillies, et al., 1992, Proc Natl Acad Sci, 89:1428-32; Bell, et al., 2015, J Autoimmun. 56:66-80) and X-Fc (Zheng, X. X., et al., 1999, J Immunol. 163:4041-8) configurations. Gavin, et al. (US 20140286898 A1) describes Fc fusion proteins containing IL-2 and certain IL-2 variants in the in the Fc-X configuration that have bioactivity similar to that of the free IL-2 cytokine, but in contrast to the results of Zheng et al, (Zheng, X. X., et al., 1999, J Immunol. 1999, 163:4041-8) found that IL-2 variant fusion proteins in the X-Fc configuration have reduced or no bioactivity. Thus, whether an N-terminal dimerization domain or a C-terminal dimerization within any given fusion protein is preferred is unpredictable.

EHD2

A recently described dimerization domain may also find use in connection with the scTNFR2 agonist described herein. This polypeptide was used to form dimers of other molecules in WO 2013/156148, which is expressly incorporated herein by reference. The EHD 2 sequence is:

```
                                        (SEQ ID NO: 23)
DFTPPTVKILQSSCDGGGHFPPTIQLLCLVSGYTPGTINITWLEDGQ

VMDVDLSTASTTQEGELASTQSELTLSQKHWLSDRTYTCQVTYQ

GHTFEDSTKKCADSN.
```

MHD2

Another recently described dimerization domain may also find use in connection with the scTNFR2 agonist described herein. This polypeptide was used to form dimers of other molecules in WO 2013/156148. The MHD2 sequence is:

```
                                        (SEQ ID NO: 24)
AELPPKVSVFVPPRDGFFGNPRKSKLICQATGFSPRQIQVSWLREG

KQVGSGVTTDQVQAEAKESGPTTYKVTSTLTIKESDWLGQSMFT

CRVDHRGLTFQQNASSMCVPD.
```

Linker

The amino acid sequence at the junction between the Fc and the fusion partner protein can be either (1) a direct fusion of the two protein sequences or (2) a fusion with an intervening linker peptide. Of the 10 Fc fusion proteins that are presently approved by the LIS FDA for clinical use (TABLE I), 8 are direct fusions of the fusion partner protein with Fc, while 2 possess linker peptides, so many Fc fusion proteins can be functional without linker peptides. Linker peptides are included as spacers between the two protein moieties. Linker peptides can promote proper protein folding and stability of the component protein moieties, improve protein expression, and enable better bioactivity of the component protein moieties (Chen, et al., 2013, Adv Drug Deliv Rev. 65:1357-69). Peptide linkers used in many fusion proteins are designed to be unstructured flexible peptides. A study of the length, sequence, and conformation of linkers peptides between independent structural domains in natural proteins has provided a theoretical basis for the design of flexible peptide linkers (Argos, 1990, J Mol Biol. 211:943-5 8). Argos provided the guidance that long flexible linker peptides be composed of small nonpolar residues like Glycine and small polar resides like Serine and Threonine, with multiple Glycine residues enabling a highly flexible conformation and Serine or Threonine providing polar surface area to limit hydrophobic interaction within the peptide or with the component fusion protein moieties.

Many peptide linkers described in the literature are rich in glycine and serine, such as repeats of the sequence GGGGS (SEQ ID NO:25), although an artisan skilled in the art will recognize that other sequences following the general recommendations of Argos (Argos, 1990, J Mol Biol. 20; 211(4):943-58) can also be used. In some embodiments polypeptide sequences from one of the fusion partners may be used as a linker. For instance, N- or C-terminal extensions from TNF-a or a dimerization domain, such as Fc, could be used all or part of the linker between the fusion partners. In some embodiments the C-terminal extension from human IgG finds use as a linker and is shown as: ELQLEESSAEA-QDGELDG (SEQ ID NO:41) or a variant of this also finds use as a linker:

ELQLEESSAEAQGG. (SEQ ID NO: 42)

TABLE I

TABLE I. US FDA-approved Fc fusion proteins and their characteristics

| Drug | FC Isotype | Fusion Partner | N vs C fusion | Linker Peptide | Half-life (days) |
|---|---|---|---|---|---|
| Romiplostim | G1 | TPO-R peptide | C | Y | 3.5 |
| Etanercept | G1 | P75 TNFa-R | N | N | 4.3 |
| Alefacept | G1 | LFA3 | N | N | 10.1 |
| Rilonacept | G1 | IL1-R | N | N | 8.6 |
| Abatacept | G1 | CTLA4 | N | N | 16.7 |
| Belatacept | G1 | CTLA4 (mut) | N | N | 9.8 |
| Aflibercept | G1 | VEGF RI + R2 | N | N | n/a |
| Dulaglutide | G4 (mut) | GLP1 | N | Y | 3.7 |
| Electate | G1 | FVIII | N | N | 0.8 |
| Alprolix | G1 | FIX | N | N | 3.6 |

In some embodiments, particularly when the fusion protein is in the DD-X configuration, the dimerization domain (DD), i.e. Fc, is directly linked to the N-terminus of the single-chain THD, i.e. TNFR2 agonist.

In some embodiments, particularly when the fusion protein is in the DD-X configuration, the linker between the N-terminus of the first THD domain of the scTNFR2 agonist is sequence from TNF-a itself. That is, sequences from the native TNF-a stalk region are used as a linker between the THD domain of the TNFR2 agonist and the C-terminus of the Fc domain. The linker between the THD domain of the TNFR2 agonist and the C-terminus of the Fc domain contains from 1 to 31 amino acids or contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids. The stalk region contains the sequences shown below and the linker using contiguous amino acids from this region may include from 1 to 31 contiguous amino acids of this sequence. The sequence from the first amino acid of the stalk region to last amino acid prior to the THD domain includes: GPQREEF-PRDLSLISPLAQAVRSSSRTPSDK (SEQ ID NO:26). In some embodiments sequences comprising at least 2, 3, 4, 5, 6, 7, 8, 9, 10, 11, 12, 13, 14, 15, 16, 17, 18, 19, 20, 21, 22, 23, 24, 25, 26, 27, 28, 29, or 30 contiguous sequences from the stalk region can be used as a linker between the N-terminus of the scTNF agonist and dimerization domain.

In some embodiments, other linkers, such as combinations of Gly and Ser find use as linkers. In some embodiments linkers using (GGGGS)$_n$, where n=1-5 (SEQ ID NO: 44) find use as linkers between the dimerization domain, i.e. Fc and first THD of the scTNFR2 agonist. In some embodiments, combinations of the stalk region sequences and Gly/Ser amino acids find use as the linker.

In some embodiments a linker peptide of 5, 10, 15, or 20 amino acids will have a maximum fully extended length of 17.5 A, 35 A, 52.5 A, or 70 A, respectively. The maximal end-to-end length of the peptide linker can also be a guide for defining the characteristics of a peptide linker in this invention. The goal of a linker peptide within the current invention is to enable attainment of an appropriate conformation and orientation of the individual fusion protein moieties to allow the engagement of the TNFR2 Selective Agonist moiety with its cognate receptor and allow the binding of the Fc moiety to the FcRn to enable fusion protein recycling and a prolonged circulating half-life. Since the factors influencing these interactions are difficult to predict, the requirement for and the proper length of a linker peptide must be empirically tested and determined. Many Fc fusion proteins do not require linker peptides, as evidenced by the 8 out of 10 US FDA-approved Fc fusion proteins lacking such peptides listed in Table I. In contrast, Dulaglutide, a fusion of GLP-1 and Fc, contains a 15 residue peptide linker which has a strong influence on bioactivity (Glaesner, U.S. Pat. No. 7,452,966 B2).

In the context of the single-chain TNFR2 agonist, other linkers may be found between the THD domains. That is, a linker may be found between the first and second and then the second third THD domain of the TNFR2 agonist. The linkers may be the same or may be different. In some embodiments the linkers may be any linker outlined herein including GGGGS (SEQ ID NO: 25) linkers. In some embodiments the linker may comprise multiple units of the GGGGS (SEQ ID NO: 25) sequence as described as (GGGGS)$_n$, wherein n=1, 2, 3, 4, 5, 6, 7, 8, 9 or 10 (SEQ ID NO: 45). In some embodiments sequences from the stalk region find use as linkers between the THDs. In addition, in some embodiments, combinations of Gly/Ser amino acids as well as contiguous amino acids from the stalk region find use as linkers between THDs. Linker between the first and second THDs may be the same or different from the linker between the second and third THD but generally both linkers will be comprised of (GGGGS)$_n$, wherein n=1, 2, 3, 4, 5, 6, 7, 8, 9 or 10 (SEQ ID NO: 45) and/or contiguous sequences from the stalk region.

In other embodiments, particularly in the X-DD configuration, a linker may be placed between the C-terminus of the third THD domain and the N-terminus of dimerization domain, i.e. Fc domain. Again this can be Gly/Ser linkers as described herein and may comprise (GGGGS)$_n$, where n=1-5 (SEQ ID NO: 44).

Fusion Proteins

Accordingly, the present disclosure provides scTNFR2 fusion proteins comprising a dimerization domain, three THD's each comprising the D143N/A145R mutations to confer selectivity for TNFR2, and a linker between each of the THDs. In some embodiments the dimerization domain is at the N-terminus of the scTNFR2 agonist domain, while in other embodiments the dimerization domain as at the C-terminus of the molecule.

Fusion proteins disclosed herein comprise the following formulas: DD-L1-THD-L2-THD-L3-THD or THD-L2-THD-L3-THD-L1-DD, where DD is a dimerization domain as described herein. Dimerization domains are selected from IgG1, IgG2 an IgG4 Fc domains lacking effector function. In one embodiment the Fc is from IgG2 and lacking effector function. In one embodiment the Fc is from IgG4. In one embodiment the dimerization domain is EHD2 or MHD2. Then the dimerization domain is at the N-terminus of the scTNFR2 agonist protein, the linker (L1) is preferably (GGGGS)$_n$ where n=1-5 (SEO ID NO: 44), although in some embodiments the L1 linker comprises some or all of the stalk region from TNF-a. All fusion proteins of the invention disclosed herein contain THD with the TNFR2 agonist selective sequences D143N/A145R and are referred to below as THD. Linkers (L2 and L3) between the first and second, and second and third THD may also be constructed from GGGGS (SEQ ID NO: 25), G/S linkers or from some or all of the stalk region. When the dimerization domain is at the C-terminus of the scTNFR2 agonist protein there may not be a linker, or the linker may comprise (GGGGS)ₙ where n=1-5 (SEQ ID NO: 44). Preferred configurations of fusion proteins include:

- DD-L1-THD-L2-THD-L3-THD, wherein DD is the IgG4 Fc with mutation(s) eliminating effector function, L1, L2 and L3 are GGGGS (SEQ ID NO: 25);
- DD-L1-THD-L2-THD-L3-THD, wherein DD is the IgG4 Fc with mutation(s) eliminating effector function, L1 is GGGGSGGGGS (SEQ ID NO:27), L2 and L3 are both GGGGs (SEQ ID NO: 25);
- DD-L1-THD-L2-THD-L3-THD, wherein DD is the IgG1 Fc with mutation(s) eliminating effector function, L1 is VRSSSRTPSDK (SEQ ID NO: 4), L2 and L3 are both GGGGS (SEQ ID NO: 25);
- DD-L1-THD-L2-THD-L3-THD, wherein DD is the IgG1 Fc with mutation(s) eliminating effector function, L1 is VRSSSRTPSDK (SEQ ID NO:4), L2 and L3 are both SSRTPSDK (SEQ ID NO: 28);
- DD-L1-THD-L2-THD-L3-THD, wherein DD is the IgG1 Fc with mutation(s) eliminating effector function, L1 is GPQREEFPRDLSLISPLAQAVRSSSRTPSDK (SEQ ID NO: 26), L2 and L3 are both GGGGS (SEQ ID NO: 25);
- DD-L1-THD-L2-THD-L3-THD, wherein DD is the IgG1 Fc with mutation(s) eliminating effector function, L1 is GPQREEFPRDLSLISPLAQAVRSSSRTPSDK (SEQ ID NO: 26), L2 and L3 are both SSRTPSDK (SEQ ID NO:28);
- DD-L1-THD-L2-THD-L3-THD, wherein DD is the IgG1 Fc with mutation(s) eliminating effector function, L1 is GPQREEFPRDLSLISPLAQAVRSSSRTPSDK (SEQ ID NO: 26), L2 and L3 are both VRSSSRTPSDK (SEQ ID NO: 4);
- DD-L1-THD-L2-THD-L3-THD, wherein DD is the IgG1 Fc with mutation(s) eliminating effector function, L1 is GGGGSVRSSSRTPSDK (SEQ ID NO:29), L2 and L3 are both VRSSSRTPSDK (SEQ ID NO: 4);
- DD-L1-THD-L2-THD-L3-THD, wherein DD is the IgG1 Fc with mutation(s) eliminating effector function, L1 is GGGGSVRSSSRTPSDK (SEQ ID NO: 29), L2 and L3 are both GGGGSSSRTPSDK (SEQ ID NQ:30);
- DD-L1-THD-L2-THD-L3-THD, wherein DD is the IgG1 Fc with mutations eliminating effector function, L1, L2 and L3 are GGGGS (SEQ ID NO: 25);
- DD-L1-THD-L2-THD-L3-THD, wherein DD is the IgG1 Fc with mutations eliminating effector function, L1 is GGGGSGGGGS (SEQ ID NO:27), L2 and L3 are both GGGGs (SEQ ID NO: 25);
- DD-L1-THD-L2-THD-L3-THD, wherein DD is the IgG1 Fc with mutations eliminating effector function, L1 is VRSSSRTPSDK (SEQ ID NO: 4), L2 and L3 are both GGGGS (SEQ ID NO: 25);
- DD-L1-THD-L2-THD-L3-THD, wherein DD is the IgG1 Fc with mutations eliminating effector function, L1 is VRSSSRTPSDK (SEQ ID NO:4), L2 and L3 are both SSRTPSDK (SEQ ID NO: 28);
- DD-L1-THD-L2-THD-L3-THD, wherein DD is the IgG1 Fc with mutations eliminating effector function, L1 is GPQREEFPRDLSLISPLAQAVRSSSRTPSDK, (SEQ ID NO: 26) L2 and L3 are both GGGGS (SEQ ID NO: 25);
- DD-L1-THD-L2-THD-L3-THD, wherein DD is the IgG1 Fc with mutations eliminating effector function, L1 is GPQREEFPRDLSLISPLAQAVRSSSRTPSDK (SEQ ID NO: 26), L2 and L3 are both SSRTPSDK (SEQ ID NO:28);
- DD-L1-THD-L2-THD-L3-THD, wherein DD is the IgG1 Fc with mutations eliminating effector function, L1 is GPQREEFPRDLSLISPLAQAVRSSSRTPSDK (SEQ ID NO: 26), L2 and L3 are both VRSSSRTPSDK (SEQ ID NO: 4);
- DD-L1-THD-L2-THD-L3-THD, wherein DD is the IgG1 Fc with mutations eliminating effector function, L1 is GGGGSVRSSSRTPSDK (SEQ ID NO:29), L2 and L3 are both VRSSSRTPSDK (SEQ ID NO: 4);
- DD-L1-THD-L2-TJID-L3-THD, wherein DD is the IgG1 Fc with mutations eliminating effector function, L1 is GGGGSVRSSSRTPSDK (SEQ ID NO: 29), L2 and L3 are both GGGGSSSRTPSDK (SEQ ID NO:30);
- DD-L1-THD-L2-THD-L3-THD, wherein DD is the IgG4 Fc, L1, L2 and L3 are GGGGS (SEQ ID NO: 25);
- DD-L1-THD-L2-THD-L3-THD, wherein DD is the IgG4 Fc, L1 is GGGGSGGGGS (SEQ ID NO: 27), L2 and L3 are both GGGGs (SEQ ID NO: 25);
- DD-L1-THD-L2-THD-L3-THD, wherein DD is the IgG4 Fc, L1 is VRSSSRTPSDK (SEQ ID NO: 4), L2 and L3 are both GGGGS (SEQ ID NO: 25);
- DD-L1-THD-L2-THD-L3-THD, wherein DD is the IgG4 Fc, L1 is VRSSSRTPSDK (SEQ ID NO: 4), L2 and L3 are both SSRTPSDK (SEQ ID NO: 28);
- DD-L1-THD-L2-THD-L3-THD, wherein DD is the IgG4 Fc, L1 is GPQREEFPRDLSLISPLAQAVRSSSRTPSDK (SEQ ID NO: 26), L2 and L3 are both GGGGS (SEQ ID NO: 25);
- DD-L1-THD-L2-THD-L3-THD, wherein DD is the IgG4 Fc, L1 is GPQREEFPRDLSLISPLAQAVRSSSRTPSDK (SEQ ID NO: 26), L2 and L3 are both SSRTPSDK (SEQ ID NO: 28);
- DD-L1-THD-L2-THD-L3-THD, wherein DD is the IgG4 Fc, L1 is GPQREEFPRDLSLISPLAQAVRSSSRTPSDK (SEQ ID NO: 26), L2 and L3 are both VRSSSRTPSDK (SEQ ID NO: 4);
- DD-L1-THD-L2-THD-L3-THD, wherein DD is the, L1 is GGGGSVRSSSRTPSDK (SEQ ID NO: 29), L2 and L3 are both VRSSSRTPSDK (SEQ ID NO: 4);
- DD-L1-THD-L2-THD-L3-THD, wherein DD is the lgG4 Fc, L1 is GGGGSVRSSSRTPSDK (SEQ ID NO: 29), L2 and L3 are both GGGGSSSRTPSDK (SEQ ID NO: 30);
- THD-L2-THD-L3-THD-L1-DD, wherein DD is the IgG1 Fc with mutations eliminating effector function, L1, L2 and L3 are GGGGS (SEQ ID NO: 25);
- THD-L2-THD-L3-THD-L1-DD, wherein DD is the IgG1 Fc with mutations eliminating effector function, L1 is GGGGS (SEQ ID NO: 25) and L2 and L3 are SSRTPSDK (SEQ ID NO: 28);
- THD-L2-THD-L3-THD-DD, wherein DD is the IgG1 Fc with mutations eliminating effector function, L2 and L3 are GGGGS (SEQ ID NO: 25) and scTNFR2 agonist domain is fused directly to DD;
- THD-L2-THD-L3-THD-DD, wherein DD is the IgG1 Fc with mutations eliminating effector function, L2 and L3 are SSRTPSDK (SEQ ID NO: 28) and scTNFR2 agonist domain is fused directly to DD;
- THD-L2-THD-L3-THD-DD, wherein DD is the IgG1 Fc with mutations eliminating effector function, L2 and L3 are GGGGSSSRTPSDK (SEQ ID NO: 30) and scTNFR2 agonist domain is fused directly to DD;
- THD-L2-THD-L3-THD-DD, wherein DD is the IgG1 Fc with mutations eliminating effector function, L2 and L3 are VRSSSRTPSDK (SEQ ID NO: 4) and scTNFR2 agonist domain is fused directly to DD;

THD-L2-THD-L3-THD-L1-DD, wherein DD is the IgG4 Fc, L1, L2 and L3 are GGGGS (SEQ ID NO: 25);

THD-L2-THD-L3-THD-L1-DD, wherein DD is the IgG4 Fc, L1 is GGGGS (SEQ ID NO: 25) and L2 and L3 are SSRTPSDK (SEQ ID NO: 28);

THD-L2-THD-L3-THD-DD, wherein DD is the IgG4 Fc, L2 and L3 are GGGGS (SEQ ID NO: 25) and scTNFR2 agonist domain is fused directly to DD;

THD-L2-THD-L3-THD-DD, wherein DD is the IgG4 Fc, L2 and L3 are SSRTPSDK (SEQ ID NO: 28) and scTNFR2 agonist domain is fused directly to DD;

THD-L2-THD-L3-THD-DD, wherein DD is the IgG4, L2 and L3 are GGGGSSSRTPSDK (SEQ ID NO: 30) and scTNFR2 agonist domain is fused directly to DD;

THD-L2-THD-L3-THD-DD, wherein DD is the IgG4 Fc, L2 and L3 are VRSSSRTPSDK (SEQ ID NO: 4) and scTNFR2 agonist domain is fused directly to DD;

THD-L2-THD-L3-THD-L1-DD, wherein DD is the IgG4 Fc with mutation(s) eliminating effector function, L1, L2 and L3 are GGGGS (SEQ ID NO: 25);

THD-L2-THD-L3-THD-L1-DD, wherein DD is the IgG4 Fc with mutation(s) eliminating effector function, L1 is GGGGS (SEQ ID NO: 25) and L2 and L3 are SSRTPSDK;

THD-L2-THD-L3-THD-DD, wherein DD is the IgG4 Fc with mutation(s) eliminating effector function, L2 and L3 are GGGGS (SEQ ID NO: 25) and scTNFR2 agonist domain is fused directly to DD;

THD-L2-THD-L3-THD-DD, wherein DD is the IgG4 Fc with mutations eliminating effector function, L2 and L3 are SSRTPSDK (SEQ ID NO: 28) and scTNFR2 agonist domain is fused directly to DD;

THD-L2-THD-L3-THD-DD, wherein DD is the IgG4 Fc with mutations eliminating effector function, L2 and L3 are GGGGSSSRTPSDK (SEQ ID NO: 30) and scTNFR2 agonist domain is fused directly to DD;

THD-L2-THD-L3-THD-DD, wherein DD is the IgG4 Fc with mutations eliminating effector function, L2 and L3 are VRSSSRTPSDK (SEQ ID NO: 4) and scTNFR2 agonist domain is fused directly to DD.

In some embodiments, the Fc-scTNFR2 agonist fusion protein comprises the sequence as shown in SEQ ID NO:31, 32, 34, or 35. In some embodiments the Fc-scTNFR2 agonist fusion protein comprises the sequence as shown in SEQ ID NOs: 101, 102, 103, 104, 105, 106, 107, 108, 109, 110, 111, 112, 118, 119 or 120. In some embodiments the scTNFR2 agonist fusion protein comprises a protein having at least 80% or 85% or 90% or 95% or 96% or 97% or 98% or 99% identity with SEQ ID NO:31, 32, 34 or 35 or SEQ IS NOs: 101, 102, 103, 104, 105, 106, 107, 108, 109, 110, 111, 112, 118, 119 or 120. In some embodiments, the present disclosure provides a nucleic acid encoding a protein as set forth in SEQ ID NO:31, 32, 34, or 35 or a protein having at least 80% or 85% or 90% or 95% or 96% or 97% or 98% or 99% identity with SEQ ID NO:31, 32, 34 or 35 or SEQ ID NOs 101, 102, 103, 104, 105, 106, 107, 108, 109, 110, 111, 112, 118, 119 or 120. In some embodiments the nucleic acid comprises a nucleic acid sequence having at least 80% or 85% or 90% or 95% or 96% or 97% or 98% or 99% identity with SEQ ID NO:36, 37, 38 or 39. In some embodiments the nucleic acid comprises the sequence shown in SEQ ID NO: 36, 27, 28 or 39.

Bioassays

Robust and quantitative bioassays are necessary for the characterization of the biological activity of candidate proteins. These assays should measure the activation of the TNFR2 30 receptor, measure the downstream functional consequences of activation in Tregs, and measure therapeutically-relevant outcomes and functions of the activated Tregs. These assays can be used the measure the therapeutic activity and potency of scTNFR2 Selective Agonist molecules, and can also be used for measurement of the pharmacodynamics of an scTNFR2 Selective Agonist in animals or in humans. One assay measures the TNF-a mediated caspase activity. In cells lacking TNFR1 or when TNFR1 cannot signal, this is a measure of TNFR2 activation. Another assay for functional activation measures TNFR2 agonist stimulated proliferation of Treg cells. One of ordinary skill in the art will recognize that Treg proliferation can be measured by tritiated thymidine incorporation into purified Treg cells, by an increase in Treg cell numbers in a mixed population of cells measured by flow cytometry and the frequencies of CD4+CD25+FOXP3+ or the CD4+CD25+CD127− marker phenotypes, by increased expression in Treg cells of proliferation-associated cell cycle proteins, such as Ki-67, or by measurement of the cell division-associated dilution of a vital fluorescent dye such as carboxyfluorescein succinimidyl ester (CFSE) by flow cytometry in Treg cells. Accordingly, in some embodiments the present disclosure provides methods of stimulating or expanding Tregs. In some embodiments the fusion proteins of described herein stimulate the expansion of Tregs more potently that EHD2-TNFR2 agonist (disclosed in Dong et al. PNAS 2016).

Other assays include the Kym-1 cell viability assay disclosed in the examples. In some embodiments the disclosure provides Fc-TNFR2 agonist fusion proteins that reduce viability of Kym-1 cells following culture as described herein. In some embodiments the Fc-TNFR2 agonists reduce the viability of Kym-1 cells more than EHD2-TNFR2 agonist (disclosed in Dong et al. PNAS 2016).

Formulation

Pharmaceutical compositions of the fusion proteins of the present invention are defined as formulated for parenteral (particularly intravenous or subcutaneous) delivery according to conventional methods. In general, pharmaceutical formulations will include fusion proteins of the present invention in combination with a pharmaceutically acceptable vehicle, such as saline, buffered saline, 5% dextrose in water, or the like. Formulations may further include one or more excipients, preservatives, solubilizers, buffering agents, albumin to prevent protein loss on vial surfaces, etc. Methods of formulation are well known in the art and are disclosed, for example, in Remington: The Science and Practice of Pharmacy, Gennaro, ed., Mack Publishing Co., Easton, Pa., 19.sup.th ed., 1995.

As an illustration, pharmaceutical formulations may be supplied as a kit comprising a container that comprises fusion proteins of the present invention. Therapeutic proteins can be provided in the form of an injectable solution for single or multiple doses, as a sterile powder that will be reconstituted before injection, or as a prefilled syringe. Such a kit may further comprise written information on indications and usage of the pharmaceutical composition. Moreover, such information may include a statement that the fusion proteins of the present invention is contraindicated in patients with known hypersensitivity to fusion proteins of the present invention.

The scTNFR2 selective agonist fusion proteins of this invention can be incorporated into compositions, including pharmaceutical compositions. Such compositions typically include the protein and a pharmaceutically acceptable carrier. As used herein, the term "pharmaceutically acceptable carrier" includes, but is not limited to, saline, solvents, dispersion media, coatings, antibacterial and antifungal agents isotonic and absorption delaying agents, and the like, compatible with pharmaceutical administration. Supplementary active compounds (e.g., antibiotics) can also be incorporated into the compositions.

A pharmaceutical composition is formulated to be compatible with its intended route of administration. The scTNFR2 selective agonist fusion proteins of the invention is likely that to be administered through a parenteral route. Examples of parenteral routes of administration include, for example, intravenous, intradermal, and subcutaneous. Solutions or suspensions used for parenteral application can include the following components: a sterile diluent such as water for injection, saline solution, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as mono- and/or dibasic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi.

The carrier can be a solvent or dispersion medium containing, for example, water, ethanol, polyol (for example, glycerol, propylene glycol, and liquid polyethylene glycol, and the like), and suitable mixtures thereof. The maintenance of the required particle size in the case of dispersion may be facilitated by the use of surfactants, e.g., Polysorbate or Tween.

Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above.

In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In one embodiment, the scTNFR2 selective agonist fusion protein is prepared with carriers that will protect the scTNFR2 selective agonist fusion protein against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques.

The pharmaceutical compositions can be included in a container, pack, or dispenser together with instructions for administration.

Administration

Fusion proteins of the present invention will preferably be administered by the parenteral route. The subcutaneous route is the preferred route, but intravenous, intramuscular, and subdermal administration can also be used. For subcutaneous or intramuscular routes, depots and depot formulations can be used. For certain diseases specialized routes of administration can be used. For instance, for eye diseases, such as but not limited to optic neuritis, intraocular injection can be used. Fusion proteins can be used in a concentration of about 0.1 to 10 mcg/ml of total volume, although concentrations in the range of 0.01 mcg/ml to 100 mcg/ml may be used. In some embodiments peripheral administration is used to treat neurological disorders. In some embodiments intrathecal administration is used, which can deliver the fusion proteins into the spinal fluid which can bypass the blood brain barrier.

Determination of dose is within the level of ordinary skill in the art. Dosing is daily or weekly over the period of treatment, or may be at another intermittent frequency. Intravenous administration will be by bolus injection or infusion over a typical period of one to several hours. Sustained release formulations can also be employed. In general, a therapeutically effective amount of fusion proteins of the present invention is an amount sufficient to produce a clinically significant change in the treated condition, such as a clinically significant change in circulating Treg cells, a clinically significant change in Treg cells present within a diseased tissue, or a clinically significant change in a disease symptom.

The data obtained from the cell culture assays and animal studies can be used in formulating a range of dosage for use in humans. The dosage of such compounds lies preferably within a range of circulating concentrations that include the half maximal effective concentration (EC50; i.e., the concentration of the test compound which achieves a half-maximal stimulation of Treg cells) with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 as determined in cell culture. Such information can be used to more accurately determine useful doses in humans. Levels in plasma may be measured, for example, by enzyme-linked immunosorbent assays.

As defined herein, a therapeutically effective amount of a scTNFR2 selective agonist fusion protein (i.e., an effective dosage) depends on the polypeptide selected and the dose frequency. For instance, single dose amounts in the range of approximately 0.01 to 50 mg/kg of patient body weight can be administered; in some embodiments, about 0.05 to 10 mg/kg, or 0.1 to 25 mg/kg of patient body weight can be administered; in some embodiments about 0.5 to 10 mg/kg of patient body weight can be administered. In some embodiments about 0.1 mg/kg, 0.5 mg/kg, 1 mg/kg, 2.5 mg/kg, 5 mg/kg, 7.5 mg/kg, 10 mg/kg, or 20 mg/kg or 40 mg/kg or 50 mg/kg of patient body can be administered. In some embodiments, for instance when intraocular administration is used, the concentration per patient body weight is in appropriate measure to use. Rather, a total of 0.5 mg, or 1 mg or 1.5 mg or 2 mg or 2.5 mg or 3 mg or 3.5 mg or 4 mg or 5 mg of fusion protein are administered in each eye. The compositions can be administered from one time per day to one or more times per week, or one or more times per month; including once every other day, or twice a week or twice a month. The skilled artisan will appreciate that certain factors may influence the dosage and timing required to effectively treat a subject, including but not limited to the severity of the disease or disorder, previous treatments, the general health and/or age of the subject, the level of Treg cells present in the patient, and other diseases present. Moreover, treatment of a subject with a therapeutically effective amount of the TNFR2 selective agonist fusion protein of the invention is likely to be a series of treatments.

Diseases

Some of the diseases that can benefit from the therapy of this invention have been noted. However, the role of Treg cells in autoimmune diseases is a very active area of research, and additional diseases will likely be identified as treatable by this invention. Autoimmune diseases are defined as human diseases in which the immune system attacks its own proteins, cells, and tissues. A comprehensive listing and review of autoimmune diseases can be found in The Autoimmune Diseases (Rose and Mackay, 2014, Academic Press).

As disclosed herein, even when administered peripherally, scTNFR2 agonist proteins may be used to treat neurological disorders, particularly those characterized by elevated TNF-a. In one embodiment the scTNFR2 molecules disclosed herein find use in treating neurological disorders, e.g., by reducing inflammation in the brain, protecting myelination of neurons and/or promoting remyelination of neurons. Accordingly, neurological disorders particularly amenable to the methods disclosed herein include art-recognized inflammatory neurodegenerative diseases, which may result in the destruction 36 of myelin or may include other neurological disorders not necessarily characterized by myelin destruction but are characterized by elevated levels of TNF-a.

In one embodiment, neurodegenerative diseases are a group of diseases typified by deterioration of neurons and/or their myelin sheath. This destruction of neurons eventually leads to dysfunction and disabilities. Often inflammation, thought to be mediated by microglial cells, is found to be a component of neurodegenerative diseases and adds to the pathogenesis of the neurodegeneration. Collectively, these diseases comprise the art-recognized neurodegenerative diseases. Neuro inflammation may occur years prior to any considerable loss of neurons in some neurodegenerative disorders. For example, 70% of dopaminergic neurons are lost from the substantia nigra before patients begin to manifest the clinical signs of Parkinson's disease, see, e.g., Factor and Weiner (2008) Parkinson's Disease: Diagnosis and Clinical Management. Many different types of immune cells, including macrophages, neutrophils, T cells, astrocytes, and microglia, can contributed to the pathology of immune-related diseases, like Multiple Sclerosis (M.S.), Parkinson's disease, Huntington's disease, dementia (including but not exclusively diseases like Alzheimer's disease, frontotemporal dementia, trauma related dementia (punch drunk), HIV-associated and Lewy Body dementia), amyotrophic lateral sclerosis (ALS), prion diseases, etc. More specifically, in MS the injury to myelin is mediated by an inflammatory response and M.S. Pathogenesis is exacerbated when leukocytes infiltrate the CNS.

Accordingly, neurodegenerative diseases include but are not limited to: multiple sclerosis (MS), Optic Neuritis, Parkinson's disease, amyloidosis (e.g., Alzheimer's disease), amyotrophic lateral sclerosis (ALS), HIV-associated dementia, stroke/cerebral ischemia, head trauma, spinal cord injury, Huntington's disease, migraine, cerebral amyloid angiopathy, AIDS, age-related cognitive decline; mild cognitive impairment and prion diseases in a mammal, and preferably in a human.

Multiple sclerosis (MS) is a chronic inflammatory neurodegenerative disease of the central nervous system (CNS) that affects approximately 1,100,000 people all over the world, in particular affects young adults. MS is characterized pathologically by demyelination of neural tissue, which results clinically in one of many forms of the disease, ranging from benign to chronic-progressive patterns of the disease state. More specifically, five main forms of multiple sclerosis have been described: 1) benign multiple sclerosis; 2) relapsing-remitting multiple sclerosis (RRMS); 3) secondary progressive multiple sclerosis (SPMS); 4) primary progressive multiple sclerosis (PPMS); and 5) progressive-relapsing multiple sclerosis (PRMS). Chronic progressive multiple sclerosis is a term used to collectively refer to SPMS, PPMS, and PRMS. The relapsing forms of multiple sclerosis are SPMS with superimposed relapses, RRMS and PRMS.

Throughout the course of the disease there is a progressive destruction of the myelin sheath surrounding axons. Since intact myelin is essential in the preservation of axonal integrity systematic destruction eventually leads, clinically, to various neurological dysfunctions including numbness and pain, problems with coordination and balance, blindness, and general cognitive impairment.

Parkinson's disease, another inflammatory neurodegenerative disease, is characterized by movement disorders, including muscle rigidity and slow physical movements.

Amyloidosis develops when certain proteins have altered structure and tend to bind to each building up in particular tissue and blocking the normal tissue functioning. These altered structured proteins are called amyloids. Often amyloidoses is split into two categories: primary or secondary. Primary amyloidoses occur from an illness with improper immune cell function. Secondary amyloidoses usually arise from a complication of some other chronic infectious or inflammatory diseases. Examples of such include Alzheimer's disease and rheumatoid arthritis. The underlying problem in secondary amyloidosis is inflammation.

Alzheimer's disease is another type of inflammatory neurodegenerative disease. It is exemplified by the increasing impairment of learning and memory, although the disease may manifest itself in other ways indicating altered cognitive ability. Throughout the disease the progressive loss of neurons and synapses in the cerebral cortex leads to gross atrophy of the neural tissue. Although the cause of Alzheimer's is unknown, many believe that inflammation plays an important role and clinical studies have shown that inflammation considerably contributes to the pathogenesis of the disease.

Amyotrophic lateral sclerosis is another debilitating neurological disorder. In ALS a link between inflammation and the disease has been suggested.

In one embodiment, the neurological disorder is any disorder characterized by elevated TNF-a, and can include disorders such as stroke, depression, post-traumatic stress syndrome and traumatic brain injury.

In some embodiments, the disorders that can be treated by the scTNFR2 fusion proteins described herein include demyelinating disorders, such as but not limited to multiple sclerosis (MS), including primary progressive or relapsing-remitting MS, or optic neuritis. Other disorders such as, but not limited to, pain, which may include neuropathic pain, may be treated with the TNFR2 agonists described herein.

Other Fusion Proteins

Because the purpose of the Fc protein moiety in this invention is solely to increase circulating half-life, one skilled in the art will recognize that the scTNFR2 selective agonist moiety could be fused to the N-terminus of other proteins to achieve the same goal of increasing molecular size and reducing the rate of renal clearance, using the structure-activity relationships discovered in this invention. The scTNFR2 selective agonist could be fused to the N-terminus of serum albumin (Sleep. D., et al., 2013, Biochim Biophys Acta. 1830:5526-34), which both increases the hydrodynamic radius of the fusion protein relative to the TNFR2 moiety and is also recycled by the FcRN. A skilled artisan would also recognize that the scTNFR2 selective agonist moiety of this invention could also be fused to the N-terminus of recombinant non-immunogenic amino acid polymers. Two examples of non-immunogenic amino acid polymers developed for this purpose are XTEN polymers, chains of A, E, G, P, S, and T amino acids (Schellenberger, V, et. al., 2009, Nat Biotechnol. 27:1186-90)), and PAS polymers, chains of P, A, and S amino acid residues (Schlapschy, M., et. al., 2007, Protein Eng Des Scl. 20:273-84).

Combination Treatments

Treatments that currently are available for MS include glatiramer acetate, interferonp, natalizumab, and mitoxanthrone. In general, these drugs suppress the immune system in a nonspecific fashion and only marginally limit the overall progression of disease. (Lubetzki et al. (2005), Curr. Opin. Neurol. 18:237-244). Thus, there exists a need for developing therapeutic strategies to better treat MS. As described herein, scTNFR2 find use in treating MS. These molecules find particular use when combined with currently available MS therapies as known in the art and as described herein. For instance, scTNFR2 agonists may be combined in a therapeutic regimen with glatiramer acetate, interferon-p, natalizumab, and mitoxanthron or other molecules, such as bardoxolone methyl or variants thereof.

As another example, in the treatment of Alzheimer's Disease (AD), a scTNFR2 agonist protein may be administered to an individual in combination therapy with one or more additional therapeutic agents for the treatment of AD. Suitable additional therapeutic agents include, but are not limited to, acetylcholinesterase inhibitors, including, but not limited to, Aricept (donepezil), Exelon (rivastigmine), metrifonate, and tacrine (Cognex); non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art. For example, Aricept is generally administered at 50 mg orally per day for 6 weeks, and, if well tolerated by the individual, at 10 mg per day thereafter.

In one embodiment, treatment of the scTNFR2 agonist in a therapeutic regimen in combination with the co-therapies as described herein results in synergistic efficacy as compared to either of the treatments alone. By "synergistic" is meant that efficacy is more than the result of additive efficacy of the two treatments alone.

In one embodiment treatment of the scTNFR2 agonist in a therapeutic regimen includes the combination of steroidal anti-inflammatory molecules, such as but not limited to dexamethasone and the like or non-steroidal anti-inflammatory molecules.

In addition, the scTNFR2 agonist may be formulated alone as a topical therapy or used in combination with or treated in a regimen with corticosteroids for treatment of autoimmune skin disorders such as psoriasis, eczema and burns (including sunburn). For instance, bath solutions and moisturizers, mineral oil and petroleum jelly which may help soothe affected skin and reduce the dryness which accompanies the build-up of skin on psoriatic plaques may be used formulated with or in a therapeutic regimen with scTNFR2 agonist as described herein. In addition, medicated creams and ointments applied directly to psoriatic plaques can help reduce inflammation, remove built-up scale, reduce skin turn over, and clear affected skin of plaques. Ointment and creams containing coal, tar, dithranol (anthralin), corticosteroids like desoximetasone (Topicort), fluocinonide, vitamin D3 analogs (for example, calcipotriol), and retinoids find use when combined with scTNFR2 agonist for topical application to the skin for treatment of autoimmune skin disorders.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present invention.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Generation and Characterization of TNFR2 Selective Agonist

Example 1 Expression of TNFR2 Agonist Molecules

Figure 10A:
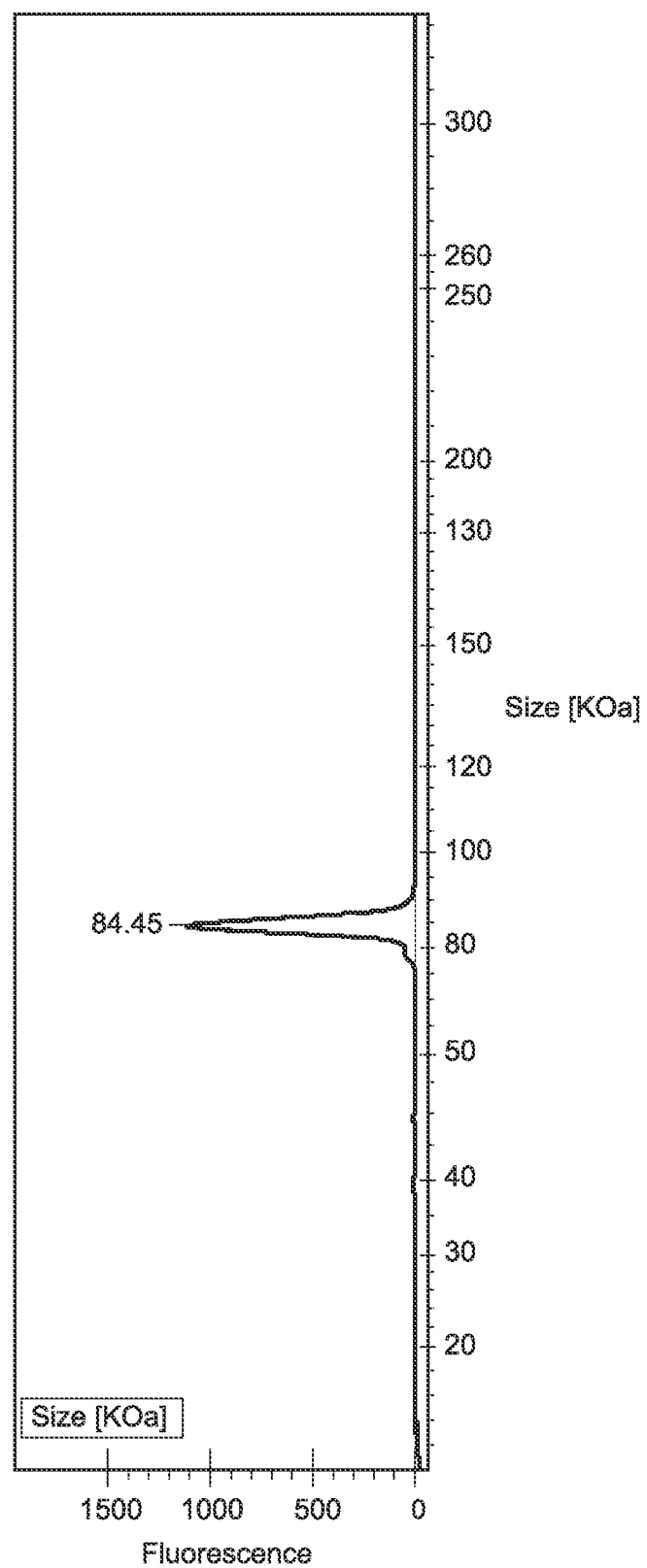
FIGS. 10a-10b—FIG. 10A Electrophoregram of SEQ ID NO: 101 under non-reducing conditions.
Figure 10B:
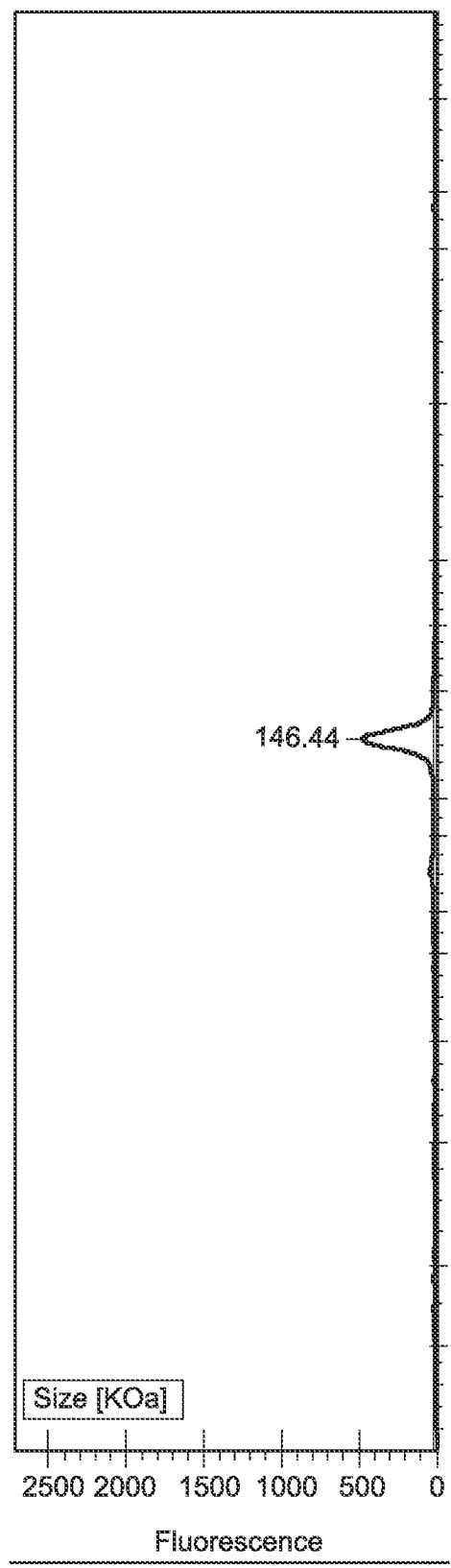

TNFR2-selective TNF variants, which are composed of a covalently stabilized human TNFR2-selective (D143N/A145R) single-chain TNF (SCTNF$_{R2}$) were fused to Fc dimerization domains resulting in a protein that is, with respect to TNF domains, hexameric (Fc-scTNFR2). The purity of the recombinant proteins was confirmed by SDS/PAGE and immunoblot analysis. Under reducing conditions, the TNF variants exhibited an appropriate molecular mass. Under nonreducing conditions the expected dimer was observed. The oligomerization state of Fc-scTNFR2 was further characterized by capillary electrophoresis. Fc-scTNFR2 elutes as a single major peak, indicating high purity. An exemplary electropherogram is shown in FIGS. 10a-10b for SEQ ID NO: 101.

Each gene sequence was cloned into a high expression mammalian vector. Each completed construct was sequence confirmed before proceeding to DNA scale up. Each DNA expression construct was scaled up to the appropriate amount for transfection. The plasmid DNA was run on agarose gel for quality assessment and sequence confirmed before proceeding to transfection. Suspension HEK293 cells were seeded in a shake flask and were expanded using serum-free chemically defined medium. On the day of transfection, the expanded cells were seeded into a new flask with fresh medium. Each DNA construct was transiently transfected into HEK293 cells using standard methods. The cells were maintained as a batch-fed culture until the end of the production run. The conditioned media from the transient production run was harvested and clarified by centrifugation and filtration. The supernatant was loaded over a Protein A column preequilibrated with binding buffer. Washing buffer was passed through the column until the OD280 value (NanoDrop, Thermo Scientific) was measured to be zero. The target protein was eluted with a low pH buffer, fractions were collected, and the OD280 value of each fraction was recorded. Fractions containing the target protein were pooled and filtered through a 0.2 pm membrane filter. The protein concentration was calculated from the OD280 value and the calculated extinction coefficient. CE-SDS analysis of the target protein was performed using LabChip GXII (Perkin Elmer).

Example 2 TNFR2 Binding

TNF receptor selectivity of FcscTNFR2 is analyzed by binding studies with immobilized huTNFR1-Fc and huTNFR2-Fc fusion proteins. Fc-scTNFR2 does not interact with huTNFR1, but the fusion protein efficiently binds to huTNFR2. In contrast, soluble human TNF (huTNF) efficiently binds to huTNFR1, whereas it less effectively with huTNFR2.

Wells were coated with 1 pg/mL hTNFR1-Fc or hTNFR2-Fc in PBS, 4° C. overnight then blocked with 3% milk in PBS, RT 1.5 hours. Primary incubation: TNF variant proteins, RT 1 hour (starting from 60 nM, 1:3 dilution). Primary detection antibody: 1 ug/mL TNF alpha monoclonal antibody (F6C5), RT 1 hour. Secondary detection antibody: HRP conjugated goat anti-mouse antibody (1:5000 dilution), RT 1 hour. Data shown in FIGS. 11A-11B. Calculated binding affinity follows:

| TNF Variant | Kd (nM) |
|---|---|
| Binding to TNFR1 | |
| TNF-a | 1.12 |
| SEQ IDNO: 101 | n/a |
| SEQ ID NO: 102 | n/a |
| EHD-scTNFr2 | n/a |
| SEQ ID NO: 113 | n/a |
| SEQ ID NO: 114 | Did not express |
| SEQ ID NO: 115 | n/a |
| SEQIDNO: 116 | n/a |
| SEQ ID NO: 117 | n/a |
| IgG4 Control | n/a |
| Binding to TNFR2 | |
| TNF-a | 0.90 |
| SEQ ID NO: 101 | 0.44 |
| SEQ ID NO: 102 | 0.27 |
| EHD-scTNFr2 | 0.33 |
| SEQ ID NO: 113 | 0.21 |
| SEQ ID NO: 114 | Did not express |
| SEQ ID NO: 115 | 0.28 |
| SEQ ID NO: 116 | 0.30 |
| SEQ ID NO: 117 | n/a |
| IgG4 Control | n/a |

Example 3 Cell Based TNFR2 Assay

Fc-scTNFR2 does not activate TNFR1-dependent cell death in L929, verifying that Fc-scTNFR2 had lost affinity for TNFR1 due to the mutations D143N/A145R. In contrast, Fc-scTNFR2 efficiently induced cell death in Kym-1 cells, which endogenously express both TNF receptors and are highly sensitive to endogenous TNF-induced TNFR1 mediated cytotoxicity. Thus, TNFR2 signaling can be measured as an increase in cell death in Kym-1 cells.

Kym-1 cells (1.5×104 cells/well) were grown in 96-well white opaque cell culture plates (Perkin Elmer) overnight. The cells were incubated with 8 concentrations of TNF muteins (100, 10, 1, 0.1, 0.01, 0.001, 0.0001 and 0.00001 ng/mL) in triplicates for 24 h at 37° C. and 5% CO2. Cell viability was analyzed at 24 h by Cell Titer Glo assay (Promega). SEQ ID NO: 114 did not express and therefore could not be tested. SEQ ID NO:117 did not induce cell death under any concentrations consistent with its inability to bind TNFR2 as shown in Example 2.

```
                         Sequence Listing

SEQ ID NO: 1 (Full length TNF-a)

MSTESMIRDVELAEEALPKKTGGPQGSRRCLFLSLFSFLIVAGATTLFCLLHFGVIGPQR
EEFPRDLSLISPLAQAVRSSSRTPSDKPVAHWANPQAEGQLQWLNRRANALLANGVEL
RDNQLWPSEGLYLIYSQVLFKGQGCPSTHVLLTHTISRIAVSYQTKVNLLSAIKSPCQRE
TPEGAEAKPWYEPIYLGGVFQLEKGDRLSAEINRPDYLDFAESGQVYFGIIAL
```

| Sequence Listing |
| --- |

SEQ ID NO: 2 (Soluble TNF-a)

VRSSSRTPSDKPVAHWANPQAEGQLQWLNRRANALLANGVELRDNQLWPSEGLYLIYS
QVLFKGQGCPSTHVLLTHTISRIAVSYQTKVNLLSAIKSPCQRETPEGAEAKPWYEPIYL
GGVFQLEKGDRLSAEINRPDYLDFAESGQVYFGIIAL

SEQ ID NO: 3 (THD Domain with TNFR2 Agonist Sequences)

PVAHVVANPQAEGQLQWLNRRANALLANGVELRDNQLVVPSEGLYLIYSQVLFKGQG
CPSTHVLLTHTISRIAVSYQTKVNLLSAIKSPCQRETPEGAEAKPWYEPIYLGGVFQLEKG
DRLSAEINRPDYLNFRESGQVYFGIIAL

SEQ ID NO: 4 (Sequence from the ADAM17 cleavage site in the
stalk region to the C-terminus of the stalk region)

VRSS SRTPSDK

SEQ ID NO: 5 (Human IgG1 Fc)

EPKSCDKTHTCPPCPAPELLGGPSVFLFPPKPKDTLMISRTPEVTCVVVDVSHEDPEVKF
NWYVDGVEVHNAKTKPREEQYNSTYRWSVLTVLHQDWLNGKEYKCKVSNKALPAPIE
KTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK

SEQ ID NO: 6 (Human IgG1 Fc with FcgR and C1q knockout)

EPKSSDKTHTCPPCPAPEAAGGPSVFLFPPKPKDTLMISRTPEVTCVWDVSHEDPEVKFN
WYVDGVEVHNAKTKPREEQYNSTYRWSVLTVLHQDWLNGKEYKCKVSNKALPASIEK
TISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK

SEQ ID NO: 7 (Human IgG1 Fc with N-terminal linker)

GGGGSEPKSCDKTHTCPPCPAPELLGGPSVFLFPPKPKDTLMISRTPEVTCVWDVSHEDP
EVKFNWYVDGVEVHNAKTKPREEQYNSTYRWSVLTVLHQDWLNGKEYKCKVSNKAL
PAPIEKTISKAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQKSLSLSPG
K

SEQ ID NO: 8 (Human IgG1 Fc with FcgR and C1q knockout and
linker)

GGGGSEPKSSDKTHTCPPCPAPEAAGGPSVFLFPPKPKDTLMISRTPEVTCVWDVSHEDP
EVKFNWYVDGVEVHNAKTKPREEQYNSTYRWSVLTVLHQDWLNGKEYKCKVSNKAL
PASIEKTISKAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQKSLSLSPG
K

SEQ ID NO: 9 (Human IgG1 Fc with C-terminal linker)

EPKSCDKTHTCPPCPAPELLGGPSVFLFPPKPKDTLMISRTPEVTCVVVDVSHEDPEVKF
NWYVDGVEVHNAKTKPREEQYNSTYRWSVLTVLHQDWLNGKEYKCKVSNKALPAPIE
KTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSP(GGGGS)
n = 1-5

SEQ ID NO: 10 (Human IgG1 Fc with FcgR and C1q knockout and
C-terminal linker)

EPKSSDKTHTCPPCPAPEAAGGPSVFLFPPKPKDTLMISRTPEVTCVWDVSHEDPEVKFN
WYVDGVEVHNAKTKPREEQYNSTYRWSVLTVLHQDWLNGKEYKCKVSNKALPASIEK
TISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSP(GGGGS)
n = 1-5

SEQ ID NO: 11 (Human IgG4 Fc)

ESKYGPPCPSCPAPEFLGGPSVFLFPPKPKDTLMISRTPEVTCVWDVSQEDPEVQFNWYV
DGVEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK

Sequence Listing

SEQ ID NO: 12 (Human IgG4 Fc with Ser to Pro mutation)

ESKYGPPCPPCPAPEFLGGPSVFLFPPKPKDTLMISRTPEVTCVVVDVSQEDPEVQFNWYV
DGVEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK

SEQ ID NO: 13 (Human IgG4 Fc with N-terminal linker)

GGGGSESKYGPPCPSCPAPEFLGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNKGLPSS
IEKTISKAKGQPREPQVYTLPPSQEEMTKNQVSLTCLVKGFYPSDIAVEWESNGQPENNY
KTTPPVLDSDGSFFLYSRLTVDKSRWQEGNVFSCSVMHEALHNHYTQKSLSLSLGK

SEQ ID NO: 14 (Human IgG4 Fc with Ser to Pro Mutation and
N-terminal linker)

GGGGSESKYGPPCPPCPAPEFLGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNKGLPSS
IEKTISKAKGQPREPQVYTLPPSQEEMTKNQVSLTCLVKGFYPSDIAVEWESNGQPENNY
KTTPPVLDSDGSFFLYSRLTVDKSRWQEGNVFSCSVMHEALHNHYTQKSLSLSLGK

SEQ ID NO: 15 (Human IgG4 Fc with C-terminal linker)

ESKYGPPCPSCPAPEFLGGPSVFLFPPKPKDTLMISRTPEVTCVVVDVSQEDPEVQFNWYV
DGVEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSL(GGGGS)
n = 1-5

SEQ ID NO: 16 (Human IgG4 Fc with Ser to Pro Mutation and
C-terminal linker)

ESKYGPPCPPCPAPEFLGGPSVFLFPPKPKDTLMISRTPEVTCVVVDVSQEDPEVQFNWYV
DGVEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSL(GGGGS)
n = 1-5

SEQ ID NO: 17 (Human IgG2 Fc)

ERKCCVECPPCPAPPVAGPSVFLFPPKPKDTLMISRTPEVTCVVVDVSHEDPEVQFNWYV
DGVEVHNAKTKPREEQFNSTFRVVSVLTVVHQDWLNGKEYKCKVSNKGLPAPIEKTIS
KTKGQPREPQVYTLPPSREEMTKNQVSLTCLVKGFYPSDIAVEWESNGQPENNYKTTPP
MLDSDGSFFLYSKLTVDKSRWQQGNVFSCSVMHEALHNHYTQKSLSLSPGK

SEQ ID NO: 18 (Human IgG2 Fc with C1q knockout)

ERKSSVECPPCPAPPVAGPSVFLFPPKPKDTLMISRTPEVTCVVVDVSHEDPEVQFNWYV
DGVEVHNAKTKPREEQFNSTFRVVSVLTVVHQDWLNGKEYKCKVSNKGLPASIEKTIS
KTKGQPREPQVYTLPPSREEMTKNQVSLTCLVKGFYPSDIAVEWESNGQPENNYKTTPP
MLDSDGSFFLYSKLTVDKSRWQQGNVFSCSVMHEALHNHYTQKSLSLSPGK

SEQ ID NO: 19 (Human IgG2 Fc with N-terminal linker)

GGGGSERKCCVECPPCPAPPVAGPSVFLFPPKPKDTLMISRTPEVTCVVVDVSHEDPEVQF
NWYVDGVEVHNAKTKPREEQFNSTFRVVSVLTVVHQDWLNGKEYKCKVSNKGLPAPI
EKTISKTKGQPREPQVYTLPPSREEMTKNQVSLTCLVKGFYPSDIAVEWESNGQPENNY
KTTPPMLDSDGSFFLYSKLTVDKSRWQQGNVFSCSVMHEALHNHYTQKSLSLSPGK

SEQ ID NO: 20 (Human IgG2 Fc with C1q knockout and N-terminal
linker)

GGGGSERKSSVECPPCPAPPVAGPSVFLFPPKPKDTLMISRTPEVTCVVVDVSHEDPEVQF
NWYVDGVEVHNAKTKPREEQFNSTFRVVSVLTVVHQDWLNGKEYKCKVSNKGLPASI
EKTISKTKGQPREPQVYTLPPSREEMTKNQVSLTCLVKGFYPSDIAVEWESNGQPENNY
KTTPPMLDSDGSFFLYSKLTVDKSRWQQGNVFSCSVMHEALHNHYTQKSLSLSPGK

SEQ ID NO: 21 (Human IgG2 Fc with C-terminal linker)

ERKCCVECPPCPAPPVAGPSVFLFPPKPKDTLMISRTPEVTCVVVDVSHEDPEVQFNWYV
DGVEVHNAKTKPREEQFNSTFRVVSVLTVVHQDWLNGKEYKCKVSNKGLPAPIEKTIS
KTKGQPREPQVYTLPPSREEMTKNQVSLTCLVKGFYPSDIAVEWESNGQPENNYKTTPP
MLDSDGSFFLYSKLTVDKSRWQQGNVFSCSVMHEALHNHYTQKSLSLSP(GGGGS)
n = 1-5

Sequence Listing

SEQ ID NO: 22 (Human IgG2 Fc with C1q knockout and C-terminal linker)

ERKSSVECPPCPAPPVAGPSVFLFPPKPKDTLMISRTPEVTCVVVDVSHEDPEVQFNWYV
DGVEVHNAKTKPRJEEQFNSTFRVVSVLTVVHQDWLNGKEYKCKVSNKGLPASIEKTIS
KTKGQPREPQVYTLPPSREEMTKNQVSLTCLVKGFYPSDIAVEWESNGQPENNYKTTPP
MLDSDGSFFLYSKLTVDKSRWQQGNVFSCSVMHEALHNHYTQKSLSLSP(GGGGS)
n = 1-5

SEQ ID NO: 23 (EHD2 dimerization domain)

DFTPPTVKILQSSCDGGGHFPPTIQLLCLVSGYTPGTINITWLEDGQVMDVDLSTASTTQE
GELASTQSELTLSQKHWLSDRTYTCQVTYQGHTFEDSTKKCADSN

SEQ ID NO: 24 (MHD2 dimerization domain)

AELPPKVSVFVPPRDGFFGNPRKSKLICQATGFSPRQIQVSWLREGKQVGSGVTTDQVQ
AEAKESGPTTYKVTSTLTIKESDWLGQSMFTCRVDHRGLTFQQNASSMCVPD

SEQ ID NO: 25 (linker)

GGGGS

SEQ ID NO: 26 (TNF-a stalk region)

GPQREEFPRDLSLISPLAQAVRSSSRTPSDK

SEQ ID NO: 27 (linker)

GGGGSGGGGS

SEQ ID NO: 28 (stalk based linker)

SSRTPSDK

SEQ ID NO: 29 (G/S Stalk based linker)

GGGGSVRSSSRTPSDK

SEQ ID NO: 30 (G/S Stalk based linker)

GGGGSSSRTPSDK

SEQ ID NO: 31 (IgG1 Fc with mutations; (GGGGS)2; THDR2; stalk linker; THDR2; stalk linker; THDR2)

EPKSSDKTHTCPPCPAPEAAGGPSVFLFPPKPKDTLMISRTPEVTCVVVDVSHEDPE
VKFNWYVDGVEVHNAKTKPREEQYNSTYRVVSVLTVLHQDWLNGKEYKCKVSN
KALPASIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYT
*QKSLSLSPGGGGSGGGGS*PVAHWANPQAEGQLQWLNRRANALLANGVELRDNQLVVPS
EGLYLIYSQVLFKGQGCPSTHVLLTHTISRIAVSYQTKVNLLSAIKSPCQRETPEGAEAKP
WYEPIYLGGVFQLEKGDRLSAEINRPDYLNFRESGHVVANPQAEGQLQWLNRRANALL
ANGVELRDNQLVVPSEGLYLIYSQVLFKGQGCPSTHVLLTHTISRIAVSYQTKVNLLSAI
KSPCQRETPEGAEAKPWYEPIYLGGVFQLEKGDRLSAEINRPDYLNFRESGQVYFGIIAL
*GGGGSSSTRPSDK*PVAHWANPQAEGQLQWLNRRANALLANGVELRDNQLVVPSEGLYL
IYSQVLFKGQGCPSTHVLLTHTISRIAVSYQTKVNLLSAIKSPCQRETPEGAEAKPWYEPI
YLGGVFQLEKGDRLSAEINRPDYLNFRESGQVYFGIIAL

SEQ ID NO: 32 (IgG1 Fc with mutations; G/S stalk linker; THDR2; G/S short stalk linker; THDR2; G/S short stalk linker; THDR2)

EPKSSDKTHTCPPCPAPEAAGGPSVFLFPPKPKDTLMISRTPEVTCVVVDVSHEDPEV
KFNWYVDGVEVHNAKTKPREEQYNSTYRVVSVLTVLHQDWLNGKEYKCKVSNK
ALPASIEKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHYTQ
KSLSLPGGGGSVRSSSTRPSDKPVAHWANPQAEGQLQWLNRRANALLANGVELRDNQL
VVPSEGLYLIYSQVLFKGQGCPSTHVLLTHTISRIAVSYQTKVNLLSAIKSPCQRETPEGA
EAKPWYEPIYLGGVFQLEKGDRLSAEINRPDYLNFRESGQVYFGIIAL*GGGGSSSRTPSDK*
PTVAHWANPQAEGQLQWLNRRANALLANGVELRDNQLVVPSEGLYLIYSQVLFKGQG
CPSTHVLLTHTISRIAVSYQTKVNLLSAIKSPCQRETPEGAEAKPWYEPIYLGGVFQLEKG
DRLSAEINRPDYLNFRESGQVYFGIIAL*GGGGSSSRTPSDK*PVAHWANPQAEGQLQWLNR
RANALLANGVELRDNQLVVPSEGLYLIYSQVLFKGQGCPSTHVLLTHTISRIAVSYQTKV
NLLSAIKSPCQRETPEGAEAKPWYEPIYLGGVFQLEKGDRLSAEINRPDYLNFRESGQVY
FGIIAL

Sequence Listing

SEQ ID NO: 33 (Soluble TNF-a sequence with TNFR2 agonist mutations)

VRSSSRTPSDKPVAHVVANPQAEGQLQWLNRRANALLANGVELRDNQLWPSEGLYLIY
SQVLFKGQGCPSTHVLLTHTISRIAVSYQTKVNLLSAIKSPCQRETPEGAEAKPWYEPIYL
GGVFQLEKGDRLSAEINRPDYLNFRESGQVYFGIIAL

SEQ ID NO: 34 (scTNFR2 agonist with C-terminal IgG1 with mutations. This is soluble TNF-a sequence, which includes VRSSSRTPSDK at N-terminus prior to THD domain.)

VRSSSRTPSDKPVAHWANPQAEGQLQWLNRRANALLANGVELRDNQLVVPSEGLYLIY
SQVLFKGQGCPSTHVLLTHTISRIAVSYQTKVNLLSAIKSPCQRETPEGAEAKPWYEPIYL
GGVFQLEKGDRLSAEINRPDYLNFRESGQVYFGIIALVRSSSRTPSDKPVAHWANPQAEG
QLQWLNRRANALLANGVELRDNQLVVPSEGLYLIYSQVLFKGQGCPSTHVLLTHTISRJ
AVSYQTKVNLLSAIKSPCQRETPEGAEAKPWYEPIYLGGVFQLEKGDRLSAEINRPDYLN
FRESGQVYFGIIALVRSSSRTPSDKPVAHVVANPQAEGQLQWLNRRANALLANGVELRD
NQLVVPSEGLYL1YSQVLFKGQGCPSTHVLLTHTISRIAVSYQTKVNLLSAIKSPCQRETP
EGAEAKPWYEPIYLGGVFQLEKGDRLSAEINRPDYLNFRESGQVYFGIIAL
EPKSSDKTHTCPPCPAPEAAGGPSVFLFPPKPKDTLMISRTPEVTCVVVDVSHEDPE
VKFNWYVDGVEVHNAKTKPREEQYNSTYRVVSVLTVLHQDWLNGKEYKCKVSN
KALPASIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYT
QKSLSLSP

SEQ ID NO: 35 (scTNFR2 agonist with C-terminal IgG1 with mutations. This is soluble TNF-a sequence, which includes VRSSSRTPSDK at N-terminus prior to THD domain and GGGGS prior to IgG1.)

VRSSSRTPSDKPVAHWANPQAEGQLQWLNRRANALLANGVELRDNQLWPSEGLYLIYS
QVLFKGQGCPSTHVLLTHTISRIAVSYQTKVNLLSAIKSPCQRETPEGAEAKPWYEPIYL
GGVFQLEKGDRLSAEINRPDYLNFRESGQVYFGIIALVRSSSRTPSDKPVAHWANPQAEG
QLQWLNRRANALLANGVELRDNQLVVPSEGLYLIYSQVLFKGQGCPSTHVLLTHTISRI
AVSYQTKVNLLSAIKSPCQRETPEGAEAKPWYEPIYLGGVFQLEKGDRLSAEINRPDYLN
FRESGQVYFGIIALVRSSSRTPSDKPVAHWANPQAEGQLQWLNRRANALLANGVELRD
NQLWPSEGLYLIYSQVLFKGQGCPSTHVLLTHTISRIAVSYQTKVNLLSAIKSPCQRETPE
GAEAKPWYEPIYLGGVFQLEKGDRLSAEINRPDYLNFRESGQVYFGIIALGGGGS' EPKS
SDKTHTCPPCPAPEAAGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPA
SIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLS
LSP

SEQ ID NO: 36 nucleic acid encoding SEQ ID NO: 31 optimized for *Mus musculus* expression by www.jcat.de GAGCCCAAGAGCAGCGACAAGACCCACACCTGCCCCCCCTGCCCCGCCCC 50
CGAGGCCGCCGGCGGCCCCAGCGTGTTCCTGTTCCCCCCCAAGCCCAAGG 100
ACACCCTGATGATCAGCAGGACCCCCGAGGTGACCTGCGTGGTGGTGGAC 150
GTGAGCCACGAGGACCCCGAGGTGAAGTTCAACTGGTACGTGGACGGCGT 200
GGAGGTGCACAACGCCAAGACCAAGCCCAGGGAGGAGCAGTACAACAGCA 250
CCTACAGGGTGGTGAGCGTGCTGACCGTGCTGCACCAGGACTGGCTGAAC 300
GGCAAGGAGTACAAGTGCAAGGTGAGCAACAAGGCCCTGCCCGCCAGCAT 350
CGAGAAGACCATCAGCAAGGCCAAGGGCCAGCCCAGGGAGCCCCAGGTGT 400
ACACCCTGCCCCCCAGCAGGGACGAGCTGACCAAGAACCAGGTGAGCCTG 450
ACCTGCCTGGTGAAGGGCTTCTACCCCAGCGACATCGCCGTGGAGTGGGA 500
GAGCAACGGCCAGCCCGAGAACAACTACAAGACCACCCCCCCCGTGCTGG 550
ACAGCGACGGCAGCTTCTTCCTGTACAGCAAGCTGACCGTGGACAAGAGC 600
AGGTGGCAGCAGGGCAACGTGTTCAGCTGCAGCGTGATGCACGAGGCCCT 650
GCACAACCACTACACCCAGAAGAGCCTGAGCCTGAGCCCCGGCGGCGGCG 700
GCAGCGGCGGCGGCGGCAGCCCCGTGGCCCACGTGGTGGCCAACCCCCAG 750
GCCGAGGGCCAGCTGCAGTGGCTGAACAGGAGGGCCAACGCCCTGCTGGC 800
CAACGGCGIGGAGCTGAGGGACAACCAGCTGGTGGTGCCCAGCGAGGGCC 850
TGTACCTGATCTACAGCCAGGTGCTGTTCAAGGGCCAGGGCTGCCCCAGC 900
ACCCACGTGCTGCTGACCCACACCATCAGCAGGATCGCCGTGAGCTACCA 950
GACCAAGGTGAACCTGCTGAGCGCCATCAAGAGCCCCTGCCAGAGGGAGA1000
CCCCCGAGGGCGCCGAGGCCAAGCCCTGGTACGAGCCCATCTACCTGGGC1050
GGCGTGTTCCAGCTGGAGAAGGGCGACAGGCTGAGCGCCGAGATCAACAG1100
GCCCGACTACCTGAACTTCAGGGAGAGCGGCCAGGTGTACTTCGGCATCA1150
TCGCCCTGGTGAGGAGCAGCAGCAGGACCCCCAGCGACAAGCCCGTGGCC1200
CACGTGGTGGCCAACCCCCAGGCCGAGGGCCAGCTGCAGTGGCTGAACAG1250
GAGGGCCAACGCCCTGCTGGCCAACGGCGTGGAGCTGAGGGACAACCAGC1300
TGGTGGTGCCCAGCGAGGGCCTGTACCTGATCTACAGCCAGGTGCTGTTC1350
AAGGGCCAGGGCTGCCCCAGCACCCACGTGCTGCTGACCCACACCATCAG1400
CAGGATCGCCGTGAGCTACCAGACCAAGGTGAACCTGCTGAGCGCCATCA1450
AGAGCCCCTGCCAGAGGGAGACCCCCGAGGGCGCCGAGGCCAAGCCCTGG1500

-continued

Sequence Listing

```
TACGAGCCCATCTACCTGGGCGGCGTGTTCCAGCTGGAGAAGGGCGACAG 1550
GCTGAGCGCCGAGATCAACAGGCCCGACTACCTGAACTTCAGGGAGAGCG 1600
GCCAGGTGTACTTCGGCATCATCGCCCTGGTGAGGAGCAGCAGCAGGACC 1650
CCCAGCGACAAGCCCGTGGCCCACGTGGTGGCCAACCCCCAGGCCGAGGG 1700
CCAGCTGCAGTGGCTGAACAGGAGGGCCAACGCCCTGCTGGCCAACGGCG 1750
TGGAGCTGAGGGACAACCAGCTGGTGGTGCCCAGCGAGGGCCTGTACCTG 1800
ATCTACAGCCAGGTGCTGTTCAAGGGCCAGGGCTGCCCCAGCACCCACGT 1850
GCTGCTGACCCACACCATCAGCAGGATCGCCGTGAGCTACCAGACCAAGG 1900
TGAACCTGCTGAGCGCCATCAAGAGCCCCTGCCAGAGGGAGACCCCCGAG 1950
GGCGCCGAGGCCAAGCCCTGGTACGAGCCCATCTACCTGGGCGGCGTGTT 2000
CCAGCTGGAGAAGGGCGACAGGCTGAGCGCCGAGATCAACAGGCCCGACT 2050
ACCTGAACTTCAGGGAGAGCGGCCAGGTGTACTTCGGCATCATCGCCCTG

SEQ ID No: 37 nucleic acid encoding SEQ ID NO: 32
optimized for Mus musculus expression by www.jcat.de GAGCCCAAGAGCAGCGACAAGACCCACACCTGCCCCCCCTGCCCCGCCCC   50
CGAGGCCGCCGGCGGCCCCAGCGTGTTCCTGTTCCCCCCCAAGCCCAAGG  100
ACACCCTGATGATCAGCAGGACCCCCGAGGTGACCTGCGTGGTGGTGGAC  150
GTGAGCCACGAGGACCCCGAGGTGAAGTTCAACTGGTACGTGGACGGCGT  200
GGAGGTGCACAACGCCAAGACCAAGCCCAGGGAGGAGCAGTACAACAGCA  250
CCTACAGGGTGGTGAGCGTGCTGACCGTGCTGCACCAGGACTGGCTGAAC  300
GGCAAGGAGTACAAGTGCAAGGTGAGCAACAAGGCCCTGCCCGCCAGCAT  350
CGAGAAGACCATCAGCAAGGCCAAGGGCCAGCCCAGGGAGCCCCAGGTGT  400
ACACCCTGCCCCCCAGCAGGGACGAGCTGACCAAGAACCAGGTGAGCCTG  450
ACCTGCCTGGTGAAGGGCTTCTACCCCAGCGACATCGCCGTGGAGTGGGA  500
GAGCAACGGCCAGCCCGAGAACAACTACAAGACCACCCCCCCCGTGCTGG  550
ACAGCGACGGCAGCTTCTTCCTGTACAGCAAGCTGACCGTGGACAAGAGC  600
AGGTGGCAGCAGGGCAACGTGTTCAGCTGCAGCGTGATGCACGAGGCCCT  650
GCACAACCACTACACCCAGAAGAGCCTGAGCCTGAGCCCCGGCGGCGGCG  700
GCAGCGTGAGGAGCAGCAGCAGGACCCCCAGCGACAAGCCCGTGGCCCAC  750
GTGGTGGCCAACCCCCAGGCCGAGGGCCAGCTGCAGTGGCTGAACAGGAG  800
GGCCAACGCCCTGCTGGCCAACGGCGTGGAGCTGAGGGACAACCAGCTGG  850
TGGTGCCCAGCGAGGGCCTGTACCTGATCTACAGCCAGGTGCTGTTCAAG  900
GGCCAGGGCTGCCCCAGCACCCACGTGCTGCTGACCCACACCATCAGCAG  950
GATCGCCGTGAGCTACCAGACCAAGGTGAACCTGCTGAGCGCCATCAAGA 1000
GCCCCTGCCAGAGGGAGACCCCCGAGGGCGCCGAGGCCAAGCCCTGGTAC 1050
GAGCCCATCTACCTGGGCGGCGTGTTCCAGCTGGAGAAGGGCGACAGGCT 1100
GAGCGCCGAGATCAACAGGCCCGACTACCTGAACTTCAGGGAGAGCGGCC 1150
AGGTGTACTTCGGCATCATCGCCCTGGGCGGCGGCGGCAGCAGCAGGCAG 1200
ACCCCCAGCGACAAGCCCGTGGCCCACGTGGTGGCCAACCCCCAGGCCGA 1250
GGGCCAGCTGCAGTGGCTGAACAGGAGGGCCAACGCCCTGCTGGCCAACG 1300
GCGTGGAGCTGAGGGACAACCAGCTGGTGGTGCCCAGCGAGGGCCTGTAC 1350
CTGATCTACAGCCAGGTGCTGTTCAAGGGCCAGGGCTGCCCCAGCACCCA 1400
CGTGCTGCTGACCCACACCATCAGCAGGATCGCCGTGAGCTACCAGACCA 1450
AGGTGAACCTGCTGAGCGCCATCAAGAGCCCCTGCCAGAGGGAGACCCCC 1500
GAGGGCGCCGAGGCCAAGCCCTGGTACGAGCCCATCTACCTGGGCGGCGT 1550
GTTCCAGCTGGAGAAGGGCGACAGGCTGAGCGCCGAGATCAACAGGCCCG 1600
ACTACCTGAACTTCAGGGAGAGCGGCCAGGTGTACTTCGGCATCATCGCC 1650
CTGGGCGGCGGCGGCAGCAGCAGGACCCCCAGCGACAAGCCCGTGGCC   1700
CCACGTGGTGGCCAACCCCCAGGCCGAGGGCCAGCTGCAGTGGCTGAACA 1750
GGAGGGCCAACGCCCTGCTGGCCAACGGCGTGGAGCTGAGGGACAACCAG 1800
CTGGTGGTGCCCAGCGAGGGCCTGTACCTGATCTACAGCCAGGTGCTGTT 1850
CAAGGGCCAGGGCTGCCCCAGCACCCACGTGCTGCTGACCCACACCATCA 1900
GCAGGATCGCCGTGAGCTACCAGACCAAGGTGAACCTGCTGAGCGCCATC 1950
AAGAGCCCCTGCCAGAGGGAGACCCCCGAGGGCGCCGAGGCCAAGCCCTG 2000
GTACGAGCCCATCTACCTGGGCGGCGTGTTCCAGCTGGAGAAGGGCGACA 2050
GGCTGAGCGCCGAGATCAACAGGCCCGACTACCTGAACTTCAGGGAGAGC 2100
GGCCAGGTGTACTTCGGGCATCATCGCCCTG SEQ ID NO: 38 nucleic acid encoding SEQ ID NO: 34
optimized for Mus musculus expression by www.jcat.de GTGAGGAGCAGCAGCAGGACCCCCAGCGACAAGCCCGTGGCCCACGTGGT   50
GGCCAACCCCCAGGCCGAGGGCCAGCTGCAGTGGCTGAACAGGAGGGCCA  100
ACGCCCTGCTGGCCAACGGCGTGGAGCTGAGGGACAACCAGCTGGTGGTG  150
CCCAGCGAGGGCCTGTACCTGATCTACAGCCAGGTGCTGTTCAAGGGCCA  200
GGGCTGCCCCAGCACCCACGTGCTGCTGACCCACACCATCAGCAGGATCG  250
CCGTGAGCTACCAGACCAAGGTGAACCTGCTGAGCGCCATCAAGAGCCCC  300
TGCCAGAGGGAGACCCCCGAGGGCGCCGAGGCCAAGCCCTGGTACGAGCC  350
CATCTACCTGGGCGGCGTGTTCCAGCTGGAGAAGGGCGACAGGCTGAGCG  400
CCGAGATCAACAGGCCCGACTACCTGAACTTCAGGGAGAGCGGCCAGGTG  450
TACTTCGGCATCATCGCCCTGGTGAGGAGCAGCAGCAGGACCCCCAGCGA  500
CAAGCCCGTGGCCCACGTGGTGGCCAACCCCCAGGCCGAGGGCCAGCTGC  550
AGTGGCTGAACAGGAGGGCCAACGCCCTGCTGGCCAACGGCGTGGAGCTG  600
AGGGACAACCAGCTGGTGGTGCCCAGCGAGGGCCTGTACCTGATCTACAG  650
CUAGGTGCTGTTCAAGGGCCAGGGCTGCCCCAGCACCCACGTGCTGCTGA  700
```

| Sequence Listing |
|---|
| CCCACACCATCAGCAGGATCGCCGTGAGCTACCAGACCAAGGTGAACCTG 750
CTGAGCGCCATCAAGAGCCCCTGCCAGAGGGAGACCCCCGAGGGCGCCGA 800
GGCCAAGCCCTGGTACGAGCCCATCTACCTGGGCGGCGTGTTCCAGCTGG 850
AGAAGGGCGACAGGCTGAGCGCCGAGATCAACAGGCCCGACTACCTGAAC 900
TTCAGGGAGAGCGGCCAGGTGTACTTCGGCATCATCGCCCTGGTGAGGAG 950
CAGCAGCAGGACCCCCAGCGACAAGCCCGTGGCCCACGTGGTGGCCAACC 1000
CCCAGGCCGAGGGCCAGCTGCAGTGGCTGAACAGGAGGGCCAACGCCCTG 1050
CTGGCCAACGGCGTGGAGCTGAGGGACAACCAGCTGGTGGTGCCCAGCGA 1100
GGGCCTGTACCTGATCTACAGCCAGGTGCTGTTCAAGGGCCAGGGCTGCC 1150
CCAGCACCCACGTGCTGCTGACCCACACCATCAGCAGGATCGCCGTGAGC 1200
TACCAGACCAAGGTGAACCTGCTGAGCGCCATCAAGAGCCCCTGCCAGAG 1250
GGAGACCCCCGAGGGCGCCGAGGCCAAGCCCTGGTACGAGCCCATCTACC 1300
TGGGCGGCGTGTTCCAGCTGGAGAAGGGCGACAGGCTGAGCGCCGAGATC 1350
AACAGGCCCGACTACCTGAACTTCAGGGAGAGCGGCCAGGTGTACTTCGG 1400
CATCATCGCCCTGGAGCCCAAGAGCAGCGACAAGACCCACCTGCCCCC 1450
CCTGCCCCGCCCCCGAGGCCGCCGGCGGCCCCAGCGTGTTCCTGTTCCCC 1500
CCCAAGCCCAAGGACACCCTGATGATCAGCAGGACCCCCGAGGTGACCTG 1550
CGTGGTGGTGGACGTGAGCCACGAGGACCCCGAGGTGAAGTTCAACTGGT 1600
ACGTGGACGGCGTGGAGGTGCACAACGCCAAGACCAAGCCCAGGGAGGAG 1650
CAGTACAACAGCACCTACAGGGTGGTGAGCGTGCTGACCGTGCTGCACCA 1700
GGACTGGCTGAACGGCAAGGAGTACAAGTGCAAGGTGAGCAACAAGGCCC 1750
TGCCCGCCAGCATCGAGAAGACCATCAGCAAGGCCAAGGGCCAGCCCAGG 1800
GAGCCCCAGGTGTACACCCTGCCCCCCAGCAGGGACGAGCTGACCAAGAA 1850
CCAGGTGAGCCTGACCTGCCTGGTGAAGGGCTTCTACCCCAGCGACATCG 1900
CCGTGGAGTGGGAGAGCAACGGCCAGCCCGAGAACAACTACAAGACCACC 1950
CCCCCCGTGCTGGACAGCGACGGCAGCTTCTTCCTGTACAGCAAGCTGAC 2000
CGTGGACAAGAGCAGGTGGCAGCAGGGCAACGTGTTCAGCTGCAGCGTGA 2050
TGCACGAGGCCCTGCACAACCACTACACCCAGAAGAGCCTGAGCCTGAGC 2051
CCC |
| SEQ ID NO: 39 nucleic acid encoding SEQ ID NO: 35
optimized for *Mus musculus* expression by www.jcat.de |
| GTGAGGAGCAGCAGCAGGACCCCCAGCGACAAGCCCGTGGCCCACGTGGT 50
GGCCAACCCCCAGGCCGAGGGCCAGCTGCAGTGGCTGAACAGGAGGGCCA 100
ACGCCCTGCTGGCCAACGGCGTGGAGCTGAGGGACAACCAGCTGGTGGTG 150
CCCAGCGAGGGCCTGTACCTGATCTACAGCCAGGTGCTGTTCAAGGGCCA 200
GGGCTGCCCCAGCACCCACGTGCTGCTGACCCACACCATCAGCAGGATCG 250
CCGTGAGCTACCAGACCAAGGTGAACCTGCTGAGCGCCATCAAGAGCCCC 300
TGCCAGAGGGAGACCCCCGAGGGCGCCGAGGCCAAGCCCTGGTACGAGCC 350
CATCTACCTGGGCGGCGTGTTCCAGCTGGAGAAGGGCGACAGGCTGAGCG 400
CCGAGATCAACAGGCCCGACTACCTGAACTTCAGGGAGAGCGGCCAGGTG 450
TACTTCGGCATCATCGCCCTGGTGAGGAGCAGCAGCAGGACCCCCAGCGA 500
CAAGCCCGTGGCCCACGTGGTGGCCAACCCCCAGGCCGAGGGCCAGCTGC 550
AGTGGCTGAACAGGAGGGCCAACGCCCTGCTGGCCAACGGCGTGGAGCTG 600
AGGGACAACCAGCTGGTGGTGCCCAGCGAGGGCCTGTACCTGATCTACAG 650
CCAGGTGCTGTTCAAGGGCCAGGGCTGCCCCAGCACCCACGTGCTGCTGA 700
CCCACACCATCAGCAGGATCGCCGTGAGCTACCAGACCAAGGTGAACCTG 750
CTGAGCGCCATCAAGAGCCCCTGCCAGAGGGAGACCCCCGAGGGCGCCGA 800
GGCCAAGCCCTGGTACGAGCCCATCTACCTGGGCGGCGTGTTCCAGCTGG 850
AGAAGGGCGACAGGCTGAGCGCCGAGATCAACAGGCCCGACTACCTGAAC 900
TTCAGGGAGAGCGGCCAGGTGTACTTCGGCATCATCGCCCTGGTGAGGAG 950
CAGCAGCAGGACCCCCAGCGACAAGCCCGTGGCCCACGTGGTGGCCAACC 1000
CCCAGGCCGAGGGCCAGCTGCAGTGGCTGAACAGGAGGGCCAACGCCCTG 1050
CTGGCCAACGGCGTGGAGCTGAGGGACAACCAGCTGGTGGTGCCCAGCGA 1100
GGGCCTGTACCTGATCTACAGCCAGGTGCTGTTCAAGGGCCAGGGCTGCC 1150
CCAGCACCCACGTGCTGCTGACCCACACCATCAGCAGGATCGCCGTGAGC 1200
TACCAGACCAAGGTGAACCTGCTGAGCGCCATCAAGAGCCCCTGCCAGAG 1250
GGAGACCCCCGAGGGCGCCGAGGCCAAGCCCTGGTACGAGCCCATCTACC 1300
TGGGCGGCGTGTTCCAGCTGGAGAAGGGCGACAGGCTGAGCGCCGAGATC 1350
AACAGGCCCGACTACCTGAACTTCAGGGAGAGCGGCCAGGTGTACTTCGG 1400
CATCATCGCCCTGGGCGGCGGCGGCAGCGAGCCCAAGAGCAGCGACAAGA 1450
CCCACACCTGCCCCCCTGCCCCGCCCCCGAGGCCGCCGGCGGCCCCAGC 1500
GTGTTCCTGTTCCCCCCCAAGCCCAAGGACACCCTGATGATCAGCAGGAC 1550
CCCCGAGGTGACCTGCGTGGTGGTGGACGTGAGCCACGAGGACCCCGAGG 1600
TGAAGTTCAACTGGTACGTGGACGGCGTGGAGGTGCACAACGCCAAGACC 1650
AAGCCCAGGGAGGAGCAGTACAACAGCACCTACAGGGTGGTGAGCGTGCT 1700
GACCGTGCTGCACCAGGACTGGCTGAACGGCAAGGAGTACAAGTGCAAGG 1750
TGAGCAACAAGGCCCTGCCCGCCAGCATCGAGAAGACCATCAGCAAGGCC 1800
AAGGGCCAGCCCAGGGAGCCCCAGGTGTACACCCTGCCCCCCAGCAGGGA 1850
CGAGCTGACCAAGAACCAGGTGAGCCTGACCTGCCTGGTGAAGGGCTTCT 1900
ACCCCAGCGACATCGCCGTGGAGTGGGAGAGCAACGGCCAGCCCGAGAAC 1950
AACTACAAGACCACCCCCCCCGTGCTGGACAGCGACGGCAGCTTCTTCCT 2000
GTACAGCAAGCTGACCGTGGACAAGAGCAGGTGGCAGCAGGGCAACGTGT 2050
TCAGCTGCAGCGTGATGCACGAGGCCCTGCACAACCACTACACCCAGAAG 2100
AGCCTGAGCCTGAGCCCC |

| Sequence Listing |
| --- |

SEQ ID NO: 40 Human IgG1 sequence including C-terminal extension

EPKSSDKTHTCPPCPAPEAAGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPASIEK
TISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPELQLEESS
AEAQDGELDG

SEQ ID NO: 41 Linker from C-terminus of Human IgG

ELQLEESSAEAQDGELDG

SEQ ID NO: 42 Linker variant derived from C-terminus of Human IgG

ELQLEESSAEAQGG

SEQ ID NO: 100:
EHD2: GGGSGGGTGSEFLA-SSRTPSDK: THDR2: GGGGS-
SSRTPSDK: THDR2: GGGGS-SSRTPSDK: THDR2

DFTPPTVKILQSSCDGGGHFPPTIQLLCLVSGYTPGTINITWLEDGQVMDVDLSTASTTQE
GELASTQSELTLSQKHWLSDRTYTCQVTYQGHTFEDSTKKCADSNGGGSGGGTGSEFL
ASSRTPSDKPVAHWANPQAEGQLQWLNRRANALLANGVELRDNQLWPSEGLYLIYSQ
VLFKGQGCPSTHVLLTHTISRIAVSYQTKVNLLSAIKSPCQRETPEGAEAKPWYEPIYLG
GVFQLEKGDRLSAEINRPDYLNFRESGQVYFGIIALGGGGSSSRTPSDKPVAHVVANPQA
EGQLQWLNRRANALLANGVELRDNQLVVPSEGLYLIYSQVLFKGQGCPSTHVLLTHTIS
RIAVSYQTKVNLLSAIKSPCQRETPEGAEAKPWYEPIYLGGVFQLEKGDRLSAEINRPDY
LNFRESGQVYFGIIALGGGGSSSRTPSDKPVAHVVANPQAEGQLQWLNRRANALLANG
VELRDNQLVVPSEGLYLIYSQVLFKGQGCPSTHVLLTHTISRIAVSYQTKVNLLSAIKSPC
QRETPEGAEAKPWYEPIYLGGVFQLEKGDRLSAEINRPDYLNFRESGQVYFGIIAL

SEQ ID NO: 101 I4SP: GGGGS: sTNFR2: GGGGS-SSRTPSDK: THDR2:
GGGGS-SSRTPSDK: THDR2

ESKYGPPCPPCPAPEFLGGPSVFLFPPKPKDTLMISRTPEVTCVVVDVSQEDPEVQFNWY
VDGVEVHNAKTKPREEQFNSTYRVVSVLTVLHQDWLNGKEYKCKVSNKGLPSSIEKTIS
KAKGQPREPQVYTLPPSQEEMTKNQVSLTCLVKGFYPSDIAVEWESNGQPENNYKTTPP
VLDSDGSFFLYSRLTVDKSRWQEGNVFSCSVMHEALHNHYTQKSLSLSLGKGGGGSVR
SSSRTPSDKPVAHVVANPQAEGQLQWLNRRANALLANGVELRDNQLWPSEGLYLIYSQ
VLFKGQGCPSTHVLLTHTISRIAVSYQTKVNLLSAIKSPCQRETPEGAEAKPWYEPIYLG
GVFQLEKGDRLSAEINRPDYLNFRESGQVYFGIIALGGGGSSSRTPSDKPVAHVVANPQA
EGQLQWLNRRANALLANGVELRDNQLVVPSEGLYLIYSQVLFKGQGCPSTHVLLTHTIS
RIAVSYQTKVNLLSAIKSPCQRETPEGAEAKPWYEPIYLGGVFQLEKGDRLSAEINRPDY
LNFRESGQVYFGIIALGGGGSSSRTPSDKPVAHWANPQAEGQLQWLNRRANALLANGV
ELRDNQLWPSEGLYLIYSQVLFKGQGCPSTHVLLTHTISRIAVSYQTKVNLLSAIKSPCQR
ETPEGAEAKPWYEPIYLGGVFQLEKGDRLSAEINRPDYLNFRESGQVYFGiiAL

SEQ ID NO: 102: I4SP: GGGGS: sTNFR2: SSRTPSDK-THDR2: SSRTPSDK:
THDR2

ESKYGPPCPPCPAPEFLGGPSVFLFPPKPKDTLMISRTPEVTCVVVDVSQEDPEVQFNWYV
DGVEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGKGGGGSVRS
SSRTPSDKPVAHVVANPQAEGQLQWLNRRANALLANGVELRDNQLWPSEGLYLIYSQV
LFKGQGCPSTHVLLTHTISRIAVSYQTKVNLLSAIKSPCQRETPEGAEAKPWYEPIYLGG
VFQLEKGDRLSAEINRPDYLNFRESGQVYFGIIALSSRTPSDKPVAHVVANPQAEGQLQ
WLNRRANALLANGVELRDNQLVVPSEGLYLIYSQVLFKGQGCPSTHVLLTHTISRIAVS
YQTKVNLLSAIKSPCQRETPEGAEAKPWYEPIYLGGVFQLEKGDRLSAEINRPDYLNFRE
SGQVYFGIIALSSRTPSDKPVAHWANPQAEGQLQWLNRRANALLANGVELRDNQLVVP
SEGLYLIYSQVLFKGQGCPSTHVLLTHTISRIAVSYQTKVNLLSAIKSPCQRETPEGAEAK
PWYEPIYLGGVFQLEKGDRLSAEINRPDYLNFRESGQVYFGIIAL

SEQ ID NO: REL103: I4SP: GGGGS: STNFR2: VRSSSRTPSDK: THDR2:
VRSSSRTPSDK: THDR2

ESKYGPPCPPCPAPEFLGGPSVFLFPPKPKDTLMISRTPEVTCVVVDVSQEDPEVQFNWYV
DGVEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGKGGGGSVRS
SSRTPSDKPVAHVVANPQAEGQLQWLNRRANALLANGVELRDNQLVVPSEGLYLIYSQ
VLFKGQGCPSTHVLLTHTISRIAVSYQTKVNLLSAIKSPCQRETPEGAEAKPWYEPIYLG
GVFQLEKGDRLSAEINRPDYLNFRESGQVYFGIIALVRSSSRTPSDKPVAHVVANPQAEG
QLQWLNRRANALLANGVELRDNQLWPSEGLYLIYSQVLFKGQGCPSTHVLLTHTISRIA
VSYQTKVNLLSAIKSPCQRETPEGAEAKPWYEPIYLGGVFQLEKGDRLSAEINRPDYLNF

-continued

Sequence Listing

RESGQVYFGIIALVRSSSRTPSDKPVAHVVANPQAEGQLQWLNRRANALLANGVELRD
NQLVVPSEGLYLIYSQVLFKGQGCPSTHVLLTHTISRIAVSYQTKVNLLSAIKSPCQRETP
EGAEAKPWYEPIYLGGVFQLEKGDRLSAEINRPDYLNFRESGQVYFGIIAL

SEQ ID NO: 104: I4SP: GGGGSGGGGS: sTNFR2: GGGGS-SSRTPSDK:
THDR2: GGGGS-SSRTPSDK: THDR2

ESKYGPPCPPCPAPEFLGGPSVFLFPPKPKDTLMISRTPEVTCVWDVSQEDPEVQFNWY
VDGVEVHNAKTKPREEQFNSTYRWSVLTVLHQDWLNGKEYKCKVSNKGLPSSIEKTIS
KAKGQPREPQVYTLPPSQEEMTKNQVSLTCLVKGFYPSDIAVEWESNGQPENNYKTTPP
VLDSDGSFFLYSRLTVDKSRWQEGNVFSCSVMHEALHNHYTQKSLSLSLGKGGGGSGG
GGSVRSSSRTPSDKPVAHVVANPQAEGQLQWLNRRANALLANGVELRDNQLVVPSEGL
YLIYSQVLFKGQGCPSTHVLLTHTISRIAVSYQTKVNLLSAIKSPCQRETPEGAEAKPWY
EPIYLGGVFQLEKGDRLSAEINRPDYLNFRESGQVYFGIIALGGGGSSSRTPSDKPVAHW
ANPQAEGQLQWLNRRANALLANGVELRDNQLWPSEGLYLIYSQVLFKGQGCPSTHVLL
THTISRIAVSYQTKVNLLSAIKSPCQRETPEGAEAKPWYEPIYLGGVFQLEKGDRLSAEIN
RPDYLNFRESGQVYFGIIALGGGGSSSRTPSDKPVAHWANPQAEGQLQWLNRRANALL
ANGVELRDNQLVVPSEGLYLIYSQVLFKGQGCPSTHVLLTHTISRIAVSYQTKVNLLSAI
KSPCQRE TPEGAEAKPWYEPIYLGGVFQLEKGDRLSAEINRPDYLNFRESGQVYFGIIAL

SEQ ID NO: 105: I4SP: GGGGSGGGGS: sTNFR2: SSRTPSDK-THDR2:
SSRTPSDK: THDR2

ESKYGPPCPPCPAPEFLGGPSVFLFPPKPKDTLMISRTPEVTCVWDVSQEDPEVQFNWYV
DGVEVHNAKTKPREEQFNSTYRWSVLTVLHQDWLNGKEYKCKVSNKGLPSSIEKTISK
AKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGKGGGGSGGG
GSVRSSSRTPSDKPVAHVVANPQAEGQLQWLNRRANALLANGVELRDNQLVVPSEGLY
LIYSQVLFKGQGCPSTHVLLTHTISRIAVSYQTKVNLLSAIKSPCQRETPEGAEAKPWYEP
IYLGGVFQLEKGDRLSAEINRPDYLNFRESGQVYFGIIALSSRTPSDKPVAHVVANPQAE
GQLQWLNRRANALLANGVELRDNQLVVPSEGLYLIYSQVLFKGQGCPSTHVLLTHTISR
IAVSYQTKVNLLSAIKSPCQRETPEGAEAKPWYEPIYLGGVFQLEKGDRLSAEINRPDYL
NFRESGQVYFGIIALSSRTPSDKPVAHWANPQAEGQLQWLNRRANALLANGVELRDNQ
LWPSEGLYLIYSQVLFKGQGCPSTHVLLTHTISRIAVSYQTKVNLLSAIKSPCQRETPEGA
EAKPWYEPIYLGGVFQLEKGDRLSAEINRPDYLNFRESGQVYFGIIAL

SEQ ID NO: 106 I4SP: GGGGSGGGGS: sTNFR2: VRSSSRTPSDK THDR2:
VRSSSRTPSDK: THDR2

ESKYGPPCPPCPAPEFLGGPSVFLFPPKPKDTLMISRTPEVTCVWDVSQEDPEVQFNWYV
DGVEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGKGGGGSGGG
GSVRSSSRTPSDKPVAHVVANPQAEGQLQWLNRRANALLANGVELRDNQLWPSEGLY
LIYSQVLFKGQGCPSTHVLLTHTISRIAVSYQTKVNLLSAIKSPCQRETPEGAEAKPWYEP
IYLGGVFQLEKGDRLSAEINRPDYLNFRESGQVYFGIIALVRSSSRTPSDKPVAHVVANP
QAEGQLQWLNRRANALLANGVELRDNQLWPSEGLYLIYSQVLFKGQGCPSTHVLLTHT
ISRIAVSYQTKVNLLSAIKSPCQRETPEGAEAKPWYEPIYLGGVFQLEKGDRLSAEINRPD
YLNFRESGQVYFGIIALVRSSSRTPSDKPVAHVVANPQAEGQLQWLNRRANALLANGV
ELRDNQLVVPSEGLYLIYSQVLFKGQGCPSTHVLLTHTISRIAVSYQTKVNLLSAIKSPCQ
RETPEGAEAKPWYEPIYLGGVFQLEKGDRLSAEINRPDYLNFRESGQVYFGIIAL

SEQ ID NO: 107 sTNFR2: GGGGS-SSRTPSDK: THDR2: GGGGS-
SSRTPSDK: THDR2: GGGGS: I4SP

VRSSSRTPSDKPVAHVVANPQAEGQLQWLNRRANALLANGVELRDNQLVVPSEGLYLI
YSQVLFKGQGCPSTHVLLTHTISRIAVSYQTKVNLLSAIKSPCQRETPEGAEAKPWYEPIY
LGGVFQLEKGDRLSAEINRPDYLNFRESGQVYFGIIALGGGGS
SSRTPSDKPVAHVVANPQAEGQLQWLNRRANALLANGVELRDNQLVVPSEGLYLIYSQ
VLFKGQGCPSTHVLLTHTISRIAVSYQTKVNLLSAIKSPCQRETPEGAEAKPWYEPIYLG
GVFQLEKGDRLSAEINRPDYLNFRESGQVYFGIIALGGGGSSSRTPSDKPVAHWANPQA
EGQLQWLNRRANALLANGVELRDNQLWPSEGLYLIYSQVLFKGQGCPSTHVLLTHTISR
IAVSYQTKVNLLSAIKSPCQRETPEGAEAKPWYEPIYLGGVFQLEKGDRLSAEINRPDYL
NFRESGQVYFGnALGGGGSESKYGPPCPPUPAPEFLGGPSVFLFPPKPKDTLMISRTPEVT
CVWDVSQEDPEVQFNWYVDGVEVHNAKTKPREEQFNSTYRVVSVLTVLHQDWLNGK
EYKCKVSNKGLPSSIEKTISKAKGQPREPQVYTLPPSQEEMTKNQVSLTCLVKGFYPSDI
AVEWESNGQPENNYKTTPPVLDSDGSFFLYSRLTVDKSRWQEGNVFSCSVMHEALHNH
YTQKSLSLSLGK

SEQ ID NO: 108: sTNFR2: SSRTPSDK: THDR2: SSRTPSDK: THDR2:
GGGGS: I4SP

VRSSSRTPSDKPVAHVVANPQAEGQLQWLNRRANALLANGVELRDNQLVVPSEGLYLI
YSQVLFKGQGCPSTHVLLTHTISRIAVSYQTKVNLLSAIKSPCQRETPEGAEAKPWYEPIY
LGGVFQLEKGDRLSAEINRPDYLNFRESGQVYFGIIALSSRTPSDKPVAHWANPQAEGQL
QWLNRRANALLANGVELRDNQLWPSEGLYLIYSQVLFKGQGCPSTHVLLTHTISRIAVS
YQTKVNLLSAIKSPCQRETPEGAEAKPWYEPIYLGGVFQLEKGDRLSAEINRPDYLNFRE

```
SGQVYFGIIALSSRTPSDKPVAHWANPQAEGQLQWLNRRANALLANGVELRDNQLWPS
EGLYLIYSQVLFKGQGCPSTHVLLTHTISRIAVSYQTKVNLLSAIKSPCQRETPEGAEAKP
WYEPIYLGGVFQLEKGDRLSAEINRPDYLNFRESGQVYFGIIALGGGGSESKYGPPCPPC
PAPEFLGGPSVFLFPPKPKDTLMISRTPEVTCVVVDVSQEDPEVQFNWYVDGVEVHNAKT
KPREEQFNSTYRVVSVLTVLHQDWLNGKEYKCKVSNKGLPSSIEKTISKAKGQPREPQV
YTLPPSQEEMTKNQVSLTCLVKGFYPSDIAVEWESNGQPENNYKTTPPVLDSDGSFFLYS
RLTVDKSRWQEGNVFSCSVMHEALHNHYTQKSLSLSLGK

SEQ ID NO: 109: sTNFR2: VRSSSRTPSDK: THDR2: VRSSSRTPSDK:
THDR2: GGGGS: I4SP

VRSSSRTPSDKPVAHVVANPQAEGQLQWLNRRANALLANGVELRDNQLWPSEGLYLIY
SQVLFKGQGCPSTHVLLTHTISRIAVSYQTKVNLLSAIKSPCQRETPEGAEAKPWYEPIYL
GGVFQLEKGDRLSAEINRPDYLNFRESGQVYFGUALVRSSSRTPSDKPVAHVVANPQAE
GQLQWLNRRANALLANGVELRDNQLWPSEGLYLIYSQVLFKGQGCPSTHVLLTHTISRI
AVSYQTKVNLLSAIKSPCQRETPEGAEAKPWYEPIYLGGVFQLEKGDRLSAEINRPDYLN
FRESGQVYFGIIALVRSSSRTPSDKPVAHWANPQAEGQLQWLNRRANALLANGVELRD
NQLWPSEGLYLIYSQVLFKGQGCPSTHVLLTHTISRIAVSYQTKVNLLSAIKSPCQRETPE
GAEAKPWYEPIYLGGVFQLEKGDRLSAEINRPDYLNFRESGQVYFGIIALGGGGSESKYG
PPCPPCPAPEFLGGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIEKTISKAKGQP
REPQVYTLPPSQEEMTKNQVSLTCLVKGFYPSDIAVEWESNGQPENNYKTTPPVLDSDG
SFFLYSRLTVDKSRWQEGNVFSCSVMHEALHNHYTQKSLSLSLGK

SEQ ID NO: 110: sTNFR2: GGGGS-SSRTPSDK.THDR2.GGGGS-SSRTPSDK:
THDR2: I4SP

VRSSSRTPSDKPVAHVVANPQAEGQLQWLNRRANALLANGVELRDNQLVVPSEGLYLI
YSQVLFKGQGCPSTHVLLTHTISRIAVSYQTKVNLLSAIKSPCQRETPEGAEAKPWYEPIY
LGGVFQLEKGDRLSAEINRPDYLNFRESGQVYFGIIALGGGGSSSRTPSDKPVAHVVANP
QAEGQLQWLNRRANALLANGVELRDNQLWPSEGLYLIYSQVLFKGQGCPSTHVLLTHT
ISRIAVSYQTKVNLLSAIKSPCQRETPEGAEAKPWYEPIYLGGVFQLEKGDRLSAEINRPD
YLNFRESGQVYFGnALGGGGSSSRTPSDKPVAHVVANPQAEGQLQWLNRRANALLAN
GVELRDNQLWPSEGLYLIYSQVLFKGQGCPSTHVLLTHTISRIAVSYQTKVNLLSAIKSP
CQRETPEGAEAKPWYEPIYLGGVFQLEKGDRLSAEINRPDYLNFRESGQVYFGnALESK
YGPPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGK

SEQ ID NO: 111: sTNFR2: SSRTPSDK: THDR2: SSRTPSDK: THDR2: I4SP

VRSSSRTPSDKPVAHVVANPQAEGQLQWLNRRANALLANGVELRDNQLWPSEGLYLIY
SQVLFKGQGCPSTHVLLTHTISRIAVSYQTKVNLLSAIKSPCQRETPEGAEAKPWYEPIYL
GGVFQLEKGDRLSAEINRPDYLNFRESGQVYFGIIALSSRTPSDKPVAHVVANPQAEGQL
QWLNRRANALLANGVELRDNQLWPSEGLYLIYSQVLFKGQGCPSTHVLLTHTISRIAVS
YQTKVNLLSAIKSPCQRETPEGAEAKPWYEPIYLGGVFQLEKGDRLSAEINRPDYLNFRE
SGQVYFGIIALSSRTPSDKPVAHWANPQAEGQLQWLNRRANALLANGVELRDNQLWPS
EGLYLIYSQVLFKGQGCPSTHVLLTHTISRIAVSYQTKVNLLSAIKSPCQRETPEGAEAKP
WYEPIYLGGVFQLEKGDRLSAEINRPDYLNFRESGQVYFGIIALESKYGPPCPPCPAPEFL
GGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPP
SQEEMTKNQVSLTCLVKGFYPSDIAVEWESNGQPENNYKTTPPVLDSDGSFFLYSRLTV
DKSRWQEGNVFSCSVMHEALHNHYTQKSLSLSLGK

SEQ ID NO: 112 STNFR2: VRSSSRTPSDK: THDR2: VRSSSRTPSDK:
THDR2: 4SP

VRSSSRTPSDKPVAHVVANPQAEGQLQWLNRRANALLANGVELRDNQLWPSEGLYLIY
SQVLFKGQGCPSTHVLLTHTISRIAVSYQTKVNLLSAIKSPCQRETPEGAEAKPWYEPIYL
GGVFQLEKGDRLSAEINRPDYLNFRESGQVYFGIIALVRSSSRTPSDKPVAHWANPQAEG
QLQWLNRRANALLANGVELRDNQLWPSEGLYLIYSQVLFKGQGCPSTHVLLTHTISRIA
VSYQTKVNLLSAIKSPCQRETPEGAEAKPWYEPIYLGGVFQLEKGDRLSAEINRPDYLNF
RESGQVYFGIIALVRSSRTPSDKPVAHVVANPQAEGQLQWLNRRANALLANGVELRDN
QLVVPSEGLYLIYSQVLFKGQGCPSTHVLLTHTISRIAVSYQTKVNLLSAIKSPCQRETPE
GAEAKPWYEPIYLGGVFQLEKGDRLSAEINRPDYLNFRESGQVYFGIIALESKYGPPCPP
CPAPEFLGGPSVFLFPPKPKDTLMISRTPEVTCVWDVSQEDPEVQFNWYVDGVEVHNAK
TKPREEQFNSTYRVVSVLTVLHQDWLNGKEYKCKVSNKGLPSSIEKTISKAKGQPREPQ
VYTLPPSQEEMTKNQVSLTCLVKGFYPSDIAVEWESNGQPENNYKTTPPVLDSDGSFFL
YSRLTVDKSRWQEGNVFSCSVMHEALHNHYTQKSLSLSLGK

SEQ ID NO: 113 IgG1: GGGGS: sTNFR2: GGGGS-SSRTPSDK: THDR2:
GGGGS-SSRTPSDK: THDR2

EPKSSDKTHTCPPCPAPEAAGGPSVFLFPPKPKDTLMISRTPEVTCVWDVSHEDPEVKFN
WYVDGVEVHNAKTKPREEQYNSTYRVVSVLTVLHQDWLNGKEYKCKVSNKALPASIE
KTISKAKGQPREPQVYTLPPSRDELTKNQVSLTCLVKGFYPSDIAVEWESNGQPENNYK
```

Sequence Listing

TTPPVLDSDGSFFLYSKLTVDKSRWQQGNVFSCSVMHEALHNHYTQKSLSLSPGKGGG
GSVRSSSRTPSDKPVAHVVANPQAEGQLQWLNRRANALLANGVELRDNQLWPSEGLY
LIYSQVLFKGQGCPSTHVLLTHTISRIAVSYQTKVNLLSAIKSPCQRETPEGAEAKPWYEP
IYLGGVFQLEKGDRLSAEINRPDYLNFRESGQVYFGIIALGGGGSSSRTPSDKPVAHWAN
PQAEGQLQWLNRRANALLANGVELRDNQLVVPSEGLYLIYSQVLFKGQGCPSTHVLLT
HTISRIAVSYQTKVNLLSAIKSPCQRETPEGAEAKPWYEPIYLGGVFQLEKGDRLSAEINR
PDYLNFRESGQVYFGIIALGGGGSSSRTPSDKPVAHWANPQAEGQLQWLNRRANALLA
NGVELRDNQLWPSEGLYLIYSQVLFKGQGCPSTHVLLTHTISRIAVSYQTKVNLLSAIKS
PCQRETPEGAEAKPWYEPIYLGGVFQLEKGDRLSAEINRPDYLNFRESGQVYFGIIAL

SEQ ID NO: 114
IgG2: GGGGS: sTNFR2: GGGGS-SSRTPSDK: THDR2: GGGGS-SSRTPSDK
THDR2

ERKSSVECPPCPAPPVAGPSVFLFPPKPKDTLMISRTPEVTCVVVDVSHEDPEVQFNWYV
DGVEVHNAKTKPREEQFNSTFRVVSVLTWHQDWLNGKEYKCKVSNKGLPASIEKTISK
TKGQPREPQVYTLPPSREEMTKNQVSLTCLVKGFYPSDIAVEWESNGQPENNYKTTPPM
LDSDGSFFLYSKLTVDKSRWQQGNVFSCSVMHEALHNHYTQKSLSLSPGKGGGGSVRS
SSRTPSDKPVAHVVANPQAEGQLQWLNRRANALLANGVELRDNQLWPSEGLYLIYSQV
LFKGQGCPSTHVLLTHTISRIAVSYQTKVNLLSAIKSPCQRETPEGAEAKPWYEPIYLGG
VFQLEKGDRLSAEINRPDYLNFRESGQVYFGIIALGGGGSSSRTPSDKPVAHWANPQAE
GQLQWLNRRANALLANGVELRDNQLVVPSEGLYLIYSQVLFKGQGCPSTHVLLTHTISR
IAVSYQTKVNLLSAIKSPCQRETPEGAEAKPWYEPIYLGGVFQLEKGDRLSAEINRPDYL
NFRESGQVYFGIIALGGGGSSSRTPSDKPVAHVVANPQAEGQLQWLNRRANALLANGV
ELRDNQLWPSEGLYLIYSQVLFKGQGCPSTHVLLTHTISRIAVSYQTKVNLLSAIKSPCQR
ETPEGAEAKPWYEPIYLGGVFQLEKGDRLSAEINRPDYLNFRESGQVYFGIIAL

SEQ ID NO: 115
STNFR2: GGGGS-SSRTPSDK: THDR2: GGGGS-SSRTPSDK: THDR: GGGGS-IgG1*

VRSSSRTPSDKPVAHVVANPQAEGQLQWLNRRANALLANGVELRDNQLWPSEGLYLIY
SQVLFKGQGCPSTHVLLTHTISRIAVSYQTKVNLLSAIKSPCQRE'1'PEGAEAKPWYEPIY
LGGVFQLEKGDRLSAEINRPDYLNFRESGQVYFGIIALGGGGSSSRTPSDKPVAHWANP
QAEGQLQWLNRRANALLANGVELRDNQLWPSEGLYLIYSQVLFKGQGCPSTHVLLTHT
ISRIAVSYQTKVNLLSAIKSPCQRETPEGAEAKPWYEPIYLGGVFQLEKGDRLSAEINRPD
YLNFRESGQVYFGIIALGGGGSSSRTPSDKPVAHWANPQAEGQLQWLNRRANALLANG
VELRDNQLWPSEGLYLIYSQVLFKGQGCPSTHVLLTHTISRIAVSYQTKVNLLSAIKSPC
QRETPEGAEAKPWYEPIYLGGVFQLEKGDRLSAEINRPDYLNFRESGQVYFGIIALGGGG
SEPKSSDKTHTCPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPASI
EKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK

SEQ ID NO: 116
STNFR2: GGGGS-SSRTPSDK: THDR2: GGGGS-SSRTPSDK: THDR: GGGGS-IgG2

VRSSSRTPSDKPVAHVVANPQAEGQLQWLNRRANALLANGVELRDNQLWPSEGLYLIY
SQVLFKGQGCPSTHVLLTHTISRIAVSYQTKVNLLSAIKSPCQRETPEGAEAKPWYEPIYL
GGVFQLEKGDRLSAEINRPDYLNFRESGQVYFGIIALGGGGSSSRTPSDKPVAHWANPQ
AEGQLQWLNRRANALLANGVELRDNQLVVPSEGLYLIYSQVLFKGQGCPSTHVLLTHTI
SRIAVSYQTKVNLLSAIKSPCQRETPEGAEAKPWYEPIYLGGVFQLEKGDRLSAEINRPD
YLNFRESGQVYFGEALGGGGSSSRTPSDKPVAHWANPQAEGQLQWLNRRANALLANG
VELRDNQLWPSEGLYLIYSQVLFKGQGCPSTHVLLTHTISRIAVSYQTKVNLLSAIKSPC
QRETPEGAEAKPWYEPIYLGGVFQLEKGDRLSAEINRPDYLNFRESGQVYFGIIALGGGG
SERKSSVECPPCPAPPVAGPSVFLFPPKPKDTLMISRTPEVTCVVVDVSHEDPEVQFNWYV
DGVEVHNAKTKPREEQFNSTFRWSVLTWHQDWLNGKEYKCKVSNKGLPASIEKTISKT
KGQPREPQVYTLPPSREEMTKNQVSLTCLVKGFYPSDIAVEWESNGQPENNYKTTPPML
DSDGSFFLYSKLTVDKSRWQQGNVFSCSVMHEALHNHYTQKSLSLSPGK

SEQ ID NO: 117:
IgG4: sTNFR2: THDR2: THDR2

ESKYGPPCPPCPAPEFLGGPSVFLFPPKPKDTLMISRTPEVTCVVVDVSQEDPEVQFNWYV
DGVEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGKVRSSSRTPS
DKPVAHVVANPQAEGQLQWLNRRANALLANGVELRDNQLWPSEGLYLIYSQVLFKGQ
GCPSTHVLLTHTISRIAVSYQTKVNLLSAIKSPCQRETPEGAEAKPWYEP1YLGGVFQLE
KGDRLSAEINRPDYLNFRESGQVYFGIIALSSRTPSDKPVAHWANPQAEGQLQWLNRRA
NALLANGVELRDNQLWPSEGLYLIYSQVLFKGQGCPSTHVLLTHTISRIAVSYQTKVNLL
SAIKSPCQRETPEGAEAKPWYEPIYLGGVFQLEKGDRLSAEINRPDYLNFRESGQVYFGII
ALSSRTPSDKPVAHWANPQAEGQLQWLNRRANALLANGVELRDNQLWPSEGLYLIYSQ
VLFKGQGCPSTHVLLTHTISRIAVSYQTKVNLLSAIKSPCQRE
TPEGAEAKPWYEPIYLGGVFQLEKGDRLSAEINRPDYLNFRESGQVYFGIIAL

-continued

Sequence Listing

SEQS ID NO: 118: I4SP: GGGGS: sTNFR2: GGGGS-THDR2: GGGGS-THDR2

ESKYGPPCPPCPAPEFLGGPSVFLFPPKPKDTLMISRTPEVTCVVVDVSQEDPEVQFNWYV
DGVEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGKGGGGSVRS
SSRTPSDKPVAHVVANPQAEGQLQWLNRRANALLANGVELRDNQLWPSEGLYLIYSQV
LFKGQGCPSTHVLLTHTISRIAVSYQTKVNLLSAIKSPCQRETPEGAEAKPWYEPIYLGG
VFQLEKGDRLSAEINRPDYLNFRESGQVYFGIIALGGGGSPVAHWANPQAEGQLQWLN
RRANALLANGVELRDNQLWPSEGLYLIYSQVLFKGQGCPSTHVLLTHTISRIAVSYQTK
VNLLSAIKSPCQRETPEGAEAKPWYEPIYLGGVFQLEKGDRLSAEINRPDYLNFRESGQV
YFGIIALGGGGSPVAHWANPQAEGQLQWLNRRANALLANGVELRDNQLVVPSEGLYLI
YSQVLFKGQGCPSTHVLLTHTISRIAVSYQTKVNLLSAIKSPCQRETPEGAEAKPWYEPIY
LGGVFQLEKGDRLSAEINRPDYLNFRESGQVYFGIIAL

SEQS ID NO: 119: I4SP: GGGGSGGGGS: sTNFR2: GGGGS-THDR2: GGGGS-THDR2

ESKYGPPCPPCPAPEFLGGPSVFLFPPKPKDTLMISRTPEVTCVVVDVSQEDPEVQFNWYV
DGVEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGKGGGGSGGG
GSVRSSSRTPSDKPVAHWANPQAEGQLQWLNRRANALLANGVELRDNQLWPSEGLYLI
YSQVLFKGQGCPSTHVLLTHTISRIAVSYQTKVNLLSAIKSPCQRETPEGAEAKPWYEPIY
LGGVFQLEKGDRLSAEINRPDYLNFRESGQVYFGIIALGGGGSPVAHWANPQAEGQLQ
WLNRRANALLANGVELRDNQLVVPSEGLYLIYSQVLFKGQGCPSTHVLLTHTISRIAVS
YQTKVNLLSAIKSPCQRETPEGAEAKPWYEPIYLGGVFQLEKGDRLSAEINRPDYLNFRE
SGQVYFGIIALGGGGSPVAHWANPQAEGQLQWLNRRANALLANGVELRDNQLVVPSE
GLYLIYSQVLFKGQGCPSTHVLLTHTISRIAVSYQTKVNLLSAIKSPCQRETPEGAEAKP
WYEPIYLGGVFQLEKGDRLSAEINRPDYLNFRESGQVYFGIIAL

SEQ ID NO: 120: I4SP: GGGGGGGGS: sTNFR2: SSRTPSDK-THDR2: SSRTPSDK: THDR2

ESKYGPPCPPCPAPEFLGGPSVFLFPPKPKDTLMISRTPEVTCVVVDVSQEDPEVQFNWYV
DGVEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGKGGGGSGGG
GSVRSSSRTPSDKPVAHWANPQAEGQLQWLNRRANALLANGVELRDNQLWPSEGLYLI
YSQVLFKGQGCPSTHVLLTHTISRIAVSYQTKVNLLSAIKSPCQRETPEGAEAKPWYEPIY
LGGVFQLEKGDRLSAEINRPDYLNFRESGQVYFGIIALSSRTPSDKPVAHVVANPQAEGQ
LQWLNRRANALLANGVELRDNQLWPSEGLYLIYSQVLFKGQGCPSTHVLLTHTISRIAV
SYQTKVNLLSAIKSPCQRETPEGAEAKPWYEPIYLGGVFQLEKGDRLSAEINRPDYLNFR
ESGQVYFGIIALSSRTPSDKPVAHVVANPQAEGQLQWLNRRANALLANGVELRDNQLW
PSEGLYLIYSQVLFKGQGCPSTHVLLTHTISRIAVSYQTKVNLLSAIKSPCQRETPEGAEA
KPWYEPIYLGGVFQLEKGDRLSAEINRPDYLNFRESGQVYFGIIAL

SEQ ID NO: 121- Codon optimized nucleic acid sequence encoding
SEQ ID NO 101

GAG TCC AAG TAT GGG CCA CCT TGT CCA TGC CCA GCC CCC GAA TTT CTT GGT
GGC CCT TCA GTC TTT CTC TTC CCA CCC AAACCC AAA GAT ACT CTT ATG ATT
TCT CGA ACC CCC GAG GTG ACA TGC GTG GTC GTA GAC GTG A GT CAG GAA GAC
CCA GAG GTT CAGTTC AAC TGG TAT GTC GAC GGC GTA GAG GTG CAT AAC GCC
AAG ACT AAA CCC CGA GAA GAG CAG TTT AAC TCC ACT TAC AGA GTGGTG AGT
GTC TTG ACC GTC CTG CAT CAG GAC TGG CTT AAC GGC AAA GAG TAT AAA TGT
AAA GTT AGC AAT AAA GGA CTC CCA AGTAGC ATT GAA AAA ACC ATC AGT AAA
GCA AAG GGC CAA CCA AGA GAG CCC CAG GTG TAT ACC CTT CCA CCC AGT CAG
GAG GAA ATGACC AAA AAC CAA GTT TCC CTT ACT TGC CTT GTT AAG GGA TTC
TAC CCC TCA GAC ATT GCT GTA GAG TGG GAG TCC AAT GGT CAGCCT GAG AAT
TAC AAA ACA CCT GTG TTG GAC AGC GAC GGA TCT TTC TTT CTC TAT AGT CGA
CTC ACT GTG GAC AAATCA AGA TGG CAG GAG GGG AAT GTG TTC TCA TGC TCA
GTA ATG CAT GAA GCC CTG CAC AAT CAC TAC ACA CAA AAG AGT CTC TCTCTG
TCC CTT GGA AAG GGT GGA CCT GGG AGC GTG CGC TCT TCA AGC CGC ACA CCA
TCT GAT AAG CCT GTG GCA CAT GTC GTT GCAAAT CCA CAA GCA GAG GGA CAA
CTT CAG TGG TTG AAC AGG CGC GCC AAC GCA TTG CTC GCC AAC GGT GTC GAG
CTG CGG GAC AACCAG CTG GTC GTA CCT AGT GAG GGT CTG TAC TT G ATC TAC
AGC CAA GTA CTG TTC AAA GGG CAG GGC TGT CCC AGC ACC CAT GTTCTC TTG
ACT CAT ACC ATA TCA CGA ATC GCA GTA AGT TAC CAG ACT AAA GTG AAC CTG
CTT TCC GCT ATC AAA AGT CCC TGT CAAAGA GAG ACT CCA GAA GGG GCT GAG
GCT AAA CCT TGG TAC GAA CCA ATT TAT CTG GGA GGT GTG TTC CAG CTT GAG
AAA GGA GATCGC CTT TCA GCT GAG ATC AAT C GA CCA GAT TAT TTG AAT TTT
CGA GAG AGC GGC CAA GTT TAT TTT GGC ATA ATC GCA TTG GGTGGT GGT AGC
TCC TCA CGC ACT CCA TCT GAC AAG CCA GTT GCT CAT GTC GTA GCT AAT CCC
CAG GCA GAG GGA CAA CTT CA ATGG CTG AAC AGA AGG GCA AAC GCC CTG TTG
GCC AAT GGT GTG GAG TTG AGA GAC AAT CAG CTG GTT GTC CCT TCT GAG GGA

| Sequence Listing |
|---|

CTTTAT CTT ATA TAT AGC CAA GTG TTG TTC AAA GGT CAA GGG TGC CCC TCA
ACT CAT GTT CTG TTG ACC CAT ACC ATA AGT CGA ATCGCA GTG AGT TAC CAA
ACA AAG TCC AAT CTC TTG TCC GCC ATA AAG AGC CCC TGC CAA CGG GAA ACA
CCC GAA G GA GCC GAG GCAAAA CCA TGG TAC GAA CCA ATA TAC CTC GGG GGA
GTG TT C CAG CTG GAG AAG GGA GAC CGA CTT TCA GCT GAA ATC AAC AGG
CCCGAC TAT CTT AAC TTC AGG GAG TCA GGG CAG GTC TAC TTT GGA ATA GCA
TTG GGC GGA GGC GGA TCC AGC AGA ACT CCTAGC GAC AAG CCC GTT GCT CAT
GTC GTA GCC AAT CCA CAA GCC GAA GGC CAG CTG CAG TGG CTT AAT CGA CGG
GCC AAT GCC CTGTTG GCA AAC GGA GTC GAG CTT AGG GAT AAT CAG CTC GTT
CCA AGT GAA GGA TTG TAT TTG ATC TAC AGC CAA GTT CTG TTCAAG GGT CAG
GGT TGC CCC TCT ACC CAT GTT TTG ACA CAC ACA ATC AGT CGC ATT GCT GTA
TCC TAT CAA ACC AAG GTC AATTTG CTG TCC GCA ATC AAG AGC CCA TGC CAG
AGA GAG ACT CCA GAA GGC GCA GAA GCT AAG CCC TGG TAC GAG CCA ATT TAC
CTTGGC GGG GTT TTC CAG CTT GAG AAA GGA GAT AGG CTG AGC GCA GAA ATC
AAT CGG CCC GAC TAC TTG AAT TTC CGC GAA AGC GGTCAA GTG TAT TTT GGT
ATC ATA GCA CTT

SEQ ID NO: 122- Codon optimized nucleic acid sequence encoding
SEQ ID NO 102

GAA TCT AAG TAC GGT CCC CCT TGT CCA TGT CCA GCC CCC GAG TTT CTC GGA
GGG CCC AGT GTC TTT CTT TTC CCT AAACCC AAG GAT ACT CTC ATG ATT AGC
CGA ACA CCT GAA GTA ACA TGT GTT GTG GAC GTT A GT CAA GAA GAC CCC GAA
GTT CAATTT AAC TGG TAT GTG GAT GGC GTA GA G GTA CAT AAC GCA AAG ACT
AAA CCA CGA GAA GAG CAG TTC AAC TCC ACT TAT CGA GTAGTT AGT GTG TTG
ACA GTA CTC CAT CAA GAC TGG CTC AAC GGC AAA GAA TAT AAG TGT AAA GTT
AGT AAC AAA GGA CTC CCC AGTAGC ATT GAA AAG ACT ATC TCC AAG GCA AAA
GGG CAA CCA AGG GAG CCC CAG GTG TAT ACC TTG CCA CCC TCA CAA GAG
ATGACA AAG AAC CAG GTC AGT CTC ACC TGT CTG GTT AAG GGT TTC TAT CCT
TCT GAC ATT GCC GTT GAA TGG GAG TCT AAC GGC CAGCCT GAA AAT AAC TAC
AAG ACT ACA CCT CCC GTC CTG GAT AGC GAT GGT AGT TTT TTC CTC TAT TCC
AGG CTC ACT GTA GAC AAGTCA AGG TGG CAG GAA GGC AAT GTT TTC AGC TGC
TCT GTC ATG CAT GAG GCA CTC CAC AAT CAT TAT ACA CAA AAA AGT CTC
AGTTTG TCC TTG GGC AAG GGT GGA GGC GGG AGC GTT CGC AGC TCC TCT CGG
ACT CCA AGC GAC AAA CCT GTT GCT CAT GTC GCCAAT CCT CAG GCA GAA GGC
CAA CTG CAA TGG CTG AAC AGA CGC GCT AAT GCA TTG GCC AAC GGC GTT GAG
TTG AGA GAC AACCAA CTC GTT GTA CCC TCC GAG GGA CTT TAT CTG ATA TAC
TCT CAA GTA TTG TTT AAG GGT CAA GGT TGT CCA TCA ACC CAC GTATTG CTG
ACC CAT ACC ATT TCT AGA ATT GCC GTA AGT TAT CAG ACT AAA GTT AAT TTG
AGC GCA ATT AAA AGT CCT TGT CAACGC GAA ACT CCT GAG GGA GCA GAA GCA
AAA CCC TGG TAC GAA CCC ATT TAT TTG GGA GGG GTA TTT CAG CTG GAA AAG
GGG GATCGG CTG TCA GCC GAA ATT AAT C GC CCT GAT TAT CTG AAC TTC AGA
GAA AGC GGT CAA GTC TAC TTC GGC ATC ATA GCC CTT TCATCT CGC ACA CCA
AGT GAT AAG CCC GTT GCT CAC GT C GTG GCA AAC CCA CAA GCC GAG GGG CAA
CTC CAG TGG TTG AAC CGC AG GGCA AAT GCT CTC TTG GCT AAC GGG GTC GAA
TTG AGG GAT AAT CAG CTC GTT GTC CCT TCC GAA GGA CTG TAT CTG ATC TAC
AGCCAA GTA CTG TTC AAG GGT CAA GGT TGC CCA AGT ACA CAT GTT TTG CTG
ACA CAT ACT ATA AGC CGC ATC GCC GTG TCT TAC CAAACA AAA GTG AAT CTG
TCA GCT ATA AAG AGC CCA TGT CAG AGG GAA ACC CGA GGA GCT AAG CCA GCA
AAG C CC TGG TAC GAACCC ATA TAC TTG GGG GGC GTC TTC CAA CTG GAG AAA
GGT GAC AGG CTC AGT GCA GAG ATA AAC CGC CCC GAC TAC CTG AAT TTTCGA
GAG AGC GGT CAA GTA TAT TTT GGT ATT GCA CTT AGT AGT CGG ACC CCA TCT
GAT AAA CCC GTC GCT CAC GTC GTC GCAAAC CCA CAA GCC GAG GGG CAG TTG
CAG TGG CTT AAT AGG CGC GCT AAC GCT CTG CTT GCT AAT GGC GTG GAG TTG
AGG GAT AATCAA TTG GTC GTT CCC AGC GAG GGT CTG T AT TTG ATC TAC AGC
CAG GTA CTT TTT AAG GGC CAA GGC TGC CCT AGT ACT CAT GTGCTT CTG ACT
CAT ACT ATA TCA AGG ATC GCC GTC AGC TAC CA A ACC AAG GTT AAT CTC CTT
AGT GCT ATC AAA AGC CCA TGT CAACGC GAG ACT CCC GAG GGC GCC GAA GCC
AAA CCC TGG TAC GAG CCC ATA TAC CTG GGT GTG TTT CAG CTG GAG AAG GGG
GACCGA CTT AGT GCA GAG ATT AAT AGA CCT GAT TAC CTG AAT TTC AGG GAG
AGC GGT CAG GTT TAT TTT GGG ATC ATC GCA CTC

SEQ ID NO: 123- - Codon optimized nucleic acid sequence encoding
SEQ ID NO 103

GAG TCA AAG TAC GGC CCA CCA TGT CCT CCT TGT CCT GCC CCC GAG TTT CTG
GGT GGC CCA TCC GTC TTC CTC TTT CCA CCT AAACCA AAA GAT ACC CTC ATG
ATC TCT CGG ACA CCC GAA GTT ACC TGC GTC GTC GTC GAC GTC A GC CAA GAA
GAT CCT GAA GTT CAGTTC AAT TGG TAC GTT GAC GGC GTT GA G GTA CAT AAC
GCC AAA ACA AAA CCC CGG GAG GAG CAA TTC AAT TCT ACT TAT CGG GTGGTT
TCA GTT TTG ACC GTG CTG CAT CAG GAC TGG CTC AAC GGG AAA GAA TAC AAA
TGT AAG GTG TCC AAC AAA GGA CTC CCT TCCAGT ATA GAG AAG ACT ATA TCA
AAG GCC AAG GGC CAG CCA CGA GAG CCT CAG GTA TAC ACC CTG CCC CCT AGC
CAA GAG GAG ATGACT AAA AAC CAA GTA AGT CTG ACA TGC CTT GTC AAG GGG
TTC TAT CCT AGT GAT ATT GCC GTA GAG TGG GAG TCT AAC GGC CAGCCC GAG
AAC AAT TAT AAG ACA ACC CCA CC C GTG CTG GAT TCA GAT GGA TCT TTT TTC
TTG TAT AGC CGG CTT ACA GTA GAT AAATCT CGA TGG CAA GAA GGT AAC GTG

| Sequence Listing |
|---|
| TTT AGT TGC TCC GTA ATG CAC GAG GCA CTC CAT AAT CAC TAT ACT CAA AAA<br>TCC CTC TCCTTG TCT CTG GGC AAA GGG GGC GGC TCC GTC CGA TCA TCT AGT<br>CGC ACT CCT TCA GAC AAG CCT GTG GCC CAC GTA GTT GCTAAT CCA CAG GCC<br>GAG GGG CAA CTC CAA TGG CTC AAC CGC AGA GCC AAG GCA TTG CTG GCT AAC<br>GGC GTA GAA TTG CGA GAC AATCAG CTT GTG GTA CCT TCC GAG GGA CTG TAC<br>CTC ATC TAC TCT CAA GTT TTG TTT AAA GGC CAA GGT TGC CCC AGT ACT CAC<br>GTACTT CTC ACT CAC ACA ATC AGC CGC ATC GCT GTG TCT TAT CAA ACC AAA<br>GTC AAT TTG CTT TCC GCC ATA AAA AGC CCT TGT CAGCGA GAA ACC CCT GAA<br>GGA GCT GAA GCT AAA CCA TGG TAC GAG CCC ATC TAT CTC GGC GGT GTT TTC<br>CAG CTT GAG AAG GGG GATCGG CTT TCC GCC GAG ATT AAT CGG CCC GAT TAC<br>TTG AAT TTC AGG GAG AGC GGG CAG GTG TAT TTT GGA ATA ATC GCT CTT<br>GTCCGG TCC TCA TCT CGA ACA CCT AGT GAT AAA CCC GTA GCC CAC GTA GTT<br>GCA AAT CCC CAG GCC GAA GGT CAA CTG CAG TGG CT TAAC CGC CGA GCA AAT<br>GCT CTT CTG GCA AAT GGG GTA GAG TTG CGC GAC AAT CAA TTG GTC GTA CCA<br>AGT GAA GGC CTC TAC CTTATC TAC TCT CAG GGT CTC TTC AAA GGT CAA GGT<br>TGT CCT TCT ACT CAC GTA CTC CTG ACA CAT ACA ATA TCT CGC ATT GCA<br>GTATCA TAC CAA ACA AAG GTG/VAT CTT CTC TCC GCT ATA AAA TCA CCC TGC<br>CAA CGA GAG ACA CCT GAA GGT GCA G AG GCC AAA CCCTGG TAC GAA CCA ATT<br>TAC CTT GGA GGA GTT TTT CAA TT G GAA AAA GGA GAT AGA CTT AGC GCC GAA<br>ATA AAT AGG CCC GAT TACTTG AAT TTT AGA GAG TCC AGC AGG ACT CCC AGC GAT AAG<br>GGC ATA ATA GCA CTG GTC AGG AGT TCC AGC AGG ACT CCC AGC GAT AAG<br>CCCGTC GCA CAC GTG GTT GCT AAT CCA CAA GCT GAA GGA CAG CTG CAA TGG<br>CTT AAT AGA AGG GCC AAT GCT CTG TTG GCT AAC GGCGTT GAA CTT CGG GAT<br>AAC CAG CTT GTG G TG CCC TCC GAA GGT TTG TAT TTG ATC TAT TCA CAA GTT<br>TTG TTC AAA G GC CAG GGTTGC CCC TCT ACC ACA CTT CTG ACA CAC ACA<br>ATC AGC CG C ATC GCT GTC TCA TAC CAG ACC AAA GTC AAC TTG TTG TCT<br>GCAATA AAA TCA CCA TGT CAG CGG GAA ACT CCT GAG GGC GCC GAG GCC AAA<br>CCC TGG TAT GAG CCA ATC TAC CTT GGT GGC GTA TTTCAG CTT GAA AAA GGA<br>GAC AGG CTT TCC GCA GAG ATA AAC AGG CCA GAT TAT CTG AAC TTT AGG GAA<br>TCA GGT CAA GTC TAC TTTGGA ATC ATA GCT CTC |

SEQ ID NO: 124 - Codon optimized nucleic acid sequence encoding
SEQ ID NO 104

| |
|---|
| GAA TCC AAG TAT GGC CCA CCA TGT CCC CCC TGC CCC GCC CCT GAA TTT CTT<br>GGC GGA CCC AGC GTA TTT CTG TTC CCA CCA AAGCCC AAG GAC ACA CTT ATG<br>ATA AGT CGG ACA CCT GAA GTA ACT TGT GTC GTC GTC GAC GTG A GT CAG GAA<br>GAC CCT GAA GTC CAATTT AAC TGG TAC GTG GAT GGC GTG GA G GTA CAC AAT<br>GCC AAG ACC AAG CCA CGC GAA GAG CAG TTC AAT TCA ACA TAT CGG GTCGTT<br>TCC GTC CTG ACC GTA CTG CAC CAA GAT TGG CTC AAT GGG AAG GAG TAC AAA<br>TGT AAA GTA TCT AAC AAA GGC CTC CCA TCCTCC ATA GAA AAA ACC ATA AGT<br>AAA GCT AAG GGA CAG CCT CGA GAA CCT CAG GTC TAC ACA CTG CCC CCA TCT<br>CAA GAA GAA ATGACC AAA AAC CAA GTG A GT CTT ACT TGT CTG GTG AAA GGT<br>TTC TAT CCA TCC GAC ATT GCC GTA G AG TGG GAA TCA AAC GGC CAACCT GAG<br>AAT AAC TAC AAA ACT ACT CCT CC C GTC CTC GAT AGT GAC GGT AGC TTC TTC<br>CTG TAC AGC AGG CTC ACA GTC GAC AAATCC AGG TGG CAA GAA GGC AAT GTT<br>TTC AGC TGT TCC GTC ATG CAT GAA GCC CTG CAC AAC CAT TAT ACA CAG AAA<br>AGC TTG AGCCTG TCC TTG GGT AAA GGT GGA GGG GGG AGT GGG GGT GGT GGG<br>TCT GTG CGA AGC AGT AGC AGA ACA CCT TCC GAC AAA CCA GTTGCA CAT GTT<br>GTT GCT AAT C CT CAG GCC GAA GGG CAG CTT CAG TGG CTC AAC AGG AGG GCT<br>AAC GCT TTG TTG GCT AAC GGT GTAGAG CTC CGC GAT AAC CAA CTT GTA GTG<br>CCT TC C GAG GGA CTC TAT CTT ATT TAC TCC CAA GTG CTG TTT AAA GGA CAA<br>GG G TGCCCT AGC ACC CAC GTA TTG CTG ACT CAC ACT ATC AGC AGG ATT GCC<br>GTC AGC TAC CAG ACT AAA GTT AAC CTT CTG TCA GCT ATAAAA TCA CCC TGT<br>CAG CGG GAA ACC CCA GAG GGA GCA GAG GCA AAA CCC TGG TAC GAA CCA ATA<br>TAC TTG GGC GGA GTA TTT CAATTG GAG AAA GGT GAT AGA CTG A GC GCT GAA<br>ATA AAT CGG CCT GAC TAT CTT AAC TTC GCC GAA TCA GGG C AG GTG TAT TTC<br>GGCATC ATT GCC CTC GGT GGC GGA GGG AGC TCC TCA AG G ACT CCA AGC AAT<br>AAG CCA GTG GCT CAC GTA GTG GCC AAT CCA CAA GC AGAA GGT CAA CTG CAA<br>TGG CTT AAC CGC CGC GCA AAC GCA TTG TTG GCT AAC GGT GTG GAA TTG AGA<br>GAT AAC CAA TTG GTG GTTCCT TCA GAA GGC CTG TAC CTG ATC TAT AGT CAA<br>GTA CTG TTC AAA GGA CAG GGT TGT CCC AGC ACT CAT GTT CTT CTG ACC<br>CACACT ATT AGT AGA ATA GCC GTA TCA T AT CAA ACC AAA GTC AAC CTT TTG<br>TCT GCC ATA AAA TCC CCC TGC CAA A GA GAA ACA CCCGAA GGA GCC GAG GCC<br>AAA CCT TGG TAC GAG CCA ATA TAC CTG GGG GGC GTT TTC CAA TTG GAA AAG<br>GGC GAT AGG TTG AGC GCTGAG ATA AAT AGG CCA GAT TAT TTG AAT TTC AGG<br>GAA AGC GGG CAA GTG TAC TTC GGG ATC ATA GCC CTG GCC GGG GGT GGG<br>TCAAGC TCT CGC ACT CCC TCA GAC AAG CCC GTT GCA CAT GTG GTG GCT AAT<br>CCA CAG GCT GAG GGA CAG CTG CAG TGG CTG AAT AGACGA GCA AAT GCA CTG<br>CTT GCT AAC GGA G TT GAG CTC CGC GAT AAC CAA CTG GTG GTA CCC TCT GAG<br>GGA CTC TAT T TG ATT TACTCC CAA GTT CTC TTC AAG GGC CAA GGC TGC CCC<br>TCC ACT CAT GTC CTG CTT ACC CAC ACT ATT TCT AGA ATA GCC GTA TCT |

Sequence Listing

TACCAG ACC AAG GTC AAC CTC TTG AGT GCA ATA AAG AGT CCC TGT CAA CGA
GAA ACT CCA GAA GGC GCC GAA GCT AAG CCA TGG TATGAG CCA ATT TAC CTC
GGG GGA GTG TTT CAG CTT GAG AAA GGG GAC AGA CTG AGT GCC GAA ATA AAC
CGG CCC GAC TAT CTC AACTTC CGC GAG AGT GGT CAA GTC TAC TTC GGT A TC
ATA GCT TTG

SEQ ID NO: 125 - Codon optimized nucleic acid sequence encoding
SEQ ID NO 105

GAG AGT AAA TAC GGC CCA CCT TGT CCT CCC TGC CCT GCT CCA GAG TTC CTT
GGC GGG CCT TCC GTC TTC CTG TTT CCC CCC AAGCCA AAG GAC ACA C TG ATG
ATT TCA AGA ACC CCA GAG GTC ACC TGT GTC GTT GTA GAT GTT AGT CAA GAG
GAT CCA GAG GTG CAATTC AAT TGG TAT GTC GAT GGG GTG GAG GTT CAC AAC
GCT AAG ACC AAA CCT CGG GAA GAG CAA TTC AAT TCT ACT TAT CGG GTGGTA
AGT GTT CTT ACT GTT TTG CAC CAG GAC TGG TTG AAC GGG AAG GAA TAT AAG
TGC AAG GTT AGT AAC AAG GGG CTT CCT TCCAGC ATC GAA AAG ACA ATT AGC
AAA GCC AAG GGA CAA CCC CGA GAG CCA CAA GTG TAT ACC CTT CCC CCC TCC
CAA GAG GAA ATGACC AAG AAC CAA GTC TCT CTG ACC TGC CTG GTG AAA GGG
TTC TAT CCA AGC GAC ATA GCT GTC G AA TGG GAA TCC AAC GGC CAACCC GAA
AAT AAC TAT AAA ACA ACA CCT CC C GTC CTG GAT TCC GAT GGG TCA TTT TTC
TTG TAT TCA AGA TTG ACC GT G GAT AAAAGC CGC TGG CAG GAG GGG AAC GTT
TTT TCA TGT AGT GTA ATG CAT GAA GCT CTT CAT AAC CAT TAT ACA CAG AAA
AGT TTG AGTTTG TCA CTC GGT AAA GGT GGA GGA GGG TCC GGT GGC GGT GGC
TCA GTG AGA AGT TCT TCT AGG ACC CCT TCC GAC AAA CCC GTTGCC CAC GTT
GTC GCA AAT C CA CAA GCT GAA GGG CAG CTT CAG TGG CTC AAT CGG AGA GCA
AAT GCT CTC CTT GCC AAC GGA GTCGAA CTG CGC GAC AAC CAA CTC GTC GTT
CCC TCC GAG GGC CTG TAT CTG ATC TAT TCA CAA GTG TTG TTC AAA GGT CAA
GGT TGTCCA AGT ACC CAT GTC TTG CTG ACA CAC ACA ATA TCA AGA ATA GCA
GTC AGC TAT CAA ACA AAA GTG AAT TTG CTC TCT GCC ATCAAA AGT CCC TGC
CAA CGC GAG ACT CCT GAA GGT GCT GAA GCA AAA CCC TGG TAT GAA CCT ATA
TAT TTG GGT GGC GTC TTT CAACTT GAA AAG GGT GAC AGA CTT TCT GCC GAG
ATA AAC CGG CCA GAC TAT CTG AAC TTT CGA GAG TCC GGT C AG GTT TAT TTC
GGTATC ATT GCC TTG AGC TCT AGA ACA CCT AGC GAC AA A CCT GTC GCC CAT
GTA GTT GCA AAT CCC CAG GCT GAG GGT CAA CTC CA ATGG CTT AAC AGG CGC
GCC AAC GCT CTT CTC GCC AAC GGT GTA GAG CTG CGC GAT AAT CAA CTG GTG
GTT CCT TCC GAG GGA CTTTAT CTG ATA TAT TCA CAA GTT CTG TTT AAA GGC
CAG GGT TGT CCC TCT ACA CAT GTA TTG TTG ACA CAC ACT ATA TCT CGG
ATAGCT GTG AGC TAC CAA ACA AAA GTA AAT TTG CTG TCT GCT ATC AAG AGT
CCA TGT CAG AGG GAA ACC CCC GAA G GA GCA GAG GCCAAA CCA TGG TAC GAA
CCA ATA TAT CTT GGG GGA GTC TT T CAA TTG GAG AAA GGG GAC CGG TTG AGT
GCC GAG ATT AAC CGA CCTGAT TAC CTT AAT TTC AGG GAG AGC GGT CAA GTT
TAC TTC GGC ATA ATA GCC CTT TCT TCA CGG ACA CCT TCA GAC AAA CCA
GTGGCT CAT GTG GTT GCA AAC CCT CAA GCA GAA GGT CAA TTG CAA TGG CTT
AAT CGC AGA GCT AAT GCC CTT TTG GCA AAC GGT GTGGAG CTT CGG GAT AAT
CAG TTG GTG GTT C CA AGT GAA GGT CTG TAC TTG ATA TAT TCC CAA GTG CTG
TTC AAA GGG C AG GGC TGCCCC TCT ACT CAT GTT CTG CTC ACC CAT ACA ATA
TCT AGA AT C GCT GTG AGC TAC CAG ACT AAG GTC AAT CTT TTG TCA GCA
ATAAAA TCA CCA TGC CAA CGG GAG ACT CCA GAA GGA GCA GAA GCC AAA CCC
TGG TAT GAA CCT ATA TAC CTC GGG GGC GTC TTT CAGCTT GAG AAG GGT GAC
AGG CTG AGC GCT GAA ATT AAT CGG CCC GAC TAC CTT AAC TTT AGA GAA TCC
GGT CAA GTA TAT TTC GGTATT ATT GCC CTC

SEQ ID NO: 126- - Codon optimized nucleic acid sequence encoding
SEQ ID NO 106

GAG AGC AAA TAT GGC CCA CCC TGC CCC CCA TGT CCT GCC CCA GAA TTC CTG
GGA GGA CCC TCA GTG TTT CTC TTT CCA CCC AAGCCA AAA GAC ACA T TG ATG
ATT TCA AGG ACT CCT GAG GTG ACA TGT GTT GTA GTA GAC GTA T CA CAG GAG
GAT CCT GAA GTC CAGTTC AAC TGG TAC GTC GAC GGC GTT GA A GTG CAC AAT
GCT AAA ACC AAG CCC CGA GAG GAG CAG TTT AAC AGC AC A TAT CGG GTCGTT
TCT GTG CTT ACC GTC TTG CAT CAG GAT TGG CTG AAC GGA AAA GAA TAT AAA
TGC AAG GTC TCA AAC AAG GGG CTT CCA TCTTCA ATA GAA AAA ACA ATT TCA
AAG GCA AAA GGA CAG CCT AGA GAG CCC CAA GTC TAC ACT CTG CCA CCC AGC
CAG GAG GAG ATGACA AAG AAC CAG GTC A GC CTG ACC TGT CTC GTC AAA GGA
TTC TAT CCA TCC GAC ATC GCC GTA G AA TGG GAG AGT AAT GGA CAGCCT GAA
AAC AAC TAT AAG ACC ACT CCC CC A GTA CTG GAC AGT GAT GGG TCA TTC TTT
TTG TAT AGT CGA CTG ACT GT A GAT AAAAGT CGA TGG CAG GAA GGT AAT GTG
TTC TCA TGC AGC GTC ATG CAC GAG GCC CTG CAC AAC CAT TAT ACA CAG AAG
AGT CTG AGTCTT AGC TTG GGT AAG GGA GGC GGG GGA TCC GGA GGC GGT GGA
TCT GTA CGG TCT TCT AGC AGA ACA CCA AGT GAT AAA CCA GTGGCT CAC GTG
GTA GCA AAC C CC CAA GCT GAG GGG CAG CTT CAA TGG CTT AAT AGA GGG GCT
AAC GCT C TT CTT GCC AAC GGG GTCGAG CTT AGG GAT AAC CAG CTG GTG GTC
CCC TC T GAA GGC TTG TAT CTG ATA TAC TCC CAG GTA CTG TTT AAA GGA CAA
GGC TGTCCC AGC ACT CAT GTA CTG TTG ACA CAT ACT ATA TCA CGC ATA GCT
GTC TCT TAT CAG ACA AAA GTT AAC TTG CTT AGC GCT ATCAAG AGT CCC TGT
CAG AGA GAA ACC CCC GAA GGT GCA GAG GCC AAG CCA TGG TAC GAA CCT ATT
TAC CTT GGA GGC GTT TTC CAACTG GAG AAA GGG GAT CGC CTC T CC GCC GAA

ATA AAC AGG CCC GAT TAT CTG AAC TTC CGA GAG AGC GGC C AA GTC TAC TTT
GGGATA ATC GCT CTC GTG CGG AGC AGT AGC AGA ACC CC C TCT GAT AAA CCA
GTT GCC CAT GTG GTT GCC AAC CCA CAG GCC GAA GG TCAG CTG CAG TGG CTG
AAT CGG AGA GCC AAC GCT CTT CTC GCC AAT GGT GTG GAA CTC AGG GAT AAC
CAA CTG GTT GTC CCA TCTGAA GGT CTT TAT CTT ATC TAT TCA CAA GTG CTC
TTT AAG GGA CAG GGC TGT CCA AGT ACA CAC GTC TTG CTC ACT CAC ACA
ATATCC AGA ATT GCT GTA AGC TAC CAG A CA AAA GTA AAC CTC CTT AGC GCC
ATT AAA AGC CCT TGT CAA AGG GAA A CA CCT GAG GGAGCC GAA GCC AAA CCA
TGG TAC GAA CCC ATA TAT CTC GGT GGC GTT TTC CAG TTG GAG AAG GGC GAT
CGA CTG TCC GCC GAG ATTAAT CGC CCT GAT TAT CTG AAC TTT CGG GAG TCC
GGG CAG GTT TAC TTT GGT ATA ATC GCA CTG GTA CGC TCA AGC AGT AGA
ACTCCC TCA GAC AAA CCA GTA GCA CAT GTT GTA GCT AAT CCA CAA GCA GAA
GGA CAG CTG CAA TGG CTG AAC CGG AGA GCT AAC GCCCTG CTG GCT AAC GGT
GTC GAG TTG CGA G AT AAT CAG CTT GTC GTG CCT AGC GAG GGG CTC TAC CTT
ATT TAT AGT C AA GTT CTCTTT AAA GGG CAG GGG TGT CCA AGT ACA CAC GTG
TTG CTC AC A CAT ACT ATT TCT CGA ATA GCC GTG TCC TAT CAA ACC AAG
GTGAAC CTT CTC TCC GCT ATC AAA AGC CCT TGC CAA AGA GAA ACA CCC GAA
GGC GCC GAG GCT AAG CCA TGG TAC GAA CCT ATC TATCTC GGG GGT GTT TTT
CAA CTC GAA AAA GGG GAC AGG TTG AGT GCT GAG ATT AAT AGA CCC GAT TAT
TTG AAT TTT AGG GAA TCTGGG CAG GTT TAT TTT GGA ATA ATT GCT CTC

SEQ ID NO: 127- Codon optimized nucleic acid sequence encoding
SEQ ID NO 107

GTA CGG AGC TCT AGA ACT CCA TCT GAC AAG CCA GTC GCT CAT GTG GTA GCA
AAT CCC CAA GCT GAG GGC CAA CTT CAG TGGTTG AAT CGC AGG G CT AAC GCT
CTG CTC GCC AAT GGA GTA GAA TTG AGG GAT AAT CAG CTC G TA GTA CCT AGC
GAA GGG CTT TACCTC ATA TAT TCT CAG GTT CTG TTT AAG GGT CAA GGC TGT
CCA AGT ACT CAC GTT CTC CTT ACT CAT ACA ATC TCT CGC ATC GCAGTT TCT
TAT CAA ACC AAG GTT AAT TTG CTG AGC GCC ATT AAG TCA CCA TGC CAG CGC
GAA ACC CCC GAA GGT GCC GAA GCA AAACCT TGG TAT GAG CCC ATT TAC CTT
GGC GGT GTG TTT CAG CTG GAG AAG GGG GAC AGG CTT TCA GCA GAA ATT AAT
AGG CCC GACTAT CTT AAT TTC CGG G AG TCC GGC CAG GTT TAT TTC GGT ATC
ATT GCC CTG GGC GGT GGC GGC TCA TCC TCA CGC ACT CCA TCTGAT AAG CCC
GTC GCA CAT GTG GTC GCC AAT CCT CAG GCA GAG GGG CAA TTG CAA TGG CTT
AAC CGC AGG GCA AAC GCT CTG CTTGCT AAT GGG GTT GAG CTT CGG GAT AAC
CAG CTC GTG GTA CCT TCA GAG GGT TTG TAC TTG ATC TAT TCT CAA GTG CTT
TTC AAAGGA CAA GGT TGC CCA AGC ACC CAT GTG TTG TTG ACC CAT ACT ATT
TCC CGG ATA GCA GTG TCA TAT CAA ACT AAG GTC AAT CTTCTG TCA GCT ATT
AAA AGT C CC TGT CAG AGA GAG ACT CCA GAG GGA GCT GAA GCC AAA CCC TGG
TAC G AG CCC ATA TAT CTT GGAGGG GTG TTC CAG CTC GAG AAA GGC GAC AGA
TT G AGC GCC GAG ATA AAC CGG CCT GAC TAT CTC AAT TTT CGA GAG TCC GG T
CAGGTT TAC TTT GGG ATA ATC GCA CTG GGT GGT GGA GGG TCT AGC TCT CGC
ACA CCA TCC GAT AAG CCA GTA GCT CAT GTG GTG GCCAAC CCT CAA GCC GAG
GGG CAA CTT CAG TGG CTG AAT AGA CGA GCT AAT GCA TTG CTG GCT AAC GGT
GTC GAA CTG AGA GAT AATCAG CTC GTA GTA CCT TCA GAA G GG CTT TAC CTC
ATA TAC TCT CAG GTT TTG TTC AAA GGA CAG GGA TGT CCT TCA ACT CAC
GTCCTT CTC ACT CAC ACT ATA AGT AGA ATC GCT GTA TC C TAC CAA ACT AAA
GTG AAC CTT TTG TCT GCT ATC AAA TCC CCT TGC CA ACGC GAA ACT CCC GAA
GGC GCA GAA GCC AAG CCT TGG TAT GAG CCA ATC TAC CTC GGA GGA GTT TTT
CAG TTG GAA AAG GGT GACAGG CTG AGT GCT GAA ATC AAC AGG CCC GAT TAT
CTG AAC TTC AGG GAA AGC GGA CAA GTG TAT TTT GGA ATA ATC GCA CTT
GGTGGG GGA GGG TCC GAG TCT AAG TAC G GG CCA CCT TGT CCT CCC TGT TCA
GCA CCT GAG TTT TTG GGC GGG CCC AGT GTA TTC CTGTTT CCA CCC AAA CCT
AAG GAT ACC CTG ATG ATA TCA CGA ACC CCT GAG GTC ACC TGT GTT GTC GTT
GAC GTA AGT CAG GAG GACCCA GAG GTT CAG TTC AAC TGG TAT GTC GAC GGG
GTA GAA GTT CAT AAT GCT AAG ACT AAG CCA AGG GAG GAA CAA TTT AAT
TCCACT TAT CGA GTT GTG AGC GTC CTG ACA GTT TTG CAT CAG GAT TGG CTT
AAC GGC AAA GAA TAT AAG TGC AAG GTT TCA AAT AAAGGT CTG CCT TCT TCC
ATA GAA AAA ACA A TC TCT AAA GCC AAA GGC CAA CCA AGA GAG CCT CAG GTG
TAC ACT CTT C CT CCC TCTCAG GAA GAG ATG ACA AAA AAC CAG GTG TCC TTG
ACC TGT CTC GTT AAG GGG TTC TAT CCA AGC GAT ATT GCT GTT GAG TGG
GAATCA AAC GGG CAG CCT GAG AAT AAT TAC AAG ACC ACA CCC CCA GTT TTG
GAT' AGC GAT GGT AGT TTC TTC CTT TAC AGT AGG TTGACC GTT GAT AAG TCC
CGG TGG CAA GAA GGA AAT GTG TTT AGT TGC TCC GTG ATG CAC GAG GCA CTG
CAT AAT CAT TAC ACT CAAAAG AGT CTT AGT CTG AGC TTG GGG AAA

SEQ ID NO: 128 - Codon optimized nucleic acid sequence encoding
SEQ ID NO 108

GTG CGG AGT AGC AGC AGA ACT CCA TCC GAT AAA CCA GTG GCA CAC GTG GTC
GCT AAT CCC CAA GCA GAA GGG CAG CTC CAA TGGCTG AAC AGG CGG GCC AAT
GCC CTT TTG GCT AAT GGC GTC GAG CTC AGA GAC AAT CAG CTC GTC GTC CCA
TCT GAG GGT CTC TACTTG ATC TAT AGT CAG GTC TTG TTC AAA GGC CAA GGC
TGT CCT AGT ACT CAT GTT CTC CTT ACA CAT ACC ATT TCA AGG ATA GCAGTC
TCA TAT CAG ACT AAA GTC AAT CTC CTG AGT GCA ATT AAG TCC CCC TGC AG
CGA GAG ACT CCA GAA GGT GCT GAG GCA AAGCCA TGG TAT GAG CCC ATA TAT

-continued

Sequence Listing

CTT GGC GGA GTC TTT CAA CTG GAG AAG GGT GAC CGG CTC TCC GCA GAG ATT
AAC CGG CCT GACTAT CTG AAT TTC AGA G AG TCT GGC CAG GTT TAC TTT GGC
ATT ATC GCA CTT TCC AGT CGG ACC C CC AGC GAC AAA CCT GTT GCCCAT GTC
GTA GCA AAT CCC CAA GCC GAA GG C CAG TTG CAG TGG CTG AAC AGA CGA GCT
AAT GCT TTG TTG GCA AAT GG G GTG GAGCTT CGG GAC AAT CAA CTC GTG GTA
CCA TCT GAA CGC TTG TAC CTG ATA TAT AGC CAG GTA CTC TTT AAG GGT CAA
GGT TGT CCTAGT ACT CAT GTG CTC TTG ACC CAC ACA ATT TCA AGA ATC GCC
GTC AGT TAC CAA ACC AAG GTT AAT CTG CTT TCT GCC ATA AAGTCT CCC TGC
CAA CGC GAA A CC CCA GAA GGT GCT GAA GCC AAG CCT TGG TAC GAG CCA ATC
TAC CTC GGT GGC GTT TTT CAA CTTGAA AAG GGG GAT CGC CTG TCT GCC GAG
ATC AA C AGG CCA GAC TAC CTG AAC TTC CGA GAA AGT GGG CAA GTC TAT TTT
GG G ATCATA GCC CTG AGC TCT CGG ACC CCC AGC GAC AAG CCT GTT GCC CAC
GTA' GTT GCT AAC CCT CAG GCT GAA GGA CAA CTT CAG TGGCTG AAC AGG AGA
GCT AAC GCC CTC CTG GCT AAT GGA GTC GAA CTG AGA GAT AAT CAA TTG GTC
GTA CCA AGC GAG GGA CTG TACCTC ATA TAC TCT CAG GTA CTG TTT AAG GGC
CAA GGA TGT CCA AGT ACC CAT GTA CTT CTC ACA CAT ACA ATA AGC CGG ATA
GCCGTC AGC TAT CAG ACT AAG GTA AAC CTG CTC AGC GCT ATT AAG AGC CCA
TGC CAG CGA GAG ACC CCA GAA GGA GCA GAA GCT AA ACCC TGG TAC GAG CCA
ATA TAT CTT GGA GGA GTC TTT CAA CTG GAG AAG GGT GAC CGA TTG AGT GCT
GAA ATT AAT CGG CCA GATTAT TTG AAC TTC CGC GAG AGC GGG CAA GTC TAT
TTC GGA ATC ATT GCA CTT GGC GGG GGC GGG AGC GAG TCC AAA TAT GGC
CCACCA TGT CCC CCC TGC CCT GCC CCA G AG TTC CTT GGG GGC CCT TCT GTA
TTT CTC TTC CCC CCA AAA CCC AAG G AT ACT CTT ATGATC AGC AGG ACT CCT
GAG GTA ACC TGT GTG GTC GTC GA C GTA TCA CAA GAG GAT CCA GAG GTA CAG
TTT AAT TGG TAT GTA GACGGC GTG GAA GTC CAC AAT GCT AAA ACT AAG CCC
AGA GAG GAG CAG TTT AAT AGT ACA TAC CGA GTA GTG AGC GTA TTG ACT
GTATTG CAT CAG GAC TGG TTG AAT GGG AAA GAG TAC AAG TGC AAA GTT TCC
AAC AAA GGT CTC CCT TCA TCT ATC GAG AAA ACC ATCTCA AAG GCC AAA GGC
CAA CCC AGA GAG C CT CAA GTA TAC ACT CTG CCA CCC AGC CAA GAA GAG ATG
ACT AAG AAT C AG GTT AGTCTC ACT TGT CTC GTC AAA GGG TTC TAT CCC TCC
GAT ATT GCT GTG GAA TGG GAG AGC AAC GGG CAA CCC GAG AAC AAC TAT
AAGACA ACC CCA CCA GTA CTT GAT AGC GAC GGG TCT TTT TTC CTT TAT TCA
CGC CTT ACA GTT GAT AAA TCT CGG TGG CAG GAA GGGAAC GTT TTC AGC TGT
TCT GTT ATG CAT GAA GCC TTG CAT AAC CAT TAC ACA CAA AAG AGT CTT AGT
TTG TCT CTT GGA AAG

SEQ ID NO: 129 - Codon optimized nucleic acid sequence encoding
SEQ ID NO 109

GTG CGC AGC AGT TCC AGA ACA CCT AGT GAC AAG CCT GTG GCA CAC GTT GTG
GCC AAT CCT CAA GCT GAA GGT CAG CTC CAA TGGCTT AAT AGA GGG GCT AAC
GCA TTG CTT GCT AAT GGG GTG GAA CTT CGA GAT AAC CAA TTG GTG GTG CCC
TCC GAG GGT CTC TACCTT ATC TAT AGC CAG GTC CTC TTT AAA GGC CAA GGT
TGC CCC AGT ACA CAC GTC CTG CTT ACA CAC ACA ATA TCC AGA ATA GCAGTC
TCA TAC CAG ACC AAG GTA AAT CTG CTT AGC GCT ATT AAG TCA CCC TGT CAG
CGG GAA ACC CCA GAG GGT GCA GAA GCA AAACCA TGG TAT GAG CCA ATT TAC
CTT GGT GGC GTT TTT CAA CTG GAA AAG GGC GAT AGG TTG AGC GCC GAG ATC
AAT AGA CCC GACTAT CTC AAT TTT CGG G AG TCA GGC CAG GTT TAT TTC GGG
ATC ATT GCT TTG GTT CGC TCC TCT A GC CGC ACC CCT TCC GAT AAACCA GTT
CCA CAT CTT CTG CCC AAT CCC CA G GCT GAA GGC CAG CTT CAG TGG CTC AAC
AGA CGG GCT AAT GCC CTC CT C GCC AATGGG GTC GAG CTG AGG GAC AAC CAA
CTT GTG GTC CCC TCA GAA GGT CTC TAC CTT ATC TAC AGC CAG GTT CTT TTC
AAA GGC CAGGGC TGT CCT TCC ACT CAC GTG CTG TTG ACC CAT ACC ATA TCC
CGC ATT GCC GTT AGC TAT CAA ACC AAA GTC AAC CTT TTG TCTGCA ATT AAG
AGT CCA TGC C AG AGA GAA ACT CCC GAA GGT GCA GAA GCA AAG CCA TGG TAT
GAA CCT ATA TAT CTC GGA GGT GTGTTT CAA CTT GAG AAA GGG GAC AGA CTG
AGT GC C GAA ATA AAT CGC CCT GAT TAT CTT AAT TTC CGA GAG TCT GGG CAA
GTA TATTTT GGA ATT ATT GCC CTC GTG CGA AGC TCT TCA AGG ACC CCA AGT
GAT AAA CCC GTA GCA CAC GTA GTT GCA AAT CCA CAA GCCGAA GGA CAG TTG
CAA TGG CTG AAT AGG CGG GCT AAT GCT TTG CTT GCT AAT GGG GTC GAG CTG
CGG GAT AAC CAG CTT GTC GTGCCA TCT GAA GGA TTG TAC CTG A TA TAC AGC
CAA GTT TTG TTT AAG GGA CAG GGA TGC CCA TCA ACC CAC G TG CTC CTC ACT
CACACT ATT TCT CGA ATT GCC GTA TCA TAT CAG ACT AAA GTC AAC TTG TTG
AGC GCA ATA AAG AGC CCT TGT CAA CGG GAA ACC CC GAG GGT GCA GAG GCC
AAA CCA TGG TAT GAA CCT ATT TAC CTC GGG GGC GTC TTT CAG TTG GAA AAA
GGT GAT CGG TTG TCC GCTGAG ATT AAC CGA CCA GAC TAT TTG AAC TTT CGG
GAA TCT GGT CAA GTC TAT TTT GGC ATA ATT GCA TTG GGG GGC GGG GGC
TCTGAA TCC AAA TAC GGG CCT CCT TGC C CC CCT TGC CCA GCA CCA GAA TTT
CTC GGG GGC CCA TCA GTT TTT CTT T TC CCC CCT AAGCCA AAA GAT ACC CTC
ATG ATA TCA AGA ACT CCA GAG GT T ACA TGT GTC GTG GTC GAC GTT AGC CAG
GAG GAT CCC GAG GTT CAGTTC AAT TGG TAC GTG GAT GGA GTT GAA GTG CAC
AAT GCC AAA ACA AAA CCA CGA GAA GAG CAA TTT AAT AGC ACC TAC AGG
GTAGTC AGC GTT CTT ACA GTT TTG CAC CAA GAT TGG CTT AAC GGC AAA GAA
TAC AAA TGT AAG GTT AGT AAT AAA GGA CTC CCC TCATCA ATA GAA AAA ACA
ATT TCC AAA GCT A AA GGC CAG CCT AGG GAA CCT CAA GTG TAC ACA CTT CCT
CCA AGT CAA G AA GAG ATGACA AAG AAC CAG GTC TCA CTC ACT TGT CTC GTC
AAA GGT TTC TAC CCC TCT GAC ATC GCC GTG GAA TGG GAG TCC AAT GGC

Sequence Listing

CAACCT GAG AAT AAT TAC AAG ACC ACA CCT CCA GTA CTC CAT AGT GAC GGG
TCT TTC TTT TTG TAT TCT AGG TTG ACA GTG GAT AAATCA AGA TGG CAA GAA
GGA AAT GTT TTC TCA TGT TCT GTG ATG CAC GAG GCT CTT CAC AAC CAC TAC
ACT CAA AAG TCT CTG TCTCTT TCC CTT GGC AAA

SEQ ID NO: 130 - Codon optimized nucleic acid sequence encoding
SEQ ID NO 110

GTC CGA TCA TCT AGT AGG ACC CCT AGC GAC AAG CCA GTT GCA CAC GTG GTA
GCA AAC CCA CAA GCA GAA GGA CAA CTG CAG TGGCTT AAT AGG CGC GCA AAT
GCA TTG CTC GCC AAT GGA GTG GAA CTC CGA GAC AAC CAA TTG G TA GTG CCT
TCC GAA GGA CTC TACCTT ATT TAT AGT CAG GTC CTG TTC AA A GGG CAA GGT
TGC CCC TCA ACA CAC GTA TTG CTG ACA CAC ACC ATA TC C CGC ATA GCAGTT
AGC TAT CAA ACA AAG GTT AAT TTG CTG TCC GCA ATA AAG AGC CCC TGC CAA
CGG GAG ACC CCC GAG GGC GCA GAG GCA AAACCC TGG TAC GAG CCC ATC TAC
TTG GGT GGC GTC TTT CAA CTT GAA AAG GGG GAT AGG CTG AGC GCT GAA ATT
AAC CCC CCC GACTAT TTG AAT TTC CGG GAA TCT GGC CAA GTA TAC TTT GGT
ATT ATT GCC TTG GGT GGT GGA GGT A GC AGT AGC CGA ACA CCA TCAGAC AAA
CCT GTG GCA CAC GTT GTC GCC AA C CCA CAA GCT GAA GGA CAA CTC CAA TGG
TTG AAC AGG CGA GCC AAT GC C CTC CTTGCA AAT GGC GTA GAA TTG CGA GAT
AAT CAG CTT GTT GTT CCT AGC GAG GGT CTT TAT CTT ATA TAC AGT CAG GTC
CTC TTT AAAGGC CAA GGA TGT CCT AGT ACA CAC GTG CTG CTG ACT CAT ACA
ATA AGC CGA ATT GCC GTA TCC TAT CAG ACT AAG GTC AAC CTTCTG AGC GCT
ATT AAA TCC C CA TGT CAA AGG GAA ACT CCA GAA GGC GCA GAA GCC AAG CCC
TGG TAT G AG CCA ATC TAT CTC GGAGGG GTT TTC CAA TTG GAG AAG GGC GAC
CGG CTT TCT GCT GAA ATC AAT CGA CCT GAT TAT CTC AAC TTT CGA GAG TCA
GGG CAGGTT TAT TTC GGT ATC ATT GCT CTC GGT GGC GGA GGG TCC AGC TCT
AGG ACC CCC TCA GAC AAA CCA GTA GCC CAC GTT GTG GCCAAT CCC CAG GCA
GAA GGT CAG TTG CAG TGG TTG AAT CGG CGC GCT AAT GCA CTC CTC GCC AAT
GGA GTT GAA CTT AGG GAT AATCAA CTC GTA GTC CCC AGC GAA G GG TTG TAT
CTT ATT TAT AGT CAG GTC CTT TTT AAG GGT CAG GGT TGC C CA TCC ACT CAC
GTGTTG CTC ACT CAC ACC ATC AGT CGC ATC GCC GTT TC C TAT CAG ACC AAG
GTT AAT CTC CTG TCC GCT ATA AAG TCC CCA TGT CA AAGA GAG ACC CCC GAA
GGA GCA GAG GCA AAG CCT TGG TAC GAG CCT ATA TAC TTG GGT GGC GTA TTT
CAG TTG GAA AAG GGT GACCGG TTG TCC GCT GAG ATA AAT CGA CCT GAC TAT
CTC AAC TTT CGG GAG TCT GGT CAG GTT TAC TTT GGG ATT ATA GCA CTG
GAGAGC AAA TAC GGA CCC CCC TGT CCT C CT TGT CCT GCC CCA GAG TTT CTC
GGT GGA CCA TCA GTC TTT CTT TTT C CT CCT AAG CCCAAG GAT ACA TTG ATG
ATC TCA CGG ACC CCC GAA GTT ACC TGC GTG GTT GTT GAT GTA AGT CAG GAG
GAT CCC GAA GTC CAA TTCAAT TGG TAT GTC TGC GAC GGC GTG GAG GTC CAC AAT
GCA AAG ACA AAG CCC CGG GAG GAA CAG TTT AAC AGC ACA TAC CGG GTC
GTTAGC GTG TTG ACC GTC CTT CAT CAA GAT TGG TTG AAC GGC AAA GAG TAC
AAG TGC AAG GTT AGC AAC AAA GGT TTG CCA TCT TCCATC GAG AAA ACA ATA
TCT AAG GCC AAA G GA CAG CCC CGC GAA CCA CAA GTT TAT ACT CTT CCT CCA
AGC CAG GAG G AA ATG ACTAAG AAT CAG GTT TCC CTC ACA TCC GTT GTA AAG
GGT TTT TA T CCC TCA GAT ATT GCA GTT GAG TGG GAG AGC AAT GGT CAG
CCCGAG AAT AAC TAT AAA ACA ACC CCA CCA GTA CTC GAC TCA GAT GGT AGT
TTC TTC CTC TAC TCC AGG TTG ACA GTA GAC AAA AGCCGC TGG CAA GAG GGC
AAC GTA TTC TCT TGC TCA GTG ATG CAT GAA GCA CTG CAT AAT CAC TAC ACA
CAA AAA TCT CTG AGC CTTTCA CTT GGC AAA

SEQ ID NO: 131 - Codon optimized nucleic acid sequence encoding
SEQ ID NO 111

GTT AGG TCT TCA TCT AGA ACA CCC AGC GAC AAG CCC GTG GCC CAC GTC GTT
GCC AAC CCC CAG GCA GAG GGT CAG CTG CAG TGGCTC AAT AGG CGA G CT AAC
GCC CTT CTC GCT AAC GGT GTG GAG TTG CGC GAT AAC CAA CTG G TC GTA CCA
TCC GAA GGA CTC TATCTG ATT TAT TCT CAA GTC CTG TTT AA G GGC CAG GGC
TGT CCT TCA ACC CAC GTC CTC CTT ACA CAT ACC ATT TCT AGA ATA GCCGTA
TCA TAT CAG ACT AAA GTA AAT CTT TTG TCA GCA ATCAAA TCT CCA TGC CAA
CGG GAG ACC CCA CAC CGA CCA GAA GCT AAACCC TGG TAC GAA CCC ATA TAT
CTG GGC GGT GTC TTC CAG CTT GAG AAG GGG GAC CGA CTC TCA GCC GAG ATA
AAT CGA CCT GACTAT TTG AAC TTC AGA GAG TCC GGG CAA GTC TAT TTC GGA
ATT ATA GCT CTC TCC TCT AGG ACC CCA TCA GAT AAA CCA GTT GCCCAT GTC
GTG GCT AAT CCC CAG GCT GAA GGC CAA CTG CAA TGG CTT AAC CGC CGG GCC
AAT GCT TTG CTC GCC AAC GG T GTA GAGTTG CGC GAC AAC CAA CTG GTA GTC
CCT AGC GAA GGG CTG TAC CTG ATC TAC TCC CAA GTT CTT TTT AAA GGC CAA
GGT TGT CCTAGT ACC CAC GTA CTT CTG ACC CAT ACT ATA TCT CGG ATA GCT
GTG AGT TAC CAG ACA AAG GTT AAC CTT CTT TCC GCC ATC AAAAGT CCT TGC
CAA AGG GAA A CA CCT GAA GGT GCA GAA GCC AAG CCC TGG TAT GAG CCA ATT
TAT CTG G GC GGA GTC TTC CAA CTCGAG AAG GGG GAT AGA CTG AGC GCT GAG
ATA AA C AGA CCA GAC TAT CTG AAT TTT AGG GAG TCA GGC CAG GTA TAC TTT
GGA ATAATC GCC CTC TCA TCA AGG ACT CCC TCC GAC AAA CCA GTA GCA CAC
GTA GTG GCA AAT CCC CAG GCA GAA GGA CAG CTC CAG TGGCTG AAT CGG CGG
GCA AAC GCC CTG CTC GCT AAC GGG GTC GAA CTT AGG GAC AAC CAG CTT GTT
GTG CCA TCC GAA GGT TTG TACCTG ATA TAT TCT CAA GTT CTC TTT AAA GGC
CAG GGG TGT CCT TCT ACT CAT GTG CTG TTG ACT CAT ACA ATA TCA CGG ATT

| Sequence Listing |
|---|
| GCAGTT TCC TAT CAA ACT AAA GTA AAC TTG CTT TCA GCT ATC AAG AGT CCA
TGC CAA AGG GAG ACA CCT GAA GGG GCA GAG GCT AA ACCC TGG TAC GAG CCT
ATT TAC CTC GGG GGC GTT TTT CAG CTG GAA AAA GGA GAT CGG TTG TCA GCT
GAA ATC AAC AGA CCC GACTAT CTG AAC TTT CGC GAG TCA GGT CAG GTT TAT
TTT GGC ATT ATT GCC CTG GAA AGC AAG TAC GGT CCT CCT TGT CCA CCA
TGCCCT GCT CCA GAA TTC TTG GGG GGA CCA TCA GTG TTT CTG TTC CCC CCC
AAA CCA AAG GAC ACC TTG ATG ATA AGC CGA ACC CCAGAA GTG ACC TGT GTC
GTA GTT GAT GTA AGT CAA GAA GAT CCA GAG GTC CAA TTC AAC TGG TAC GTT
GAC GGT GTC GAG GTA CATAAC GCC AAA ACC AAG CCT CGC GAA GAG CAG TTT
AAC TCC ACA TAT AGG GTG GTA AGT GTG CTC ACA GTG CTG CAT CAA GAC
TGGCTT AAC GGG AAG GAA TAC AAG TGT AAA GTC TCC AAT AAG GGA CTT CCC
TCT AGC ATA GAA AAA ACT ATA TCT AAA GCA AAG GGTCAA CCA CGC GAA CCA
CAG GTA TAT ACA C TC CCC CCT AGC CAG GAG GAA ATG ACC AAA AAC CAA GTA
TCT TTG ACC TGT CTG GTGAAA GGC TTT TAC CCA TCT GAT ATC GCA GTT GAA
TGG GAG TC AAAT GGC CAA CCC GAA AAT AAC TAC AAG ACA ACT CCT CCC
GTGCTC GAC TCT GAC GGA TCA TTC TTC CTT TCT CGC CTC ACC GTA GAT
AAG AGC CGC TGG CAA GAG GGT AAC GTA TTC AGT TGTAGC GTG ATG CAT GAG
GCT CTT CAT AAC CAT TAT ACA CAA AAG TCC CTC AGC CTT TCT CTG GGA AAG |

SEQ ID NO: 132 - Codon optimized nucleic acid sequence encoding
SEQ ID NO 112

| GTC CGC TCA TCA TCA AGA ACC CCA AGC GAC AAA CCT GTG GCC CAC GTT GTT
GCC AAT CCA CAA GCC GAG GGG CAG CTG CAG TGGCTT AAC AGG AGA G CA AAC
GCT CTT CTT GCC AAC GGC GTA GAG CTT CGA GAC AAC CAA CTT G TC GTA CCT
TCT GAA GGT CTG TACCTC ATC TAT AGT CAA GTA CTT TTT AA A GGA CAG GGT
TGT CCA AGT ACA CAT GTA CTT CTG ACC CAC ACA ATA TC C AGG ATA GCCGTG
TCA TAC CAC ACA AAG GTC AAT CTG TTG TCT GCA ATT AAG TCA CCA TGC CAA
AGA GAA ACC CCA GAA GGT GCA GAA GCA AAGCCA TGG TAT GAG CCA ATA TAT
CTG GGC GGC GTC TTT CAG CTC GAG AAG GGA GAC CGG CTG TCT GCA GAA ATC
AAC AGG CCT GACTAC CTC AAC TTC AGG GAG AGT GGC CAG GTG TAT TTT GGA
ATA ATT GCA TTG GTT AGA AGT TCT CGC ACA CCA TCC GAT AAA CCAGTC GCC
CAC GTT GTA GCT AAT CCA CAA GC C GAG GGA CAG CTG CAA TGG CTG AAT CGA
CGG GCC AAT GCA TTG CTG GC T AAT GGGGTA GAG CTT CGC GAT AAT CAA CTT
GTG GTC CCA TCA GAG GGT CTT TAC CTC ATA TAC TCC CAA GTC CTT TTC AAA
GGC CAA GGTTGT CCT TCT ACA CAT GTG CTT TTG ACC CAC ACT ATT TCT AGA
ATC GCA GTG TCA TAC CAG ACT AAG GTC AAC CTG CTC TCA GCTATT AAG TCA
CCC TGC CAA A GG GAA ACT CCC GAG GGT GCC GAG GCC AAA CCT TGG TAT GAA
CCT ATC T AC CTT GGG GGA GTG TTCCAA CTG GAG AAG GGC GAT AGA TTG AGT
GCC GA G ATA AAT CGG CCA GAT TAT TTG AAC TTC AGA GAG AGC GGA CAA GTC
TAC TTCGGT ATA ATA GCA TTG GTG CGC AGT GGC CGA ACT CCC TCC GAT AAG
CCA GTC GCC CAT GTT GTC GCA AAC CCT CAG GCA GAG GGACAG CTT CAA TGG
CTC AAT CGC CGC GCC AAT GCC TTG CTT GCC AAC GGT GTT GAA CTG AGG GAC
AAC CAG TTG GTC GTT CCT AGCGAA GGT TTG TAT CTT ATC TAT AGC CAG GTA
CTG TTC AAA GGG CAA GGG TGT CCT AGT ACC CAT GTG CTC C TC ACA CAT ACC
ATATCA AGA ATT GCA GTT AGT TAT CAG ACC AAG GTA AA T CTC CTG AGT GCA
ATA AAA TCC CCC TGC CAG CGG GAG ACT CCA GAG GG GGCT GAG GCC AAA CCA
TGG TAC GAG CCC ATC TAT CTC GGT GGA GTC TTT CAG CTG GAA AAG GGA GAT
CGC CTT TCT GCA GAG ATTAAT AGG CCA GAT TAC CTG AAT TTC CGC GAG AGT
GGG CAA GTT TAC TTC GGT ATC ATA GCC CTT GAA AGC AAA TAC GGC CCT
CCATGC CCC CCC TGC CCT GCA CCC GAG T TC CTG GGC GGT CCC TCT GTG TTC
TTG TTC CCC CCA AAG CCC AAG GAC A CC CTC ATG ATATCC AGG ACA CCA GAA
GTA ACT TGC GTT GTC GTC GAT GTG TCC CAG GAA GAT CCA GAA GTT CAA TTT
AAC TGG TAT GTC GAT GGTGTG GAA GTG CAT AAT GCA AAA ACT AAG CCT CGA
GAA GAA CAA TTC AAC TCT ACA TAT CGC GTC GTC AGT GTG TTG ACT GTC
CTCCAC CAA GAC TGG CTG AAT GGC AAA GAG TAC AAG TGC AAA GTG TCC AAT
AAG GGC CTT CCA TCT TCA ATT GAG AAA ACC ATT AGTAAG GCA AAG GGT CAG
CCC CGG GAA CCA C AG GTC TAT ACA TTG CCC CCT AGC CAA GAG GAG ATG ACC
AAG AAC CAA G TC TCA CTCACC TGT CTG GTA AAG GGA TTT TAC CCT AGT GAT
ATC GCT GT C GAA TGG GAA AGC AAC GGT CAG CCC GAG AAC AAT TAC AAA
ACCACT CCA CCA GTG CTC GAC TCA GAC GGC TCT TTT TTC CTT TAC TCA CGG
TTG ACT GTA GAT AAA TCC CGC TGG CAG GAG GGC AATGTT TTC AGC TGT AGT
GTT ATG CAC GAA GCA CTT CAC AAT CAT TAT ACC CAG AAG TCA CTG TCT CTT
TCC CTT GGG AAG |

SEQ ID NO: 133 - Codon optimized nucleic acid sequence encoding
SEQ ID NO 113

| GAG CCA AAG TCC AGC GAC AAG ACA CAT ACT TGT CCA CCC TGT CCA GCT CCA
GAG GCA GCC GGC GGT CCT TCC GTG TTC TTG TTTCCT CCC AAG CCA A AG GAC
ACA CTG ATG ATC TCT AGA ACT CCC GAG GTT ACA TGC GTT GTG G TT GAC GTG
TCT CAT GAG GAC CCTGAA GTG AAG TTT AAT TCC TAC GTC GA C GGT GTC GAG
GTA CAT AAT GCA AAA ACT AAG CCA CGC GAG GAA CAA TA T AAT AGC ACATAC
CGA GTG GTC AGC GTC TTG ACA GTG CTT CAC CAA GAC TGG CTC AAT GGT AAG
GAG TAT AAA TGC AAA GTA TCA AAC AAA GCCTTG CCC GCA TCC ATC GAA AAA
ACA ATA AGC AAG GCT AAG GGA CAA CCA CGG GAG CCA CAA GTG TAT ACT CTC
CCC CCT TCA AGAGAC GAG CTC ACA AAA A AC CAA GTT TCA CTG ACT TGC CTG |

-continued

| Sequence Listing |
|---|
| GTT AAA GGT TTT TAT CCC TCC GAT ATA GCT GTT GAA TGG GAG AGTAAT GGA<br>CAA CCA GAA AAT AAC TAT AAA ACT ACT CCT CCC GTG CTT GAC AGT GAC GGG<br>TCT TTT TTC TTG TAT TCT AA A CTC ACCGTT GAT AAA AGT AGA TGG CAG GGC<br>AAT GTT TTC TCC TGC TCA GTG ATG CAT GAA GCT CTG CAC AAT CAC TAC ACA<br>CAA AAATCA CTG TCC CTG TCT CCT GGT AAG GGT GGC GGT GGC AGC GTC AGG<br>TCA AGT TCC AGA ACA CCT AGT GAT AAA CCA GTA GCC CATGTA GTT GCT AAC<br>CCC CAG G CT GAG GGA CAA CTT CAG TGG CTT AAC CGC CGC GCT AAT GCT CTT<br>CTT G CT AAC GGA GTC GAA CTGAGA GAT AAC CAA CTT GTC GTG CCT AGT GAG<br>GG G TTG TAT CTC ATT TAC TCT CAG GTG CTG TTC AAG GGC CAG GGC TGT CC A<br>TCAACT CAC GTA CTG CTT ACA CAT ACT ATT AGC AGG ATA GCA GTG AGC TAC<br>CAA ACC AAA GTT AAC TTG TTG TCT GCC ATT AAA AGCCCT TGT CAG AGG GAA<br>ACC CCT GAG GGG GCA GAA GCT AAG CCA TGG TAC GAA CCT ATT TAC CTT GGT<br>GGG GTG TTT CAG TTG GAGAAA GGG GAT CGG CTT AGT GCT G AA ATA AAT AGA<br>CCC GAT TAT TTG AAC TTC CGG GAG AGT GGT CAG GTT TAC TTC GGA ATC<br>ATCGCC CTG GGA GGG GGG GGT TCT AGC TCA AGG ACA CCA AGC GAT AAA CCA<br>GTG GCA CAT GTG GTC GCT AAT CCC CAA GCA GGG GCAA CTT CAG TGG TTG<br>AAC CGC CGG GCT AAT GCA CTG CTC GCA AAC GGT GTA GAG TTG AGG GAC AAT<br>CAA CTC GTT GTA CCA AGTGAG GGC TTG TAT CTC ATA TAC AGC AGG TGC CTT<br>TTT AAA GGC CAG GGG TGT CCC AGT ACA CAC GTG TTG CTC ACC CAC ACA<br>ATATCA AGA ATA GCA GTC TCA TAC CAA ACT AAG ATT AAC CTC CTC TCA GCA<br>ATT AAA TCC CCT TGT CAG CGG GAG A CC CCC GAA GGCGCT GAG GCT AAG CCC<br>TGG TAC GAA CCC ATC TAT CTT GG T GGG GTT TTT CAA CTG GAG AAA GGC GAT<br>CGA TTG TCA GCC GAG ATTAAT CGC CCA GAT TAC CTG AAC TTT CGC GAA TCC<br>GGA CAG GTA TAC TTC GCC ATT ATC GCA TTG GGT GGC GGT GGC AGC AGC<br>AGTAGG ACT CCT AGC GAT AAA CCC GTT GCT CAT GTT GTT GCA AAC CCA CAG<br>GCA GAA GGG CAG CTC CAA TGG CTC AAT CGG CGC GCAAAC GCA TTG CTG GCC<br>AAC GGA GTA GAG C TG CGG GAC AAC CAA CTT GTT GTT CCC AGC GAA GGT CTT<br>TAC CTC ATT T AT TCC CAAGTC CTT TTC AAG GGC CAA GGC TGT CCA AGT ACA<br>CAC GTA CT T CTT ACT CAC ACA ATA AGT CGC ATA GCA GTC TCT TAC CAA<br>ACAAAA GTC AAT CTC CTG TCT GCA ATT AAA TCC CCA TGT CAA AGA GAA ACC<br>CCA GAA GGG GCA GAG GCC AAG CCT TGG TAT GAG CCTATC TAT TTG GGC GGG<br>GTT TTC CAA CTT GAG AAG GGA GAC CGG CTT TCA GCT GAA ATC AAC AGG CCC<br>GAT TAT CTC AAC TTC AGGGAG AGT GGA CAA GTC TAC TTC GGA ATT ATA G CC<br>CTG |

SEQ ID NO: 134 - Codon optimized nucleic acid sequence encoding
SEQ ID NO 114

| GAA AGG AAG TCA AGC GTG GAA TGC CCT CCC TCT CCA CCA CCA CCC GTC GCT<br>GGA CCC AGC GTG TTC CTG TTC CCA CCC AAA CCCAAG GAT ACT CTC A TG ATC<br>AGC CGG ACA CCA GGA GTA ACT TGT GTA GTA GTA GAT GTT AGC GAC CAT GAG GAT<br>CCT GAG GTG CAG TTTAAT TGG TAC GTT GAC GGG GTG GAG GTA CAT AAC GCA<br>AAA ACC AAA CCA CGA GAG GAG CAG TTC AAC AGC ACC TTT CGC GTA GTGTCA<br>GTC CTG ACC GTA GTC CAC CAG GAC TGG fTG AAC GGT AAG GAA TAC AAG TGT<br>AAG GTT TCC AAC AAG GGT CTG CCT GCC TCTATC GAG AAA ACA ATA AGC AAG<br>ACA AAA GGC CAA CCT CGG GAA CCT CAG GTA TAT ACA CTT CCC CCA AGT CGA<br>GAG GAG ATG ACTAAG AAC CAG GTA AGC CTT ACT TGC CTG GTA AAA GGT TTT<br>TAT CCC AGC GAC ATC GCC GTC GAA T GG GAA TCC AAT GGA CAG CCTGAG AAT<br>AAC TAT AAG ACA ACC CCC CCT ATG CTG GAT TCA GAC GGT AGC TTC TTT CTT<br>TAT TCC AAA CTT ACC GTG GA T AAA TCAAGG TGG CAG CAA GGG AAT GTT TTC<br>TCT TGT AGT GTC ATG CAC GAA GCC CTT CAC AAC CAT TAC ACT CAG AAA TCC<br>CTC AGC TTGTCA CCT GGA AAA GGG GGC GGC GGA AGT GTC CGA TCC TCC TCT<br>CGG ACC CCA TCT GAC AAG CCA GTT GCC CAT GTG GCT AATCCA CAG GCT<br>GAG GGG CAA C TC CAG TGG CTG AAT AGG AGA GCT AAT GCT CTC CTT GCT AAT<br>GGA GTT G AA CTT AGA GAC AAT CAGCTT GTC GTC CCC TCT GAA GGG CTC TAT<br>TTG AT A TAC AGC CAG GTT CTT TTT AAG GGT CAG GGC TGT CCC TCC ACT CAT<br>GT G CTTCTC ACA CAC ACA ATC AGC CGC ATC GCA GTG AGT TAT CAA ACC AAA<br>GTT AAC CTG CTT TCC GCA ATC AAA AGC CCT TGT CAG AGAGAA ACC CCA GAA<br>GGA GCA GAA GCC AAA CCC TGG TAT GAG CCC ATC TAT CTC GGA GGA GTA TTC<br>CAA CTG GAA AAG GGT GAT AGGTTG AGC GCT GAG ATA AAT AGA C CC GAC TAT<br>CTG AAC TTC AGG GAG AGT GGT CAA GTA TAC TTT GGC ATT A TT GCC CTC GGC<br>GGCGGC GGC AGT TCC AGT CGG ACA CCC TCA GAT AAG CC A GTT GCT CAC GTT<br>GTG GCC AAC CCC CAA GCC GAA GGC CAG TTG CAG TG GTTG AAT AGG CGG GCT<br>AAT GCT CTG CTG GCA AAC GGT GTA GAA CTT CGA GAT AAT CAA CTC GTT GTG<br>CCC TCA GAG GGA CTC TATCTC ATT TAC AGC CAG GTG CTT TTC AAA GGG CAG<br>GGG TGT CCC TCT ACA CAT GTC CTT CTG ACA CAT ACA ATC TCA CGA ATA<br>GCTGTC TCC TAC CAA ACA AAA GTT AAT TTG CTC AGT GCT ATA AAA TCC CCT<br>TGC CAG CGG GAG ACA CCT GAG GGG G CT GAG GCC AAACCT TGG TAC GAG CCT<br>ATC TAT CTC GGC GGG GTA TTC CAA CTT GAA AAA GGG GAC AGA CTT AGT GCC<br>GAA ATA AAC CGC CCA GACTAC CTT AAC TTC CGC GAG TCC GGG CAG GTT TAC<br>TTT GGG ATA ATC GCA CTG GGG GGA GGT GGA TTT TCA TCT AGA ACC CCA<br>AGCGAC AAA CCA GTT GCT CAT GTG GTC GCC AAT CCT CAA GCT GAA GGA CAG<br>CTT CAA TGG CTT AAT CGC CGG GCA AAC GCC CTT TTGGCA AAT GGC GTT GAG<br>CTG CGG GAT AAT C AA CTG GTA GTT CCA AGT GAG GGC TTG TAC TTG ATC TAT<br>AGT CAA GTA C TG TTC AAGGGC CAA GGC TGC CCA TCT ACA CAC GTT CTT TTG<br>ACC CAC ACT ATT TCA AGG ATT GCC GTC AGC TAT CAA ACT AAA GTG AAC<br>CTCCTG TCT GCT ATC AAG TCA CCC TGT CAA CGA GAA ACC CCT GAG GGT GCT |

| Sequence Listing |
|---|

GAA GCC AAG CCC TGG TAT GAG CCC ATA TAT CTC GGCGGA GTC TTT CAA CTG
GAG AAG GGT GAC AGG CTG TCT GCC GAA ATC AAT CGG CCT GAC TAT CTG AAC
TTT CGG GAG AGC GGC CAGGTC TAC TTC GGC ATT ATT GCT CTC

SEQ ID NO: 135 - Codon optimized nucleic acid sequence encoding
SEQ ID NO 115

GTC AGG AGT AGC TCT AGG ACC CCA TCC GAT AAG CCC GTC GCA CAT GTG GTG
GCC AAC CCC CAG GCA GAA GGC CAA CTC CAG TGGCTT AAT AGA CGA G CC AAT
GCC CTT TTG GCT AAT GGC GTC GAG CTC AGG GAC AAT CAA CTT GTG GTG CCT
AGT GAG GGA CTC TATTTG ATT TAT -AGC CAA GTA CTT TTC AA G GGA CAG GGT
TGT CCA TCT ACA CAC GTG CTT CTT ACC CAC ACT ATT TC T CGG ATC GCAGTT
TCT TAT CAA ACC AAA GTC AAC CTT TTG TCC GCT ATC AAG AGT CCA TGT CAG
AGA GAG ACA CCC GAG GGC GCT GAA GCT AAGCCC TGG TAT GAG CCA ATC TAT
CTT GGG GGA GTT TTC CAG CTC GAA AAA GGG GAC CGG CTG TCT GCC GAA ATT
AAC CGC CCT GACTAC CTC AAC TTT AGG G AG AGT GGT CAG GTG TAT TTC GGA
ATA ATC GCC TTG GGC GGT GGC GGG TCA TCT AGC AGA ACC CCA TCCGAC AAG
CCA GTC GCC CAT GTA GTG GCC AA T CCA CAG GCA GAG GGA CAA TTG CAG TGG
TTG AAT CGG CGA GCC AAT GC A TTG CTCGCA AAC GGG GTG GAG CTC CGC GAT
AAC CAG CTT GTA GTG CCA TCC GAA GGA TTG TAT TTG ATT TAT TCT CAA GTG
CTG TTC AAAGGA CAA GGG TGC CCA TCT ACC CAT GTC TTG CTG ACA CAC ACA
ATT TCC CGG ATC GCT GTA TCC TAC CAA ACC AAG GTG AAT CTTTTG TCA GCA
ATC AAA AGC C CA TGT CAA CGC GAA ACA CCA GAG GGA GCA GAG GCC AAG
CCT TGG TAC G AG CCT ATT TAC CTG GGCGGT GTC TTT CAA CTT GAG AAG GGA
GAT CGC TT G AGC GCA GAA ATT AAT AGG CCT GAC TAC CTT AAC TTT AGG GAA
AGT GGA CAGGTA TAT TTT GGA ATA ATT GCA CTC GGT GGT GGG GGA TCA TCA
AGC CGC ACA CCT TCC GAT AAA CCC GTT GCC CAC GTA GTG GCAAAT CCC CAG
GCC GAA GGC CAA TTG CAA TGG CTG AAC CGA AGA GCC AAC GCC CTT CTC GCA
AAT GGT GTA GAA CTC CGG GAT AACCAG TTG GTG GTG CCC AGC GAG G GC CTT
TAT CTC ATA TAC TCT CAA GTC CTT TTC AAA GGG CAG GGA TGT C CT AGT ACC
CAT GTACTT CTC ACT CAC ACA ATC TCC AGG ATC GCC GTT TCA TAT CAA ACA
AAA GTT AAT TTG CTC AGC GCT ATA AAG AGT CCA TGT CA ACGC GAA ACA CCT
GAG GGG GCC GAA GCA AAA CCT TGG TAC GAG CCT ATT TAT CTT GGT GGA GTA
TTC CAA CTT GAA AAA GGT GACAGG TTG TCA GCT GAG ATT AAT AGA CCA GAT
TAT CTG AAT TTT CGC GAA TCT GGG CAC GTT TAC TTC GGG ATA ATC GCT CTG
GGAGGA GGA GGG AGT GAA CCA AAG TCC A GC GAT AAA ACT CAT ACC TGT CCA
CCT TGT CCA GCC CCC GAA GCT GCA G GA GGC CCT AGCGTG TTC TTG TTT CCT
CCC AAA CCC AAA GAC ACA TTG ATG ATT AGT CGC ACT CCT GAA GTG ACA TGT
GTT GTC GTA GAC GTA TCTCAT GAA GAC CCC GAA GTC AAG TTT AAC TGG TAT
GTC GAT GGA GTG GAG GTG CAC AAT GCA AAG ACT AAG CCT AGG GAA GAA
CAATAT AAC AGT ACC TAC AGA GTT GTG TCA GTG CTT ACC GTC TTG CAT CAG
GAT TGG CTC AAT GGA AAA GAG TAT AAG TGT AAG GTAAGT AAC AAG GCA' TTG
CCC GCT AGC ATA G AG AAA ACA ATA AGC AAG GCA AAG GGG CAG CCC AGG
GAA CCC CAA GTC TAT ACC CTTCCA CCA AGT CGG GAT GAA CTG ACT AAA AAT
CAG GTG TCC TT G ACT TGC CTT GTA AAG GGA TTC TAC CCC TCA GAT ATC GCA
GTGGAG TGG GAG AGC AAC GGA CAG CCA GAA AAC AAT TAC AAA ACC ACC CCC
CCT GTC CTG GAT TCA GAC GGT TCT TTC TTT TTG TACTCC AAA CTT ACA GTA
GAC AAG TCC AGG TGG CAA CAA GGC AAT GTC TTT AGC TGT TCT GTC ATG CAC
GAA GCC CTT CAC AAC CACTAT ACT CAA AAG TCA CTT TCT CTT TCC CCT G GA
AAA

SEQ ID NO: 136 - Codon optimized nucleic acid sequence encoding
SEQ ID NO 116

GTA AGA TCA TCT AGT CGG ACT CCA TCA GAC AAA CCA GTA GCC CAT GTT GTT
GCA AAC CCA CAA GCC GAG GGT CAA CTT CAG TGGCTC AAT AGG CGC GCC AAT
GCA CTG CTC GCT AAT GGA GTC GAA TTG CGC GAT AAC CAA TTG G TG GTA CCT
AGT GAG GGA CTT TATTTG ATC TAT AGT CAG GTG CTC TTT AA A GGT CAG GGT
TGC CCC TCC ACC CAC GTT CTC CTG ACA CAT ACC ATT AG C AGG ATA GCTGTA
AGT TAC CAG ACT AAA GTC AAC CTC CTT AGC GCT ATC AAA AGT CCA TGT CAA
AGA GAA ACT CCA GAA GGA GCA GAA GCC AAACCT TGG TAC GAG CCT ATC TAC
CTC GGA GGA GTA TTT CAG CTT GAA AAG GGG GAT CGA CTG AGC GCC GAA ATC
AAC AGA CCC GATTAC CTT AAC TTC CGA G AA TCC GGC CAA GTA TAC TTC GGG
ATT ATT GCC CTT GGG GGA GGT GGC T CT TCA AGC AGA ACC CCA TCAGAC AAG
CCA GTG GCT CAC GTC GTT GCC AA T CCC CAA GCT GAA GGG CAA CTT CAA TGG
CTT AAT CGA AGG GCT AAT GC A CTT TTGGCC AAC GGT GTA GAA CTC CGA GAC
AAC CAA TTG GTC GTG CCA TCA GAA GGC CTT TAC CTC ATA TAC TCC CAG GTT
CTT TTC AAGGGT CAG GGA TGT CCT AGT ACA CAC GTA TTG TTG ACC CAT ACA
ATT TCA AGG ATA GCA GTA AGC TAC CAG ACT AAA GTT AAT CTGCTT AGT GCT
ATA AAG TCT C CT TGT CAG CGA GAG ACA CCC GAA GGC GCT GAG GCA AAA CCC
TGG TAC GAG CCC ATC TAC CTC GGGGGT GTT TTT CAA CTG GAG AAG GGA GAC
CGA CTG TCC GCC GAA ATT AAC CGG CCC GAC TAC CTC AAT TTT CGC GAA TCC
GGG CAAGTT TAT TTT GGT ATC ATT GCA TTG GGT GGT GGA GGC TCC AGT AGC
CGG ACT CCC TCC GAT AAA CCA GTG GCA CAT GTA GTC GCCAAC CCT CAA GCA
GAA GGG CAA TTG CAG TGG CTG AAT AGA CGC GCC AAT GCC CTC CTG GCT AAT
GGC GTA GAG CTT AGA GAT AATCAA TTG GTG GTG CCT AGT GAA- G GT CTG TAC
CTC ATT TAC TCT CAG GTT CTC TTT AAG GGC CAA GGA TGT CCC TCA ACT CAC

| Sequence Listing |
|---|
| GTACTG CTG ACT CAT ACT ATA TCA CGG ATA GCC GTC TC T TAC CAG ACA AAA
GTG AAT TTG CTG TCA GCC ATC AAG AGT CCA TGC CA GCGA AAA ACC CCT GAG
GGG GCT GAA GCT AAA CCA TGG TAT GAA CCA TAC CTT GGT GGC GTT TTC
CAG CTC GAG AAG GGC GATAGA CTT AGC GCC GAA ATT AAT CGA CCA GAC TAT
CTC AAT TTT AGA GAG TCA GGA CAA GTG TAC TTT GGT ATT ATA GCC TTG
GGTGGG GGC GGT TCT GAA CGG AAA AGT TCT GTT GAA TGC CCT CCA TGT CCT
GCC CCC CCT GTG GCC GGT CCC TCA GTC TTT CTC TTCCCA CCC AAG CCC AAA
GAT ACA TTG ATG ATT AGT AGG AC T CCC GAG GTG ACT TGC GTA GTT GTC GAT
GTT TCC CAT GAA GAT CCAGAA GTG CAA TTT AAC TGG TAT GTA GAC GGC GTC
GAG GTC CAT AAT GCT AAA ACT AAG CCC GCG GAG GAG CAG TTT AAT TCA
ACCTTT AGA GTT GTG AGC GTT CTG ACC GTT GTA CAC CAG GAT TGG CTT AAT
GGT AAA GAG TAC AAG TGC AAG GTG TCC AAC AAG GGACTT CCA GCA TCC ATT
GAA AAG ACC ATT T CC AAG ACT AAA GGG CAA CCA CGG GAA CCA CAA GTC TAC
ACC CTC CCA C CC AGC CGCGAA GAG ATG ACT AAA AAT CAG GTA TCA CTT ACT
TGC CTG GTT AAG GGT TTC TAC CCA TCT GAC ATT GCT GTC GAG TGG GAA
TCTAAT GGG CAA CCT GAA AAC AAT TAC AAG ACA ACA CCT ATG CTG GAT
TCC GAT GGG AGT TTC TTC CTG TAC AGT AAA CTC ACTGTT GAC AAG TCC CGA
TGG CAG CAG GGA AAT GTC TTT TCA TGC TCC GTT ATG CAT GAG GCC CTC CAC
AAC CAT TAT ACC CAA AAGTCT CTG TCC CTG TCA CCA GGA AAG |
| SEQ ID NO: 137 - Codon optimized nucleic acid sequence encoding SEQ ID NO 117 |
| GAA TCA AAG TAC GGT CCA CCT TGT CCT CCC TGT CCC GCC CCC GAG TTT CTG
GGG GGT CCC TCT GTC TTT CTG TTT CCA CCA AAGCCC AAG GAC ACT C TG ATG
ATT AGC AGA ACA CCA GAA GTA ACC TGT GTC GTC GTG GAT GTC T CA CAG GAG
GAT CCC GAG GTA CAGTTC AAC TGG TAC GTG GAT GGT GTA GA G GTG CAT AAT
GCA AAG ACT AAA CCA AGG GAA GAA CAA TTC AAT TCT ACT TAC CGG GTC GTA
TCT GTC TTG ACC GTG CTT CAC CAA GAT TGG CTG AAC GGC AAG GAG TAT AAA
TGT AAA GTT TCT AAT AAG GGG CTC CCA TCAAGT ATC GAG AAA ACC ATT TCA
AAA GCA AAA GGG CAA CCT CGA GAG CCT CAA GTT TAC ACA CTC CCT CCA TCA
CAA GAA GAA ATGACA AAG AAT CAA GTC A GC CTC ACC TGC CTT GTA AAG GGC
TTC TAT CCC TCC GAC ATT GCA GTG GAA TGG GAG TCA AAC GGA CAACCT GAG
AAT AAT TAT AAG ACC ACA CCT CCA GTG CTG GAC TCA GAT GGG TCA TTT TTC
CTG TAC TCC CGC TTG ACC GTG GAC AAGTCT CGA TGG CAG GAA GGT AAT GTG
TTC AGC TGT AGT GTG ATG CAC GAA GCA CTG CAC AAC CAT TAT ACC CAG AAA
TCC CTG TCATTG TCC CTC GGT AAG GTG AGA TCC AGT AGC CGC ACA CCA AGT
GAT AAA CCT GTA GCC CAC GTA GTG GCA AAT CCA CAA GCT GAAGGG CAG CTC
CAG TGG CTG AAT CGC CGC GCA AAC GCA CTG CTG GCA AAT GGG GTA GAG CTT
AGG GAC AAT CAG CTC GTA GTG CCCAGT GAA GGC CTC TAT CTC ATT TAT TCA
CAA GTA CTT TTC AAA GGC CAG GGA TGC CCT AGT ACC GTC CTT TTG ACA
CAC ACCATC TCC CGA ATA GCC GTA AGC TAC CAA ACT AAG GTT AAT CTC CTT
AGC GCA ATC AAA TCT CCT TGC CAA AGG GAA ACC CCC GAAGGC GCC GAA GCC
AAG CCC TGG TAT GAA CCT ATA TAC CTT GGC GGG GTT TTT CAG CTG GAA AAG
GGA GAC AGG TTG AGT GCC GAGATT AAT CGA CCA GAC TAC CTT AAT TTT AGA
GAG TCC GGC CAG GTC TAT TTC GGG ATA ATC GCT CTG TCT TCT AGA ACT CCC
AGTGAT AAA CCC GTT GCC CAC GTG GTG GCC AAC CCA CAG GCC GAA GGG CAA
CTG CAG TGG CTG AAC AGA CGA GCA AAT GCA TTG TT GGCC AAC GGT GTT GAA
CTG CGC GAC AAC CAA CTT GTG GTG CCT AGT GAG GGT CTC TAC TTG ATT TAT
TCC CAA GTC CTC TTT AAAGGG CAA GGG TGT CCC TCT ACT CAT GTC CTG CTC
ACT CAC ACC ATC TCC AGA ATT GCA GTA TCT TAT CAG ACA AAA GTA AAC
TTGCTG TCA GCC ATT AAA TCA CCA TGT C AG AGG GAG ACA CCT GAA GGT GCA
GAA GCT AAG CCT TGG TAT GAA CCT ATT TAT CTC GGCGGG GTG TTC CAA TTG
GAG AAA GGG GAC CGA CTG AGC GC T GAA ATC AAT AGA CCC GAT TAT TTG AAC
TTT AGA GAG AGT GGC CAGGTA TAC TTC GGT ATA ATA GCC CTG TCC AGT CGA
ACT CCT TCT GAT AAG CCT GTC GCA CAT GTT GTG GCA AAT CCT CAA GCT
GAGGGA CAG CTC CAA TGG TTG AAT AGA CGC AAC GCA CTC CTC CCT AAC
GGG GTT GAG CTC CGA GAC AAT CAG CTT GTC GTC CCAAGC GAG GGG CTG TAC
CTT ATT TAC TCC C AG GTA TTG TTT AAG GGA CAG GGT TGC CCC TCC ACA CAT
GTG CTC CTG ACC CAC ACTATC AGC CGA ATA GCC GTT AGC TAT CAA ACA AAG
GTC AAT CTC CTG AGT GCA ATA AAG TCT CCT TGT CAG CGA GAA ACC CCC
GAAGGC GCC GAG GCC AAG CCC TGG TAC GAG CCA ATT TAC CTC GGT GGA GTC
TTT CAG TTG GAG AAG GGG GAT AGA TTG AGC GCA GAAATT AAC CGA CCT GAC
TAT TTG AAC TTC AGA GAA AGC GGA CAA GTC TAT TTT GGT ATC ATC GCC CTG |
| SEQ ID NO: 138 - Codon optimized nucleic acid sequence encoding SEQ ID NO 118 |
| GAA TCA AAG TAC GGC CCT CCA TGT CCA CCC TGT CCT GCC CCT GAG TTT CTC
GGA GGA CCC AGT GTA TTC CTC TTC CCA CCA AAACCC AAG GAT ACC CTC ATG
ATC AGC AGG ACT CCC GAA GTT ACA TGC GTT GTC GAC GTA TCA CAG GAA
GAT CCT GAG GTC CAATTT AAT TGG TAC GTC GAC GGA GTC GAA GTT CAT AAC
GCC AAA ACA AAA CCA CGA GAA GAG CAA TTT AAC AGT AC A TAT CGC GTGGTC
TCA GTG CTG ACC GTG CTC CAC CAG GAC TGG CTC AAT GGG AAA GAA TAC AAA
TGT AAG GTT TCC AAT AAG GGA CTC CCT AGCTCA ATA GAA AAG ACC ATT TCA
AAA GCT AAA GGC CAA CCC CGG GAG CCC CAA GTC TAC ACC CTT CCC CCC TCT
CAG GAA GAA ATGACC AAA AAT CAG GTG T CC CTG ACC TGT CTT GTG AAA GGG |

| Sequence Listing |
| --- |

TTT TAT CCC TCA GAC ATT GCC GTA G AG TGG GAA TCA AAT GGA CAACCC GAG
AAC AAC TAT AAA ACT ACT CCA CC T GTT CTG GAC TCC GAT GGT TCC TTT TTC
CTG TAC AGC CGC CTT ACC GT T GAC AAATCA CGA TGG CAG GAA GGG AAT GTC
TTC AGT TGT TCA GTA ATG CAT GAA GCT CTC CAT AAC CAC TAT ACT CAG AAG
TCC CTG TCCCTC TCT CTG GGC AAG GGC GGC GGT GGT TCC GTC CGC AGT TCT
TCT CGG ACT CCC TCC GAC AAG CCA GTC GCA CAT GTA GTC GCCAAC CCA CAA
GCA GAG GGA CAG CTT CAG TGG CTC AAT CGA AGA GCA AAC GCC CTC CTT GCA
AAC GGC G TC GAA CTT CGC GAC AACCAA CTG GTT GTT CCA TCA GAA GGC TTG
TAT CTG ATC TAC TCT CAG GTG CTG TTT AAG GGA CAG GGA TGT CCT AGC ACA
CAT GTGCTC CTT ACT CAT ACA ATT TCA AGG ATC GCA GTA AGC TAC CAA ACT
AAA GTG AAC CTC CTT AGC GCC ATA AAG TCC CCA TGC CAAAGG GAG ACA CCC
GAG GGA GCA GAA GCA AAG CCA TGG TAT GAA CCT ATC TAT CTC GGT GGA GTT
TTC CAG TTG GAG AAA GGT GATAGA CTC TCT GCT GAG ATC AAT C GC CCC GAC
TAT CTG AAT TTC GCC GAA TCT GGG CAG GTC TAC TTT GGG ATA ATA GCA CTG
GGTGGC GGT GGA TCT CCC GTA GCT CAC GTG GTC GCT AAC CCA CAG GCT GAG
GGG CAA TTG CAA TGG TTG AAC CGG CGG GCT AAT GC TTTG TTG GCA AAC GGC
GTA GAA TTG AGA GAC AAC CAA TTG GTC GTT CCT TCA GAA GGA TTG TAT CTC
ATC TAC AGC CAA GTC TTGTTT AAA GGC CAA GGC TGT CCA TCT ACA CAC GTG
CTT CTT ACT CAC ACA ATC TCA CGA ATC GCA GTA TCT TAT CAG ACC AAA
GTGAAC TTG CTC TCT GCA ATA AAA AGC C CT TGT CAA CGC GAA ACT CCA GAA
GGG GCT GAA GCA AAG CCA TGG TAC G AA CCT ATT TATCTC GGG GGG GTG TTC
CAA CTC GAG AAA GGG GAC CGA CT G TCC GCT GAA ATC AAC CGC CCT GAC TAT
CTT AAT TTC CGG GAG TCTGGG CAG GTA TAT TTC GGT ATA ATT GCA CTT GGA
GGC GGG GGG TCA CCT GTG GCA CAT GTA GTC GCC AAC CCC CAA GCT GAA
GGACAA CTT CAA TGG CTC AAT AGG CGC GCA AAT GCT CTG CTC GCA AAT GGA
GTA GAA CTC CGG GAT AAT CAA CTG GTT GTG CCT TCTGAA GGA CTG TAT CTG
ATC TAT AGC CAA G TT TTG TTC AAG GGC CAG GGG TGC CCA TCT ACA CAC GTA
CTT CTT ACC C AC ACA ATATCC CGC ATC GCC GTC AGT TAT CAG ACA AAA GTG
AAC CTT TTG TCC GCC ATC AAG AGC CCA TGT CAG CGC GAA ACT CCC GAG
GGTGCT GAG GCT AAA CCA TGG TAT GAG CCC ATC TAT TTG GGA GGC GTA TTT
CAA CTG GAA AAA GGG GAT CGA CTG AGC GCA GAG ATCAAT AGG CCC GAT TAT
CTT AAT TTC AGG GAG TCT GGT CAA GTG TAT TTT GGG ATA ATT GCT CTG

SEQ ID NO: 139 - Codon optimized nucleic acid sequence encoding
SEQ ID NO 119

GAA TCT AAG TAT GGG CCA CCA TGC CCA CCA TGC CCA GCC CCA GAA TTC CTG
GGC GGA CCT TCC GTT TTC TTG TTC CCA CCA AAGCCA AAA GAT ACT C TG ATG
ATT TCC AGG ACC CCT GAA GTT ACC TGT GTG GTA GTG GAT GTC A GC CAG GAG
GAT CCA GAA GTT CAATTT AAT TGG TAT GTA GAC GGA GTC GA A GTC CAT AAC
GCT AAA ACT AAA CCT CGA GAA GAG CAG TTT AAT TCA ACC TAC AGG GTTGTT
TCC GTA CTG ACA GTT TTG CAT CAG GAC TGG CTG AAT GGC AAG GAA TAC AAA
TGC AAG GTC AGC AAC AAA GGA CTC CCA AGTTCA ATA GAA AAG ACC ATT TCA
AAA GCT AAA GGG CAA CCA CGA GAA CCT CAG GTC TAC ACT CTC CCT CCC TCT
CAG GAA GAG ATGACT AAA AAT CAG GTT TCA CTT ACA TGC CTC GTG AAG GGC
TTT TAC CCC AGC GAC ATT GCT GTT GAG TGG GAA AGT AAC GGA CAACCT GAG
AAC AAC TAC AAG ACT ACA CCT CCT GTG CTG GAC TCA GAT GGT TCC TTC TTT
TTG TAT AGC AGG CTT ACC GT T GAT AAGTCC CGC TGG CAA GAA GGC AAC GTT
TTC AGT TGT TCA GTA ATG CAC GAA GCT CTC CAC AAT CAT TAT ACA CAG AAG
AGT CTT AGCCTG TCC CTG GGT AAG GGA GGC GGG GGG TCC GGG GGC GGG GGC
TCA GTT CGC TCA TCA AGC CGA ACA CCC TCA GAC AAG CCA GTTGCC CAC GTC
GTA GCC AAC CCC CAA GCT GAA GGA CAG TTG CAA TGG CTG AAT AGG CGA GCT
AAT GCA TTG TTG GCA AAT GGA GTAGAA CTG CGC GAT AAT CAA TTG GTT GTG
CCC TCA GAA GGG CTG TAC CTT ATT TAC TCC CAG GTG CTC TTC AAA GGG CAG
GGT TGCCCT TCA ACC CAC GTA CTT CTT ACC CAC ACA ATA AGC AGG ATT GCC
GTC TCC TAC CAA ACT AAA GTA AAC CTG TTG AGC GCT ATCAAG AGT CCT TGC
CAA CGG GAG ACC CCT GAA GGT GCA GAG GCA AAA CCA TGG TAC GAA CCC ATT
TAT CTC GGA GGG GTG TTC CAGTTG GAG AAG GGG GAC CGC CTG TCT GCC GAA
ATC AAT AGG CCA GAC TAC CTC AAC TTT CGC GAG TCC GGG C AG GTG TAT TTT
GGGATC ATA GCT TTG GGC GGT GGG GGA TCT CCT GTT GC T CAT GTC GTT GCA
AAC CCT CAG GCT GAA GGC CAA TTG CAA TGG CTC AA CAGG AGA GCT AAC GCA
TTG CTG GCC AAC GGG GTT GAG CTC CGC GAT AAC CAG CTG GTA GTT CCC TCA
GAG GGC TTG TAC CTT ATCTAT TCA CAG GTT CTC TTC AAA GGA CAA GGA TGT
CCT AGC ACA CAC GTC TTG CTT ACA CAT ACC ATT AGC CGG ATA GCA GTT
TCTTAT CAG ACT AAA GTT AAT CTC CTC TCT GCC ATA AAG TCA CCC TGT CAG
CGG GAA ACA CCT GAG GGT GCT GAA GCA AAA CCT TGGTAT GAA CCA ATA TAC
CTC GGT GGA GTT TTT CAA CTG GAG AAG GGC GAC AGA CTG AGC GAT GAA
ATA'AAC AGA CCT GAC TAC CTTAAT TTC CGA GAA TCA CCT CAA GTA TAC TTC
GGG ATT ATA GCC TTG GGG GGT GGA GGC TCC CCA GTG GCT CAT GTA GTC GCT
AATCCC CAA GCT GAA GGC CAA CTC CAA TGG CTT AAC AGG AGG GCC AAC GCA
CTC CTC GCA AAT GGA GTC GAG CTT AGG GAT AAT CAATTG GTG GTT CCC TCT
GAG GGC TTG TAT CTT ATT TAT TCA CAG GTC CTG TTT AAA GGC CAA GGC TGT
CCT TCT ACA CAT GTC CTGTTG ACT CAT ACC ATA AGT AGA ATA GCC GTG AGT

-continued

| Sequence Listing |
|---|

TAC CAG ACA AAG GTT AAC CTG CTT TCC GCA ATC AAA TCT CCA TGC CAA
CGCGAG ACCCCA GAA GGG GCA GAA GCA AAG CCT TGG TAC GAG CCC ATA TAT
CTC GGTGGG GTC TTT CAG CTC GAG AAA GGC GAC CGGCTT AGC GCT GAA ATC
AAC CGC CCA GAC TAT TTG AAC TTT CGG GAA AGT GGA CAA GTC TAC TTC GGT
ATC ATA GCA CTC

SEQ ID NO: 140 - Codon optimized nucleic acid sequence encoding
SEQ ID NO 120

GAA TCT AAG TAT GGA CCT CCT TGT CCA CCA TGT CCA GCT CCC GAG TTC CTG
GGA GGC CCA TCC GTG TTT TTG TTC CCC CCT AAGCCA AAA GAC ACA CTT ATG
ATA TCA AGA ACC CCA GAA GTT ACT TGT GTA GTC GTG GAC GTA TCC CAG GAA
GAC CCC GAG GTT CAATTT AAC TGG TAT GTA GAC GGC GTG GAA GTC CAT AAT
GCT AAG ACA AAG CCC CGG GAG GAA CAA TTC AAC TCC ACA TAC CGA GTAGTA
TCC GTA TTG ACC GTG CTC CAT CAG GAT TGG TTG AAT GGA AAG GAA TAC AAG
TGC AAA GTT TCT AAT AAG GGC CTG CCT TCTAGC ATC GAG AAG ACC ATC AGC
AAG GCT AAG GGA CAG CCT CGC GAA CCC CAA GTT TAT ACC CTT CCT CCT AGC
CAA GAG GAG ATGACT AAA AAT CAG GTG T CA CTC ACC TGC CTC GTC AAA GGA
TTC TAC CCA TCA GAT ATA GCA GTG GAA TGG GAG TCC AAC GGG CAACCT GAG
AAT AAC TAC AAA ACA ACT CCA CCT GTC CTG GAC TCC GAC GGC TCC TTC TTT
CTT TAT TCC AGA CTT ACC GTG GAC AAAAGC AGA TGG CAA GAG GGG AAT GTG
TTT AGC TGC AGT GTT ATG CAT GAA GCT TTG CAT AAT CAT TAC ACC CAA AAA
TCA CTT TCACTC TCT CTT GGT AAG GGG GGT GGG GGA TCT GGT GGG GGA GGC
TCC GTG CGA TCA AGC TCT AGG ACA CCC TCT GAT AAT CCT GTTGCC CAC GTC
GTC GCA AAT C CC CAG GCC GAA GGA CAG TTG CAG TGG CTG AAT CGA AGA GCT
AAC GCA CTG TTG GCA AAC GGG GTGGAG CTC AGG GAT AAC CAG TTG GTG GTG
CCT TCA GAA GGG CTT TAT CTC ATT TAC TCA CAA GTA CTC TTT AAA GGG CAA
GGG TGCCCA TCT ACT CAC GTG TTG CTG ACT CAC ACT ATT TCT CGA ATC GCA
GTT AGC TAT CAA ACC AAG GTA AAC TTG CTC AGT GCC ATAAAA AGT CCT TGT
CAA AGG GAG ACA CCC GAA GGA GCA GAA GCA AAG CCC TGG TAC GAG CCC ATT
TAC CTC GGT GGT GTC TTC CAGCTG GAG AAA GGA GAC CGG CTC TCT GCA GAG
ATA AAC AGA CCT GAC TAT CTC AAC TTT AGA GAA TCA GGC CAG GTT TAT TTC
GGGATC ATC GCA CTC TCC AGC CGG ACC CCC TCA GAC AAG CCC GTT GCA CAC
GTC GTT GCT AAC CCA CAA GCT GAA GGG CAG TTG CA GTGG TTG AAT CGA AGA
GCA AAC GCT CTC TTG GCC AAC GGT GTA GAA CTC GCG GAC AAC CAA CTG GTT
GTA CCT TCA GAA GGG CTCTAT CTG ATT TAC TCT CAG GTG CTT TTC AAG GGC
CAA GGG TGC CCT AGT ACA CAT GTT CTG CTT ACC CAC ACA ATT TCT AGA
ATTGCA GTT AGC TAC CAG ACT AAA GTC AAC CTG TTG AGT GCT ATC AAG TCC
CCT TGT CAG AGA GAA ACC CCA GAG G GA GCT GAG GCTAAA CCT TGG TAT GAG
CCC ATA TAC CTC GGT GGT GTA TTC CAA TTG GAG AAA GGT GAT CGA TTG TCA
GCT GAA ATC AAC AGA CCAGAC TAT CTG AAT GTC AGA GAG TCA GGA CAA GTT
TAC TTC GGC ATA ATC GCA TTG AGT AGT CGG ACA CCC TCC GAT AAA CCT
GTGGCA CAT GTT GTA GCT AAC CCT CAA GCA GAG GGG CAG CTC CAA TGG CTG
AAC CGG CGC GCT AAT GCC CTG TTG GCT AAC GGC GTTGAG TTG CGA GAT AAC
CAG CTG GTT GTG CCC TCT GAA GGT CTG TAC TTG ATC TAC TCC CAA GTC CTG
TTT AAG GGT C AA GGC TGTCCC AGC ACA CAC GTG TTG CTC ACC CAC ACT ATC
AGC CGG ATT GCC GTA AGC TAT CAA ACT AAA GTC AAT CTT CTG TCC GCC
ATCAAA AGT CCA TGT CAG CGC GAA ACC CCT GAG GGT GCC GAA GCC AAG CCT
TGG TAC GAG CCA ATC TAC CTG GGT GGC GTC TTT CAGCTC GAA AAG GGG GAC
CGG CTC TCT GCA GAG ATA AAT CGC CCT GAT TAT CTT AAC TTT CGC GAG TCC
GGG CAG GTA TAC TTT GGGATT ATA GCT CTT

---

The invention claimed is:

1. A nucleic acid encoding a fusion protein, wherein the nucleic acid comprises the sequence of SEQ ID NO: 36, SEQ ID NO: 37, SEQ ID NO: 38 or SEQ ID NO: 39.

2. An isolated host cell comprising the nucleic acid according to claim 1.

3. The nucleic acid of claim 1, wherein the fusion protein comprises SEQ ID NO: 31, SEQ ID NO: 32, SEQ ID NO: 34 or SEQ ID NO: 35.

4. A pharmaceutical composition comprising the nucleic acid of claim 1 and a pharmaceutically acceptable carrier.

5. A nucleic acid encoding a fusion protein, wherein the fusion protein comprises the sequence selected from the group consisting of SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 118, SEQ ID NO: 119 and SEQ ID NO: 120.

6. A pharmaceutical composition comprising the nucleic acid of claim 5 and a pharmaceutically acceptable carrier.

7. An isolated host cell comprising the nucleic acid according to claim 5.

* * * * *

SEQUENCE LISTING

Sequence total quantity: 140
SEQ ID NO: 1                moltype = AA  length = 233
FEATURE                     Location/Qualifiers
source                      1..233
                            mol_type = protein
                            organism = Homo sapiens
                            note = Full length TNF-alpha
SEQUENCE: 1
MSTESMIRDV ELAEEALPKK TGGPQGSRRC LFLSLFSFLI VAGATTLFCL LHFGVIGPQR   60
EEFPRDLSLI SPLAQAVRSS SRTPSDKPVA HVVANPQAEG QLQWLNRRAN ALLANGVELR  120
DNQLVVPSEG LYLIYSQVLF KGQGCPSTHV LLTHTISRIA VSYQTKVNLL SAIKSPCQRE  180
TPEGAEAKPW YEPIYLGGVF QLEKGDRLSA EINRPDYLDF AESGQVYFGI IAL         233

SEQ ID NO: 2                moltype = AA  length = 157
FEATURE                     Location/Qualifiers
source                      1..157
                            mol_type = protein
                            organism = Homo sapiens
                            note = Soluble TNF-alpha

```
SEQUENCE: 2
VRSSSRTPSD KPVAHVVANP QAEGQLQWLN RRANALLANG VELRDNQLVV PSEGLYLIYS    60
QVLFKGQGCP STHVLLTHTI SRIAVSYQTK VNLLSAIKSP CQRETPEGAE AKPWYEPIYL   120
GGVFQLEKGD RLSAEINRPD YLDFAESGQV YFGIIAL                            157

SEQ ID NO: 3           moltype = AA   length = 146
FEATURE                Location/Qualifiers
source                 1..146
                       mol_type = protein
                       organism = Homo sapiens
                       note = THD Domain with TNFR2 Agonist Sequences
SEQUENCE: 3
PVAHVVANPQ AEGQLQWLNR RANALLANGV ELRDNQLVVP SEGLYLIYSQ VLFKGQGCPS    60
THVLLTHTIS RIAVSYQTKV NLLSAIKSPC QRETPEGAEA KPWYEPIYLG GVFQLEKGDR   120
LSAEINRPDY LNFRESGQVY FGIIAL                                       146

SEQ ID NO: 4           moltype = AA   length = 11
FEATURE                Location/Qualifiers
source                 1..11
                       mol_type = protein
                       organism = Homo sapiens
                       note = Sequence from the ADAM17 cleavage site in the stalk
                        region to the C-terminus of the stalk region
SEQUENCE: 4
VRSSSRTPSD K                                                        11

SEQ ID NO: 5           moltype = AA   length = 232
FEATURE                Location/Qualifiers
source                 1..232
                       mol_type = protein
                       organism = Homo sapiens
                       note = Human IgG1 Fc
SEQUENCE: 5
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 6           moltype = AA   length = 232
FEATURE                Location/Qualifiers
source                 1..232
                       mol_type = protein
                       organism = Homo sapiens
                       note = Human IgG1 Fc with FcyR and C1q knockout
SEQUENCE: 6
EPKSSDKTHT CPPCPAPEAA GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPASIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 7           moltype = AA   length = 237
FEATURE                Location/Qualifiers
source                 1..237
                       mol_type = protein
                       organism = Homo sapiens
                       note = Human IgG1 Fc with N-terminal linker
SEQUENCE: 7
GGGGSEPKSC DKTHTCPPCP APELLGGPSV FLFPPKPKDT LMISRTPEVT CVVVDVSHED    60
PEVKFNWYVD GVEVHNAKTK PREEQYNSTY RVVSVLTVLH QDWLNGKEYK CKVSNKALPA   120
PIEKTISKAK GQPREPQVYT LPPSRDELTK NQVSLTCLVK GFYPSDIAVE WESNGQPENN   180
YKTTPPVLDS DGSFFLYSKL TVDKSRWQQG NVFSCSVMHE ALHNHYTQKS LSLSPGK      237

SEQ ID NO: 8           moltype = AA   length = 237
FEATURE                Location/Qualifiers
source                 1..237
                       mol_type = protein
                       organism = Homo sapiens
                       note = Human IgG1 Fc with FcyR and C1q knockout and linker
SEQUENCE: 8
GGGGSEPKSS DKTHTCPPCP APEAAGGPSV FLFPPKPKDT LMISRTPEVT CVVVDVSHED    60
PEVKFNWYVD GVEVHNAKTK PREEQYNSTY RVVSVLTVLH QDWLNGKEYK CKVSNKALPA   120
SIEKTISKAK GQPREPQVYT LPPSRDELTK NQVSLTCLVK GFYPSDIAVE WESNGQPENN   180
YKTTPPVLDS DGSFFLYSKL TVDKSRWQQG NVFSCSVMHE ALHNHYTQKS LSLSPGK      237

SEQ ID NO: 9           moltype = AA   length = 255
FEATURE                Location/Qualifiers
VARIANT                235..255
                       note = GGGGS repeats may be deleted
source                 1..255
```

```
                              mol_type = protein
                              organism = Homo sapiens
                              note = Human IgG1 Fc with C-terminal linker
SEQUENCE: 9
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GGGGSGGGGS   240
GGGGSGGGGS GGGGS                                                   255

SEQ ID NO: 10                 moltype = AA  length = 255
FEATURE                       Location/Qualifiers
VARIANT                       235..255
                              note = GGGGS repeats may be deleted
source                        1..255
                              mol_type = protein
                              organism = Homo sapiens
                              note = Human IgG1 Fc with FcyR and C1q knockout and
                                     C-terminal linker
SEQUENCE: 10
EPKSSDKTHT CPPCPAPEAA GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPASIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GGGGSGGGGS   240
GGGGSGGGGS GGGGS                                                   255

SEQ ID NO: 11                 moltype = AA  length = 229
FEATURE                       Location/Qualifiers
source                        1..229
                              mol_type = protein
                              organism = Homo sapiens
                              note = Human IgG4 Fc
SEQUENCE: 11
ESKYGPPCPS CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGK              229

SEQ ID NO: 12                 moltype = AA  length = 229
FEATURE                       Location/Qualifiers
source                        1..229
                              mol_type = protein
                              organism = Homo sapiens
                              note = Human IgG4 Fc with Ser to Pro mutation
SEQUENCE: 12
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGK              229

SEQ ID NO: 13                 moltype = AA  length = 234
FEATURE                       Location/Qualifiers
source                        1..234
                              mol_type = protein
                              organism = Homo sapiens
                              note = Human IgG4 Fc with N-terminal linker
SEQUENCE: 13
GGGGSESKYG PPCPSCPAPE FLGGPSVFLF PPKPKDTLMI SRTPEVTCVV VDSQEDPEV     60
QFNWYVDGVE VHNAKTKPRE EQFNSTYRVV SVLTVLHQDW LNGKEYKCKV SNKGLPSSIE   120
KTISKAKGQP REPQVYTLPP SQEEMTKNQV SLTCLVKGFY PSDIAVEWES NGQPENNYKT   180
TPPVLDSDGS FFLYSRLTVD KSRWQEGNVF SCSVMHEALH NHYTQKSLSL SLGK         234

SEQ ID NO: 14                 moltype = AA  length = 234
FEATURE                       Location/Qualifiers
source                        1..234
                              mol_type = protein
                              organism = Homo sapiens
                              note = Human IgG4 Fc with Ser to Pro Mutation and
                                     N-terminal linker
SEQUENCE: 14
GGGGSESKYG PPCPPCPAPE FLGGPSVFLF PPKPKDTLMI SRTPEVTCVV VDSQEDPEV     60
QFNWYVDGVE VHNAKTKPRE EQFNSTYRVV SVLTVLHQDW LNGKEYKCKV SNKGLPSSIE   120
KTISKAKGQP REPQVYTLPP SQEEMTKNQV SLTCLVKGFY PSDIAVEWES NGQPENNYKT   180
TPPVLDSDGS FFLYSRLTVD KSRWQEGNVF SCSVMHEALH NHYTQKSLSL SLGK         234

SEQ ID NO: 15                 moltype = AA  length = 252
FEATURE                       Location/Qualifiers
VARIANT                       233..252
                              note = GGGGS repeats may be deleted
```

```
source                  1..252
                        mol_type = protein
                        organism = Homo sapiens
                        note = Human IgG4 Fc with C-terminal linker
SEQUENCE: 15
ESKYGPPCPS CPAPEFLGGP SVFLFPPKPK DTLMISRTPE VTCVVVDVSQ EDPEVQFNWY      60
VDGVEVHNAK TKPREEQFNS TYRVVSVLTV LHQDWLNGKE YKCKVSNKGL PSSIEKTISK     120
AKGQPREPQV YTLPPSQEEM TKNQVSLTCL VKGFYPSDIA VEWESNGQPE NNYKTTPPVL     180
DSDGSFFLYS RLTVDKSRWQ EGNVFSCSVM HEALHNHYTQ KSLSLSLGGG GSGGGGSGGG     240
GSGGGGSGGG GS                                                        252

SEQ ID NO: 16           moltype = AA  length = 252
FEATURE                 Location/Qualifiers
VARIANT                 232..252
                        note = GGGGS repeats may be deleted
source                  1..252
                        mol_type = protein
                        organism = Homo sapiens
                        note = Human IgG4 Fc with Ser to Pro Mutation and
                         C-terminal linker
SEQUENCE: 16
ESKYGPPCPP CPAPEFLGGP SVFLFPPKPK DTLMISRTPE VTCVVVDVSQ EDPEVQFNWY      60
VDGVEVHNAK TKPREEQFNS TYRVVSVLTV LHQDWLNGKE YKCKVSNKGL PSSIEKTISK     120
AKGQPREPQV YTLPPSQEEM TKNQVSLTCL VKGFYPSDIA VEWESNGQPE NNYKTTPPVL     180
DSDGSFFLYS RLTVDKSRWQ EGNVFSCSVM HEALHNHYTQ KSLSLSLGGG GSGGGGSGGG     240
GSGGGGSGGG GS                                                        252

SEQ ID NO: 17           moltype = AA  length = 228
FEATURE                 Location/Qualifiers
source                  1..228
                        mol_type = protein
                        organism = Homo sapiens
                        note = Human IgG2 Fc
SEQUENCE: 17
ERKCCVECPP CPAPPVAGPS VFLFPPKPKD TLMISRTPEV TCVVVDVSHE DPEVQFNWYV      60
DGVEVHNAKT KPREEQFNST FRVVSVLTVV HQDWLNGKEY KCKVSNKGLP APIEKTISKT     120
KGQPREPQVY TLPPSREEMT KNQVSLTCLV KGFYPSDIAV EWESNGQPEN NYKTTPPMLD     180
SDGSFFLYSK LTVDKSRWQQ GNVFSCSVMH EALHNHYTQK SLSLSPGK                  228

SEQ ID NO: 18           moltype = AA  length = 228
FEATURE                 Location/Qualifiers
source                  1..228
                        mol_type = protein
                        organism = Homo sapiens
                        note = Human IgG2 Fc with C1q knockout
SEQUENCE: 18
ERKSSVECPP CPAPPVAGPS VFLFPPKPKD TLMISRTPEV TCVVVDVSHE DPEVQFNWYV      60
DGVEVHNAKT KPREEQFNST FRVVSVLTVV HQDWLNGKEY KCKVSNKGLP ASIEKTISKT     120
KGQPREPQVY TLPPSREEMT KNQVSLTCLV KGFYPSDIAV EWESNGQPEN NYKTTPPMLD     180
SDGSFFLYSK LTVDKSRWQQ GNVFSCSVMH EALHNHYTQK SLSLSPGK                  228

SEQ ID NO: 19           moltype = AA  length = 233
FEATURE                 Location/Qualifiers
source                  1..233
                        mol_type = protein
                        organism = Homo sapiens
                        note = Human IgG2 Fc with N-terminal linker
SEQUENCE: 19
GGGGSERKCC VECPPCPAPP VAGPSVFLFP PKPKDTLMIS RTPEVTCVVV DVSHEDPEVQ      60
FNWYVDGVEV HNAKTKPREE QFNSTFRVVS VLTVVHQDWL NGKEYKCKVS NKGLPAPIEK     120
TISKTKGQPR EPQVYTLPPS REEMTKNQVS LTCLVKGFYP SDIAVEWESN GQPENNYKTT     180
PPMLDSDGSF FLYSKLTVDK SRWQQGNVFS CSVMHEALHN HYTQKSLSLS PGK            233

SEQ ID NO: 20           moltype = AA  length = 233
FEATURE                 Location/Qualifiers
source                  1..233
                        mol_type = protein
                        organism = Homo sapiens
                        note = Human IgG2 Fc with C1q knockout and N-terminal linker
SEQUENCE: 20
GGGGSERKSS VECPPCPAPP VAGPSVFLFP PKPKDTLMIS RTPEVTCVVV DVSHEDPEVQ      60
FNWYVDGVEV HNAKTKPREE QFNSTFRVVS VLTVVHQDWL NGKEYKCKVS NKGLPASIEK     120
TISKTKGQPR EPQVYTLPPS REEMTKNQVS LTCLVKGFYP SDIAVEWESN GQPENNYKTT     180
PPMLDSDGSF FLYSKLTVDK SRWQQGNVFS CSVMHEALHN HYTQKSLSLS PGK            233

SEQ ID NO: 21           moltype = AA  length = 251
FEATURE                 Location/Qualifiers
VARIANT                 232..251
                        note = GGGGS repeats may be deleted
```

```
source                    1..251
                          mol_type = protein
                          organism = Homo sapiens
                          note = Human IgG2 Fc with C-terminal linker
SEQUENCE: 21
ERKCCVECPP CPAPPVAGPS VFLFPPKPKD TLMISRTPEV TCVVVDVSHE DPEVQFNWYV    60
DGVEVHNAKT KPREEQFNST FRVVSVLTVV HQDWLNGKEY KCKVSNKGLP APIEKTISKT   120
KGQPREPQVY TLPPSREEMT KNQVSLTCLV KGFYPSDIAV EWESNGQPEN NYKTTPPMLD   180
SDGSFFLYSK LTVDKSRWQQ GNVFSCSVMH EALHNHYTQK SLSLSPGGGG SGGGGSGGGG   240
SGGGGSGGGG S                                                       251

SEQ ID NO: 22             moltype = AA  length = 251
FEATURE                   Location/Qualifiers
REGION                    232..251
                          note = GGGGS repeats may be deleted
source                    1..251
                          mol_type = protein
                          organism = Homo sapiens
                          note = Human IgG2 Fc with C1q knockout and C-terminal linker
SEQUENCE: 22
ERKSSVECPP CPAPPVAGPS VFLFPPKPKD TLMISRTPEV TCVVVDVSHE DPEVQFNWYV    60
DGVEVHNAKT KPREEQFNST FRVVSVLTVV HQDWLNGKEY KCKVSNKGLP ASIEKTISKT   120
KGQPREPQVY TLPPSREEMT KNQVSLTCLV KGFYPSDIAV EWESNGQPEN NYKTTPPMLD   180
SDGSFFLYSK LTVDKSRWQQ GNVFSCSVMH EALHNHYTQK SLSLSPGGGG SGGGGSGGGG   240
SGGGGSGGGG S                                                       251

SEQ ID NO: 23             moltype = AA  length = 106
FEATURE                   Location/Qualifiers
source                    1..106
                          mol_type = protein
                          organism = synthetic construct
                          note = EHD2 dimerization domain
SEQUENCE: 23
DFTPPTVKIL QSSCDGGGHF PPTIQLLCLV SGYTPGTINI TWLEDGQVMD VDLSTASTTQ    60
EGELASTQSE LTLSQKHWLS DRTYTCQVTY QGHTFEDSTK KCADSN                 106

SEQ ID NO: 24             moltype = AA  length = 111
FEATURE                   Location/Qualifiers
source                    1..111
                          mol_type = protein
                          organism = synthetic construct
                          note = MHD2 dimerization domain
SEQUENCE: 24
AELPPKVSVF VPPRDGFFGN PRKSKLICQA TGFSPRQIQV SWLREGKQVG SGVTTDQVQA    60
EAKESGPTTY KVTSTLTIKE SDWLGQSMFT CRVDHRGLTF QQNASSMCVP D           111

SEQ ID NO: 25             moltype = AA  length = 5
FEATURE                   Location/Qualifiers
source                    1..5
                          mol_type = protein
                          organism = synthetic construct
                          note = linker
SEQUENCE: 25
GGGGS                                                                5

SEQ ID NO: 26             moltype = AA  length = 31
FEATURE                   Location/Qualifiers
source                    1..31
                          mol_type = protein
                          organism = synthetic construct
                          note = TNF-a stalk region
SEQUENCE: 26
GPQREEFPRD LSLISPLAQA VRSSSRTPSD K                                  31

SEQ ID NO: 27             moltype = AA  length = 10
FEATURE                   Location/Qualifiers
source                    1..10
                          mol_type = protein
                          organism = synthetic construct
                          note = linker
SEQUENCE: 27
GGGGSGGGGS                                                          10

SEQ ID NO: 28             moltype = AA  length = 8
FEATURE                   Location/Qualifiers
source                    1..8
                          mol_type = protein
                          organism = synthetic construct
                          note = stalk based linker
```

-continued

```
SEQUENCE: 28
SSRTPSDK                                                                     8

SEQ ID NO: 29          moltype = AA   length = 16
FEATURE                Location/Qualifiers
source                 1..16
                       mol_type = protein
                       organism = synthetic construct
                       note = G/S Stalk based linker
SEQUENCE: 29
GGGGSVRSSS RTPSDK                                                           16

SEQ ID NO: 30          moltype = AA   length = 13
FEATURE                Location/Qualifiers
source                 1..13
                       mol_type = protein
                       organism = synthetic construct
                       note = G/S Stalk based linker
SEQUENCE: 30
GGGGSSSRTP SDK                                                              13

SEQ ID NO: 31          moltype = AA   length = 700
FEATURE                Location/Qualifiers
source                 1..700
                       mol_type = protein
                       organism = synthetic construct
                       note = IgG1 Fc with mutations;GGGGS2; THDR2; stalk
                         linker;THDR2; stalk linker; THDR2
SEQUENCE: 31
EPKSSDKTHT CPPCPAPEAA GGPSVFLFPP KPKDTLMISR TPEVTCVVVD VSHEDPEVKF            60
NWYVDGVEVH NAKTKPREEQ YNSTYRVVSV LTVLHQDWLN GKEYKCKVSN KALPASIEKT           120
ISKAKGQPRE PQVYTLPPSR DELTKNQVSL TCLVKGFYPS DIAVEWESNG QPENNYKTTP           180
PVLDSDGSFF LYSKLTVDKS RWQQGNVFSC SVMHEALHNH YTQKSLSLSP GGGGSGGGGS           240
PVAHVVANPQ AEGQLQWLNR RANALLANGV ELRDNQLVVP SEGLYLIYSQ VLFKGQGCPS           300
THVLLTHTIS RIAVSYQTKV NLLSAIKSPC QRETPEGAEA KPWYEPIYLG GVFQLEKGDR           360
LSAEINRPDY LNFRESGQVY FGIIALVRSS SRTPSDKPVA HVVANPQAEG QLQWLNRRAN           420
ALLANGVELR DNQLVVPSEG LYLIYSQVLF KGQGCPSTHV LLTHTISRIA VSYQTKVNLL           480
SAIKSPCQRE TPEGAEAKPW YEPIYLGGVF QLEKGDRLSA EINRPDYLNF RESGQVYFGI           540
IALVRSSSRT PSDKPVAHVV ANPQAEGQLQ WLNRRANALL ANGVELRDNQ LVVPSEGLYL           600
IYSQVLFKGQ GCPSTHVLLT HTISRIAVSY QTKVNLLSAI KSPCQRETPE GAEAKPWYEP           660
IYLGGVFQLE KGDRLSAEIN RPDYLNFRES GQVYFGIIAL                                 700

SEQ ID NO: 32          moltype = AA   length = 710
FEATURE                Location/Qualifiers
source                 1..710
                       mol_type = protein
                       organism = synthetic construct
                       note = IgG1 Fc with mutations; G/S stalk linker; THDR2;
                         G/Sshort stalk linker; THDR2; G/S short stalk linker; THDR2
SEQUENCE: 32
EPKSSDKTHT CPPCPAPEAA GGPSVFLFPP KPKDTLMISR TPEVTCVVVD VSHEDPEVKF            60
NWYVDGVEVH NAKTKPREEQ YNSTYRVVSV LTVLHQDWLN GKEYKCKVSN KALPASIEKT           120
ISKAKGQPRE PQVYTLPPSR DELTKNQVSL TCLVKGFYPS DIAVEWESNG QPENNYKTTP           180
PVLDSDGSFF LYSKLTVDKS RWQQGNVFSC SVMHEALHNH YTQKSLSLSP GGGGSVRSSS           240
RTPSDKPVAH VVANPQAEGQ LQWLNRRANA LLANGVELRD NQLVVPSEGL YLIYSQVLFK           300
GQGCPSTHVL LTHTISRIAV SYQTKVNLLS AIKSPCQRET PEGAEAKPWY EPIYLGGVFQ           360
LEKGDRLSAE INRPDYLNFR ESGQVYFGII ALGGGGSSSR TPSDKPVAHV VANPQAEGQL           420
QWLNRRANAL LANGVELRDN QLVVPSEGLY LIYSQVLFKG QGCPSTHVLL THTISRIAVS           480
YQTKVNLLSA IKSPCQRETP EGAEAKPWYE PIYLGGVFQL EKGDRLSAEI NRPDYLNFRE           540
SGQVYFGIIA LGGGGSSSRT PSDKPVAHVV ANPQAEGQLQ WLNRRANALL ANGVELRDNQ           600
LVVPSEGLYL IYSQVLFKGQ GCPSTHVLLT HTISRIAVSY QTKVNLLSAI KSPCQRETPE           660
GAEAKPWYEP IYLGGVFQLE KGDRLSAEIN RPDYLNFRES GQVYFGIIAL                     710

SEQ ID NO: 33          moltype = AA   length = 157
FEATURE                Location/Qualifiers
source                 1..157
                       mol_type = protein
                       organism = synthetic construct
                       note = Soluble TNF-a sequence with TNFR2 agonist mutations
SEQUENCE: 33
VRSSSRTPSD KPVAHVVANP QAEGQLQWLN RRANALLANG VELRDNQLVV PSEGLYLIYS            60
QVLFKGQGCP STHVLLTHTI SRIAVSYQTK VNLLSAIKSP CQRETPEGAE AKPWYEPIYL           120
GGVFQLEKGD RLSAEINRPD YLNFRESGQV YFGIIAL                                   157

SEQ ID NO: 34          moltype = AA   length = 701
FEATURE                Location/Qualifiers
source                 1..701
                       mol_type = protein
                       organism = synthetic construct
```

```
                            note = scTNFR2 agonist with C-terminal IgG1 with
                                mutations.This is soluble TNF-a sequence, which includes
                                VRSSSRTPSDK atN-terminus prior to THD domain.
SEQUENCE: 34
VRSSSRTPSD KPVAHVVANP QAEGQLQWLN RRANALLANG VELRDNQLVV PSEGLYLIYS    60
QVLFKGQGCP STHVLLTHTI SRIAVSYQTK VNLLSAIKSP CQRETPEGAE AKPWYEPIYL   120
GGVFQLEKGD RLSAEINRPD YLNFRESGQV YFGIIALVRS SSRTPSDKPV AHVVANPQAE   180
GQLQWLNRRA NALLANGVEL RDNQLVVPSE GLYLIYSQVL FKGQGCPSTH VLLTHTISRI   240
AVSYQTKVNL LSAIKSPCQR ETPEGAEAKP WYEPIYLGGV FQLEKGDRLS AEINRPDYLN   300
FRESGQVYFG IIALVRSSSR TPSDKPVAHV VANPQAEGQL QWLNRRANAL LANGVELRDN   360
QLVVPSEGLY LIYSQVLFKG QGCPSTHVLL THTISRIAVS YQTKVNLLSA IKSPCQRETP   420
EGAEAKPWYE PIYLGGVFQL EKGDRLSAEI NRPDYLNFRE SGQVYFGIIA LEPKSSDKTH   480
TCPPCPAPEA AGGPSVFLFP PKPKDTLMIS RTPEVTCVVV DVSHEDPEVK FNWYVDGVEV   540
HNAKTKPREE QYNSTYRVVS VLTVLHQDWL NGKEYKCKVS NKALPASIEK TISKAKGQPR   600
EPQVYTLPPS RDELTKNQVS LTCLVKGFYP SDIAVEWESN GQPENNYKTT PPVLDSDGSF   660
FLYSKLTVDK SRWQQGNVFS CSVMHEALHN HYTQKSLSLS P                      701

SEQ ID NO: 35           moltype = AA  length = 706
FEATURE                 Location/Qualifiers
source                  1..706
                        mol_type = protein
                        organism = synthetic construct
                        note = scTNFR2 agonist with C-terminal IgG1 with
                            mutations.This is soluble TNF-a sequence, which includes
                            VRSSSRTPSDK atN-terminus prior to THD domain and GGGGS
                            prior to IgG1.
SEQUENCE: 35
VRSSSRTPSD KPVAHVVANP QAEGQLQWLN RRANALLANG VELRDNQLVV PSEGLYLIYS    60
QVLFKGQGCP STHVLLTHTI SRIAVSYQTK VNLLSAIKSP CQRETPEGAE AKPWYEPIYL   120
GGVFQLEKGD RLSAEINRPD YLNFRESGQV YFGIIALVRS SSRTPSDKPV AHVVANPQAE   180
GQLQWLNRRA NALLANGVEL RDNQLVVPSE GLYLIYSQVL FKGQGCPSTH VLLTHTISRI   240
AVSYQTKVNL LSAIKSPCQR ETPEGAEAKP WYEPIYLGGV FQLEKGDRLS AEINRPDYLN   300
FRESGQVYFG IIALVRSSSR TPSDKPVAHV VANPQAEGQL QWLNRRANAL LANGVELRDN   360
QLVVPSEGLY LIYSQVLFKG QGCPSTHVLL THTISRIAVS YQTKVNLLSA IKSPCQRETP   420
EGAEAKPWYE PIYLGGVFQL EKGDRLSAEI NRPDYLNFRE SGQVYFGIIA LGGGGSEPKS   480
SDKTHTCPPC PAPEAAGGPS VFLFPPKPKD TLMISRTPEV TCVVVDVSHE DPEVKFNWYV   540
DGVEVHNAKT KPREEQYNST YRVVSVLTVL HQDWLNGKEY KCKVSNKALP ASIEKTISKA   600
KGQPREPQVY TLPPSRDELT KNQVSLTCLV KGFYPSDIAV EWESNGQPEN NYKTTPPVLD   660
SDGSFFLYSK LTVDKSRWQQ GNVFSCSVMH EALHNHYTQK SLSLSP                 706

SEQ ID NO: 36           moltype = DNA  length = 2100
FEATURE                 Location/Qualifiers
source                  1..2100
                        mol_type = other DNA
                        organism = synthetic construct
                        note = nucleic acid encoding SEQ ID NO:31 optimized for
                            Musmusculus expression by www.jcat.de
SEQUENCE: 36
gagcccaaga gcagcgacaa gacccacacc tgcccccct gccccgcccc cgaggccgcc     60
ggcggcccca gcgtgttcct gttccccccc aagcccaagg acaccctgat gatcagcagg   120
acccccgagg tgacctgcgt ggtggtggac gtgagccacg aggacccga ggtgaagttc   180
aactggtacg tggacggcgt ggaggtgcac aacgccaaga ccaagcccag ggaggagcag   240
tacaacagca cctacagggt ggtgagcgtg ctgaccgtgc tgcaccagga ctggctgaac   300
ggcaaggagt acaagtgcaa ggtgagcaac aaggccctgc cgccagcat cgagaagacc   360
atcagcaagg ccaagggcca gccccaggtg tacaccctgc ccccagcagg   420
gacgagctga ccaagaacca ggtgagcctg acctgcctgg tgaagggctt ctaccccagc   480
gacatcgccg tggagtggga gagcaacggc cagcccgaga caactacaa gaccacccc   540
cccgtgctgg acagcgacgg cagcttcttc ctgtacagca agctgaccgt ggacaagagc   600
aggtggcagc agggcaacgt gttcagctgc agcgtgatgc acgaggccct gcacaaccac   660
tacacccaga agagcctgag cctgagcccc ggcggcggcg gcagcggcgg cggcggccac   720
cccgtggccc acgtggtggc caaccccag gccgagggcc agctgcagtg gctgaacagg   780
agggccaacg ccctgctggc caacggcgtg gagctgaggg acaaccagct ggtggtgccc   840
agcgagggcc tgtacctgat ctacagccag gtgctgttca agggccaggg ctgccccagc   900
acccacgtgc tgctgaccca caccatcagc aggatcgccg tgagctacca gaccaaggtg   960
aacctgctga gcgccatcaa gagccccgc cagagggaga cccccgaggg cgccgaggcc  1020
aagccctggt acgagcccat ctaccctggg ggcgtgttcc agctggagaa gggcgacagg  1080
ctgagcgccg agatcaacag gcccgactac ctgaacttca gggagagcgg ccaggtgtac  1140
ttcggcatca tcgcccctgg tgaggagcag cagggaccc ccagcgacaa gcccgtgcc  1200
cacgtggtgg ccaaccccca ggccgagggc cagctgcagt ggctgaacag gagggccaac  1260
gccctgctgg ccaacggcgt ggagctgagg gacaaccagc tggtggtgcc cagcgagggc  1320
ctgtacctga tctacagcca ggtgctgttc aagggccagg gctgccccag cacccacgtg  1380
ctgctgaccc acaccatcag caggatcgcc gtgagctacc agaccaaggt gaacctgctg  1440
agcgccatca agagcccctg ccagagggag acccccgagg gcgccgaggc caagccctgg  1500
tacgagccca tctacctggg cggcgtgttc cagctggagaa gggcgacagg ctgagcgcc  1560
gagatcaaca ggcccgacta cctgaacttc agggagagcg gccaggtgta cttcggcatc  1620
atcgccctgg tgaggagcag cagcaggacc cccagcgaca agcccgtggc ccacgtggtg  1680
gccaaccccc aggccgaggg ccagctgcag tggctgaaca ggagggccaa cgccctgctg  1740
gccaacggcg tggagctgag ggacaaccag ctggtggtgc ccagcgaggg cctgtacctg  1800
atctacagcc aggtgctgtt caagggccag ggctgcccca gcacccacgt gctgctgacc  1860
```

```
cacaccatca gcaggatcgc cgtgagctac cagaccaagg tgaacctgct gagcgccatc    1920
aagagcccct gccagaggga gaccccgag ggcgccgagg ccaagccctg gtacgagccc    1980
atctacctgg gcggcgtgtt ccagctggag aagggcgaca ggctgagcgc cgagatcaac    2040
aggcccgact acctgaactt cagggagagc ggccaggtgt acttcggcat catcgccctg    2100
```

| | | |
|---|---|---|
| SEQ ID NO: 37 | moltype = DNA   length = 2130 | |
| FEATURE | Location/Qualifiers | |
| source | 1..2130 | |
| | mol_type = other DNA | |
| | organism = synthetic construct | |
| | note = nucleic acid encoding SEQ ID NO:32 optimized for Musmusculus expression by www.jcat.de | |

SEQUENCE: 37
```
gagcccaaga gcagcgacaa gacccacacc tgccccccct gccccgcccc cgaggccgcc     60
ggcggcccca gcgtgttcct gttccccccc aagcccaagg acaccctgat gatcagcagg    120
accccccgag tgacctgcgt ggtggtggac gtgagccacg aggaccccga ggtgaagttc    180
aactggtacg tggacggcgt ggaggtgcac aacgccaaga ccaagcccag ggaggagcag    240
tacaacagca cctacagggt ggtgagcgtg ctgaccgtgc tgcaccagga ctggctgaac    300
ggcaaggagt acaagtgcaa ggtgagcaac aaggccctgc cgccagcat cgagaagacc     360
atcagcaagg ccaaggggcca gcccaggag ccccaggtgt acaccctgcc ccccagcagg    420
gacgagctga ccaagaacca ggtgagcctg acctgcctgg tgaagggctt ctaccccagc    480
gacatcgccg tggagtggga gagcaacggc cagcccgaga acaactacaa gaccacccc    540
cccgtgctgg acagcgacgg cagcttcttc ctgtacagca gctgaccgt ggacaagagc     600
aggtggcagc agggcaacgt gttcagctgc agcgtgatgc acgaggccct gcacaaccac    660
tacacccaga gagcctgag cctgagcccc ggcggcggcg gcagcgtgag gagcagcagc     720
aggaccccca gcgacaagcc cgtgccccac gtggtggcca cccccaggcc gcagggcgag    780
ctgcagtggc tgaacaggag ggccaacgcc ctgctggcca acggcgtgga gctgagggac    840
aaccagctgg tggtgcccag cgagggcctg tacctgatct acagccaggt gctgttcaag    900
ggccagggct gccccagcac ccacgtgctg ctgacccaca ccatcagcag gatcgccgtg    960
agctaccaga ccaaggtgaa cctgctgagc gccatcaaga gcccctgcca gagggagacc   1020
cccgagggcg ccgaggccaa gccctggtac gagcccatct acctgggcgg cgtgttccag   1080
ctggagaagg gcgacaggct gagcgccgag atcaacaggc ccgactacct gaacttcagg   1140
gagagcggcc aggtgtactt cggcatcatc gccctgggcg cggcggcag cagcagcagg    1200
accccagcg acaagcccgt ggcccacgtg gtggccaacg cccaggccga gggccagctg   1260
cagtggctga acaggagggc caaccctg ctggccaacg gcgtggagct gagggacaac    1320
cagctggtgg tgcccagcga gggcctgtac ctgatctaca gccaggtgct gttcaagggc   1380
cagggctgcc ccagcaccca cgtgctgctg acccacacca tcagcaggat cgccgtgagc   1440
taccagacca aggtgaacct gctgagcgcc atcaagagcc cctgccagag ggagaccccc   1500
gagggcgccg aggccaagcc ctggtacgag cccatctacc tgggcggcgt gttccagctg   1560
gagaagggcg acaggctgag cgccgagatc aacaggcccg actacctgaa cttcaggag    1620
agcggccagg tgtacttcgg catcatcgcc ctggcggcg cggcagcag cagcaggacc     1680
cccagcgaca agcccgtggc ccacgtggtg gccaacccc aggccgaggg ccagctgcag   1740
tggctgaaca ggagggccaa cgccctgctg gccaacggcg tggagctgag ggacaacagc  1800
ctggtggtgc ccagcgaggg cctgtacctg atctacagcc aggtgctgtt caagggccag   1860
ggctgcccca gcacccacgt gctgctgacc cacaccatca gcaggatcgc cgtgagctac   1920
cagaccaagg tgaacctgct gagcgccatc aagagcccct gccagaggga gaccccgag   1980
ggcgccgagg ccaagccctg gtacgagccc atctacctgg gcggcgtgtt ccagctggag   2040
aagggcgaca ggctgagcgc cgagatcaac aggcccgact acctgaactt cagggagagc   2100
ggccaggtgt acttcggcat catcgccctg                                   2130
```

| | | |
|---|---|---|
| SEQ ID NO: 38 | moltype = DNA   length = 2103 | |
| FEATURE | Location/Qualifiers | |
| source | 1..2103 | |
| | mol_type = other DNA | |
| | organism = synthetic construct | |
| | note = nucleic acid encoding SEQ ID NO:34 optimized for Musmusculus expression by www.jcat.de | |

SEQUENCE: 38
```
gtgaggagca gcagcaggac ccccagcgac aagcccgtgg cccacgtggt ggccaacccc     60
caggccgagg gccagctgca gtggctgaac aggagggcca acgccctgct ggccaacggc    120
gtggagctga gggacaacca gctggtggtg cccagcgagg gcctgtacct gatctacagc    180
caggtgctgt tcaagggcca gggctgcccc agcacccacg tgctgctgac ccacaccatc    240
agcaggatcg ccgtgagcta ccagaccaag gtgaacctgc tgagcgccat caagagcccc    300
tgccagaggg agaccccga gggcgccgag gccaagcctg gtacgagcc catctacctg     360
ggcggcgtgt tccagctgga aagggcgac aggctgagcg ccgagatcaa caggcccgac   420
tacctgaact tcagggagag cggccaggtg tacttcggca tcatcgccct ggtgaggagc    480
agcagcagga ccccagcga caagcccgtg gcccacgtg tggccaaccc caggccgag     540
ggccagctgc agtggctgaa caggagggcc aacgccctgc tggccaacgg cgtggagctg    600
agggacaacc agctggtggt gcccagcgag ggcctgtacc tgatctacag ccaggtgctg    660
ttcaagggcc agggctgccc cagcacccac gtgctgctga cccacaccat cagcaggatc    720
gccgtgagct accagaccaa ggtgaacctg ctgagcgcca tcaagagccc ctgccagagg    780
gagacccccg agggcgccga ggccaagccc tggtacgagc ccatctacct gggcggcgtg    840
ttccagctgg agaagggcga caggctgagc gccgagatca acaggcccga ctacctgaac    900
ttcagggaga gcggccaggt gtacttcggc atcatcgccc tggtgaggag cagcagcagg    960
acccccagcg acaagcccgt ggcccacgtg gtggccaacc ccaggccgag ggccagctg   1020
cagtggctga acaggagggc caacgccctg ctggccaacg gcgtggagct gagggacaac   1080
cagctggtgg tgcccagcga gggcctgtac ctgatctaca gccaggtgct gttcaagggc   1140
cagggctgcc ccagcaccca cgtgctgctg acccacacca tcagcaggat cgccgtgagc   1200
taccagacca aggtgaacct gctgagcgcc atcaagagcc cctgccagag ggagaccccc   1260
```

-continued

```
gagggcgccg aggccaagcc ctggtacgag cccatctacc tgggcggcgt gttccagctg 1320
gagaagggcg acaggctgag cgccgagatc aacaggcccg actacctgaa cttcagggag 1380
agcggccagg tgtacttcgg catcatcgcc ctggagccca gagcagcga caagacccac 1440
acctgccccc cctgccccgc ccccgaggcc gccggcggcc ccagcgtgtt cctgttcccc 1500
cccaagccca aggacaccct gatgatcagc aggacccccg aggtgacctg cgtggtggtg 1560
gacgtgagcc acgaggaccc cgaggtgaag ttcaactggt acgtggacgg cgtggaggtg 1620
cacaacgcca agaccaagcc cagggaggag cagtacaaca gcacctacag ggtggtgagc 1680
gtgctgaccg tgctgcacca ggactggctg aacggcaagg agtacaagtg caaggtgagc 1740
aacaaggccc tgcccgccag catcgagaag accatcagca aggccaaggg ccagccccgg 1800
gagccccagg tgtacaccct gccccccagc agggacgagc tgaccaagaa ccaggtgagc 1860
ctgacctgcc tggtgaaggg cttctacccc agcgacatcg ccgtggagtg ggagagcaac 1920
ggccagcccg agaacaacta caagaccacc ccccccgtgc tggacagcga cggcagcttc 1980
ttcctgtaca gcaagctgac cgtggacaag agcaggtggc agcagggcaa cgtgttcagc 2040
tgcagcgtga tgcacgaggc cctgcacaac cactacaccc agaagagcct gagcctgagc 2100
ccc                                                                2103

SEQ ID NO: 39          moltype = DNA  length = 2118
FEATURE                Location/Qualifiers
source                 1..2118
                       mol_type = other DNA
                       organism = synthetic construct
                       note = nucleic acid encoding SEQ ID NO:35 optimized for
                       Musmusculus expression by www.jcat.de
SEQUENCE: 39
gtgaggagca gcagcaggac ccccagcgac aagcccgtgg cccacgtggt ggccaacccc 60
caggccgagg gccagctgca gtggctgaac aggagggcca acgccctgct ggccaacggc 120
gtggagctga gggacaacca gctggtggtg cccagcgagg gcctgtacct gatctacagc 180
caggtgctgt tcaagggcca gggctgcccc agcacccacg tgctgctgac ccacaccatc 240
agcaggatcc ccgtgagcta ccagaccaag gtgaacctgc tgagcgccat caagagcccc 300
tgccagaggg agaccccccga gggcgccgag gccaagccct ggtacgagcc catctacctg 360
ggcggcgtgt tccagctgga agggcgcag aggctgagcg ccgagatcaa caggcccgac 420
tacctgaact tcagggagag cggccaggtg tacttcggca tcatcgccct ggtgaggagc 480
agcagcagga cccccagcga caagcccgtg gcccacgtgg tggccaaccc caggccgag 540
ggcagctgc agtggctgaa caggagggcc aacgccctgc tggccaacgg cgtggagctg 600
agggacaacc agctggtggt gcccagcgag ggcctgtacc tgatctacag ccaggtgctg 660
ttcaagggcc agggctgccc cagcacccac gtgctgctga cccacaccat cagcaggatc 720
gccgtgagct accagaccaa ggtgaacctg ctgagcgcca tcaagagccc ctgccagagg 780
gagacccccg agggcgccga ggccaagccc tggtacgagc ccatctacct gggcggcgtg 840
ttccagctgg agaagggcga caggctgagc gccgagatca acaggcccga ctacctgaac 900
ttcagggaga gcggccaggt gtacttcggc atcatcgccc tggtgaggag cagcagcagg 960
accccccagcg acaagcccgt ggcccacgtg gtggccaacc ccaggccgag ggccagctg 1020
cagtggctga acaggagggc caacgccctg ctggccaacg gcgtggagct gagggacaac 1080
cagctggtgg tgcccagcga gggcctgtac ctgatctaca gccaggtgct gttcaagggc 1140
cagggctgcc ccagcaccca cgtgctgctg acccacacca tcagcaggat cgccgtgagc 1200
taccagacca aggtgaacct gctgagcgcc atcaagagcc cctgccagag ggagacccc 1260
gagggcgccg aggccaagcc ctggtacgag cccatctacc tgggcggcgt gttccagctg 1320
gagaagggcg acaggctgag cgccgagatc aacaggcccg actacctgaa cttcagggag 1380
agcggccagg tgtacttcgg catcatcgcc ctgggcggcg cgcagcga gccaagagc 1440
agcgacaaga cccacacctg ccccccctgc cccgccccg aggccgccgg cggcccagc 1500
gtgttcctgt tcccccccaa gcccaaggac accctgatga tcagcaggac ccccgaggtg 1560
acctgcgtgg tggtggacgt gagccacgag gaccccgagg tgaagttcaa ctggtacgtg 1620
gacgtggtgg aggtgcacaa cgccaagacc aagcccaggg aggagcagta caacagcacc 1680
tacagggtgg tgagcgtgct gaccgtgctg caccaggact ggctgaacgg caaggagtac 1740
aagtgcaagg tgagcaacaa ggccctgccc gccagcatcg agaagaccat cagcaaggcc 1800
aagggccagc ccagggagcc caggtgtac accctgcccc ccagcaggga cgagctgacc 1860
aagaaccagg tgagcctgac ctgcctggtg aagggcttct accccagcga catcgccgtg 1920
gagtgggaga gcaacggcca gcccgagaac aactacaaga ccaccccccc cgtgctggac 1980
agcgacggca gcttcttcct gtacagcaag ctgaccgtgg acaagagcag gtggcagcag 2040
ggcaacgtgt tcagctgcag cgtgatgcac gaggccctgc acaaccacta cacccagaag 2100
agcctgagcc tgagccccc                                                2118

SEQ ID NO: 40          moltype = AA  length = 248
FEATURE                Location/Qualifiers
source                 1..248
                       mol_type = protein
                       organism = Homo sapiens
                       note = Human IgG1 sequence including C-terminal extension
SEQUENCE: 40
EPKSSDKTHT CPPCPAPEAA GGPSVFLFPP KPKDTLMISR TPEVTCVVVD VSHEDPEVKF 60
NWYVDGVEVH NAKTKPREEQ YNSTYRVVSV LTVLHQDWLN GKEYKCKVSN KALPASIEKT 120
ISKAKGQPRE PQVYTLPPSR DELTKNQVSL TCLVKGFYPS DIAVEWESNG QPENNYKTTP 180
PVLDSDGSFF LYSKLTVDKS RWQQGNVFSC SVMHEALHNH YTQKSLSLSP ELQLEESSAE 240
AQDGELDG                                                            248

SEQ ID NO: 41          moltype = AA  length = 18
FEATURE                Location/Qualifiers
source                 1..18
                       mol_type = protein
                       organism = Homo sapiens
```

```
                    note = Linker from C-terminus of Human IgG
SEQUENCE: 41
ELQLEESSAE AQDGELDG                                                         18

SEQ ID NO: 42           moltype = AA  length = 14
FEATURE                 Location/Qualifiers
source                  1..14
                        mol_type = protein
                        organism = Homo sapiens
                        note = Linker variant derived from C-terminus of Human IgG
SEQUENCE: 42
ELQLEESSAE AQGG                                                             14

SEQ ID NO: 43           moltype = AA  length = 22
FEATURE                 Location/Qualifiers
source                  1..22
                        mol_type = protein
                        organism = Homo sapiens
SEQUENCE: 43
GGGSGGGTGS EFLASSRTPS DK                                                    22

SEQ ID NO: 44           moltype = AA  length = 25
FEATURE                 Location/Qualifiers
VARIANT                 6..25
                        note = GGGGS repeats may be deleted
source                  1..25
                        mol_type = protein
                        organism = synthetic construct
                        note = linker
SEQUENCE: 44
GGGGSGGGGS GGGGSGGGGS GGGGS                                                 25

SEQ ID NO: 45           moltype = AA  length = 50
FEATURE                 Location/Qualifiers
VARIANT                 6..50
                        note = GGGGS repeats may be deleted
source                  1..50
                        mol_type = protein
                        organism = synthetic construct
                        note = linker
SEQUENCE: 45
GGGGSGGGGS GGGGSGGGGS GGGGSGGGGS GGGGSGGGGS GGGGSGGGGS                      50

SEQ ID NO: 46           moltype =     length =
SEQUENCE: 46
000

SEQ ID NO: 47           moltype =     length =
SEQUENCE: 47
000

SEQ ID NO: 48           moltype =     length =
SEQUENCE: 48
000

SEQ ID NO: 49           moltype =     length =
SEQUENCE: 49
000

SEQ ID NO: 50           moltype =     length =
SEQUENCE: 50
000

SEQ ID NO: 51           moltype =     length =
SEQUENCE: 51
000

SEQ ID NO: 52           moltype =     length =
SEQUENCE: 52
000

SEQ ID NO: 53           moltype =     length =
SEQUENCE: 53
000

SEQ ID NO: 54           moltype =     length =
SEQUENCE: 54
000
```

| | | |
|---|---|---|
| SEQ ID NO: 55<br>SEQUENCE: 55<br>000 | moltype = | length = |
| SEQ ID NO: 56<br>SEQUENCE: 56<br>000 | moltype = | length = |
| SEQ ID NO: 57<br>SEQUENCE: 57<br>000 | moltype = | length = |
| SEQ ID NO: 58<br>SEQUENCE: 58<br>000 | moltype = | length = |
| SEQ ID NO: 59<br>SEQUENCE: 59<br>000 | moltype = | length = |
| SEQ ID NO: 60<br>SEQUENCE: 60<br>000 | moltype = | length = |
| SEQ ID NO: 61<br>SEQUENCE: 61<br>000 | moltype = | length = |
| SEQ ID NO: 62<br>SEQUENCE: 62<br>000 | moltype = | length = |
| SEQ ID NO: 63<br>SEQUENCE: 63<br>000 | moltype = | length = |
| SEQ ID NO: 64<br>SEQUENCE: 64<br>000 | moltype = | length = |
| SEQ ID NO: 65<br>SEQUENCE: 65<br>000 | moltype = | length = |
| SEQ ID NO: 66<br>SEQUENCE: 66<br>000 | moltype = | length = |
| SEQ ID NO: 67<br>SEQUENCE: 67<br>000 | moltype = | length = |
| SEQ ID NO: 68<br>SEQUENCE: 68<br>000 | moltype = | length = |
| SEQ ID NO: 69<br>SEQUENCE: 69<br>000 | moltype = | length = |
| SEQ ID NO: 70<br>SEQUENCE: 70<br>000 | moltype = | length = |
| SEQ ID NO: 71<br>SEQUENCE: 71<br>000 | moltype = | length = |
| SEQ ID NO: 72<br>SEQUENCE: 72<br>000 | moltype = | length = |
| SEQ ID NO: 73<br>SEQUENCE: 73<br>000 | moltype = | length = |
| SEQ ID NO: 74<br>SEQUENCE: 74<br>000 | moltype = | length = |

| | | |
|---|---|---|
| SEQ ID NO: 75<br>SEQUENCE: 75<br>000 | moltype = | length = |
| SEQ ID NO: 76<br>SEQUENCE: 76<br>000 | moltype = | length = |
| SEQ ID NO: 77<br>SEQUENCE: 77<br>000 | moltype = | length = |
| SEQ ID NO: 78<br>SEQUENCE: 78<br>000 | moltype = | length = |
| SEQ ID NO: 79<br>SEQUENCE: 79<br>000 | moltype = | length = |
| SEQ ID NO: 80<br>SEQUENCE: 80<br>000 | moltype = | length = |
| SEQ ID NO: 81<br>SEQUENCE: 81<br>000 | moltype = | length = |
| SEQ ID NO: 82<br>SEQUENCE: 82<br>000 | moltype = | length = |
| SEQ ID NO: 83<br>SEQUENCE: 83<br>000 | moltype = | length = |
| SEQ ID NO: 84<br>SEQUENCE: 84<br>000 | moltype = | length = |
| SEQ ID NO: 85<br>SEQUENCE: 85<br>000 | moltype = | length = |
| SEQ ID NO: 86<br>SEQUENCE: 86<br>000 | moltype = | length = |
| SEQ ID NO: 87<br>SEQUENCE: 87<br>000 | moltype = | length = |
| SEQ ID NO: 88<br>SEQUENCE: 88<br>000 | moltype = | length = |
| SEQ ID NO: 89<br>SEQUENCE: 89<br>000 | moltype = | length = |
| SEQ ID NO: 90<br>SEQUENCE: 90<br>000 | moltype = | length = |
| SEQ ID NO: 91<br>SEQUENCE: 91<br>000 | moltype = | length = |
| SEQ ID NO: 92<br>SEQUENCE: 92<br>000 | moltype = | length = |
| SEQ ID NO: 93<br>SEQUENCE: 93<br>000 | moltype = | length = |
| SEQ ID NO: 94<br>SEQUENCE: 94 | moltype = | length = |

```
SEQ ID NO: 95              moltype =    length =
SEQUENCE: 95
000

SEQ ID NO: 96              moltype =    length =
SEQUENCE: 96
000

SEQ ID NO: 97              moltype =    length =
SEQUENCE: 97
000

SEQ ID NO: 98              moltype =    length =
SEQUENCE: 98
000

SEQ ID NO: 99              moltype =    length =
SEQUENCE: 99
000

SEQ ID NO: 100             moltype = AA   length = 592
FEATURE                    Location/Qualifiers
source                     1..592
                           mol_type = protein
                           organism = synthetic construct
                           note = fusion protein
SEQUENCE: 100
DFTPPTVKIL QSSCDGGGHF PPTIQLLCLV SGYTPGTINI TWLEDGQVMD VDLSTASTTQ    60
EGELASTQSE LTLSQKHWLS DRTYTCQVTY QGHTFEDSTK KCADSNGGGS GGGTGSEFLA   120
SSRTPSDKPV AHVVANPQAE GQLQWLNRRA NALLANGVEL RDNQLVVPSE GLYLIYSQVL   180
FKGQGCPSTH VLLTHTISRI AVSYQTKVNL LSAIKSPCQR ETPEGAEAKP WYEPIYLGGV   240
FQLEKGDRLS AEINRPDYLN FRESGQVYFG IIALGGGGSS SRTPSDKPVA HVVANPQAEG   300
QLQWLNRRAN ALLANGVELR DNQLVVPSEG LYLIYSQVLF KGQGCPSTHV LLTHTISRIA   360
VSYQTKVNLL SAIKSPCQRE TPEGAEAKPW YEPIYLGGVF QLEKGDRLSA EINRPDYLNF   420
RESGQVYFGI IALGGGGSSS RTPSDKPVAH VVANPQAEGQ LQWLNRRANA LLANGVELRD   480
NQLVVPSEGL YLIYSQVLFK GQGCPSTHVL LTHTISRIAV SYQTKVNLLS AIKSPCQRET   540
PEGAEAKPWY EPIYLGGVFQ LEKGDRLSAE INRPDYLNFR ESGQVYFGII AL           592

SEQ ID NO: 101             moltype = AA   length = 709
FEATURE                    Location/Qualifiers
source                     1..709
                           mol_type = protein
                           organism = synthetic construct
                           note = fusion protein
SEQUENCE: 101
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKG GGGSVRSSSR   240
TPSDKPVAHV VANPQAEGQL QWLNRRANAL LANGVELRDN QLVVPSEGLY LIYSQVLFKG   300
QGCPSTHVLL THTISRIAVS YQTKVNLLSA IKSPCQRETP EGAEAKPWYE PIYLGGVFQL   360
EKGDRLSAEI NRPDYLNFRE SGQVYFGIIA LGGGGSSSRT PSDKPVAHVV ANPQAEGQLQ   420
WLNRRANALL ANGVELRDNQ LVVPSEGLYL IYSQVLFKGQ GCPSTHVLLT HTISRIAVSY   480
QTKVNLLSAI KSPCQRETPE GAEAKPWYEP IYLGGVFQLE KGDRLSAEIN RPDYLNFRES   540
GQVYFGIIAL GGGGSSSRTP SDKPVAHVVA NPQAEGQLQW LNRRANALLA NGVELRDNQL   600
VVPSEGLYLI YSQVLFKGQG CPSTHVLLTH TISRIAVSYQ TKVNLLSAIK SPCQRETPEG   660
AEAKPWYEPI YLGGVFQLEK GDRLSAEINR PDYLNFRESG QVYFGIIAL               709

SEQ ID NO: 102             moltype = AA   length = 699
FEATURE                    Location/Qualifiers
source                     1..699
                           mol_type = protein
                           organism = synthetic construct
                           note = fusion protein
SEQUENCE: 102
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKG GGSVRSSSR    240
TPSDKPVAHV VANPQAEGQL QWLNRRANAL LANGVELRDN QLVVPSEGLY LIYSQVLFKG   300
QGCPSTHVLL THTISRIAVS YQTKVNLLSA IKSPCQRETP EGAEAKPWYE PIYLGGVFQL   360
EKGDRLSAEI NRPDYLNFRE SGQVYFGIIA LSSRTPSDKP VAHVANPQA EGQLQWLNRR    420
ANALLANGVE LRDNQLVVPS EGLYLIYSQV LFKGQGCPST HVLLTHTISR IAVSYQTKVN   480
LLSAIKSPCQ RETPEGAEAK PWYEPIYLGG VFQLEKGDRL SAEINRPDYL NFRESGQVYF   540
GIIALSSRTP SDKPVAHVVA NPQAEGQLQW LNRRANALLA NGVELRDNQL VVPSEGLYLI   600
YSQVLFKGQG CPSTHVLLTH TISRIAVSYQ TKVNLLSAIK SPCQRETPEG AEAKPWYEPI   660
YLGGVFQLEK GDRLSAEINR PDYLNFRESG QVYFGIIAL                         699
```

```
SEQ ID NO: 103           moltype = AA  length = 705
FEATURE                  Location/Qualifiers
source                   1..705
                         mol_type = protein
                         organism = synthetic construct
                         note = fusion protein
SEQUENCE: 103
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKG GGSVRSSSR    240
TPSDKPVAHV VANPQAEGQL QWLNRRANAL LANGVELRDN QLVVPSEGLY LIYSQVLFKG   300
QGCPSTHVLL THTISRIAVS YQTKVNLLSA IKSPCQRETP EGAEAKPWYE PIYLGGVFQL   360
EKGDRLSAEI NRPDYLNFRE SGQVYFGIIA LVRSSSRTPS DKPVAHVVAN PQAEGQLQWL   420
NRRANALLAN GVELRDNQLV VPSEGLYLIY SQVLFKGQGC PSTHVLLTHT ISRIAVSYQT   480
KVNLLSAIKS PCQRETPEGA EAKPWYEPIY LGGVFQLEKG DRLSAEINRP DYLNFRESGQ   540
VYFGIIALVR SSSRTPSDKP VAHVVANPQA EGQLQWLNRR ANALLANGVE LRDNQLVVPS   600
EGLYLIYSQV LFKGQGCPST HVLLTHTISR IAVSYQTKVN LLSAIKSPCQ RETPEGAEAK   660
PWYEPIYLGG VFQLEKGDRL SAEINRPDYL NFRESGQVYF GIIAL                   705

SEQ ID NO: 104           moltype = AA  length = 714
FEATURE                  Location/Qualifiers
source                   1..714
                         mol_type = protein
                         organism = synthetic construct
                         note = fusion protein
SEQUENCE: 104
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKG GGSGGGGSV    240
RSSSRTPSDK PVAHVVANPQ AEGQLQWLNR RANALLANGV ELRDNQLVVP SEGLYLIYSQ   300
VLFKGQGCPS THVLLTHTIS RIAVSYQTKV NLLSAIKSPC QRETPEGAEA KPWYEPIYLG   360
GVFQLEKGDR LSAEINRPDY LNFRESGQVY FGIIALGGGG SSSRTPSDKP VAHVVANPQA   420
EGQLQWLNRR ANALLANGVE LRDNQLVVPS EGLYLIYSQV LFKGQGCPST HVLLTHTISR   480
IAVSYQTKVN LLSAIKSPCQ RETPEGAEAK PWYEPIYLGG VFQLEKGDRL SAEINRPDYL   540
NFRESGQVYF GIIALGGGGS SSRTPSDKPV AHVVANPQAE GQLQWLNRRA NALLANGVEL   600
RDNQLVVPSE GLYLIYSQVL FKGQGCPSTH VLLTHTISRI AVSYQTKVNL LSAIKSPCQR   660
ETPEGAEAKP WYEPIYLGGV FQLEKGDRLS AEINRPDYLN FRESGQVYFG IIAL          714

SEQ ID NO: 105           moltype = AA  length = 704
FEATURE                  Location/Qualifiers
source                   1..704
                         mol_type = protein
                         organism = synthetic construct
                         note = fusion protein
SEQUENCE: 105
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKG GGSGGGGSV    240
RSSSRTPSDK PVAHVVANPQ AEGQLQWLNR RANALLANGV ELRDNQLVVP SEGLYLIYSQ   300
VLFKGQGCPS THVLLTHTIS RIAVSYQTKV NLLSAIKSPC QRETPEGAEA KPWYEPIYLG   360
GVFQLEKGDR LSAEINRPDY LNFRESGQVY FGIIALSSRT PSDKPVAHVV ANPQAEGQLQ   420
WLNRRANALL ANGVELRDNQ LVVPSEGLYL IYSQVLFKGQ GCPSTHVLLT HTISRIAVSY   480
QTKVNLLSAI KSPCQRETPE GAEAKPWYEP IYLGGVFQLE KGDRLSAEIN RPDYLNFRES   540
GQVYFGIIAL SSRTPSDKPV AHVVANPQAE GQLQWLNRRA NALLANGVEL RDNQLVVPSE   600
GLYLIYSQVL FKGQGCPSTH VLLTHTISRI AVSYQTKVNL LSAIKSPCQR ETPEGAEAKP   660
WYEPIYLGGV FQLEKGDRLS AEINRPDYLN FRESGQVYFG IIAL                    704

SEQ ID NO: 106           moltype = AA  length = 710
FEATURE                  Location/Qualifiers
source                   1..710
                         mol_type = protein
                         organism = synthetic construct
                         note = fusion protein
SEQUENCE: 106
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKG GGSGGGGSV    240
RSSSRTPSDK PVAHVVANPQ AEGQLQWLNR RANALLANGV ELRDNQLVVP SEGLYLIYSQ   300
VLFKGQGCPS THVLLTHTIS RIAVSYQTKV NLLSAIKSPC QRETPEGAEA KPWYEPIYLG   360
GVFQLEKGDR LSAEINRPDY LNFRESGQVY FGIIALVRSS SRTPSDKPVA HVVANPQAEG   420
QLQWLNRRAN ALLANGVELR DNQLVVPSEG LYLIYSQVLF KGQGCPSTHV LLTHTISRIA   480
VSYQTKVNLL SAIKSPCQRE TPEGAEAKPW YEPIYLGGVF QLEKGDRLSA EINRPDYLNF   540
RESGQVYFGI IALVRSSSRT PSDKPVAHVV ANPQAEGQLQ WLNRRANALL ANGVELRDNQ   600
LVVPSEGLYL IYSQVLFKGQ GCPSTHVLLT HTISRIAVSY QTKVNLLSAI KSPCQRETPE   660
```

```
GAEAKPWYEP IYLGGVFQLE KGDRLSAEIN RPDYLNFRES GQVYFGIIAL            710

SEQ ID NO: 107          moltype = AA  length = 709
FEATURE                 Location/Qualifiers
source                  1..709
                        mol_type = protein
                        organism = synthetic construct
                        note = fusion protein
SEQUENCE: 107
VRSSSRTPSD KPVAHVVANP QAEGQLQWLN RRANALLANG VELRDNQLVV PSEGLYLIYS  60
QVLFKGQGCP STHVLLTHTI SRIAVSYQTK VNLLSAIKSP CQRETPEGAE AKPWYEPIYL 120
GGVFQLEKGD RLSAEINRPD YLNFRESGQV YFGIIALGGG GSSSRTPSDK PVAHVVANPQ 180
AEGQLQWLNR RANALLANGV ELRDNQLVVP SEGLYLIYSQ VLFKGQGCPS THVLLTHTIS 240
RIAVSYQTKV NLLSAIKSPC QRETPEGAEA KPWYEPIYLG GVFQLEKGDR LSAEINRPDY 300
LNFRESGQVY FGIIALGGGG SSSRTPSDKP VAHVVANPQA EGQLQWLNRR ANALLANGVE 360
LRDNQLVVPS EGLYLIYSQV LFKGQGCPST HVLLTHTISR IAVSYQTKVN LLSAIKSPCQ 420
RETPEGAEAK PWYEPIYLGG VFQLEKGDRL SAEINRPDYL NFRESGQVYF GIIALGGGGS 480
ESKYGPPCPP CPAPEFLGGP SVFLFPPKPK DTLMISRTPE VTCVVVDVSQ EDPEVQFNWY 540
VDGVEVHNAK TKPREEQFNS TYRVVSVLTV LHQDWLNGKE YKCKVSNKGL PSSIEKTISK 600
AKGQPREPQV YTLPPSQEEM TKNQVSLTCL VKGFYPSDIA VEWESNGQPE NNYKTTPPVL 660
DSDGSFFLYS RLTVDKSRWQ EGNVFSCSVM HEALHNHYTQ KSLSLSLGK            709

SEQ ID NO: 108          moltype = AA  length = 699
FEATURE                 Location/Qualifiers
source                  1..699
                        mol_type = protein
                        organism = synthetic construct
                        note = fusion protein
SEQUENCE: 108
VRSSSRTPSD KPVAHVVANP QAEGQLQWLN RRANALLANG VELRDNQLVV PSEGLYLIYS  60
QVLFKGQGCP STHVLLTHTI SRIAVSYQTK VNLLSAIKSP CQRETPEGAE AKPWYEPIYL 120
GGVFQLEKGD RLSAEINRPD YLNFRESGQV YFGIIALSSR TPSDKPVAHV VANPQAEGQL 180
QWLNRRANAL LANGVELRDN QLVVPSEGLY LIYSQVLFKG QGCPSTHVLL THTISRIAVS 240
YQTKVNLLSA IKSPCQRETP EGAEAKPWYE PIYLGGVFQL EKGDRLSAEI NRPDYLNFRE 300
SGQVYFGIIA LSSRTPSDKP VAHVVANPQA EGQLQWLNRR ANALLANGVE LRDNQLVVPS 360
EGLYLIYSQV LFKGQGCPST HVLLTHTISR IAVSYQTKVN LLSAIKSPCQ RETPEGAEAK 420
PWYEPIYLGG VFQLEKGDRL SAEINRPDYL NFRESGQVYF GIIALGGGGS ESKYGPPCPP 480
CPAPEFLGGP SVFLFPPKPK DTLMISRTPE VTCVVVDVSQ EDPEVQFNWY VDGVEVHNAK 540
TKPREEQFNS TYRVVSVLTV LHQDWLNGKE YKCKVSNKGL PSSIEKTISK AKGQPREPQV 600
YTLPPSQEEM TKNQVSLTCL VKGFYPSDIA VEWESNGQPE NNYKTTPPVL DSDGSFFLYS 660
RLTVDKSRWQ EGNVFSCSVM HEALHNHYTQ KSLSLSLGK                       699

SEQ ID NO: 109          moltype = AA  length = 705
FEATURE                 Location/Qualifiers
source                  1..705
                        mol_type = protein
                        organism = synthetic construct
                        note = fusion protein
SEQUENCE: 109
VRSSSRTPSD KPVAHVVANP QAEGQLQWLN RRANALLANG VELRDNQLVV PSEGLYLIYS  60
QVLFKGQGCP STHVLLTHTI SRIAVSYQTK VNLLSAIKSP CQRETPEGAE AKPWYEPIYL 120
GGVFQLEKGD RLSAEINRPD YLNFRESGQV YFGIIALVRS SSRTPSDKPV AHVVANPQAE 180
GQLQWLNRRA NALLANGVEL RDNQLVVPSE GLYLIYSQVL FKGQGCPSTH VLLTHTISRI 240
AVSYQTKVNL LSAIKSPCQR ETPEGAEAKP WYEPIYLGGV FQLEKGDRLS AEINRPDYLN 300
FRESGQVYFG IIALVRSSSR TPSDKPVAHV VANPQAEGQL QWLNRRANAL LANGVELRDN 360
QLVVPSEGLY LIYSQVLFKG QGCPSTHVLL THTISRIAVS YQTKVNLLSA IKSPCQRETP 420
EGAEAKPWYE PIYLGGVFQL EKGDRLSAEI NRPDYLNFRE SGQVYFGIIA LGGGGSESKY 480
GPPCPPCPAP EFLGGPSVFL FPPKPKDTLM ISRTPEVTCV VVDVSQEDPE VQFNWYVDGV 540
EVHNAKTKPR EEQFNSTYRV VSVLTVLHQD WLNGKEYKCK VSNKGLPSSI EKTISKAKGQ 600
PREPQVYTLP PSQEEMTKNQ VSLTCLVKGF YPSDIAVEWE SNGQPENNYK TTPPVLDSDG 660
SFFLYSRLTV DKSRWQEGNV FSCSVMHEAL HNHYTQKSLS LSLGK                705

SEQ ID NO: 110          moltype = AA  length = 704
FEATURE                 Location/Qualifiers
source                  1..704
                        mol_type = protein
                        organism = synthetic construct
                        note = fusion protein
SEQUENCE: 110
VRSSSRTPSD KPVAHVVANP QAEGQLQWLN RRANALLANG VELRDNQLVV PSEGLYLIYS  60
QVLFKGQGCP STHVLLTHTI SRIAVSYQTK VNLLSAIKSP CQRETPEGAE AKPWYEPIYL 120
GGVFQLEKGD RLSAEINRPD YLNFRESGQV YFGIIALGGG GSSSRTPSDK PVAHVVANPQ 180
AEGQLQWLNR RANALLANGV ELRDNQLVVP SEGLYLIYSQ VLFKGQGCPS THVLLTHTIS 240
RIAVSYQTKV NLLSAIKSPC QRETPEGAEA KPWYEPIYLG GVFQLEKGDR LSAEINRPDY 300
LNFRESGQVY FGIIALGGGG SSSRTPSDKP VAHVVANPQA EGQLQWLNRR ANALLANGVE 360
LRDNQLVVPS EGLYLIYSQV LFKGQGCPST HVLLTHTISR IAVSYQTKVN LLSAIKSPCQ 420
RETPEGAEAK PWYEPIYLGG VFQLEKGDRL SAEINRPDYL NFRESGQVYF GIIALESKYG 480
PPCPPCPAPE FLGGPSVFLF PPKPKDTLMI SRTPEVTCVV VDVSQEDPEV QFNWYVDGVE 540
VHNAKTKPRE EQFNSTYRVV SVLTVLHQDW LNGKEYKCKV SNKGLPSSIE KTISKAKGQP 600
```

```
REPQVYTLPP SQEEMTKNQV SLTCLVKGFY PSDIAVEWES NGQPENNYKT TPPVLDSDGS   660
FFLYSRLTVD KSRWQEGNVF SCSVMHEALH NHYTQKSLSL SLGK                   704

SEQ ID NO: 111             moltype = AA   length = 694
FEATURE                    Location/Qualifiers
source                     1..694
                           mol_type = protein
                           organism = synthetic construct
                           note = fusion protein
SEQUENCE: 111
VRSSSRTPSD KPVAHVVANP QAEGQLQWLN RRANALLANG VELRDNQLVV PSEGLYLIYS    60
QVLFKGQGCP STHVLLTHTI SRIAVSYQTK VNLLSAIKSP CQRETPEGAE AKPWYEPIYL   120
GGVFQLEKGD RLSAEINRPD YLNFRESGQV YFGIIALSSR TPSDKPVAHV VANPQAEGQL   180
QWLNRRANAL LANGVELRDN QLVVPSEGLY LIYSQVLFKG QGCPSTHVLL THTISRIAVS   240
YQTKVNLLSA IKSPCQRETP EGAEAKPWYE PIYLGGVFQL EKGDRLSAEI NRPDYLNFRE   300
SGQVYFGIIA LSSRTPSDKP VAHVVANPQA EGQLQWLNRR ANALLANGVE LRDNQLVVPS   360
EGLYLIYSQV LFKGQGCPST HVLLTHTISR IAVSYQTKVN LLSAIKSPCQ RETPEGAEAK   420
PWYEPIYLGG VFQLEKGDRL SAEINRPDYL NFRESGQVYF GIIALESKYG PPCPPCPAPE   480
FLGGPSVFLF PPKPKDTLMI SRTPEVTCVV VDVSQEDPEV QFNWYVDGVE VHNAKTKPRE   540
EQFNSTYRVV SVLTVLHQDW LNGKEYKCKV SNKGLPSSIE KTISKAKGQP REPQVYTLPP   600
SQEEMTKNQV SLTCLVKGFY PSDIAVEWES NGQPENNYKT TPPVLDSDGS FFLYSRLTVD   660
KSRWQEGNVF SCSVMHEALH NHYTQKSLSL SLGK                              694

SEQ ID NO: 112             moltype = AA   length = 698
FEATURE                    Location/Qualifiers
source                     1..698
                           mol_type = protein
                           organism = synthetic construct
                           note = fusion protein
SEQUENCE: 112
VRSSSRTPSD KPVAHVVANP QAEGQLQWLN RRANALLANG VELRDNQLVV PSEGLYLIYS    60
QVLFKGQGCP STHVLLTHTI SRIAVSYQTK VNLLSAIKSP CQRETPEGAE AKPWYEPIYL   120
GGVFQLEKGD RLSAEINRPD YLNFRESGQV YFGIIALVRS SRTPSDKPVA HVVANPQAEG   180
QLQWLNRRAN ALLANGVELR DNQLVVPSEG LYLIYSQVLF KGQGCPSTHV LLTHTISRIA   240
VSYQTKVNLL SAIKSPCQRE TPEGAEAKPW YEPIYLGGVF QLEKGDRLSA EINRPDYLNF   300
RESGQVYFGI IALVRSSRTP SDKPVAHVVA NPQAEGQLQW LNRRANALLA NGVELRDNQL   360
VVPSEGLYLI YSQVLFKGQG CPSTHVLLTH TISRIAVSYQ TKVNLLSAIK SPCQRETPEG   420
AEAKPWYEPI YLGGVFQLEK GDRLSAEINR PDYLNFRESG QVYFGIIALE SKYGPPCPPC   480
PAPEFLGGPS VFLFPPKPKD TLMISRTPEV TCVVVDVSQE DPEVQFNWYV DGVEVHNAKT   540
KPREEQFNST YRVVSVLTVL HQDWLNGKEY KCKVSNKGLP SSIEKTISKA KGQPREPQVY   600
TLPPSQEEMT KNQVSLTCLV KGFYPSDIAV EWESNGQPEN NYKTTPPVLD SDGSFFLYSR   660
LTVDKSRWQE GNVFSCSVMH EALHNHYTQK SLSLSLGK                          698

SEQ ID NO: 113             moltype = AA   length = 712
FEATURE                    Location/Qualifiers
source                     1..712
                           mol_type = protein
                           organism = synthetic construct
                           note = fusion protein
SEQUENCE: 113
EPKSSDKTHT CPPCPAPEAA GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPASIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GKGGGGSVRS   240
SSRTPSDKPV AHVVANPQAE GQLQWLNRRA NALLANGVEL RDNQLVVPSE GLYLIYSQVL   300
FKGQGCPSTH VLLTHTISRI AVSYQTKVNL LSAIKSPCQR ETPEGAEAKP WYEPIYLGGV   360
FQLEKGDRLS AEINRPDYLN FRESGQVYFG IIALGGGGSS SRTPSDKPVA HVVANPQAEG   420
QLQWLNRRAN ALLANGVELR DNQLVVPSEG LYLIYSQVLF KGQGCPSTHV LLTHTISRIA   480
VSYQTKVNLL SAIKSPCQRE TPEGAEAKPW YEPIYLGGVF QLEKGDRLSA EINRPDYLNF   540
RESGQVYFGI IALGGGGSSS RTPSDKPVAH VVANPQAEGQ LQWLNRRANA LLANGVELRD   600
NQLVVPSEGL YLIYSQVLFK GQGCPSTHVL LTHTISRIAV SYQTKVNLLS AIKSPCQRET   660
PEGAEAKPWY EPIYLGGVFQ LEKGDRLSAE INRPDYLNFR ESGQVYFGII AL           712

SEQ ID NO: 114             moltype = AA   length = 708
FEATURE                    Location/Qualifiers
source                     1..708
                           mol_type = protein
                           organism = synthetic construct
                           note = fusion protein
SEQUENCE: 114
ERKSSVECPP CPAPPVAGPS VFLFPPKPKD TLMISRTPEV TCVVVDVSHE DPEVQFNWYV    60
DGVEVHNAKT KPREEQFNST FRVVSVLTVV HQDWLNGKEY KCKVSNKGLP ASIEKTISKT   120
KGQPREPQVY TLPPSREEMT KNQVSLTCLV KGFYPSDIAV EWESNGQPEN NYKTTPPMLD   180
SDGSFFLYSK LTVDKSRWQQ GNVFSCSVMH EALHNHYTQK SLSLSPGKGG GGSVRSSSRT   240
PSDKPVAHVV ANPQAEGQLQ WLNRRANALL ANGVELRDNQ LVVPSEGLYL IYSQVLFKGQ   300
GCPSTHVLLT HTISRIAVSY QTKVNLLSAI KSPCQRETPE GAEAKPWYEP IYLGGVFQLE   360
KGDRLSAEIN RPDYLNFRES GQVYFGIIAL GGGGSSSRTP SDKPVAHVVA NPQAEGQLQW   420
LNRRANALLA NGVELRDNQL VVPSEGLYLI YSQVLFKGQG CPSTHVLLTH TISRIAVSYQ   480
TKVNLLSAIK SPCQRETPEG AEAKPWYEPI YLGGVFQLEK GDRLSAEINR PDYLNFRESG   540
```

```
QVYFGIIALG GGGSSSRTPS DKPVAHVVAN PQAEGQLQWL NRRANALLAN GVELRDNQLV    600
VPSEGLYLIY SQVLFKGQGC PSTHVLLTHT ISRIAVSYQT KVNLLSAIKS PCQRETPEGA    660
EAKPWYEPIY LGGVFQLEKG DRLSAEINRP DYLNFRESGQ VYFGIIAL                708

SEQ ID NO: 115            moltype = AA   length = 712
FEATURE                   Location/Qualifiers
source                    1..712
                          mol_type = protein
                          organism = synthetic construct
                          note = fusion protein
SEQUENCE: 115
VRSSSRTPSD KPVAHVVANP QAEGQLQWLN RRANALLANG VELRDNQLVV PSEGLYLIYS    60
QVLFKGQGCP STHVLLTHTI SRIAVSYQTK VNLLSAIKSP CQRETPEGAE AKPWYEPIYL    120
GGVFQLEKGD RLSAEINRPD YLNFRESGQV YFGIIALGGG SSSRTPSDKP VAHVVANPQ     180
AEGQLQWLNR RANALLANGV ELRDNQLVVP SEGLYLIYSQ VLFKGQGCPS THVLLTHTIS    240
RIAVSYQTKV NLLSAIKSPC QRETPEGAEA KPWYEPIYLG GVFQLEKGDR LSAEINRPDY    300
LNFRESGQVY FGIIALGGGG SSSRTPSDKP VAHVVANPQA EGQLQWLNRR ANALLANGVE    360
LRDNQLVVPS EGLYLIYSQV LFKGQGCPST HVLLTHTISR IAVSYQTKVN LLSAIKSPCQ    420
RETPEGAEAK PWYEPIYLGG VFQLEKGDRL SAEINRPDYL NFRESGQVYF GIIALGGGGS    480
EPKSSDKTHT CPPCPAPEAA GGPSVFLFPP KPKDTLMISR TPEVTCVVVD VSHEDPEVKF    540
NWYVDGVEVH NAKTKPREEQ YNSTYRVVSV LTVLHQDWLN GKEYKCKVSN KALPASIEKT    600
ISKAKGQPRE PQVYTLPPSR DELTKNQVSL TCLVKGFYPS DIAVEWESNG QPENNYKTTP    660
PVLDSDGSFF LYSKLTVDKS RWQQGNVFSC SVMHEALHNH YTQKSLSLSP GK            712

SEQ ID NO: 116            moltype = AA   length = 708
FEATURE                   Location/Qualifiers
source                    1..708
                          mol_type = protein
                          organism = synthetic construct
                          note = fusion protein
SEQUENCE: 116
VRSSSRTPSD KPVAHVVANP QAEGQLQWLN RRANALLANG VELRDNQLVV PSEGLYLIYS    60
QVLFKGQGCP STHVLLTHTI SRIAVSYQTK VNLLSAIKSP CQRETPEGAE AKPWYEPIYL    120
GGVFQLEKGD RLSAEINRPD YLNFRESGQV YFGIIALGGG SSSRTPSDKP VAHVVANPQ     180
AEGQLQWLNR RANALLANGV ELRDNQLVVP SEGLYLIYSQ VLFKGQGCPS THVLLTHTIS    240
RIAVSYQTKV NLLSAIKSPC QRETPEGAEA KPWYEPIYLG GVFQLEKGDR LSAEINRPDY    300
LNFRESGQVY FGIIALGGGG SSSRTPSDKP VAHVVANPQA EGQLQWLNRR ANALLANGVE    360
LRDNQLVVPS EGLYLIYSQV LFKGQGCPST HVLLTHTISR IAVSYQTKVN LLSAIKSPCQ    420
RETPEGAEAK PWYEPIYLGG VFQLEKGDRL SAEINRPDYL NFRESGQVYF GIIALGGGGS    480
ERKSSVECPP CPAPPVAGPS VFLFPPKPKD TLMISRTPEV TCVVVDVSHE DPEVQFNWYV    540
DGVEVHNAKT KPREEQFNST FRVVSVLTVV HQDWLNGKEY KCKVSNKGLP ASIEKTISKT    600
KGQPREPQVY TLPPSREEMT KNQVSLTCLV KGFYPSDIAV EWESNGQPEN NYKTTPPMLD    660
SDGSFFLYSK LTVDKSRWQQ GNVFSCSVMH EALHNHYTQK SLSLSPGK                708

SEQ ID NO: 117            moltype = AA   length = 694
FEATURE                   Location/Qualifiers
source                    1..694
                          mol_type = protein
                          organism = synthetic construct
                          note = fusion protein
SEQUENCE: 117
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKV RSSSRTPSDK    240
PVAHVVANPQ AEGQLQWLNR RANALLANGV ELRDNQLVVP SEGLYLIYSQ VLFKGQGCPS    300
THVLLTHTIS RIAVSYQTKV NLLSAIKSPC QRETPEGAEA KPWYEPIYLG GVFQLEKGDR    360
LSAEINRPDY LNFRESGQVY FGIIALSSRT PSDKPVAHVV ANPQAEGQLQ WLNRRANALL    420
ANGVELRDNQ LVVPSEGLYL IYSQVLFKGQ GCPSTHVLLT HTISRIAVSY QTKVNLLSAI    480
KSPCQRETPE GAEAKPWYEP IYLGGVFQLE KGDRLSAEIN RPDYLNFRES GQVYFGIIAL    540
SSRTPSDKPV AHVVANPQAE GQLQWLNRRA NALLANGVEL RDNQLVVPSE GLYLIYSQVL    600
FKGQGCPSTH VLLTHTISRI AVSYQTKVNL LSAIKSPCQR ETPEGAEAKP WYEPIYLGGV    660
FQLEKGDRLS AEINRPDYLN FRESGQVYFG IIAL                              694

SEQ ID NO: 118            moltype = AA   length = 693
FEATURE                   Location/Qualifiers
source                    1..693
                          mol_type = protein
                          organism = synthetic construct
                          note = fusion protein
SEQUENCE: 118
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKG GGSVRSSSR     240
TPSDKPVAHV VANPQAEGQL QWLNRRANAL LANGVELRDN QLVVPSEGLY LIYSQVLFKG    300
QGCPSTHVLL THTISRIAVS YQTKVNLLSA IKSPCQRETP EGAEAKPWYE PIYLGGVFQL    360
EKGDRLSAEI NRPDYLNFRE SGQVYFGIIA LGGGGSPVAH VVANPQAEGQ LQWLNRRANA    420
LLANGVELRD NQLVVPSEGL YLIYSQVLFK GQGCPSTHVL LTHTISRIAV SYQTKVNLLS    480
```

```
AIKSPCQRET PEGAEAKPWY EPIYLGGVFQ LEKGDRLSAE INRPDYLNFR ESGQVYFGII   540
ALGGGGSPVA HVVANPQAEG QLQWLNRRAN ALLANGVELR DNQLVVPSEG LYLIYSQVLF   600
KGQGCPSTHV LLTHTISRIA VSYQTKVNLL SAIKSPCQRE TPEGAEAKPW YEPIYLGGVF   660
QLEKGDRLSA EINRPDYLNF RESGQVYFGI IAL                                693

SEQ ID NO: 119            moltype = AA   length = 698
FEATURE                   Location/Qualifiers
source                    1..698
                          mol_type = protein
                          organism = synthetic construct
                          note = fusion protein
SEQUENCE: 119
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKG GGSGGGGSV    240
RSSSRTPSDK PVAHVVANPQ AEGQLQWLNR RANALLANGV ELRDNQLVVP SEGLYLIYSQ   300
VLFKGQGCPS THVLLTHTIS RIAVSYQTKV NLLSAIKSPC QRETPEGAEA KPWYEPIYLG   360
GVFQLEKGDR LSAEINRPDY LNFRESGQVY FGIIALGGGG SPVAHVVANP QAEGQLQWLN   420
RRANALLANG VELRDNQLVV PSEGLYLIYS QVLFKGQGCP STHVLLTHTI SRIAVSYQTK   480
VNLLSAIKSP CQRETPEGAE AKPWYEPIYL GGVFQLEKGD RLSAEINRPD YLNFRESGQV   540
YFGIIALGGG GSPVAHVVAN PQAEGQLQWL NRRANALLAN GVELRDNQLV VPSEGLYLIY   600
SQVLFKGQGC PSTHVLLTHT ISRIAVSYQT KVNLLSAIKS PCQRETPEGA EAKPWYEPIY   660
LGGVFQLEKG DRLSAEINRP DYLNFRESGQ VYFGIIAL                           698

SEQ ID NO: 120            moltype = AA   length = 704
FEATURE                   Location/Qualifiers
source                    1..704
                          mol_type = protein
                          organism = synthetic construct
                          note = fusion protein
SEQUENCE: 120
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKG GGSGGGGSV    240
RSSSRTPSDK PVAHVVANPQ AEGQLQWLNR RANALLANGV ELRDNQLVVP SEGLYLIYSQ   300
VLFKGQGCPS THVLLTHTIS RIAVSYQTKV NLLSAIKSPC QRETPEGAEA KPWYEPIYLG   360
GVFQLEKGDR LSAEINRPDY LNFRESGQVY FGIIALSSRT PSDKPVAHVV ANPQAEGQLQ   420
WLNRRANALL ANGVELRDNQ LVVPSEGLYL IYSQVLFKGQ GCPSTHVLLT HTISRIAVSY   480
QTKVNLLSAI KSPCQRETPE GAEAKPWYEP IYLGGVFQLE KGDRLSAEIN RPDYLNFRES   540
GQVYFGIIAL SSRTPSDKPV AHVVANPQAE GQLQWLNRRA NALLANGVEL RDNQLVVPSE   600
GLYLIYSQVL FKGQGCPSTH VLLTHTISRI AVSYQTKVNL LSAIKSPCQR ETPEGAEAKP   660
WYEPIYLGGV FQLEKGDRLS AEINRPDYLN FRESGQVYFG IIAL                    704

SEQ ID NO: 121            moltype = DNA   length = 2127
FEATURE                   Location/Qualifiers
source                    1..2127
                          mol_type = other DNA
                          organism = synthetic construct
                          note = Codon optimized nucleic acid sequence encoding SEQ
                          IDNO 101
SEQUENCE: 121
gagtccaagt atgggccacc ttgtccacca tgcccagccc ccgaatttct tggtggccct    60
tcagtctttc tcttcccacc caaacccaaa gatactctta tgatttctcg aaccccgag   120
gtgacatgcg tggtcgtaga cgtgagtcag gaagacccag aggttcagtt caactgctat   180
gtcgacggcg tagaggtgca taacgccaag actaaacccc gagaagagca gtttaactcc   240
acttacagag tggtgagtgt cttgaccgtc ctgcatcagg actggcttaa cggcaaagag   300
tataaatgta agttagcaa taaaggactc ccaagtagca ttgaaaaaac catcagtaaa   360
gcaaagggcc aaccaagaga gccccaggtg tataccctc cacccagtca ggaggaaatg   420
accaaaaacc aagtttccct tacttgcctt gttaagggat tctacccctc agacattgct   480
gtagagtggg agtccaatgg tcagcctgag aataattaca aaacaacacc tcctgtgttg   540
gacagcgacg gatctttctt tctctatagt cgactcactg tggacaaatc aagatggcag   600
gagggggaatg tgttctcatg ctcagtaatg catgaagcc tgcacaatca ctacacacaa   660
aagagtctct ctctgtccct tggaaagggt ggaggtggga gcgtgcgctc ttcaagccgc   720
acaccatctg ataagcctgt ggcacatgtc gttgcaaatc cacaagcaga gggacaactt   780
cagtggttga caggcgcgc caacgcattg ctcgccaacg tgtcgagct gcgggacaac   840
cagctggtcg tacctagtga gggtctgtac ttgatctaca gccaagtgct gttcaaaggg   900
cagggctgtc ccagcaccca tgttctcttg actcatacca tatcacgaat cgcagtaagt   960
taccagacta aagtgaacct gctttccgct atcaaaagtc cctgtcaaag agagactcca  1020
gaaggggctg aggctaaacc ttggtacgaa ccaatttatc tgggaggtgt gttccagctt  1080
gagaaaggag atcgccttc agctgagatc aatcgaccag attatttgaa ttttcgagag  1140
agcggccaag tttattttgg cataatcgca ttgggtggtg gtgtagctc ctcacgcact  1200
ccatctgaca agccagttgc tcatgtcgta gctaatccaa aggcaggaca acaactttcaa  1260
tggctgaaca aagggcaaa cgccctgttg gccaatggtg tggagttgag agacaatcag  1320
ctggttgtcc cttctgaggg actttatctt atatatagcc aagtgttgtt caaaggtcaa  1380
gggtgcccct caactcatgt tctgttgacc ataccataa gtcgaatcgc agtgagttac  1440
caaacaaagg tcaatctctt gtccgccata agagccccct gccaacggga acacccgaa   1500
ggagccgagg caaaaccatg gtacgaacca atatacctcg ggggagtgtt ccagctgag   1560
```

```
aagggagacc gactttcagc tgaaatcaac aggcccgact atcttaactt caggggagtca  1620
gggcaggtct actttggaat aatagcattg ggcggaggcg gatccagcag cagaactcct  1680
agcgacaagc ccgttgctca tgtcgtagcc aatccacaag ccgaaggcca gctgcagtgg  1740
cttaatcgac gggccaatgc cctgttggca aacggagtcg agcttaggga taatcagctc  1800
gttgttccaa gtgaaggatt gtatttgatc tacagccaag ttctgttcaa gggtcagggt  1860
tgcccctcta cccatgtttt gttgacacac acaatcagtc gcattgctgt atcctatcaa  1920
accaaggtca atttgctgtc cgcaatcaag agcccatgcc agagagagac tccagaaggc  1980
gcagaagcta agccctggta cgagccaatt taccttggcg gggttttcca gcttgagaaa  2040
ggagataggc tgagcgcaga aatcaatcgg cccgactact tgaatttccg cgaaagcggt  2100
caagtgtatt ttggtatcat agcactt                                      2127

SEQ ID NO: 122         moltype = DNA   length = 2097
FEATURE                Location/Qualifiers
source                 1..2097
                       mol_type = other DNA
                       organism = synthetic construct
                       note = Codon optimized nucleic acid sequence encoding SEQ
                       IDNO 102
SEQUENCE: 122
gaatctaagt acgtccccc ttgtccacca tgtccagccc ccgagtttct cggagggccc   60
agtgtctttc ttttccctcc taaacccaag gatactctca tgattagccg aacacctgaa  120
gtaacatgtg ttgttgtgga cgttagtcaa gaagaccccg aagttcaatt taactggtat  180
gtggatggcg tagaggtaca caacgcaaag actaaaccac gagaagagca gttcaactcc  240
acttatcgag tagttagtgt gttgacagta ctccatcaag actggctcaa cggcaaagaa  300
tataagtgta aagttagtaa caaggactc cccagtagca ttgaaaagac tatctccaag  360
gcaaaagggc aaccaaggga gccccaggtg tataccttgc caccctcaca agaggagatg  420
acaaagaacc aggtcagtct cacctgtctg gttaagggtt tctatcctc tgacattgcc  480
gttgaatggg agtctaacgg ccagcctgaa ataactaca agactacacc tcccgtcctg  540
gatagcgatg gtagtttttt cctctattcc aggctcactg tagacaagtc aaggtggcag  600
gaaggcaatg ttttcagctg ctctgtcatg catgaggcac tccacaatca ttatacacaa  660
aaaagtctca gtttgtcctt gggcaagggt ggaggcggga gcgttcgcag ctcctctcgg  720
actccaagcg acaaacctgt tgctcatgtc gtcgccaatc ctcaggcaga aggccaactg  780
caatggctga cagacgcgc taatgcattg ttggccaacg gcgttgagtt gagagacaac  840
caactcgttg taccctccga gggactttat ctgatatact ctcaagtatt gtttaagggt  900
caaggttgtc catcaaccca cgtattgctg acccatacca tttctagaat tgccgtaagt  960
tatcagacta aagttaattt gttgagcgca attaaaagtc cttgtcaacg cgaaactcct 1020
gagggagcag aagcaaaacc ctggtacgaa cccatttatt gggagggggt atttcagctg 1080
gaaaagggg atcggctgtc agccgaaatt aatcgccctg attatctgaa cttcagagaa 1140
agcggtcaag tctacttcgg catcatagcc ctttcatctc gcacaccaag tgataagccc 1200
gttgctcacg tcgtgcaaa cccacaagcc gaggggcaac tccagtggtt gaaccgcagg 1260
gcaaatgctc tcttggctaa cggggtcgaa ttgagggata atcagctcgt tgtcccttcc 1320
gaaggactgt atctgatcta cagccaagta ctgttcaagg gtcaaggttg cccaagtaca 1380
catgttttgc tgacacatac tataagccgc atcgccgtgt cttaccaaac aaaagtgaat 1440
ctgctgtcag ctataaagag cccatgtcag agggaaacac ccgggggagc tgaggcaaag 1500
ccctggtacg aacccatata cttggggggc gtcttccaac tggagaaagg tgacaggctc 1560
agtgcagaga taaccgccc cgactacctg aatttcgag agagcggtca agtatatttt 1620
ggtattattg cacttagtag tcggaccca tctgataaac ccgtcgctca gtcgtcgca 1680
aacccacaag ctgaggggca gttgcagtgg cttaataggc gcgctaacgc tctgcttgct 1740
aatggcgtgg agttgaggga taatcaattg gtcgttccca gcgagggtct gtatttgatc 1800
tacagccagg tactttttaa gggccaaggc tgccctagta ctcatgtgct tctgactcat 1860
actatatcaa ggatcgccgt cagctaccaa accaaggtta atctcctag tgctatcaaa 1920
agcccatgtc aacgcgagac tcccgagggc gccgaagcca aaccctggta cgagcccata 1980
tacctggtg tgtgtttca gctgagaag ggggaccgac ttagtgcaga gattaataga 2040
cctgattacc tgaatttcag ggagagcggt caggtttatt ttgggatcat cgcactc    2097

SEQ ID NO: 123         moltype = DNA   length = 2115
FEATURE                Location/Qualifiers
source                 1..2115
                       mol_type = other DNA
                       organism = synthetic construct
                       note = Codon optimized nucleic acid sequence encoding SEQ
                       IDNO 103
SEQUENCE: 123
gagtcaaagt acggcccacc atgtcctcct tgtcctgccc ccgagtttct gggtggccca   60
tccgtcttcc tctttccacc taaaccaaaa gataccctca tgatctctcg gacacccgaa  120
gttacctgcg tcgtcgtcga cgtcagccaa gaagatcctg aagttcagtt caattggtac  180
gttgacggcg ttgaggtaca taacgccaaa acaaaacccc gggaggagca attcaattcc  240
acttatcggg tggtttcagt tttgaccgtg ctgcatcagg actggctcaa cggcaaagaa  300
tacaaatgta aggtgtccaa caaggactc ccttccagta tagaagact tatatcaaag  360
gccaagggcc agccacgaga gcctcaggta tacaccctgc cccctagcca agaggagatg  420
actaaaaacc aagtaagtct gacatgcctt gtcaagggt tctatcctag tgatattgcc  480
gtagagtggg agtctaacgg ccagcccgag aacaattata gacaaccccc accgtgctg  540
gattcagatg gatctttttt cttgtatagc cggcttacag tagataaatc tcgatggcaa  600
gaaggtaacg tgttttagttg ctccgtaatg cacgaggcac tccataatca ctatactaa  660
aaatccctct ccttgtctct gggcaaaggg ggggcggct ccgtcgatc atctagtcgc  720
actcctcag acaagcctgt ggcccacgta gttgctaatc cacaggccga ggggcaactc  780
caatggctca accgcagagc caacgcattg ctggctaacg gcgtagaatt gcgagacaat  840
cagcttgtgg taccttccga gggactgtac ctcatctact ctcaagtttt gtttaaaggc  900
caaggttgcc ccagtactca cgtacttctc actcacacaa tcagccgcat cgctgtgtct  960
```

```
tatcaaacca aagtcaattt gctttccgcc ataaaaagcc cttgtcagcg agaaacccct  1020
gaaggagctg aagctaaacc atggtacgag cccatctatc tcggcggtgt tttccagctt  1080
gagaaggggg atcggctttc cgccgagatt aatcggccg  attacttgaa tttcagggag  1140
agcgggcagg tgtattttgg aataatcgct cttgtccggt cctcatctcg aacacctagt  1200
gataaaccg  tagcccacgt agttgcaaat ccccaggccg aaggtcaact gcagtggctt  1260
aaccgccgag caaatgctct tctggcaaat ggggtagagt tgcgcgacaa tcaattggtc  1320
gtaccaagtg aaggcctcta cctatctac  tctcaggtcc tcttcaaagg tcaaggttgt  1380
ccttctactc acgtactcct gacacataca atatctcgca ttgcagtatc ataccaaaca  1440
aaggtgaatc ttctctccgc tataaaatca ccctgccaac gagagacacc tgaaggtaca  1500
gaggccaaac cctggtacga accaatttac cttggaggag ttttttcaatt ggaaaaagga  1560
gatagactta gcgccgaaat aaataggccc gattacttga attttagaga gtccgggcag  1620
gtatatttcg gcataatagc actggtcagg agttccagca ggactcccag cgataagccc  1680
gtcgcacacg tggttgctaa tccacaagct gaaggacagc tgcaatggct taatagaagg  1740
gccaatgctc tgttggctaa cggcgttgaa cttcgggata accagccttgt ggtgccctcc  1800
gaaggtttgt atttgatcta ttcacaagtt ttgttcaaag gccagggttg ccctctacc   1860
cacgtacttc tgcacacacac aatcagccgc atcgctgtct cataccagac caaagtcaac  1920
ttgttgtctg caataaaatc accatgtcag cgggaaactc ctgagggcgc cgaggccaaa  1980
ccctggtatg agccaatcta ccttggtggc gtatttcagc ttgaaaaagg agacaggctt  2040
tccgcagaga taaacaggcc agattatctg aactttaggg aatcaggtca agtctacttt  2100
ggaatcatag ctctc                                                   2115

SEQ ID NO: 124          moltype = DNA length = 2142
FEATURE                 Location/Qualifiers
source                  1..2142
                        mol_type = other DNA
                        organism = synthetic construct
                        note = Codon optimized nucleic acid sequence encoding SEQ
                        IDNO 104
SEQUENCE: 124
gaatccaagt atggcccacc atgtccccc  tgccccgccc ctgaattcct tggcggaccc  60
agcgtatttc tgttcccacc aaagcccaag gacacactta tgataagtcg gacacctgaa  120
gtaacttgtg tcgtcgtcga cgtgagtcag gaagacctg  aagtccaatt taactggtac  180
gtggatggcg tggaggtaca caatgccaag accaagccac gcgaagagca gttcaattca  240
acatatcggg tcgtttccgt cctgaccgta ctgcaccaag attggctcaa tgggaaggag  300
tacaaatgta aagtatctaa caaaggcctc ccatcctca  tagaaaaaac cataagtaaa  360
gctaagggac agcctcgaga acctcaggtc tacacactgc cccatcctca agaagaaatg  420
accaaaaacc aagtgagtct tacttgtctg gtgaaaggtt tctatccatc gacattgcc   480
gtagagtggg aatcaaacgg ccaacctgag aataactaca aaactactcc tcccgtcctc  540
gatagtgacg gtagcttctt cctgtacagc aggctcacag tcgacaaatc caggtggcaa  600
gaaggcaatg ttttcagctg ttccgtcatg catgaagccc tgcacaacca ttatacacag  660
aaaagcttga gcctgtcctt gggtaaaggt ggagggggga gtgggggtgg tgggtctgtg  720
cgaagcagta gcagaacacc ttccgacaaa ccagttcac  atgttgttgc taatcctcag  780
gcccaaaggc agcttcagtg gctcaacagg agggctaacg ctttgttggc taacggtgta  840
gagctccgcg ataaccaact tgtagtgcct tccgagggac tctatcttat ttactcccaa  900
gtgctgtttta aggacaagg  gtgccctagc acccacgtat tgctgactca cactatcagc  960
aggattgccg tcagctacca gactaaagtt aaccttctgt cagctataaa atcaccctgt  1020
cagcgggaaa cccccagggg agcagaggca aaacccttgg acgaaccaat atacttggcg  1080
ggagtatttc aattggagaa aggtgataga ctgagcgctg aaataaatcg gcctgactat  1140
cttaacttcc gcgaatcagg gcaggtgtat tcggcatca  ttgccctcgg tgggggaggg  1200
agctcctcaa ggactccaag cgataagcca gtggctcacg tagtggccaa tccacaagca  1260
gaaggtcaac tgcaatggct taaccgccgc gcaaaccgat tgttggctaa cggtgtgaa   1320
ttgagagata accaattggt ggttccttca gaaggcctgt acctgatcta tagtcaagta  1380
ctgttcaaag gacagggttg tcccagcact catgttcttc tgacccacac tattagtaga  1440
atagccgtat catatcaaac caaagtcaac cttttgtctg ccataaaatc ccctgccaa   1500
agagaaacac ccgaaggagc cgaggccaaa ccttggtacg agccaatata cctgggggc   1560
gttttccaat tggaaaaggg cgataggttg agcgctgaga taaataggcc agattatttg  1620
aatttcaggg aaagcgggca agtgtacttc gggatcatag ccctgggcgg gggtgggtca  1680
agctctcgca ctccctcaga caagcccgtt gcacatgtgg tggctaatcc acaggctgag  1740
ggacagctgc agtggctgaa tagacgagca aatgcactgc ttgctaacgg agttgagctc  1800
cgcgataacc aactggtggt acctctgag  ggactctatt tgatttactc ccaagttctc  1860
ttcaagggcc aaggctgccc ctccactcat gtcctgctta cccacactat ttctagaata  1920
gccgtatctt accagaccaa ggtcaacctc ttgagtgcaa taaagagtcc ctgtcaacga  1980
gaaactccag aaggcgccga agctaagcca tggtatgagc caatttaccct cggggagtg  2040
tttcagcttg agaaggggga cagactgagt gccgaaataa accggcccga ctatctcaac  2100
ttccgcgaga gtggtcaagt ctacttcggt atcatagctt tg                     2142

SEQ ID NO: 125          moltype = DNA length = 2112
FEATURE                 Location/Qualifiers
source                  1..2112
                        mol_type = other DNA
                        organism = synthetic construct
                        note = Codon optimized nucleic acid sequence encoding SEQ
                        IDNO 105
SEQUENCE: 125
gagagtaaat acggcccacc ttgtcctccc tgccctgctc cagagttcct tggcgggcct  60
tccgtcttcc tgtttccccc caagccaaag gacacactga tgatttcaag aaccccagag  120
gtcacctgtg tcgttgtaga tgttagtcaa gaggatccag aggtgcaatt caattggtat  180
gtcgatgggg tggaggttca caacgctaag accaaacctc gggaagagca attcaattct  240
acttatcggg tggtaagtgt tcttactgtt ttgcaccagg actggttgaa cgggaaggaa  300
```

```
tataagtgca aggttagtaa caaggggctt ccttccagca tcgaaaagac aattagcaaa    360
gccaagggac aacccgaga gccacaagtg tataccttc  cccctccca agaggaaatg     420
accaagaacc aagtctctct gacctgcctg gtgaaaggt tctatccaag cgacatagct    480
gtcgaatggg aatccaacgg ccaacccgaa ataactata aaacaacacc tcccgtcctg    540
gattccgatg ggtcattttt cttgtattca agattgaccg tggataaaag ccgctggcag   600
gaggggaacg ttttttcatg tagtgtaatg catgaagctc ttcataacca ttatacacag   660
aaaagtttga gtttgtcact cggtaaaggt ggaggagggt ccggtggcgg tggctcagtg   720
agaagttctt ctaggacccc ttccgacaaa cccgttgccc acgttgtcgc aaatccacaa   780
gctgaagggc agcttcagtg gctcaatcgg agagcaaatg ctctccttgc caacggagtc   840
gaactgcgcg acaaccaact cgtcgttccc tccgagggcc tgtatctgat ctattccaaa   900
gtgttgttca aaggtcaagg ttgtccaagt acccatgtct tgctgacaca cacaatatca   960
agaatagcag tcagctatca aacaaaagtg aatttgctct ctgccatcaa aagtccctgc  1020
caacgcgaga ctcctgaagg tgctgaagca aaaccctggt atgaacctat atatttgggt  1080
ggcgtctttc aacttgaaaa gggtgacaga cttttctgccg agataaaccg gccagactat 1140
ctgaactttc gagagtccgg tcaggtttat ttcggtatca ttgccttgag ctctagaaca  1200
cctagcgaca aacctgtcgc ccatgtagtt gcaaatcccc aggctgaggg tcaactccaa  1260
tggcttaaca ggcgcgccaa cgctcttctc gccaacggtg tagagctgcg cgataatcaa  1320
ctggtggttc cttccgaggg acttttatctg atatattcac aggttctgtt taaaggccag 1380
ggttgtccct ctacacatgt attgttgaca cacactatat ctcggatagc tgtgagctac  1440
caaacaaaag taaatttgct gtctgctatc aagagtccat gtcagaggga aaccccgaa   1500
ggagcagagg ccaaaccatg gtacgaacca atatatcttg ggggagtctt tcaattggag  1560
aaaggggacc ggttgagtgc cgagattaac cgacctgatt accttaattt caggagagc   1620
ggtcaagttt acttcggcat aatagccctt tcttcacgga caccttcaga caaaccagtg  1680
gctcatgtgg ttgcaaaccc tcaagcagaa ggtcaattgc aatggcttaa tcgcagagct  1740
aatgcccttt tggcaaacgg tgtggagctt cgggataatc agttggtggt tccaagtgaa  1800
ggtctgtact tgatatattc ccaagtgctg ttcaaaggc agggctgccc ctctactcat  1860
gttctgctca cccatacaat atctagaatc gctgtgagct accagactaa ggtcaatctt  1920
ttgtcagcaa taaaatcacc atgccaacgg gagactccag aaggagcaga agccaaaccc  1980
tggtatgaac ctatataccct cggggggcgtc tttcagcttg agaagggtga caggctgagc  2040
gctgaaatta atcggcccga ctaccttaac tttagagaat ccggtcaagt atatttcggt  2100
attattgccc tc                                                      2112

SEQ ID NO: 126          moltype = DNA   length = 2130
FEATURE                 Location/Qualifiers
source                  1..2130
                        mol_type = other DNA
                        organism = synthetic construct
                        note = Codon optimized nucleic acid sequence encoding SEQ
                          IDNO 106
SEQUENCE: 126
gagagcaaat atgcccacc  ctgcccccca tgtcctgccc cagaattcct gggaggaccc    60
tcagtgtttc tctttccacc caagccaaaa gacacattga tgatttcaag gactcctgag   120
gtgacatgtg ttgtagtaga cgtatcacag gaggatcctg aagtccagtt caactggtac   180
gtcgacggcg ttgaagtgca caatgctaaa accaagcccc gagaggagca gtttaacagc   240
acatatcggg tcgtttctgt gcttaccgtc ttgcatcagg attggctgaa cggaaaagaa   300
tataaatgca aggtctcaaa caaggggctt ccatcttcaa tagaaaaaac aatttcaaag   360
gcaaaaggac agcctagaga gccccaagtc tacactctgc cacccagcca ggaggagatg   420
acaaagaacc aggtcagcct gacctgtctc gtcaaaggat tctatccatc cgacatcgcc   480
gtagaatggg agagtaatgg acagcctgaa acaactata agaccactcc cccagtactg   540
gacagtgatg ggtcattctt tttgtatagt cgactgactg tagataaaag tcgatggcag   600
gaaggtaatg tgttctcatg cagcgtcatg cacgaggccc tgcacaacca ttatacacag   660
aagagtctga gtcttagctt gggtaaggga ggcgggggat ccggaggcgg tggatctgta   720
cggtcttcta gcagaacacc aagtgataaa ccagtggctc acgtggtagc aaaccccaa    780
gctgaggggc agcttcaatg gcttaataga agggctaacg ctcttcttgc caacgggtc   840
gagcttaggg ataaccagct ggtggtcccc tctgaaggct tgtatctgat atactcccag   900
gtactgtttta aaggacaagg ctgtcccagc actcatgtac tgttgacaca tactatatca   960
cgcatagctg tctcttatca gacaaaagtt aacttgctta gcgctatcaa gagtccctgt  1020
cagagagaaa ccccgaagg tgcagaggcc aagccatggt acgaacctat taccttgga   1080
ggcgttttcc aactggagaa aggggatcgc ctctccgccg aaataaacag gcccgattat  1140
ctgaacttcc gagagagcgg ccaagtctac tttgggataa tcgctctcgt gcggaacagt  1200
agcagaaccc cctctgataa accagttgcc catgtggttg ccaacccaca ggccgaaggt  1260
cagctgcagt ggctgaatcg gagagccaac gctcttctcg ccaatggtgt ggaactcagg  1320
gataaccaac tggttgtccc atctgaaggt ctttatctta tctattcaca agtgctcttt  1380
aagggacagg gctgtccaag tacacacgtc ttgctcactc acacaatatc cagaattgct  1440
gtaagctacc agacaaaagt aaacctccta gcgccatta aaagcccttg tcaaagggaa   1500
acacctgagg gagccgaagc caaaccatgg tacgaaccca tatctcgg  tggcgttttc    1560
cagttggaga agggcgatcg actgtccgcc gagattaatc gccctgatta tctgaactt   1620
cgggagtccg gcaggtttat cttttggtata atcgctagtg tacgctcaag cagtagaact  1680
ccctcagaca aaccagtagc acatgttgta gctaatccac aagcagaagg acagctgcaa  1740
tggctgaacc ggagagctaa cgccctgctg ctaacggtg tcgagttgcg agataatcag   1800
cttgtcgtgc ctagcgaggg gctctacctt atttatagtc aagttctctt taagggcag   1860
gggtgtccaa gtacacacgt gttgctcaca catactattt ctcgaatagc cgtgtcctat  1920
caaaccaagt gaaccttct ctccgctatc aaagccctg  gccaaagaga aacacccgaa   1980
ggcgccgagg ctaagccatg gtacgaacct atctatcctg ggggtgtttt tcaactcgaa  2040
aaaggggaca ggttgagtgc tgagattaat agacccgatt atttgaattt tagggaatct  2100
ggcaggttt  atttttggaat aattgctctc                                  2130

SEQ ID NO: 127          moltype = DNA   length = 2127
FEATURE                 Location/Qualifiers
```

| source | 1..2127 |
| --- | --- |
| | mol_type = other DNA |
| | organism = synthetic construct |
| | note = Codon optimized nucleic acid sequence encoding SEQ IDNO 107 |

SEQUENCE: 127

```
gtacggagca gctctagaac tccatctgac aagccagtcg ctcatgtggt agcaaatccc    60
caagctgagg gccaacttca gtggttgaat cgcagggcta acgctctgct cgccaatgga   120
gtagaattga gggataatca gctcgtagta cctagcgaag ggctttacct catatattct   180
caggttctgt ttaagggtca aggctgtcca agtactcacg ttctccttac tcatacaatc   240
tctcgcatcg cagtttctta tcaaaccaag gttaatttgc tgagcgccat taagtcacca   300
tgccagcgcg aaaccccga aggtgccgaa gcaaaccttt ggtatgagcc catttacctt   360
ggcggtgtgt ttcagctgga aaggggggac aggctttcag cagaaattaa taggcccgac   420
tatcttaatt tccgggagtc cggccaggtt tatttcggta tcattgccct gggcggtggc   480
ggctcatcct cacgcactcc atctgataag cccgtcgcac atgtggtcgc caatcctcag   540
gcagaggggc aattgcaatg gcttaaccgc agggcaaacg ctctgcttgc taatggggtt   600
gagcttcggg ataaccagct cgtggtacct tcagagggtt gtacttgat ctattctcaa   660
gtgcttttca aaggacaagg ttgcccaagc acccatgtgt tgttgaccca tactatttcc   720
cggatagcag tgtcatatca aactaaggtc aatcttctgt cagctattaa aagtccctgt   780
cagagagaga ctccagaggg agctgaagcc aaacccctgt acgagcccat atatcttgga   840
ggggtgttcc agctcgagaa aggcgacaga ttgagcgccg agataaaccg gcctgactat   900
ctcaatttc gagagtccgg tcaggtttac tttgggataa tgcactggg tggtggaggg   960
tctagctctc gcacaccatc cgataagcca gtagctcatg tggtggccaa ccctcaagcc  1020
gaggggcaac ttcagtggct gaatagcgac gctaatgcat tgctggctaa cggtgtcgaa  1080
ctgagagata atcagctcgt agtaccttca gaagggcttt acctcatata ctctcaggtt  1140
tgttcaaag gacaggatg tccttcaact cacgtcctc tcactcacac tataagtaga  1200
atcgctgtat cctaccaaac taaagtgaac cttttgtctg ctatcaaatc cccttgccaa  1260
cgcgaaactc ccgaaggcgc agaagccaag ccttggtatg agccaatcta cctcggagga  1320
gtttttcagt tggaaaaggg tgacaggctg agtgctgaaa tcaacaggcc cgattatctg  1380
aacttcaggg aaagcggaca agtgtattt tggaataatcg cacttggtgg gggagggtcc  1440
gagtctaagt acgggccacc ttgtcctccc tgtccagcac ctgagttttt tggcggggccc  1500
agtgtattcc tgtttccacc caaacctaag gataccctga tgatatcacg aacccctgag  1560
gtcacctgtg ttgtcgttga cgtaagtcag gaggacccag aggttcagtt caactggtat  1620
gtcgacgggg tagaagttca taatgctaag actaagccaa gggaggaaca atttaattcc  1680
acttatcgag ttgtgagcgt cctgacagtt ttgcatcagg attggcttaa cggcaaagaa  1740
tataagtgca aggttcaaa taaaggtctg cctttcttcca tagaaaaaac aatctctaaa  1800
gccaaaggcc aaccaagaga gcctcaggtg tacactcttc ctccctctca ggaagagatg  1860
acaaaaaacc aggtgtcctt gacctgtctc gttaaggggt tctatccaag cgatattgct  1920
gttgagtggg aatcaaacgg gcagcctgag aataattaca agccacacc ccagttttg  1980
gatagcgatg gtagtttctt cctttacagt aggttgaccg ttgataagtc ccggtggcaa  2040
gaaggaaatg tgtttagttg ctccgtgatg cacgaggcac tgcataatca ttacactcaa  2100
aagagtctta gtctgagctt ggggaaa                                      2127
```

| SEQ ID NO: 128 | moltype = DNA length = 2097 |
| --- | --- |
| FEATURE | Location/Qualifiers |
| source | 1..2097 |
| | mol_type = other DNA |
| | organism = synthetic construct |
| | note = Codon optimized nucleic acid sequence encoding SEQ IDNO 108 |

SEQUENCE: 128

```
gtgcggagta gcagcagaac tccatccgat aaaccagtgg cacacgtggt cgctaatccc    60
caagcagaag ggcagctcca atggctgaac aggcgggcca atgccctttt ggctaatggc   120
gtcgagctca gagacaatca gctcgtcgtc ccatctgagg gtctctactt gatctatagt   180
caggtcttgt tcaaaggcca aggctgtcct agtactcatg ttctccttac acataccatt   240
tcaaggatag cagtctccata tcagactaaa gtcaatctcc tgagtgcaat taagtccccc   300
tgccagcgag agactccaga aggtgctgag gcaaagccat ggtatgagcc catatatctt   360
ggcggagtct ttcaactgga aagggtgac cggctctccg cagagattaa ccggcctgac   420
tatctgaatt tcagagagtc tggccaggtt tactttggca ttatcgcact tccagtcgg   480
accccccagcg acaaacctgt tgcccatgtc gtagcaaatc ccaagccga aggccagttg   540
cagtggctga acagacgagc taatgctttg ttggcaaatg gggtggagct tcgggacaat   600
caactcgtgg taccatctga agggttgtac ctgatatata gccaggtact ctttaagggt   660
caaggttgtc ctagtactca tgtgctcttg acccacacaa tttcaagaat cgccgtcagt   720
taccaaacca aggttaatct gctttctgcc ataaagtctc ctgccaacg cgaaactcca   780
gaaggtgctg aagccaagcc ttggtacgag ccaatctacc tcggtggcgt ttttcaactt   840
gaaaagggg atcgcctgtc tgccgagatc aacaggccag actacctgaa cttccgagaa   900
agtgggcaag tctattttgg gatcatagcc ctgagctctc ggaccccag cgacaagcct   960
gttgcccacg tagttgctaa ccctcaggct gaaggacaac ttcatggctg gaacaggaga  1020
gctaacgccc tcctggctaa tggagtcgaa ctgacagaga atcaattggt cgtaccaagc  1080
gagggactgt acctcatata ctctcaggta ctgtttaagg gccaaggatg tccaagtacc  1140
catgtacttc tcacacatac aataagccgg atagccgtca gctatcagac taaggtaaac  1200
ctgctcagcg ctattaagag cccatgccag cgagagaccc cagaaggagc agaagctaaa  1260
ccctggtacg agccaatata tcttggagga gtcttttcaac tggagaaggg tgaccgattg  1320
agtgctgaaa ttaatcggcc agattattttg aacttccgaga agagcggaca agtgtatttc  1380
ggaatcattg cacttggcgg gggcgggagc gagtccaaat atgggcccac catgtccccc  1440
tgccctgccc cagagttcct tgggggccct tctgtatttc tcttcccccc aaacccaag  1500
gatactctta tgatcagcag gactcctgag gtaacctgtg tggtcgtcga cgtatcacaa  1560
gaggatccaa aggtacagtt taattggtat gtagacggct ggaagtcca caatgctaaa  1620
actaagccca gagaggagca gtttaatagt acataccgag tagtgagcgt attgactgta  1680
```

```
ttgcatcagg actggttgaa tgggaaagag tacaagtgca aagtttccaa caaaggtctc  1740
ccttcatcta tcgagaaaac catctcaaag gccaaaggcc aacccagaga gcctcaagta  1800
tacactctgc cacccagcca agaagagatg actaagaatc aggttagtct cacttgtctc  1860
gtcaaagggt tctatccctc cgatattgct gtggaatggg agagcaacgg gcaacccgag  1920
aacaactata agacaacccc accagtactt gatagcgacg ggtctttttt cctttattca  1980
cgccttacag ttgataaatc tcggtggcag aagggaacg ttttcagctg ttctgttatg  2040
catgaagcct tgcataacca ttacacacaa aagagtctta gtttgtctct tggaaag     2097

SEQ ID NO: 129         moltype = DNA  length = 2115
FEATURE                Location/Qualifiers
source                 1..2115
                       mol_type = other DNA
                       organism = synthetic construct
                       note = Codon optimized nucleic acid sequence encoding SEQ
                           IDNO 109
SEQUENCE: 129
gtgcgcagca gttccagaac acctagtgac aagcctgtgg cacacgttgt ggccaatcct    60
caagctgaag gtcagctcca atggcttaat agaagggcta acgcattgct tgctaatggg   120
gtggaacttc gagataacca attggtggtg ccctccgagg gtctctacct tatctatagc   180
caggtcctct ttaaaggcca aggttgcccc agtacacacg tcctgcttac acacacaata   240
tccagaatag cagtctcata ccagaccaag gtaaatctgc ttagcgctat taagtcaccc   300
tgtcagcggg aaaccccaga gggtcagaaa gcaaaaccat ggtatgagcc aatttaccct   360
ggtggcgttt tcaactgga aaagggcgat aggttgagcg ccgagatcaa tagacccgac   420
tatctcaatt tcgggagtc aggccaggtt tatttcggga tcattgcttt ggttcgctcc   480
tctagccgca cccccttccga taaaccagtt gcacatgttg tggccaatcc ccaggctgaa   540
ggccagcttc agtggctcaa cagacgggct aatgccctcc tcgccaatgg gtcgagctg    600
agggacaacc aacttgtggt ccctcagaa ggtctctacc ttatctacag ccaggttctt   660
ttcaaaggcc agggctgtcc ttccactcac gtgctgttga cccataccat atcccgcatt   720
gccgttagct atcaaaccaa agtcaacctt ttgtctgcaa ttaagagtcc atgccagaga   780
gaaactcccg aaggtgcaga agcaaagcca tggtatgaac ctatatatct cggaggtgtg   840
tttcaacttg agaaagggga cagactgagt gccgaaataa atcgccctga ttatcttaat   900
ttccgagagt ctgggcaagt atattttgga attattgccc tcgtgcgaag ctcttcaagg   960
accccaagtg ataaacccgt agcacacgta gttgcaaatc cacaagccga aggacagttg  1020
caatggctga ataggcgggc taatgctttg cttgctaatg gggtgagctc gcgggataac  1080
cagcttgtcg tgccatctga aggattgtac ctgatataca gccaagtttt gtttaaggga  1140
cagggatgcc catcaaccca cgtgctcctc actcacacta tttctcgaat tgccgtatca  1200
tatcagacta aagtcaactt gttgagcgca ataaagagcc cttgtcaacg ggaaaccccc  1260
gagggtgcag aggccaaacc atggtatgaa cctatttacc tcgggggcgt cttttcagttg  1320
gaaaaaggtg atcggttgtc cgctgagatt aaccgaccag actatcttaa cttttcgggaa  1380
tctggtcaag tctattttgg cataattgca ttggggggcg gggctctga atccaaatac  1440
gggcctcctt gccccccttg cccagcacca gaatttctcg ggggcccatc agtttttctt  1500
ttcccccta agcaaaaga taccctcatg atatcaagaa ctccagaggt tacatgtgtc  1560
gtggtcgacg ttagccagga ggatcccgag gttcagttca attggtacgt ggatggaatt  1620
gaagtgcaca atgccaaaac aaaaccacga gaagagcaat taatagcac ctacagggta   1680
gtcagcgttc ttacagttt gcaccaagat tggcttaacg gcaaagaata caaatgtaag  1740
gttagtaata aaggactccc ctcatcaata gaaaaaacaa tttccaaagc taaaggccag  1800
cctaggaac ctcaagtgta cacacttcct ccaagtcaag aagagatgaa aagaaccag   1860
gtctcactca cttgtctcgt caaaggtttc taccccctcg acatcgccgt ggaatgggag  1920
tccaatggcc aacctgagaa taattacaag accacacctc cagtactcga tagtgacggg  1980
tcttttcttttt tgtattctag gttgacagtg gataaatcca gatggcaaga aggaaatgtt  2040
ttctcatgtt ctgtgatgca cgaggctctt cacaaccact acactcaaaa gtctctgtct  2100
cttttcccttg gcaaa                                                   2115

SEQ ID NO: 130         moltype = DNA  length = 2112
FEATURE                Location/Qualifiers
source                 1..2112
                       mol_type = other DNA
                       organism = synthetic construct
                       note = Codon optimized nucleic acid sequence encoding SEQ
                           IDNO 110
SEQUENCE: 130
gtccgatcat ctagtaggac ccctagcgac aagccagttg cacacgtggt agcaaaccca    60
caagcagaag gacaactgca gtggcttaat aggcgcgcaa atgcattgct cgccaatgga   120
gtggaactcc gagacaacca attggtagtg ccttccgaga gactctacct tatttatagt   180
caggtcctgt tcaaagggca aggttgcccc tcaacacacg tattgctgac acacaccata   240
tcccgcatag cagttagcta tcaaacaaag gttaatttgc tgtccgcaat aaagagcccc   300
tgccaacggg agacccccga gggcgcagag gcaaaaccct ggtacgagcc catctacttg   360
ggtggcgtct ttcaacttga aaagggggat aggctgagcg ctgaaattaa ccggcccgac   420
tatttgaatt tccgggaatc tggccaagta tactttggta tttgcctt gggtggttga    480
ggtagcagta gccgaacacc atcagacaaa cctgtggcac acgttgtcgc caacccacaa   540
gctgaaggac aactccaatg gttgaacagg cgagccaatg cctccttgc aaatgcgta    600
gaattgcgag ataatcagct tgttgttcct agcgagggtc tttatcttat atacagtcag   660
gtcctcttta aggccaagg atgtcctagt acacacgtgc tgctgactca tacaataagc   720
cgaattgccg tatcctatca gactaaggtc aaccttctga gcgcattaa atccccatgt   780
caaagggaaa ctccagaagg cgcagaagcc aagcccggt atgagccaat ctatctcgga   840
ggggttttcc aattggagaa gggcgaccgg ctttctgctg aaatcaatcg acctgattat   900
ctcaactttc gagagtcagg gcaggtttat ttcggtatca ttgctctcgg tggcggaggg   960
tccagctcta ggacccccctc agacaaacca gtagcccacg ttgtgccaa tcccaggca   1020
gaaggtcagt tgcagtggtt gaatcggcgc gctaatgcac tcctgccaa tggagttgaa  1080
```

```
cttagggata atcaactcgt agtccccagc gaagggttgt atcttattta tagtcaggtc  1140
cttttaagg  gtcagggttg cccatccact cacgtgttgc tcactcacac catcagtcgc  1200
atcgccgttt cctatcagac caaggttaat ctcctgtccg ctataaagtc cccatgtcaa  1260
agagagaccc ccgaaggagc agaggcaaag ccttggtacg agcctatata cttgggtggc  1320
gtatttcagt tggaaaaggg tgaccggttg tccgctgaga taaatcgacc tgactatctc  1380
aactttcggg agtctggtca ggtttacttt gggattatag cactggagag caaatacgga  1440
cccccctgtc ctccttgtcc tgccccagag tttctcggtg gaccatcagt ctttcttttt  1500
cctcctaagc caaggatac  attgatgatc tcacggaccc ccgaagttac ctgcgtggtt  1560
gttgatgtaa gtcaggagga tcccgaagtc caattcaatt ggtatgtcga cggcgtggag  1620
gtccacaatg caaagacaaa gccccggag  gaacagttta acagcacata ccgggtcgtt  1680
agcgtgttga ccgtccttca tcaagattgg ttgaacggca aagagtacaa gtgcaaggtt  1740
agcaacaaag gtttgccatc ttccatcgag aaaacaatat ctaaggccaa aggacagccc  1800
cgcgaaccac aagtttatac tcttcctcca agccaggagg aaatgactaa gaatcaggtt  1860
tccctcacat gccttgtaaa gggtttttat ccctcagata ttgcagttga gtgggagagc  1920
aatggtcagc ccgagaataa ctataaaaca accccaccag tactcgactc agatggtagt  1980
ttcttcctct actccaggtt gacagtagac aaaagccgct ggcaagaggg caacgtattc  2040
tcttgctcag tgatgcatga agcactgcat aatcactaca cacaaaaatc tctgagcctt  2100
tcacttggca aa                                                     2112

SEQ ID NO: 131      moltype = DNA  length = 2082
FEATURE             Location/Qualifiers
source              1..2082
                    mol_type = other DNA
                    organism = synthetic construct
                    note = Codon optimized nucleic acid sequence encoding SEQ
                    IDNO 111
SEQUENCE: 131
gttaggtctt catctagaac acccagcgac aagcccgtgg cccacgtcgt tgccaacccc  60
caggcagagg gtcagctgca gtggctcaat aggcgagcta acgcccttct cgctaacggt  120
gtggagttgc gcgataacca acttggtcgta ccatccgaag gactctatct gatttattct  180
caagtcctgt ttaagggcca gggctgtcct tcaacccacg tcctccttac acataccatt  240
tctagaatag ccgtatcata tcagactaaa gtaaatcttt tgtcagcaat caaatctcca  300
tgccaacggg agaccccaga gggagcagaa gctaaaccct ggtacgaacc catatatctg  360
ggcggtgtct tccagcttga aaggggggac cgactctcga ccgagataaa tcgacctgac  420
tatttgaact tcagagagtc cgggcaagtc tatttcggaa ttatagctct ctcctctagg  480
accccatcag ataaaccagt tgcccatgtc gtggctaatc cccaggctga aggccaactg  540
caatggctta accgccggc  caatgctttg ctcgccaacg tgtagagtt  gcgcgacaac  600
caactggtag tccctagcga agggctgtac ctgatctact cccaagttct ttttaaaggc  660
caaggttgtc ctagtaccca cgtacttctg acccatacta tatctcggat agctgtgagt  720
taccagacaa aggttaacct tcttttccgcc atcaaaagtc cttgccaaag ggaaacacct  780
gaaggtgcag aagccaagcc ctggtatgag ccaatttatc tgggcggagt cttccaactc  840
gagaagggg  atagactgag cgctgagata aacagaccag actatctgaa ttttaggag   900
tcaggccagg tatactttgg aataatcgcc tctcatcaag ggactcccctc cgcaaaacca  960
gtagcacacg tagtggcaaa tccccaggca gaaggacagc tccagtggct gaatcggcgg  1020
gcaaacgccc tgctcgctaa cggggtcgaa cttaggggac accagcttgt tgtgccatcc  1080
gaaggtttgt acctgatata ttctcaagtt ctctttaaag gccaggggtg tccttctact  1140
catgtgctgt tgactcatac aatatcacgg attgcagttt cctatcaaac taaagtaaac  1200
ttgctttcag ctatcaagag tccatgccaa agggagacac ctgaaggggc agaggctaaa  1260
ccctggtacg agcctattta cctcgggggc gtttttcagc tggaaaaagg agatcggttg  1320
tcagctgaaa tcaacagacc cgactatctg aactttcgcg agtcaggtca ggtttatttt  1380
ggcattattg ccctggaaag caagtacggt cctccttgtc caccatgcc  tgctccagaa  1440
ttcttggggg gaccatcagt gtttctgttc cccccaaaac caaaggacac cttgatgata  1500
agccgaaccc cagaagtgac ctgtgtcgta gttgatgtaa gtcaagaaga tccgaggtc   1560
caattcaact ggtacgttga cggtgtcgag gtacataacg ccaaaccaa  gcctcgcgaa  1620
gagcagttta actccacata tagggtggta agtgtgctca cagtgctgcca tcaagactgg  1680
cttaacggga aggaatacaa gtgtaaagtc tccaataagg gacttccctc tagcatagaa  1740
aaaactatat ctaaagcaaa gggtcaacca cgcgaaccac aggtatatac actccccct   1800
agccaggagg aaatgaccaa aaaccaagta tctttgacct gtctggtgaa aggcttttac  1860
ccatctgata tcgcagttga atgggagtca aatggcaac  ccgaaaataa ctacaagaca  1920
actcctcccg tgctcgactc tgacggatca ttcttccttt actctcgcct caccgtagat  1980
aagagccgct ggcaagaggg taacgtattc agttgtagcg tgatgcatga ggctcttcat  2040
aaccattata cacaaaagtc cctcagcctt tctctgggaa ag                    2082

SEQ ID NO: 132      moltype = DNA  length = 2094
FEATURE             Location/Qualifiers
source              1..2094
                    mol_type = other DNA
                    organism = synthetic construct
                    note = Codon optimized nucleic acid sequence encoding SEQ
                    IDNO 112
SEQUENCE: 132
gtccgctcat catcaagaac cccagcgac  aaacctgtgg cccacgttgt tgccaatcca  60
caagccgagg ggcagctgca gtggcttaac aggagagcaa acgctcttct tgccaacggc  120
gtagagcttc gagacaacca acttgtcgta ccttctgaag gtctgtacct catctatagt  180
caagtacttt ttaaggaca  gggttgtcca agtacacatg tacttctgac ccacacaata  240
tccaggatag ccgtgtcata ccagacaaag gtcaatctgt tgtctgcaat taagtcacca  300
tgccaaagag aaaccccaga aggtgcagaa gcaaagccat ggtatgagcc aatatatctg  360
ggcggcgtct tcagctcgga aaggggagac cggctgtctg cagaaatcaa caggcctgac  420
tacctcaact tcagggagag tggccaggtg tatttttgaa taattgcatt ggttagaagt  480
```

```
tctcgcacac catccgataa accagtcgcc cacgttgtag ctaatccaca agccgaggga    540
cagctgcaat ggctgaatcg acgggccaat gcattgctgg ctaatggggt agagcttcgc    600
gataatcaac ttgtggtccc atcagagggt ctttacctca tatactccca agtccttttc    660
aaaggccaag gttgtccttc tacacatgtg cttttgaccc acactatttc tagaatcgca    720
gtgtcatacc agactaaggt caacctgctc tcagctatta agtcaccctg ccaaagggaa    780
actcccgagg gtgccgaggc caaaccttgg tatgaaccta tctaccttgg gggagtgttc    840
caactggaga agggcgatag attgagtgcc gagataaatc ggccagatta tttgaacttc    900
agagagagcg gacaagtcta cttcggtata atagcattgg tgcgcagtag ccgaactccc    960
tccgataagc cagtcgccca tgttgtcgca aaccctcagg cagagggaca gcttcaatgg   1020
ctcaatcgcc gcgccaatgc cttgcttgcc aacggtgttg aactgaggga caaccagttg   1080
gtcgttccta gcgaaggttt gtatcttatc tatagccagg tactgttcaa agggcaaggg   1140
tgtcctagta cccatgtgct cctcacacat accatatcaa gaattgcagt tagttatcag   1200
accaaggtaa atctcctgag tgcaataaaa tcccctgcc agcgggagac tccagagggg   1260
gctgaggcca aaccatggta cgagcccatc tatctcgatg gagtctttca gctggaaaag   1320
ggagatcgcc tttctgcaga gattaatagg ccagattacc tgaatttccg cgagagtggg   1380
caagtttact tcggtatcat agcccttgaa agcaaatacg ccctccatg ccccccctgc    1440
cctgcacccg agttcctggg cggtccctct gtgttcttgt tcccccaaa gcccaaggac    1500
accctcatga tatccaggac accagaagta acttgcgttg tcgtcgatgt gtccaggaa    1560
gatccagaag ttcaatttaa ctggtatgtc gatggtgtgg aagtgcataa tgcaaaaact   1620
aagcctcgag aagaacaatt caactctaca tatcgcgtcg tcagtgtgtt gactgtcctc   1680
caccaagact ggctgaatgg caaagagtac aagtgcaaag tgtccaataa gggccttcca   1740
tcttcaattg agaaaaccat tagtaaggca aagggtcagc cccgggaacc acaggtctat   1800
acattgcccc ctagccaaga ggagatgacc aagaaccaag tctcactcac ctgtctggta   1860
aagggatttt accctagtga tatcgctgtc gaatgggaaa gcaacggtca gcccgagaac   1920
aattacaaaa ccactccacc agtgctcgac tcagacggct cttttttcct ttactcacgg   1980
ttgactgtag ataaatcccg ctggcaggag ggcaatgttt tcagctgtag tgttatgcac   2040
gaagcacttc acaatcatta tacccagaag tcactgtctc tttcccttgg gaag         2094

SEQ ID NO: 133         moltype = DNA   length = 2136
FEATURE                Location/Qualifiers
source                 1..2136
                       mol_type = other DNA
                       organism = synthetic construct
                       note = Codon optimized nucleic acid sequence encoding SEQ
                           IDNO 113

SEQUENCE: 133
gagccaaagt ccagcgacaa gacacatact tgtccaccct gtccagctcc agaggcagcc      60
ggcggtcctt ccgtgttctt gtttcctccc aagccaaagg cacacactgat gatctctaga    120
actcccgagg ttacatgcgt tgtggttgac gtgtctcatg aggaccctga agtgaagttt     180
aattggtacg tcgacggtgt cgaggtacat aatgcaaaaa ctaagccacg cgaggaacaa     240
tataatagca cataccgagt ggtcagcgtc ttgacagtgc ttcaccaaga ctggctcaat     300
ggtaaggagt ataaatgcaa agtatcaaac aaagccttgc ccgcatccat cgaaaaaaca     360
ataagcaagg ctaagggaca accacggagg ccacaagtgt atactctccc cccttcaaga    420
gacgagctca caaaaaacca agtttcactg acttgcctgg ttaaaggttt ttatccctcc     480
gatatagctg ttgaatggga gagtaatgga caaccagaaa ataactataa aactactcct     540
cccgtgcttg acagtgacgg gtcttttttc ttgtattcta aactcaccgt tgataaaagt     600
agatggcagc agggcaatgt tttctcctgc tcagtgatgc atgaagctct gcacaatcac     660
tacacacaaa aatcactgtc cctgtctcct ggtaagggtg gcggtggcag cgtcaggtca     720
agttccagaa cacctagtga taaaccagta gcccatgtag ttgctaaccc ccaggctgag     780
ggacaacttc agtggcttaa ccgccgcgct aatgctcttc ttgctaacgg agtcgaactg     840
agagataacc aacttgtcgt gcctagtgag gggttgtatc tcatttactc tcggtgctg     900
ttcaagggcc agggctgtcc atcaactcac gtactgctta cacatactat tagcaggata    960
gcagtgagct accaaaccaa agtaacttg tgtctgccac ttaaaagccc ttgtcagagg    1020
gaaacccctg aggggcaga agctaagcca tggtacgaac ctatttacct tggtggggtg    1080
tttcagttgg agaaagggga tcggcttagt gctgaaataa atagacccga ttattgaac    1140
ttccgggaga gtggtcaggt ttacttcgga atcatcgccc tgggagggg gggttctagc    1200
tcaaggacac caagcgataa accagtggca catgtggtcg ctaatcccca agcagaggg    1260
caacttcagt ggttgaaccg ccgggctaat gcactgctcg caaacggtgt agagttgagg    1320
gacaatcaac tcgttgtacc aagtgagggc ttgtatctca tatacagcca ggtgcttttt    1380
aaaggccagg ggtgtcccag tacacagtg ttgctcaccc acacaatatc aagaatagca    1440
gtctcatacc aaactaaggt taatctcctc tcagcaatta atccccttg tcagcggag    1500
acccccgaag gcgctgaggc taagccctgg tacgaaccca tctatcttgg tggggttttt    1560
caactggaga aaggcgatcg attgtcagcc gagattaatc gcccagatta cctgaacttt    1620
cgcgaatccg gacaggtata cttcggcatt atcgcattg gtggcggtgg cagcagcagt    1680
aggactccta gcgataaacc cgttgctcat gttgttgcaa acccacaggc agaagggcag    1740
ctccaatggc tcaatcggcg cgcaaacgca ttgctggcca acggagtaga gctgcgggac    1800
aaccaacttg ttgttcccag cgaaggtctt tacctcattt attcccaagt cctttttcaag    1860
ggccaaggct gtccaagtac acacgtactt cttactcaca caataagtcg catgcagtc    1920
tcttaccaaa caaaagtcaa tctcctgtct gcaattaaat ccccatgtca aagagaaacc    1980
ccagaagggg cagaggccaa gcttggtat gagcctatct atttgggcgg ggttttccaa    2040
cttgagaagg gagaccggct ttcagctgaa atcaacaggc ccgattatct caacttcagg    2100
gagagtggac aagtctactt cggaattata gccctg                              2136

SEQ ID NO: 134         moltype = DNA   length = 2124
FEATURE                Location/Qualifiers
source                 1..2124
                       mol_type = other DNA
                       organism = synthetic construct
                       note = Codon optimized nucleic acid sequence encoding SEQ
```

-continued

IDNO 114
SEQUENCE: 134
gaaaggaagt caagcgtgga atgccctccc tgtccagcac cacccgtcgc tggacccagc 60
gtgttcctgt tcccacccaa acccaaggat actctcatga tcagccggac accagaggta 120
acttgtgtag tagtagatgt tagccatgag gatcctgagg tgcagtttaa ttggtacgtt 180
gacggggtgg aggtacataa cgcaaaaacc aaaccacgag aggagcagtt caacagcacc 240
tttcgcgtag tgtcagtcct gaccgtagtc caccaggact ggttgaacgg taaggaatac 300
aagtgtaagg tttccaacaa gggtctgcct gcctctatcg agaaaacaat aagcaagaca 360
aaaggccaac ctcgggaacc tcaggtatat acacttcccc caagtcgaga ggagatgact 420
aagaaccagg taagccttac ttgcctggta aaaggttttt atcccagcga catcgccgtc 480
gaatgggaat ccaatggaca gcctgagaat aactataaga caacccccc tatgctggat 540
tcagacggta gcttctttct ttattccaaa cttaccgtgg ataaatcaag gtggcagcaa 600
gggaatgttt tctcttgtag tgtcatgcac gaagcccttc acaaccatta cactcagaaa 660
tccctcagct tgtcacctgg aaaagggggc ggcggaagtg tccgatcctc ctctcggacc 720
ccatctgaca agccagttgc ccatgtggtg gctaatccac aggctgaggg gcaactccag 780
tggctgaata ggagagctaa tgctctcctt gctaatggag ttgaacttag agacaatcag 840
cttgtcgtcc cctctgaagg gctctatttg atatacagcc aggttctttt taagggtcag 900
ggctgtccct ccactcatgt gcttctcaca cacacaatca gccgcatcgc agtgagttat 960
caaaccaaag ttaacctgct ttccgcaatc aaaagccctt gtcagagaga acccccagaa 1020
ggagcagaag ccaaaccctg gtatgagccc atctatctcg gaggagtatt ccaactggaa 1080
aagggtgata ggttgagcgc tgagataaat agacccgact atctgaactt cagggagagt 1140
ggtcaagtat actttggcat tattgccctc ggcggcggcg gcagttccag tcggacaccc 1200
tcagataagc cagttgctca cgttgtggcc aaccccaag ccgaaggcca gttgcagtgg 1260
ttgaataggc gggctaatgc tctgctggca acggtgtag aacttcgaga taatcaactc 1320
gttgtgccct cagagggact ctatctcatt tacagccagg tgcttttcaa agggcagggg 1380
tgtccctcta cacatgtcct tctgacacat acaatctgat aatagctgt ctcctaccaa 1440
acaaaagtta atttgctcag tgctataaaa tcccccttgcc agcgggagac acctgagggg 1500
gctgaggcca aaccttggta cgagcctatc tatctcggcg gggtattcca acttgaaaaa 1560
ggggacagac ttagtgccga aataaaccgc ccagactacc ttaacttccg cgagtccggg 1620
caggtttact ttgggataat cgcactgggg ggaggtggat cttcatctag aaccccaagc 1680
gacaaaccag ttgctcatgt ggtcgccaat cctcaagctg aaggacagct tcaatggctt 1740
aatcgccggg caaacgccct tttggcaaat ggcgttgagc tgcgggataa tcaactggta 1800
gttccaagtg agggcttgta cttgatctat agtcaagtac tgttcaaggg ccaaggctgc 1860
ccatctacac acgttctttt gacccacact atttcaagga ttgccgtcag ctatcaaact 1920
aaagtgaacc tcctgtctgc tatcaagtca ccctgtcaac gagaaacccc tgagggtgct 1980
gaagccaagc cctggtatga gcccatatat ctcggcggag tctttcaact ggagaagggt 2040
gacaggctgt ctgccgaaat caatcggcct gactatctga actttcggga gagcggccag 2100
gtctacttcg gcattattgc tctc 2124

SEQ ID NO: 135          moltype = DNA   length = 2136
FEATURE                 Location/Qualifiers
source                  1..2136
                        mol_type = other DNA
                        organism = synthetic construct
                        note = Codon optimized nucleic acid sequence encoding SEQ
                        IDNO 115
SEQUENCE: 135
gtcaggagta gctctaggac cccatccgat aagcccgtcg cacatgtggt ggccaacccc 60
caggcagaag gccaactcca gtggcttaat agacgagcca atgcccttt ggctaatggc 120
gtcgagctca gggacaatca acttgtggtg cctagtgagg gactctattt gatttatagc 180
caagtacttt tcaagggaca gggttgtcca tctcacacta tgcttcttac ccacactatt 240
tctcggatcg cagtttctta tcaaaccaaa gtcaaccttt tgtccgctat caagagtcca 300
tgtcagagag agacacccga gggcgctgaa gctaagccct ggtatgagcc aatctatctt 360
gggggagttt tccagctcga aaaggggac cggctgtctg ccgaaattaa ccgccctgac 420
tacctcaact ttagggagag tggtcaggtg tatttcggaa ttgccttt gggcggtggc 480
gggtcatcta gcagaacccc atccgacaag ccagtcgccc atgtagtggc caatccacag 540
gcagagggac aattgcagtg gttgaatcgg cgagccaatg cattgctcgc aaacggggtg 600
gagctccgcg ataaccagct tgtagtgcca tccgaaggat tgtatttgat ttattctcaa 660
gtgctgttca aaggacaagg gtgccatct acccatgtct tgctgacaca cacaatttcc 720
cggatcgctg tatcctacca aaccaaggtg aatcttttgt cagcaatcaa aagcccatgt 780
caacgcgaaa caccgagggg agcagaggcc aagccttggt acgagcctat ttacctgggc 840
ggtgtctttc aacttgagaa gggagatcgc ttgagcgcag aaattaatag gcctgactac 900
cttaacttta gggaaagtgg acaggtatat tttggaataa ttgcactcgg tggtggggga 960
tcatcaagcc gcacaccttc cgataaaccc gttgcccacg tagtgccaca tcccaggcc 1020
gaaggccaat tgcaatggct gaaccgaaga gccaacgctc ttctcgcaaa tggtgtagaa 1080
ctccgggata ccagttggt ggtgcccagc gagggccttt atctcatata ctctcaagtc 1140
cttttcaaag gcagggatg tcctagtacc catgtacttc tcactcacac aatctccagg 1200
atcgccgttt catatcaaac aaaagtgaat ttgctcagcg ctataaagag tccatgcaa 1260
cgcgaaacac ctgagggggc gcaagcaaaa ccttggtaca gcctattta tcttggtgta 1320
gtattccaac ttgaaaaagg tgacaggttg tcagctgaga ttaatagacc agattatctg 1380
aattttcgcg aatctgggca ggtttacttc gggataatcg ctctgggagg aggagggagt 1440
gaaccaaagt ccagcgataa aactcatacc tgtccacctt gtccagcccc gaagctgca 1500
ggaggcccta gcgtgttctt gtttcctccc aaacccaaag acacattgat gattagtcgc 1560
actcctgaag tgacatgtgt tgtcgtagac gtatctcatg aagacccgga agtcaagttt 1620
aactggtatg tcgatggagt ggaggtgcac aatgcaaaga ctaagcctag ggaagaacaa 1680
tataacagta cctacagagt tgtgtcagtg cttaccgtct tgcatcagga ttggctcaat 1740
ggaaaagagt ataagtgtaa ggtaagtaac aaggcattgc ccgctagcat agagaaaaca 1800
ataagcaagg caaaggggca gccccaggga ccccaagtct atcccttcc accaagtcgg 1860
gatgaactga ctaaaaatca ggtgtccttg acttgccttg taaaggggatt ctaccccta 1920

```
gatatcgcag tggagtggga gagcaacgga cagccagaaa acaattacaa aaccaccccc  1980
cctgtcctgg attcagacgg ttctttcttt ttgtactcca aacttacagt agacaagtcc  2040
aggtggcaac aaggcaatgt ctttagctgt tctgtcatgc acgaagccct tcacaaccac  2100
tatactcaaa agtcactttc tctttcccct ggaaaa                            2136
```

| SEQ ID NO: 136 | moltype = DNA length = 2124 |
|---|---|
| FEATURE | Location/Qualifiers |
| source | 1..2124 |
| | mol_type = other DNA |
| | organism = synthetic construct |
| | note = Codon optimized nucleic acid sequence encoding SEQ IDNO 116 |

SEQUENCE: 136
```
gtaagatcat ctagtcggac tccatcagac aaaccagtag cccatgttgt tgcaaaccca   60
caagccgagg gtcaacttca gtggctcaat aggcgcgcca atgcactgct cgctaatgga  120
gtcgaattgc gcgataacca attggtggta cctagtgagg gactttattt gatctatagt  180
caggtgctct ttaaaggtca gggttgcccc tccacccacg ttctcctgac acataccatt  240
agcaggatag ctgtaagtta ccagactaaa gtcaacctcc ttagcgctat caaaagtcca  300
tgtcaaagag aaactccaga aggagcagaa gccaaacctt ggtacgagcc tatctacctc  360
ggaggagtat ttcagcttga aaggggggat cgactgagcg ccgaaatcaa cagacccgat  420
taccttaact tccgagaatc cggccaagta tacttcggga ttattgccct ggggggaggt  480
ggctcttcaa gcagaacccc atcagacaag ccagtgctca acgtcgttgc caatcccaa   540
gctgaagggc aacttcaatg gcttaatcga agggctaatg cacttttggc caacggtgta  600
gaactccgag acaaccaatt ggtcgtgcca tcagaaggcc tttacctcat atactcccag  660
gttctttttca agggtcaggg atgtcctagt acacacgtat tgttgaccca tacaatttca  720
aggatagcca taagctacca gactaaagtt aatctgctta gtgctataaa gtctccttgt  780
cagcgagaga caccegaagg cgctgaggca aaaccctggt acgagcccat ctacctcgga  840
ggtgttttc aactggagaa gggagaccga ctgtccgccg aaattaaccg gcccgactac  900
ctcaatttc gcgaatccgg gcaagtttat tttggtatca ttgcattggg tggtggaggc  960
tccagtagcc ggactccctc cgataaacca gtggcacata tagtcgccaa ccctcaagca 1020
gaagggcaat tgcagtggct aatagacgc gccaatgccc tcctggctaa tggcgtagag 1080
cttagagata atcaattggt ggtgcctagt gaaggtctgt acctcattta ctctcaggtt 1140
ctctttaagg gccaaggatg tccctcaact cacgtactgc tgactcatac tatatcacgg 1200
atagccgtct cttaccagac aaaagtgaat ttgctgccac ccatcaagag tccatgccag 1260
cgagaaaccc ctgaggggggc tgaagctaaa ccatgtgtatg aaccaatcta ccttggtgtc 1320
gttttccagc tcgagaaggg cgatagactt agccgccgaaa ttaatcgacc agactatctc 1380
aattttagag agtcaggaca agtgtacttt ggtattatag ccttgggtgg gggcggttct 1440
gaacggaaaa gttctgttga atgccctcca tgtcctgccc cctgtggc cggtccctca 1500
gtctttctct tcccaccaa gcccaaagat acattgatga ttagtaggac tccgaggtg 1560
acttgcgtag ttgtcgatgt tccccatgaa gatccagaag tgcaatttaa ctggtatgta 1620
gacggcgtcg aggtccataa tgctaaaact aagccccgcg aggagcagtt taattcaacc 1680
tttagagttg tgagcgttct gaccgttgta caccaggatt ggcttaatgg taaagagtac 1740
aagtgcaagg tgtccaacaa gggacttcca gcatccattg aaaagaccat tccaagact 1800
aaagggcaac cacgggaacc acaagtctac accctcccac ccagccgcga agagatgact 1860
aaaaatcagg tatcacttac ttgcctggtt aagggtttct acccatctga cattgctgtc 1920
gagtgggaat ctaatgggca acctgaaaac aattacaaga caacaccacc tatgctggat 1980
tccgatggga gtttcttcct gtacagtaaa ctcactgttg acaagtcccg atggcagcag 2040
ggaaatgtct tttcatgctc cgttatgcat gaggccctcc acaaccatta tacccaaaag 2100
tctctgtccc tgtcaccagg aaag                                        2124
```

| SEQ ID NO: 137 | moltype = DNA length = 2082 |
|---|---|
| FEATURE | Location/Qualifiers |
| source | 1..2082 |
| | mol_type = other DNA |
| | organism = synthetic construct |
| | note = Codon optimized nucleic acid sequence encoding SEQ IDNO 117 |

SEQUENCE: 137
```
gaatcaaagt acggtccacc ttgtcctccc tgtcccgccc ccgagtttct gggggggtccc   60
tctgtctttc tgttttccacc aaagcccaag gacactctga tgattagcag aacaccagaa  120
gtaacctgtg tcgtcgtgga tgtctcacag gaggatcccg aggtacagtt caactggtac  180
gtggatggtg tagaggtgca taatgcaaag actaaaccaa gggaagaaca attcaattct  240
acttaccggg tcgtatctgt cttgaccgtg cttaccaag attggctgaa cggcaaggag  300
tataaatgta aagtttctaa taagggggctc ccatcaagta tcgagaaaac catttcaaaa  360
gcaaaagggc aacctcgaga gcctcaagtt tacacactcc ctccatcaca agaagaaatg  420
acaaagaatc aagtcagcct cacctgcctt gtaaagggct tctatccctc cgacattgca  480
gtggaatggg agtcaaacgg acaacctgag aataattata gaccacacac tccagtgctg  540
gactcagatg ggtcattttt cctgtactcc cgcttgaccg tggacaagtc tcgatggcag  600
gaaggtaatg tgttcagctg tagtgtgatg cacgaagcac tgcacaacca ttatacccag  660
aaatccctgt cattgtccct cggtaaggtg agatccagta gccgcacacc aagtgataaa  720
cctgtagccc acgtagtggc aaatccacaa gctgaagggc agctccagtg gctgaatcgc  780
cgcgcaaacg cactgctggc aaatgggtta gagcttaggg acaatcagct cgtagtgccc  840
agtgaaggcc tctatctcat ttattcacaa gtactttttca aaggcaggg atgcccctagt  900
acccatgtcc ttttgacaca caccatctcc cgaatagcca taagcaagaa aactaaggtt  960
aatctcctta gcgcaatcaa atctccttgc caaagggaaa ccccegaagg cgccgaagcc 1020
aagccctggt atgaacctat ataccttggc ggggttttc agctggaaaa gggagacagg 1080
ttgagtgccg agattaatcg accagactac cttaatttta gagagtccgg ccaggtctat 1140
ttcgggataa tcgctctgtc ttctagaact cccagtgata aacccgttgc cacgtggtg 1200
gccaacccac aggccgaagg gcaactgcag tggctgaaca gacgagcaaa tgcattgttg 1260
```

```
gccaacggtg ttgaactgcg cgacaaccaa cttgtggtgc ctagtgaggg tctctacttg 1320
atttattccc aagtcctctt taaagggcaa gggtgtccct ctactcatgt cctgctcact 1380
cacaccatct ccagaattgc agtatcttat cagacaaaag taaacttgct gtcagccatt 1440
aaatcaccat gtcagaggga gacacctgaa ggtgcagaag ctaagccttg gtatgaacct 1500
atttatctcg gcggggtgtt ccaattggag aaagggacc gactgagcgc tgaaatcaat 1560
agacccgatt atttgaactt tagagagagt ggccaggtat acttcggtat aatagccctg 1620
tccagtcgaa ctccttctga taagcctgtc gcacatgttg tggcaaatcc tcaagctgag 1680
ggacagctcc aatggttgaa tagacgcgcc aacgcactcc tcgctaacgg ggttgagctc 1740
cgagacaatc agcttgtcgt cccaagcgag gggctgtacc ttatttactc ccaggtattg 1800
tttaagggac aggggttgccc ctccacacat gtgctcctga cccacactat cagccgaata 1860
gccgttagct atcaaacaaa ggtcaatctc ctgagtgcaa taaagtctcc ttgtcagcga 1920
gaaaccccccg aaggcgccga ggccaagccc tggtacgagc caatttacct cggtggagtc 1980
tttcagttgg agaaggggga tagattgagc gcagaaatta accgacctga ctatttgaac 2040
ttcagagaaa gcggacaagt ctattttggt atcatcgccc tg                     2082

SEQ ID NO: 138          moltype = DNA   length = 2079
FEATURE                 Location/Qualifiers
source                  1..2079
                        mol_type = other DNA
                        organism = synthetic construct
                        note = Codon optimized nucleic acid sequence encoding SEQ
                        IDNO 118
SEQUENCE: 138
gaatcaaagt acggccctcc atgtccaccc tgtcctgccc ctgagtttct cggaggaccc 60
agtgtattcc tcttcccacc aaaacccaag gatacccctca tgatcagcag gactcccgaa 120
gttacatgcg ttgtcgtaga cgtatcacag gaagatctcg aggtccaatt taattggtac 180
gtcgacggag tcgaagttca taacgccaaa acaaaaccac gagaagagca atttaacagt 240
acatatcgcg tggtctcagt gctgaccgtg ctccaccagg actggctcaa tgggaaagaa 300
tacaaatgta aggtttccaa taagggactc cctagctcaa tagaaaagac catttcaaaa 360
gctaaaggcc aaccccggga gccccaagtc tacacccttc cccccctctca ggaagaaatg 420
accaaaaatc aggtgtccct gacctgtctt gtgaaagggt tttatccctc agacattgcc 480
gtagagtggg aatcaaatgg acaacccgag aacaactata aaactactcc acctgttctg 540
gactccgatg gttccttttt cctgtacagc cgccttaccg ttgacaaatc acgatggcag 600
gaagggaatg tcttcagttg ttcagtaatg catgaagctc tccataacca ctatactgag 660
aagtccctgt ccctctctct gggcaagggc ggcggtggtt ccgtccgcag ttcttctcgg 720
actccctccg acaagccagt cgcacatgta gtcgccaacc cacaagcaga gggacagctt 780
cagtggctca atcgaagagc aaacgccctc cttgcaaacg cgtcgaact tcgcgacaac 840
caactggttg ttccatcaga aggcttgtat ctgatctact ctcaggtgct gtttaaggga 900
caggggatgtc ctagcacaca tgtgctcctt actcatacaa tttcaaggat gcagtaagc 960
taccaaacta aagtgaacct ccttagcgcg ataaagtccc catgccaaag ggagacaccc 1020
gagggagcag aagcaaagcc atggtatgaa cctatctatc tcggtggagt tttccagttg 1080
gagaaaggtg atagactctc tgctgagatc aatcgcccg actatctgaa tttccgcgaa 1140
tctgggcagg tctactttgg gataatagca ctgggtgggg gtggatctcc cgtagctcac 1200
gtggtcgcta acccacaggc tgaggggcaa ttgcaatggt tgaaccggcg ggctaatgct 1260
ttgttggcaa acggcgtaga attgagagac aaccaattgg tcgttccttc agaaggattg 1320
tatctcatct acagccaagt cttgtttaaa ggccaaggct gtccatctac acacgtgctt 1380
cttactcaca caatctcacg aatcgcagta tcttatcaga ccaaagtgaa cttgctctct 1440
gcaataaaaa gcccttgtca acgcgaaact ccagaagggg ctgaagcaaa gccatggtac 1500
gaacctattt atctcggggg ggtgttccaa ctcgagaaag ggaccgact gtccgctgaa 1560
atcaaccgcc ctgactatct taatttccgg gagtctgggc aggtatattt cggtataatt 1620
gcacttggag gcgggggtc acctgtggca catgtagtcg ccaaccccca agctgaagga 1680
caacttcaat ggctcaatag gcgcgcaaat gctctgctcg caaatggagt agaactccgg 1740
gataatcaac tggttgtgcc ttctgaagga ctgtatctga tctatagcca agtttgttc 1800
aagggccagg ggtgcccatc tacacacgta cttcttaccc acacaatatc ccgcatcgcc 1860
gtcagttatc agacaaaagt gaaccttttg tccgccatca gagcccatg tcagcgcgaa 1920
actcccgagg gtgctgaggc taaaccatgg tatgagccca tctatttggg aggcgtatttt 1980
caactggaaa aaggggatcg actgagcgca gagatcaata ggcccgatta tcttaatttc 2040
agggagtctg tcaagtgta ttttgggata attgctctg                         2079

SEQ ID NO: 139          moltype = DNA   length = 2094
FEATURE                 Location/Qualifiers
source                  1..2094
                        mol_type = other DNA
                        organism = synthetic construct
                        note = Codon optimized nucleic acid sequence encoding SEQ
                        IDNO 119
SEQUENCE: 139
gaatctaagt atgggccacc atgcccacca tgcccagccc cagaattcct gggcggacct 60
tccgttttct tgttcccacc aaagccaaaa gatactctga tgatttccag gacccctgaa 120
gttacctgtg tggtagtgga tgtcagccaa gaggatccag aagttcaatt taattggtat 180
gtagacggag tcgaagttca taacgctaaa actaaacctc gagaagagca gtttaattca 240
acctacaggg ttgtttccgt actgacagtt ttgcatcagg actggctgaa tggcaaggaa 300
tacaaatgca aggtcagcaa caaaggactc ccagttcaa tagaaaagac catttcaaaa 360
gctaaaggcc aaccacgaga acctcaggtc tacactctcc ctccctctca ggaagagatg 420
actaaaaatc aggtttcact tacatgcctc gtgaagggct tttacccag cgacattgct 480
gttgagtggg agagtaacgg acaacctgag aacaactaca gactacacc tcctgtgctg 540
gactcagatg gttccttctt ttgtatagc aggcttaccg ttgataagtc cgctggcaa 600
gaaggcaacg ttttcagttg ttcagtaatg cacgaagctc tccacaatca ttatacacag 660
aagagtctta gcctgtccct gggtaaggga ggcgggggt ccggggggcgg gggctcagtt 720
```

-continued

```
cgctcatcaa gccgaacacc ctcagacaag ccagttgccc acgtcgtagc caaccccaa    780
gctgaaggac agttgcaatg gctgaatagg cgagctaatg cattgttggc aaatggagta    840
gaactgcgcg ataatcaatt ggttgtgccc tcagaagggc tgtaccttat ttactcccag    900
gtgctcttca aagggcaggg ttgcccttca acccacgtac ttcttaccca cacaataagc    960
aggattgccg tctcctacca aactaaagta aacctgttga gcgctatcaa gagtccttgc   1020
caacgggaga cccctgaagg tgcagaggca aaaccatggt acgaacccat ttatctcgga   1080
ggggtgttcc agttggagaa ggggaccgc ctgtctgccg aaatcaatag gccagactac    1140
ctcaactttc gcgagtccgg gcaggtgtat tttgggatca tagctttggg cggtggggga   1200
tctcctgttg ctcatgtcgt tgcaaaccct caggctgaag gccaattgca atggctcaac   1260
aggagagcta acgcattgct ggccaacggg gttgagctcc gcgataacca gctggtagtt   1320
ccctcagagg gcttgtacct tatctattca caggttctct tcaaaggaca aggatgtcct   1380
agcacacacg tcttgcttac acataccatt agccggatag cagtttctta tcagactaaa   1440
gttaatctcc tctctgccat aaagtcaccc tgtcagcggg aaacacctga gggtgctgaa   1500
gcaaaacctt ggtatgaacc aatataccct ggtgagttt ttcaactgga aagggcgac    1560
agactgagcg ctgaaataaa cagacctgac taccttaatt tccgaaatc aggtcaagta    1620
tacttcggga ttatagcctt gggggtggga ggctcccag tggctcatgt agtcgctaat    1680
ccccaagctg aaggccaact ccaatggctt aacaggaggg ccaacgcact cctcgcaaat   1740
ggagtcgagc ttagggataa tcaattggtg gttccctctg agggcttgta tcttatttat   1800
tcacaggtcc tgtttaaagg ccaaggctgt ccttctacac atgtcctgtt gactcatacc   1860
ataagtagaa tagccgtgag ttaccagaca aaggttaacc tgctttccgc aatcaaatct   1920
ccatgccaac gcgagacccc agaagggca gaagcaaagc cttggtacga gcccatatat   1980
ctcggtgggg tctttcagct cgagaaaggc gaccggctta gcgctgaaat caaccgccca   2040
gactatttga actttcggga aagtggacaa gtctacttcg gtatcatagc actc         2094
```

SEQ ID NO: 140          moltype = DNA   length = 2112
FEATURE                 Location/Qualifiers
source                  1..2112
                        mol_type = other DNA
                        organism = synthetic construct
                        note = Codon optimized nucleic acid sequence encoding SEQ
                           IDNO 120
SEQUENCE: 140

```
gaatctaagt atggacctcc ttgtccacca tgtccagctc ccgagttcct gggaggccca    60
tccgtgtttt tgttcccccc taagccaaaa gacacactta tgatatcaag aaccccagaa   120
gttacttgtg tagtcgtgga cgtatcccag aagaccccg aggttcaatt taactggtat    180
gtagacgcg tggaagtcca taatgctaag acaaaagccc gggaggaaca attcaactcc    240
acataccgag tagtatccgt attgaccgtg ctccatcagg attggttgaa tggaaaggaa    300
tacaagtgca aagtttctaa taagggcctg ccttctagca tcgagaagac catcagcaag    360
gctaagggac agcctcgcga accccaagtt tataccttc ctcctagcca agaggagatg    420
actaaaaatc aggtgtcact cacctgcctc gtcaaaggat tctacccatc agatatagca    480
gtggaatggg agtccaacgg gcaacctgag aataactaca aaacaactcc acctgtcctg   540
gactccgacg gctccttctt tctttattcc agacttaccg tggacaaaag cagatggcaa   600
gagggaatg tgtttagctg cagtgttatg catgaagctt tgcataatca ttacacccaa    660
aaatcacttt cactctctct tggtaagggg ggtggggat ctggtggggg aggctccgtg    720
cgatcaagct ctaggacacc ctctgataaa cctgttgccc acgtcgtcgc aaatcccag    780
gccgaaggac agttgcagtg gctgaatcga agagctaacg cactgttggc aaacggggtg    840
gagctcaggg ataaccagtt ggtggtgcct tcagaaggc tttatctcat ttactcacaa    900
gtactcttta aagggcaagg gtgcccatct actcacgtgt tgctgactca cactatttct    960
cgaatcgcag ttagctatca aaccaaggta aacttgctca gtgccataaa aagtccttgt   1020
caaagggaga caccgaagg agcagaagca agccctggt acgagcccat ttactccggt   1080
ggtgtcttcc agctggagaa aggagaccgg ctctctgcag agataaacag acctgactat   1140
ctcaacttta gagaatcagg ccaggtttat ttcgggatca tcgcactctc cagccggacc   1200
ccctcagaca caccccgttgc acacgtcgtt gctaacccaac aagctgaagg gcagttgcag   1260
tggttgaatc gaagagcaaa cgctctcttg gccaacggtg tagaactccg cgacaaccaa   1320
ctggttgtac cttcagaagg gctctatctg atttactctc aggtgctttt caagggccaa   1380
gggtgcccta gtacacatgt tctgcttacc cacacaattt ctagaattgc agttagctac   1440
cagactaaag tcaacctgtt gagtgctatc aagtcccctt gtcagagaga accccagag   1500
ggagctgagg ctaaaccttg gtatgagccc atataccctcg gtggtgtatt ccaattggag   1560
aaaggtgatc gattgtcagc tgaaatcaac agaccagact atctgaattt cagagagtca   1620
ggacaagttt acttcggcat aatcgcattg agtagtcgga caccctccga taaacctgtg   1680
gcacatgttg tagctaaccc tcaagcagag gggcagctcc aatggctgaa ccggcgcgct   1740
aatgccctgt tggctaacgg cgttgagttg cgagataacc agctggttgt gccctctgaa   1800
ggtctgtact tgatctactc ccaagtcctg tttaaggtcc aaggctgtcc cagcacacac   1860
gtgttgctca cccacactat cagccggatt gccgtaagct atcaaactaa agtcaattt   1920
ctgtccgcca tcaaagtcc atgtcagcgc gaaacccctg agggtgccga agccaagcct   1980
tggtacgagc caatctacct gggtggcgtc tttcagctcg aaaaggggga ccggctctct   2040
gcagagataa atcgccctga ttatcttaac tttcgcgagt ccgggcaggt atactttggg   2100
attatagctc tt                                                       2112
```